(12) United States Patent
Koizumi et al.

(10) Patent No.: US 9,885,036 B2
(45) Date of Patent: Feb. 6, 2018

(54) DOUBLE-STRANDED POLYNUCLEOTIDE

(75) Inventors: Makoto Koizumi, Kanagawa (JP); Yasuhide Hirota, Sakura (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 746 days.

(21) Appl. No.: 13/001,714

(22) PCT Filed: Jun. 30, 2009

(86) PCT No.: PCT/JP2009/061998
§ 371 (c)(1),
(2), (4) Date: Jan. 27, 2011

(87) PCT Pub. No.: WO2010/001909
PCT Pub. Date: Jan. 7, 2010

(65) Prior Publication Data
US 2011/0152353 A1    Jun. 23, 2011

(30) Foreign Application Priority Data

Jul. 1, 2008 (JP) ................................ 2008-172174
May 21, 2009 (JP) ................................ 2009-122742

(51) Int. Cl.
*C12N 15/11* (2006.01)
*A61K 31/713* (2006.01)

(52) U.S. Cl.
CPC .......... *C12N 15/111* (2013.01); *A61K 31/713* (2013.01); *C12N 2310/14* (2013.01); *C12N 2310/321* (2013.01); *C12N 2310/343* (2013.01); *C12N 2320/51* (2013.01)

(58) Field of Classification Search
None
See application file for complete search history.

(56) References Cited

U.S. PATENT DOCUMENTS

2007/0265220 A1   11/2007   Rossi et al.

FOREIGN PATENT DOCUMENTS

| CA | 2504929 | 5/2004 |
|----|---------|--------|
| CA | 2701845 | 4/2009 |
| JP | 2003-219893 | 8/2003 |
| WO | WO 1999-054459 | 10/1999 |
| WO | WO 2000-044895 | 8/2000 |
| WO | WO 2001-036646 | 5/2001 |
| WO | WO 2001-075164 | 10/2001 |
| WO | WO 2002-044321 | 6/2002 |
| WO | WO 2002-055693 | 7/2002 |
| WO | WO 2003-044188 | 5/2003 |
| WO | WO 2003-070918 | 8/2003 |
| WO | WO 2004-015107 | 2/2004 |
| WO | WO 2004-027030 | 4/2004 |
| WO | WO 2004-044136 | 5/2004 |
| WO | WO 2004/044136 A2 | 5/2004 |
| WO | WO 2004045543 A2 * | 6/2004 |
| WO | WO 2004-090105 | 10/2004 |
| WO | WO 2004-113496 | 12/2004 |
| WO | WO 2005-121372 | 12/2005 |
| WO | WO 2008-152636 | 12/2008 |
| WO | WO 2009-044392 | 4/2009 |
| WO | WO 2009-102427 | 8/2009 |

OTHER PUBLICATIONS

Manoharan, RNA interference and chemically modified small interfering RNAs, 2004, Current Opinion in Chemical Biology, 8:570-579.*

Addepalli et al, Modulation of thermal stability can enhance the potency of siRNA, 2010, Nucleic Acid Research, vol. 38, 20:7320-7331.*

Allerson, Charles R. et al. "Fully 2'-Modified Oligonucleotide Duplexes with Improved in Vitro Potency and Stability Compared to Unmodified Small Interfering RNA," Journal of Medicinal Chemistry, 2005, vol. 48, p. 901-904.

Amarzguioui, Mohammed et al. "Tolerance for Mutations and Chemical Modifications in a siRNA," Nucleic Acids Research, 2003, vol. 31, No. 2, p. 589-595.

Baigude, Huricha et al. "Design and Creation of New Nanomaterials for Therapeutic RNAi," ACS Chemical Biology, 2007, vol. 2, No. 4, p. 237-241.

Beaucage, Serge L. "Solid-Phase Synthesis of siRNA Oligonucleotides," Current Opinion in Drug Discovery & Development, 2008, vol. 11, No. 2, p. 203-216.

Blidner, Richard A. et al. "Fully 2'-Deoxy-2'-Fluoro Substituted Nucleic Acids Induce RNA Interference in Mammalian Cell Culture," Chemical Biology & Drug Design, 2007, vol. 70, p. 113-122.

Blume, Gabriele et al. "Liposomes for the Sustained Drug Release In Vivo," Biochimica et Biophysica Acta (BBA), 1990, vol. 1029, p. 91-97.

Braasch, Dwaine A. et al. "RNA Interference in mammalian Cells by Chemically-Modified RNA," Biochemistry, 2003, vol. 42, No. 26, p. 7967-7975.

Burmeister, Paula E. et al. "2'-Deoxy Purine, 2'-O-Methyl Pyrimidine (dRmY) Aptamers as Candidate Therapeutics," Oligonucleotides, 2006, vol. 16, p. 337-351.

Chiu, Ya-Lin et al. "siRNA Function in RNAi: A Chemical Modification Analysis," RNA, 2003, vol. 9, p. 1034-1048.

Chonn, Arcadio et al. "Recent Advances in Liposomal Drug-Delivery Systems," Current Opinion in Biotechnology, 1995, vol. 6, p. 698-708.

Chu, Chia-Ying et al. "Potent RNAi by Short RNA Triggers," RNA, 2008, vol. 14, p. 1714-1719.

Czauderna, Frank et al. "Structural Variations and Stabilising Modifications of Synthetic siRNAs in Mammalian Cells," Nucleic Acids Research, 2003, vol. 31, No. 11, p. 2705-2716.

Dande, Prasad et al. "Improving RNA Interference in Mammalian Cells by 4'-Thio-Modified Small Interfering RNA (siRNA): Effect on siRNA Activity and Nuclease Stability When Used in Combination with 2'-O-Alkyl Modifications," J. Medicinal Chemistry, 2006, vol. 49, p. 1624-1634.

(Continued)

*Primary Examiner* — Ekaterina Poliakova-Georgantas
(74) *Attorney, Agent, or Firm* — Dorsey & Whitney LLP

(57) ABSTRACT

It is intended to provide a double-stranded polynucleotide that is resistant to RNase and has RNA interference effect, etc. The present invention provides a double-stranded polynucleotide comprising sense and antisense strands comprising polynucleotides comprising a nucleotide unit of DNAs and 2'-O-methyl RNAs alternately combined.

40 Claims, 28 Drawing Sheets

(56) References Cited

OTHER PUBLICATIONS

Eckstein, Fritz. "Phosphorothioate Oligodeoxynucleotides: What is their Origin and What is Unique About Them?" Antisense and Nucleic Acid Drug Development, 2000, vol. 10, p. 117-121.

Elbashir, Sayda et al. "Functional Anatomy of siRNAs for Mediating Efficient RNAi in *Drosophila melanogaster* Embryo Lysate," EMBO Journal, 2001, vol. 20, p. 6877-6888.

Elbashir, Sayda M. "Duplexes of 21-Nucleotide RNAs Mediate RNA Interference in Cultured Mammalian Cells," Nature, 2001, vol. 411, p. 494-498.

Fire, Andrew et al. "Potent and Specific Genetic Interference by Double-Stranded RNA in Caenorhabditis elegans," Nature, 1998, vol. 391, p. 806-811.

Funakoshi News, Mar. 15, 2007, p. 3 (English translation).

Hamada, Makiko, et al. "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, 2002, vol. 12, p. 301-309.

Hamilton, Andrew J. et al. "A Species of Small Antisense RNA in Posttranscriptional Gene Silencing in Plants," Science, 1999, vol. 286, p. 950-952.

Harborth, Jens, et al. "Sequence, Chemical, and Structural Variation of Small Interfering RNAs and Short Hairpin RNAs and the Effect on mammalian Gene Silencing," Antisense Nucleic Acid Drug Development, 2003, vol. 13, p. 83-105.

Heil, Florian et al. "Species-Specific Recognition of Single-Stranded RNA via Toll-Like Receptor 7 and 8," Science, Mar. 2004, vol. 303, p. 1526-1529.

Hogrefe, Richard I. et al. "Chemically Modified Short Interfering Hybrids (siHYBRIDS): Nanoimmunoliposome Delivery In Vitro and In Vivo for RNAi of HER-2," Nucleosides, Nucleotides, and Nucleic Acids, 2006, vol. 25, p. 889-907.

Hohjoh, Hirohiko. "RNA Interference (RNAi) Induction with Various Types of Synthetic Oligonucleotide Duplexes in Cultured Human Cells," FEBS Letters, 2002, vol. 521, p. 195-199.

Holen, Torgeir et al. "Positional Effects of Short Interfering RNAs Targeting the Human Coagulation Trigger Tissue Factor," Nucleic Acids Research, 2002, vol. 30, No. 8, p. 1757-1766.

Hornung, Veit et al. "Sequence-Specific Potent Induction of IFN-α by Short Interfering RNA in Plasmacytoid Dendritic Cells Through TLR7," Nature Medicine, Mar. 2005, vol. 11, No. 3, p. 263-270.

Hoshika, Shuichi et al. "RNA Interference Induced by siRNAs Modified with 4'-thioribonucleosides in Cultured Mammalian Cells," FEBS Letters, 2005, vol. 579, p. 3115-3118.

Hoshika, Shuichi et al. "Study of Modification Pattern-RNAi Activity Relationships by Using siRNAs Modified with 4'-Thioribonucleosides," ChemBioChem, 2007, vol. 8, p. 2133-2138.

Inoue, Hideo et al. "Synthesis and Hybridization Studies on Two Complementary Nona(2'-O-methyl)ribonucleotides," Nucleic Acids Research, 1987, vol. 15, No. 15, p. 6131-6148.

Judge, Adam D. et al. "Sequence-Dependent Stimulation of the Mammalian Innate Immune Response by Synthetic siRNA," Nature Biotechnology, Apr. 2005, vol. 23, No. 4, p. 457-462.

Karwowski, Boleslaw et al. "Stereocontrolled Synthesis of LNA Dinucleoside Phosphorothioate by the Oxathiaphospholane Approach," Bioorganic & Medicinal Chemistry Letters, 2001, vol. 11, p. 1001-1003.

Kawasaki, Andrew M. et al. "Uniformly Modified 2'-Deoxy-2'-fluoro Phosphorothioate Oligonucleotides as Nuclease-Resistant Antisense Compounds with high Affinity and Specificity for RNA Targets," Journal of Medicinal Chemistry, 1993, vol. 36, p. 831-841.

Koshkin, Alexei A. et al. "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, 1998, vol. 54, p. 3607-3630.

Kraynack, Bryan A. et al. "Small Interfering RNAs Containing Full 2'-O-Methylribonucleotide-Modified Sense Strands Display Argonaute2/eIF2C2-Dependent Activity," RNA, 2006, vol. 12, p. 163-176.

Kubo, Takanori et al. "Chemically Modified Symmetric and Asymmetric Duplex RNAs: An Enhanced Stability to Nuclease Degradation and Gene Silencing Effect," Biochemical and Biophysical Research Communications, 2008, vol. 365, p. 54-61.

Kubo, Takanori et al. "Modified 27-nt dsRNAs with Dramatically Enhanced Stability in Serum and Long-Term RNAi Activity," Oligonucleotides, 2007, vol. 17, p. 445-464.

Kumar, Priti et al. "Transvascular Delivery of Small Interfering RNA to the Central Nervous System," Nature, 2007, vol. 448, p. 39-43.

Lappalainen, Katriina et al. "Cationic Liposomes Mediated Delivery of Antisense Oligonucleotides Targeted to HPV 16 E7 mRNA in CaSki Cells," Antiviral Research., 1994, vol. 23, p. 119-130.

Layzer, Juliana M. et al. "In Vivo Activity of Nuclease-Resistant siRNAs," RNA, 2004, vol. p. 766-771.

Leng, Qixin et al. "Highly Branched HK Peptides are Effective Carriers of siRNA," Journal of Gene Medicine, 2005, vol. 7, p. 977-986.

Lorenz, Christina et al. "Steroid and Lipid Conjugates of siRNAs to Enhance Cellular Uptake and Gene Silencing in Liver Cells," Bioorganic & Medicinal Chemistry Letters, 2004, vol. 14, p. 4975-4977.

Mannino, Raphael et al. "Liposome Mediated Gene Transfer," BioTechniques, 1988, vol. 6, p. 682-690.

Matsugami, Akimasa et al. "Unexpected A-Form Formation of 4'-thioDNA in Solution, Revealed by NMR, and the Implications as to the Mechanism of Nuclease Resistance," Nucleic Acids Research, 2008, vol. 36, No. 6, p. 1805-1812.

Morita, Koji et al. "2'-O,4'-C-Ethylene-Bridged Nucleic Acids (ENA): Highly Nuclease-Resistant and Thermodynamically Stable Oligonucleotides fro Antisense Drug," Bioorganic & Medicinal Chemistry Letters, 2002, vol. 12, p. 73-76.

Morita, Koji et al. "Synthesis and Properties of 2'-O,4'-C-Ethylene-Bridged Nucleic Acids (ENA) as Effective Antisense Oligonucleotides," Bioorganic & Medicinal Chemistry, 2003, vol. p. 2211-2226.

Morrissey, David V. et al. "Potent and Persistent In Vivo Anti-HBV Activity of Chemically Modified siRNAs," Nature Biotechnology, Aug. 2005, vol. 23, No. 8, p. 1002-1007.

Muhonen, Pirkko et al. "RNA Interference Tolerates 2'-Fluoro Modifications at the Argonaute2 Cleavage Site," Chemistry & Biodiversity, 2007, vol. 4, p. 858-873.

Nishina, Kazutaka et al. "Efficient In Vivo Delivery of siRNA to the Liver by Conjugation of α-Tocopherol," Molecular Therapy, 2008, vol. 16, p. 734-740.

Nykanen, Antti et al. "ATP Requirements and Small Interfering RNA Structure in the RNA Interference Pathway," Cell, 2001, vol. 107, p. 309-321.

Obika, Satoshi et al. "Stability and Structural Features of the Duplexes Containing nucleoside Analogues with a Fixed N-Type Conformation, 2'-O,4'-C-Methyleneribonucleosides," Tetrahedron Letters, 1998, vol. 39, p. 5401-5404.

Obika, Satoshi et al. "Synthesis of 2'-O,4'-C-Methyleneuridine and -cytidine. Novel Bicyclic nucleosides Having a Fixed $C_3$,-endo Sugar Puckering," Tetrahedron Letters, 1997, vol. 38, No. 50, p. 8735-8738.

Parker, James S. "Structural Insights into mRNA Recognition from a PIWI Domain-siRNA Guide Complex," Nature, 2005, vol. 434, p. 663-666.

Prakash, Thazha P. et al. "Positional Effect of Chemical Modifications on Short Interference RNA Activity in Mammalian Cells," Journal of Medicinal Chemistry, 2005, vol. 48, p. 4247-4253.

Richardson, Frank C. "An Evaluation of the Toxicities of 2'-Fluorouridine and 2'-Fluorocytidine-HC1 in F344 Rats and Woodchucks (*Marmota monax*)," Toxicologic Pathology, 1999, vol. 27, No. 6, p. 607-617.

Richardson, Frank C. "Polymerization of 2'-Fluoro- and 2'-O-Methyl-dNTPs by Human DNA Polymerase α, Polymerase γ, and Primase," Biochemical Pharmacology, 2000, vol. 59, p. 1045-1052.

(56) References Cited

OTHER PUBLICATIONS

Richardson, Frank C. "Quantification of 2'-Fluoro-2'-Deoxyuridine and 2'-Fluoro-2'-Deoxycytidine in DNA and RNA Isolated from Rats and Woodchucks Using LC/MS/MS," Chemical Research in Toxicology, 2002, vol. 15, p. 922-926.
Sano, Masayuki et al. "Effect of Asymmetric Terminal Structures of Short RNA Duplexes on the RNA Interference Activity and Strand Selection," Nucleic Acids Research, 2008, vol. 36, No. 18, p. 5812-5821.
Sekine, M. and Taira K., ed., "RNAi Method and Antisense Method", Kodansha Ltd., published on Jun. 20, 2005, paragraph 2.4 RNAi Therapy—Application of siRNA to Therapeutic Drugs for Cancer, p. 76-87 (Japanese; with English Translation).
Sioud, Mouldy et al. "Suppression of Immunostimulatory siRNA-Driven Innate Immune Activation by 2'-Modified RNAs," Biochemical and Biophysical Research Communications, 2007, vol. 361, p. 122-126.
Sioud, Mouldy. "Induction of Inflammatory Cytokines and Interferon Responses by Double-Stranded and Single-Stranded siRNAs is Sequence-Dependent and Requires Endosomal Localization," Journal of Molecular Biology, 2005, vol. 348, p. 1079-1090.
Song, Erwei et al. "Antibody mediated in vivo Delivery of Small Interfering RNAs via Cell-Surface Receptors," Nature Biotechnology, Jun. 2005, vol. 23, No. 6, p. 709-717.
Soutschek, Jurgen et al. "Therapeutic Silencing of an Endogenous Gene by Systemic Administration of Modified siRNAs," Nature, 2004, vol. 432, p. 173-178.
Tsui, Nancy B.Y. et al. "Stability of Endogenous and Added RNA in Blood Specimens, Serum, and Plasma," Clinical Chemistry, 2002, vol. 48, No. 10, p. 1647-1653.
Ui-Tei, Kumiko et al. "Functional Dissection of siRNA Sequence by Systematic DNA Substitution: Modified siRNA with a DNA Seed Arm is a Powerful Tool for Mammalian Gene Silencing with Significantly Reduced Off-Target Effect," Nucleic Acids Research, 2008, vol. 36, No. 7, p. 2136-2151.

Weitzer, Stefan et al. "The Human RNA Kinase hClp1 is Active on 3' Transfer RNA Exons and Short Interfering RNAs," Nature, 2007, vol. 447, p. 222-226.
Wolfrum, Christian et al. "Mechanisms and Optimization of In Vivo Delivery of Lipophilic siRNAs," Nature Biotechnology, Oct. 2007, vol. 25, No. 10, p. 1149-1157.
Xia, Chun-Fang et al. "Intravenous siRNA of Brain Cancer with Receptor Targetign and Avidin-Biotin Technology," Pharmaceutical Research, 2007, vol. 24, No. 12, p. 2309-2316.
Yadava, Preeti et al. "Evaluation of Two Cationic Delivery Systems for siRNA," Oligonucleotide, 2007, vol. 17, p. 213-222.
Han et al., "The Effectiveness of siRNA Depends on the Target Sites of mRNA," *China Biotechnology* (2004), 24(12): pp. 6-9 (English language Abstract provided).
Sun, L. et al., "Chemical Modification and Clinical Application of siRNA," *Chemistry of Life*, 25(4):339-342 (2005).
Course on Biochemical Experiments 2 (Seikagaku Jikken Kouza 2) Chemistry of Nucleic Acids II, Nucleolytic enzyme and primary structure, (1976), published by Tokyo Kagaku-Dojin Publishing Co., Ltd., Tokyo, Japan, from line 5, p. 68, to line 10, p. 69, 5 pages including English translation.
Funakoshi News, Funakoshi Co., Ltd., Mar. 15, 2007, p. 3 with English translation, 6 pages.
Koizumi, Certificate of Experimental Results, Aug. 8, 2014, Daiichi Sankyo Company, Limited, 3 pages.
Prakash et al., "Positional Effect of Chemical Modifications on Short Interference RNA Activity in Mammalian Cells," *J. Med. Chem.*, (2005) 48:4247-4253.
Sioud et al., "Suppression of immunostimulatory siRNA-driven innate immune activation by 2'-modified RNAs," *Biochemical and Biophysical Research Communications*, (2007), 361:122-126.
Ui-Tei et al., "Functional dissection of siRNA sequence by systematic DNA substitution: modified siRNA with a DNA seed arm is a powerful tool for mammalian gene silencing with significantly reduced off-target effect," *Nucleic Acids Research*, (2008), 36(7):2136-2151.

* cited by examiner

CT-169S  5' GCA CAA GAA UGG AUC ACA  SEQ ID NO: 113
CT-157S  UT CGU GUT CTU ACC UAG TGT Up5'  SEQ ID NO: 114 ent filed under 35 U.S.C. 371 of International Patent Application No. PCT/JP2009/061998, filed Jun. 30, 2009, entitled "Double-Stranded Polynucleotide," which claims priority to Japanese Application No. 2008-172174 filed Jul. 1, 2008, and to Japanese Application No. 2009-122742 filed May 21, 2009, the contents of all of which are hereby incorporated by reference in their entirety.

SEQUENCE LISTING

```
<160> NUMBER OF SEQ ID NOS: 118

<210> SEQ ID NO 1
<211> LENGTH: 21
<212> TYPE: DNA
<213> ORGANISM: Artificial Sequence
<220> FEATURE:
<223> OTHER INFORMATION: CT-095
<220> FEATURE:
<221> NAME/KEY: modified_base
<222> LOCATION: (2)..(2)
<223> OTHER INFORMATION: cm
```

```
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 1
gcacaagaau ggaucacaat t                                             21

<210> SEQ ID NO 2
<211> LENGTH: 3720
<212> TYPE: DNA
<213> ORGANISM: Homo sapiens
<220> FEATURE:
<221> NAME/KEY: CDS
<222> LOCATION: (269)..(2614)

<400> SEQUENCE: 2
aggatacagc ggcttctgcg cgacttataa gagctccttg tgcggcgcca ttttaagcct    60
ctcggtctgt ggcagcagcg ttggcccggc cccgggagcg gagagcgagg ggaggcggag   120
acggaggaag gtctgaggag cagcttcagt ccccgccgag ccgccaccgc aggtcgagga   180
cggtcggact cccgcggcgg gaggagcctg ttcccctgag ggtatttgaa gtataccata   240
caactgtttt gaaaatccag cgtggaca atg gct act caa gct gat ttg atg      292
                                Met Ala Thr Gln Ala Asp Leu Met
                                1               5 gag ttg gac atg gcc atg gaa cca gac aga aaa gcg gct gtt agt cac    340
Glu Leu Asp Met Ala Met Glu Pro Asp Arg Lys Ala Ala Val Ser His
    10                  15                  20 tgg cag caa cag tct tac ctg gac tct gga atc cat tct ggt gcc act    388
Trp Gln Gln Gln Ser Tyr Leu Asp Ser Gly Ile His Ser Gly Ala Thr
25                  30                  35                  40 acc aca gct cct tct ctg agt ggt aaa ggc aat cct gag gaa gag gat    436
Thr Thr Ala Pro Ser Leu Ser Gly Lys Gly Asn Pro Glu Glu Glu Asp
                45                  50                  55 gtg gat acc tcc caa gtc ctg tat gag tgg gaa cag gga ttt tct cag    484
Val Asp Thr Ser Gln Val Leu Tyr Glu Trp Glu Gln Gly Phe Ser Gln
            60                  65                  70 tcc ttc act caa gaa caa gta gct gat att gat gga cag tat gca atg    532
Ser Phe Thr Gln Glu Gln Val Ala Asp Ile Asp Gly Gln Tyr Ala Met
        75                  80                  85
```

```
act cga gct cag agg gta cga gct gct atg ttc cct gag aca tta gat       580
Thr Arg Ala Gln Arg Val Arg Ala Ala Met Phe Pro Glu Thr Leu Asp
     90              95                 100 gag ggc atg cag atc cca tct aca cag ttt gat gct gct cat ccc act       628
Glu Gly Met Gln Ile Pro Ser Thr Gln Phe Asp Ala Ala His Pro Thr
105             110                 115                 120 aat gtc cag cgt ttg gct gaa cca tca cag atg ctg aaa cat gca gtt       676
Asn Val Gln Arg Leu Ala Glu Pro Ser Gln Met Leu Lys His Ala Val
                125                 130                 135 gta aac ttg att aac tat caa gat gat gca gaa ctt gcc aca cgt gca       724
Val Asn Leu Ile Asn Tyr Gln Asp Asp Ala Glu Leu Ala Thr Arg Ala
            140                 145                 150 atc cct gaa ctg aca aaa ctg cta aat gac gag gac cag gtg gtg gtt       772
Ile Pro Glu Leu Thr Lys Leu Leu Asn Asp Glu Asp Gln Val Val Val
        155                 160                 165 aat aag gct gca gtt atg gtc cat cag ctt tct aaa aag gaa gct tcc       820
Asn Lys Ala Ala Val Met Val His Gln Leu Ser Lys Lys Glu Ala Ser
    170                 175                 180 aga cac gct atc atg cgt tct cct cag atg gtg tct gct att gta cgt       868
Arg His Ala Ile Met Arg Ser Pro Gln Met Val Ser Ala Ile Val Arg
185                 190                 195                 200 acc atg cag aat aca aat gat gta gaa aca gct cgt tgt acc gct ggg       916
Thr Met Gln Asn Thr Asn Asp Val Glu Thr Ala Arg Cys Thr Ala Gly
                205                 210                 215 acc ttg cat aac ctt tcc cat cat cgt gag ggc tta ctg gcc atc ttt       964
Thr Leu His Asn Leu Ser His His Arg Glu Gly Leu Leu Ala Ile Phe
            220                 225                 230 aag tct gga ggc att cct gcc ctg gtg aaa atg ctt ggt tca cca gtg      1012
Lys Ser Gly Gly Ile Pro Ala Leu Val Lys Met Leu Gly Ser Pro Val
        235                 240                 245 gat tct gtg ttg ttt tat gcc att aca act ctc cac aac ctt tta tta      1060
Asp Ser Val Leu Phe Tyr Ala Ile Thr Thr Leu His Asn Leu Leu Leu
    250                 255                 260 cat caa gaa gga gct aaa atg gca gtg cgt tta gct ggt ggg ctg cag      1108
His Gln Glu Gly Ala Lys Met Ala Val Arg Leu Ala Gly Gly Leu Gln
265                 270                 275                 280 aaa atg gtt gcc ttg ctc aac aaa aca aat gtt aaa ttc ttg gct att      1156
Lys Met Val Ala Leu Leu Asn Lys Thr Asn Val Lys Phe Leu Ala Ile
                285                 290                 295 acg aca gac tgc ctt caa att tta gct tat ggc aac caa gaa agc aag      1204
Thr Thr Asp Cys Leu Gln Ile Leu Ala Tyr Gly Asn Gln Glu Ser Lys
            300                 305                 310 ctc atc ata ctg gct agt ggt gga ccc caa gct tta gta aat ata atg      1252
Leu Ile Ile Leu Ala Ser Gly Gly Pro Gln Ala Leu Val Asn Ile Met
        315                 320                 325 agg acc tat act tac gaa aaa cta ctg tgg acc aca agc aga gtg ctg      1300
Arg Thr Tyr Thr Tyr Glu Lys Leu Leu Trp Thr Thr Ser Arg Val Leu
    330                 335                 340 aag gtg cta tct gtc tgc tct agt aat aag ccg gct att gta gaa gct      1348
Lys Val Leu Ser Val Cys Ser Ser Asn Lys Pro Ala Ile Val Glu Ala
345                 350                 355                 360 ggt gga atg caa gct tta gga ctt cac ctg aca gat cca agt caa cgt      1396
Gly Gly Met Gln Ala Leu Gly Leu His Leu Thr Asp Pro Ser Gln Arg
                365                 370                 375 ctt gtt cag aac tgt ctt tgg act ctc agg aat ctt tca gat gct gca      1444
Leu Val Gln Asn Cys Leu Trp Thr Leu Arg Asn Leu Ser Asp Ala Ala
            380                 385                 390 act aaa cag gaa ggg atg gaa ggt ctc ctt ggg act ctt gtt cag ctt      1492
Thr Lys Gln Glu Gly Met Glu Gly Leu Leu Gly Thr Leu Val Gln Leu
```

```
                395                 400                 405
ctg ggt tca gat gat ata aat gtg gtc acc tgt gca gct gga att ctt      1540
Leu Gly Ser Asp Asp Ile Asn Val Val Thr Cys Ala Ala Gly Ile Leu
    410                 415                 420 tct aac ctc act tgc aat aat tat aag aac aag atg atg gtc tgc caa      1588
Ser Asn Leu Thr Cys Asn Asn Tyr Lys Asn Lys Met Met Val Cys Gln
425                 430                 435                 440 gtg ggt ggt ata gag gct ctt gtg cgt act gtc ctt cgg gct ggt gac      1636
Val Gly Gly Ile Glu Ala Leu Val Arg Thr Val Leu Arg Ala Gly Asp
                445                 450                 455 agg gaa gac atc act gag cct gcc atc tgt gct ctt cgt cat ctg acc      1684
Arg Glu Asp Ile Thr Glu Pro Ala Ile Cys Ala Leu Arg His Leu Thr
                    460                 465                 470 agc cga cac caa gaa gca gag atg gcc cag aat gca gtt cgc ctt cac      1732
Ser Arg His Gln Glu Ala Glu Met Ala Gln Asn Ala Val Arg Leu His
            475                 480                 485 tat gga cta cca gtt gtg gtt aag ctc tta cac cca cca tcc cac tgg      1780
Tyr Gly Leu Pro Val Val Val Lys Leu Leu His Pro Pro Ser His Trp
        490                 495                 500 cct ctg ata aag gct act gtt gga ttg att cga aat ctt gcc ctt tgt      1828
Pro Leu Ile Lys Ala Thr Val Gly Leu Ile Arg Asn Leu Ala Leu Cys
505                 510                 515                 520 ccc gca aat cat gca cct ttg cgt gag cag ggt gcc att cca cga cta      1876
Pro Ala Asn His Ala Pro Leu Arg Glu Gln Gly Ala Ile Pro Arg Leu
                525                 530                 535 gtt cag ttg ctt gtt cgt gca cat cag gat acc cag cgc cgt acg tcc      1924
Val Gln Leu Leu Val Arg Ala His Gln Asp Thr Gln Arg Arg Thr Ser
                540                 545                 550 atg ggt ggg aca cag cag caa ttt gtg gag ggg gtc cgc atg gaa gaa      1972
Met Gly Gly Thr Gln Gln Gln Phe Val Glu Gly Val Arg Met Glu Glu
            555                 560                 565 ata gtt gaa ggt tgt acc gga gcc ctt cac atc cta gct cgg gat gtt      2020
Ile Val Glu Gly Cys Thr Gly Ala Leu His Ile Leu Ala Arg Asp Val
        570                 575                 580 cac aac cga att gtt atc aga gga cta aat acc att cca ttg ttt gtg      2068
His Asn Arg Ile Val Ile Arg Gly Leu Asn Thr Ile Pro Leu Phe Val
585                 590                 595                 600 cag ctg ctt tat tct ccc att gaa aac atc caa aga gta gct gca ggg      2116
Gln Leu Leu Tyr Ser Pro Ile Glu Asn Ile Gln Arg Val Ala Ala Gly
                605                 610                 615 gtc ctc tgt gaa ctt gct cag gac aag gaa gct gca gaa gct att gaa      2164
Val Leu Cys Glu Leu Ala Gln Asp Lys Glu Ala Ala Glu Ala Ile Glu
                620                 625                 630 gct gag gga gcc aca gct cct ctg aca gag tta ctt cac tct agg aat      2212
Ala Glu Gly Ala Thr Ala Pro Leu Thr Glu Leu Leu His Ser Arg Asn
            635                 640                 645 gaa ggt gtg gcg aca tat gca gct gct gtt ttg ttc cga atg tct gag      2260
Glu Gly Val Ala Thr Tyr Ala Ala Ala Val Leu Phe Arg Met Ser Glu
        650                 655                 660 gac aag cca caa gat tac aag aaa cgg ctt tca gtt gag ctg acc agc      2308
Asp Lys Pro Gln Asp Tyr Lys Lys Arg Leu Ser Val Glu Leu Thr Ser
665                 670                 675                 680 tct ctc ttc aga aca gag cca atg gct tgg aat gag act gct gat ctt      2356
Ser Leu Phe Arg Thr Glu Pro Met Ala Trp Asn Glu Thr Ala Asp Leu
                685                 690                 695 gga ctt gat att ggt gcc cag gga gaa ccc ctt gga tat cgc cag gat      2404
Gly Leu Asp Ile Gly Ala Gln Gly Glu Pro Leu Gly Tyr Arg Gln Asp
                    700                 705                 710 gat cct agc tat cgt tct ttt cac tct ggt gga tat ggc cag gat gcc      2452
```

|  |  |  |  |  |  |  |  |  |  |  |  |  |  |
|---|---|---|---|---|---|---|---|---|---|---|---|---|---|
| Asp | Pro | Ser | Tyr | Arg | Ser | Phe | His | Ser | Gly | Gly | Tyr | Gln | Asp | Ala |
|  |  | 715 |  |  |  | 720 |  |  |  | 725 |  |  |  |

```
ttg ggt atg gac ccc atg atg gaa cat gag atg ggt ggc cac cac cct    2500
Leu Gly Met Asp Pro Met Met Glu His Glu Met Gly Gly His His Pro
        730                 735                 740 ggt gct gac tat cca gtt gat ggg ctg cca gat ctg ggg cat gcc cag    2548
Gly Ala Asp Tyr Pro Val Asp Gly Leu Pro Asp Leu Gly His Ala Gln
745                 750                 755                 760 gac ctc atg gat ggg ctg cct cca ggt gac agc aat cag ctg gcc tgg    2596
Asp Leu Met Asp Gly Leu Pro Pro Gly Asp Ser Asn Gln Leu Ala Trp
                765                 770                 775 ttt gat act gac ctg taa atcatccttt aggtaagaag ttttaaaaag           2644
Phe Asp Thr Asp Leu
                780 ccagtttggg taaatactt ttactctgcc tacagaactt cagaaagact tggttggtag    2704
ggtgggagtg gtttaggcta tttgtaaatc tgccacaaaa acaggtatat actttgaaag   2764
gagatgtctt ggaacattgg aatgttctca gatttctggt tgttatgtga tcatgtgtgg   2824
aagttattaa ctttaatgtt ttttgccaca gcttttgcaa cttaatactc aaatgagtaa   2884
catttgctgt tttaaacatt aatagcagcc tttctctctt tatacagctg tattgtctga   2944
acttgcattg tgattggcct gtagagttgc tgagagggct cgaggggtgg gctggtatct   3004
cagaaagtgc ctgacacact aaccaagctg agtttcctat gggaacaatt gaagtaaact   3064
ttttgttctg gtccttttg gtcgaggagt aacaatacaa atggattttg ggagtgactc    3124
aagaagtgaa gaatgcacaa gaatggatca caagatggaa tttatcaaac cctagccttg   3184
cttgttaaat tttttttttt ttttttttaa gaatatctgt aatggtactg actttgcttg   3244
ctttgaagta gctcttttt tttttttttt ttttttttg cagtaactgt ttttaagtc     3304
tctcgtagtg ttaagttata gtgaatactg ctacagcaat ttctaatttt taagaattga   3364
gtaatggtgt agaacactaa ttcataatca ctctaattaa ttgtaatctg ataaagtgt    3424
aacaattgtg tagcctttttt gtataaaata gacaaataga aaatggtcca attagtttcc  3484
ttttttaatat gcttaaaata agcaggtgga tctatttcat gttttgatc aaaactatt    3544
tgggatatgt atgggtaggg taaatcagta agaggtgtta tttggaacct tgttttggac   3604
agtttaccag ttgccttta tcccaaagtt gttgtaacct gctgtgatac gatgcttcaa    3664
gagaaaatgc ggttataaaa aatggttcag aattaaactt ttaattcatt cgattg       3720
```

<210> SEQ ID NO 3
<211> LENGTH: 781
<212> TYPE: PRT
<213> ORGANISM: Homo sapiens

<400> SEQUENCE: 3

|  |  |  |  |  |  |  |  |  |  |  |  |  |  |  |
|---|---|---|---|---|---|---|---|---|---|---|---|---|---|---|
| Met | Ala | Thr | Gln | Ala | Asp | Leu | Met | Glu | Leu | Asp | Met | Ala | Met | Glu | Pro |
| 1 |  |  |  | 5 |  |  |  |  | 10 |  |  |  |  | 15 |  |

|  |  |  |  |  |  |  |  |  |  |  |  |  |  |
|---|---|---|---|---|---|---|---|---|---|---|---|---|---|
| Asp | Arg | Lys | Ala | Ala | Val | Ser | His | Trp | Gln | Gln | Gln | Ser | Tyr | Leu | Asp |
|  |  |  | 20 |  |  |  |  | 25 |  |  |  |  | 30 |  |  |

|  |  |  |  |  |  |  |  |  |  |  |  |  |  |
|---|---|---|---|---|---|---|---|---|---|---|---|---|---|
| Ser | Gly | Ile | His | Ser | Gly | Ala | Thr | Thr | Thr | Ala | Pro | Ser | Leu | Ser | Gly |
|  |  |  |  | 35 |  |  |  |  | 40 |  |  |  |  | 45 |  |

|  |  |  |  |  |  |  |  |  |  |  |  |  |  |
|---|---|---|---|---|---|---|---|---|---|---|---|---|---|
| Lys | Gly | Asn | Pro | Glu | Glu | Glu | Asp | Val | Asp | Thr | Ser | Gln | Val | Leu | Tyr |
|  |  |  | 50 |  |  |  |  | 55 |  |  |  |  | 60 |  |  |

|  |  |  |  |  |  |  |  |  |  |  |  |  |  |
|---|---|---|---|---|---|---|---|---|---|---|---|---|---|
| Glu | Trp | Glu | Gln | Gly | Phe | Ser | Gln | Ser | Phe | Thr | Gln | Glu | Gln | Val | Ala |
| 65 |  |  |  |  | 70 |  |  |  |  | 75 |  |  |  |  | 80 |

|  |  |  |  |  |  |  |  |  |  |  |  |  |  |
|---|---|---|---|---|---|---|---|---|---|---|---|---|---|
| Asp | Ile | Asp | Gly | Gln | Tyr | Ala | Met | Thr | Arg | Ala | Gln | Arg | Val | Arg | Ala |

```
                    85                  90                  95
Ala Met Phe Pro Glu Thr Leu Asp Glu Gly Met Gln Ile Pro Ser Thr
                100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
        130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
                195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
                260                 265                 270

Val Arg Leu Ala Gly Gly Leu Gln Lys Met Val Ala Leu Leu Asn Lys
                275                 280                 285

Thr Asn Val Lys Phe Leu Ala Ile Thr Thr Asp Cys Leu Gln Ile Leu
            290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
                340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
        450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510
```

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780

<210> SEQ ID NO 4
<211> LENGTH: 21
<212> TYPE: DNA
<213> ORGANISM: Artificial Sequence
<220> FEATURE:
<223> OTHER INFORMATION: CT-096
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm

```
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 4
utgtgaucca uuctugugct t                                              21

<210> SEQ ID NO 5
<211> LENGTH: 21
<212> TYPE: DNA
<213> ORGANISM: Artificial Sequence
<220> FEATURE:
<223> OTHER INFORMATION: CT-097
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 5
gcacaagaau ggaucacaat t                                              21

<210> SEQ ID NO 6
<211> LENGTH: 21
<212> TYPE: DNA
<213> ORGANISM: Artificial Sequence
<220> FEATURE:
```

<223> OTHER INFORMATION: CT-098
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 6
utgtgaucca uucuugugct t                                              21

<210> SEQ ID NO 7
<211> LENGTH: 21
<212> TYPE: DNA
<213> ORGANISM: Artificial Sequence
<220> FEATURE:
<223> OTHER INFORMATION: CT-099
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 7
gcacaagaau ggaucacaat t                                              21

<210> SEQ ID NO 8
<211> LENGTH: 21
<212> TYPE: DNA
<213> ORGANISM: Artificial Sequence
<220> FEATURE:
<223> OTHER INFORMATION: CT-100
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 8
utgtgaucca uucuugugct t                                              21

<210> SEQ ID NO 9
<211> LENGTH: 21
<212> TYPE: DNA
<213> ORGANISM: Artificial Sequence
<220> FEATURE:
<223> OTHER INFORMATION: CT-112
<220> FEATURE:
<221> NAME/KEY: modified_base
<222> LOCATION: (2)..(2)
<223> OTHER INFORMATION: cm
<220> FEATURE:

```
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-O, 4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 9
gcacaagaat ggaucacaat t                                              21

<210> SEQ ID NO 10
<211> LENGTH: 21
<212> TYPE: DNA
<213> ORGANISM: Artificial Sequence
<220> FEATURE:
<223> OTHER INFORMATION: CT-113
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
```

```
<220> FEATURE:
<221> NAME/KEY: modified_base
<222> LOCATION: (18)..(18)
<223> OTHER INFORMATION: 2'-O-methyladenosine

<400> SEQUENCE: 10
gcacaagaau ggaucacaat t                                              21

<210> SEQ ID NO 11
<211> LENGTH: 21
<212> TYPE: DNA
<213> ORGANISM: Artificial Sequence
<220> FEATURE:
<223> OTHER INFORMATION: CT-114
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 11
gcacaagaau ggaucacaat t                                              21

<210> SEQ ID NO 12
<211> LENGTH: 21
<212> TYPE: DNA
<213> ORGANISM: Artificial Sequence
<220> FEATURE:
<223> OTHER INFORMATION: CT-115
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O,4'-C-ethylene-5-methylcytidine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
```

-continued

```
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 12
gcacaagaau ggaucacaat t                                     21

<210> SEQ ID NO 13
<211> LENGTH: 21
<212> TYPE: DNA
<213> ORGANISM: Artificial Sequence
<220> FEATURE:
<223> OTHER INFORMATION: CT-116
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O,4'-C-ethyleneadenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 13
```
utgtgaucca utctugugct t                                          21

<210> SEQ ID NO 14
<211> LENGTH: 21
<212> TYPE: DNA
<213> ORGANISM: Artificial Sequence
<220> FEATURE:
<223> OTHER INFORMATION: CT-117
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O,4'-C-ethylene-5-methyluridine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 14
utgtgaucca ttctugugct t                                          21

<210> SEQ ID NO 15
<211> LENGTH: 21
<212> TYPE: DNA
<213> ORGANISM: Artificial Sequence
<220> FEATURE:
<223> OTHER INFORMATION: CT-118
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:

```
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: 2'-O,4'-C-ethylenethymidine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: 2'-O,4'-C-ethylenethymidine
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 15
utgtgaucca ttcttgugct t                                              21

<210> SEQ ID NO 16
<211> LENGTH: 21
<212> TYPE: DNA
<213> ORGANISM: Artificial Sequence
<220> FEATURE:
<223> OTHER INFORMATION: CT-091
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 16
gcacaagaau ggaucacaat t                                              21

<210> SEQ ID NO 17
<211> LENGTH: 21
```

```
<212> TYPE: DNA
<213> ORGANISM: Artificial Sequence
<220> FEATURE:
<223> OTHER INFORMATION: CT-092
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 17
utgtgaucca utctugugct t                                              21

<210> SEQ ID NO 18
<211> LENGTH: 21
<212> TYPE: DNA
<213> ORGANISM: Artificial Sequence
<220> FEATURE:
<223> OTHER INFORMATION: CT-101
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
```

-continued

```
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-Methyladenosine
<220> FEATURE:
<221> NAME/KEY: modified_base
<222> LOCATION: (18)..(18)
<223> OTHER INFORMATION: 2'-O-methyladenosine

<400> SEQUENCE: 18
gcacaagaau ggaucacaat t                                    21

<210> SEQ ID NO 19
<211> LENGTH: 21
<212> TYPE: DNA
<213> ORGANISM: Artificial Sequence
<220> FEATURE:
<223> OTHER INFORMATION: CT-102
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 19
gcacaagaau ggaucacaat t                                    21

<210> SEQ ID NO 20
<211> LENGTH: 21
<212> TYPE: DNA
<213> ORGANISM: Artificial Sequence
<220> FEATURE:
<223> OTHER INFORMATION: CT-107
<220> FEATURE:
<221> NAME/KEY: modified_base
```

```
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 20
utgtgaucca utctugugct t                                                   21

<210> SEQ ID NO 21
<211> LENGTH: 21
<212> TYPE: DNA
<213> ORGANISM: Artificial Sequence
<220> FEATURE:
<223> OTHER INFORMATION: CT-108
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
```

```
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 21
utgtgaucca utctugugct t                                              21

<210> SEQ ID NO 22
<211> LENGTH: 19
<212> TYPE: DNA
<213> ORGANISM: Artificial Sequence
<220> FEATURE:
<223> OTHER INFORMATION: CT-103
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 22
gcacaagaau ggaucacaa                                                 19

<210> SEQ ID NO 23
<211> LENGTH: 19
<212> TYPE: DNA
<213> ORGANISM: Artificial Sequence
<220> FEATURE:
<223> OTHER INFORMATION: CT-109
<220> FEATURE:
<221> NAME/KEY: modified_base
<222> LOCATION: (1)..(1)
<223> OTHER INFORMATION: um
```

```
-continued

<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 23
utgtgaucca utctugugc                                              19

<210> SEQ ID NO 24
<211> LENGTH: 21
<212> TYPE: DNA
<213> ORGANISM: Artificial Sequence
<220> FEATURE:
<223> OTHER INFORMATION: CT-127
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
```

```
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 24
gcacaagaau ggaucacaat t                                          21

<210> SEQ ID NO 25
<211> LENGTH: 21
<212> TYPE: DNA
<213> ORGANISM: Artificial Sequence
<220> FEATURE:
<223> OTHER INFORMATION: CT-128
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 25
gcacaagaau ggaucacaat t                                          21
```

```
<210> SEQ ID NO 26
<211> LENGTH: 21
<212> TYPE: DNA
<213> ORGANISM: Artificial Sequence
<220> FEATURE:
<223> OTHER INFORMATION: CT-129
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 26
gcacaagaau ggaucacaat t                                              21

<210> SEQ ID NO 27
<211> LENGTH: 21
<212> TYPE: DNA
<213> ORGANISM: Artificial Sequence
<220> FEATURE:
<223> OTHER INFORMATION: CT-130
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
```

<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 27
gcacaagaau ggaucacaat t                                              21

<210> SEQ ID NO 28
<211> LENGTH: 21
<212> TYPE: DNA
<213> ORGANISM: Artificial Sequence
<220> FEATURE:
<223> OTHER INFORMATION: CT-131
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 28
gcacaagaau ggaucacaat t                                       21

<210> SEQ ID NO 29
<211> LENGTH: 21
<212> TYPE: DNA
<213> ORGANISM: Artificial Sequence
<220> FEATURE:
<223> OTHER INFORMATION: CT-132
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-4'-C-ethyleneadenosine
<220> FEATURE:
<221> NAME/KEY: modified_base
<222> LOCATION: (10)..(10)
<223> OTHER INFORMATION: 2'-O-4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 29
gcacaagaat ggaucacaat t                                       21

<210> SEQ ID NO 30
<211> LENGTH: 21
<212> TYPE: DNA
<213> ORGANISM: Artificial Sequence
<220> FEATURE:
<223> OTHER INFORMATION: CT-133
<220> FEATURE:
<221> NAME/KEY: modified_base
<222> LOCATION: (2)..(2)

```
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O,4'-C-ethyleneadenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 30
gcacaagaau ggaucacaat t                                       21

<210> SEQ ID NO 31
<211> LENGTH: 21
<212> TYPE: DNA
<213> ORGANISM: Artificial Sequence
<220> FEATURE:
<223> OTHER INFORMATION: CT-134
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O,4'-C-ethyleneadenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-O,4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
```

```
<222> LOCATION: (18)..(18)
<223> OTHER INFORMATION: 2'-O-methyladenosine

<400> SEQUENCE: 31
gcacaagaat ggaucacaat t                                              21

<210> SEQ ID NO 32
<211> LENGTH: 21
<212> TYPE: DNA
<213> ORGANISM: Artificial Sequence
<220> FEATURE:
<223> OTHER INFORMATION: CT-135
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O,4'-C-ethyleneadenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: 2'-O,4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 32
gcacaagaat ggaucacaat t                                              21

<210> SEQ ID NO 33
<211> LENGTH: 21
<212> TYPE: DNA
<213> ORGANISM: Artificial Sequence
<220> FEATURE:
<223> OTHER INFORMATION: CT-137
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O,4'-C-ethylene-5-methylcytidine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
```

```
<221> NAME/KEY: modified_base
<222> LOCATION: (10)..(10)
<223> OTHER INFORMATION: 2'-O,4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 33
gcacaagaat ggaucacaat t                                              21

<210> SEQ ID NO 34
<211> LENGTH: 21
<212> TYPE: DNA
<213> ORGANISM: Artificial Sequence
<220> FEATURE:
<223> OTHER INFORMATION: CT-136
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O,4'-C-ethylene-5-methylcytidine
<220> FEATURE:
<221> NAME/KEY: modified_base
<222> LOCATION: (6)..(6)
<223> OTHER INFORMATION: 2'-O,4'-C-ethyleneadenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 34
gcacaagaau ggaucacaat t                                              21

<210> SEQ ID NO 35
<211> LENGTH: 21
<212> TYPE: DNA
<213> ORGANISM: Artificial Sequence
<220> FEATURE:
<223> OTHER INFORMATION: CT-138
```

-continued

```
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O,4'-C-ethylene-5-methylcytidine
<220> FEATURE:
<221> NAME/KEY: modified_base
<222> LOCATION: (6)..(6)
<223> OTHER INFORMATION: 2'-O,4'-C-ethyleneadenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: 2'-O,4'-C-ethylene-5-methyluridine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 35
gcacaagaat ggaucacaat t                                              21

<210> SEQ ID NO 36
<211> LENGTH: 21
<212> TYPE: DNA
<213> ORGANISM: Artificial Sequence
<220> FEATURE:
<223> OTHER INFORMATION: CT-119
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (15)..(15)
```

```
<223> OTHER INFORMATION: cm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: 2'-O-methyladenosine

<400> SEQUENCE: 36
gcacaagaat ggatcacaat t                                          21

<210> SEQ ID NO 37
<211> LENGTH: 21
<212> TYPE: DNA
<213> ORGANISM: Artificial Sequence
<220> FEATURE:
<223> OTHER INFORMATION: CT-120
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: gm

<400> SEQUENCE: 37
tugugatcca tucutgtgct t                                          21

<210> SEQ ID NO 38
<211> LENGTH: 21
<212> TYPE: DNA
<213> ORGANISM: Artificial Sequence
<220> FEATURE:
<223> OTHER INFORMATION: CT-097S
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
```

```
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 38
gcacaagaau ggaucacaat t                                              21

<210> SEQ ID NO 39
<211> LENGTH: 21
<212> TYPE: DNA
<213> ORGANISM: Artificial Sequence
<220> FEATURE:
<223> OTHER INFORMATION: CT-098S
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
```

-continued

```
<400> SEQUENCE: 39
utgtgaucca uucuugugct t                                              21

<210> SEQ ID NO 40
<211> LENGTH: 21
<212> TYPE: DNA
<213> ORGANISM: Artificial Sequence
<220> FEATURE:
<223> OTHER INFORMATION: CT-139
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-ethyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 40
gcacaagaau ggaucacaat t                                              21

<210> SEQ ID NO 41
<211> LENGTH: 21
<212> TYPE: DNA
<213> ORGANISM: Artificial Sequence
<220> FEATURE:
<223> OTHER INFORMATION: CT-141
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
```

```
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 41
utgtgaucca utctugugct t                                            21

<210> SEQ ID NO 42
<211> LENGTH: 21
<212> TYPE: DNA
<213> ORGANISM: Artificial Sequence
<220> FEATURE:
<223> OTHER INFORMATION: CT-140
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 42
```
gcacaagaau ggaucacaat t                                              21

<210> SEQ ID NO 43
<211> LENGTH: 21
<212> TYPE: DNA
<213> ORGANISM: Artificial Sequence
<220> FEATURE:
<223> OTHER INFORMATION: CT-114L
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O,4'-C-methyleneadenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 43
gcacaagaau ggaucacaat t                                              21

<210> SEQ ID NO 44
<211> LENGTH: 21
<212> TYPE: DNA
<213> ORGANISM: Artificial Sequence
<220> FEATURE:
<223> OTHER INFORMATION: CT-001
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base

```
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 44
gcacaagaau ggaucacaat t                                            21

<210> SEQ ID NO 45
<211> LENGTH: 21
<212> TYPE: DNA
<213> ORGANISM: Artificial Sequence
<220> FEATURE:
<223> OTHER INFORMATION: CT-005
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 45
uugugaucca uucuugugct t                                            21

<210> SEQ ID NO 46
<211> LENGTH: 21
<212> TYPE: RNA
<213> ORGANISM: Artificial Sequence
<220> FEATURE:
<223> OTHER INFORMATION: CT-106
```

```
<400> SEQUENCE: 46
gcacaagaau ggaucacaau u                                              21

<210> SEQ ID NO 47
<211> LENGTH: 21
<212> TYPE: RNA
<213> ORGANISM: Artificial Sequence
<220> FEATURE:
<223> OTHER INFORMATION: CT-041

<400> SEQUENCE: 47
uugugaucca uucuugugcu u                                              21

<210> SEQ ID NO 48
<211> LENGTH: 21
<212> TYPE: DNA
<213> ORGANISM: Artificial Sequence
<220> FEATURE:
<223> OTHER INFORMATION: CT-104

<400> SEQUENCE: 48
gcacaagaau ggatcacaat t                                              21

<210> SEQ ID NO 49
<211> LENGTH: 21
<212> TYPE: DNA
<213> ORGANISM: Artificial Sequence
<220> FEATURE:
<223> OTHER INFORMATION: CT-110

<400> SEQUENCE: 49
ttgtgatcca uucuugugct t                                              21

<210> SEQ ID NO 50
<211> LENGTH: 21
<212> TYPE: DNA
<213> ORGANISM: Artificial Sequence
<220> FEATURE:
<223> OTHER INFORMATION: CT-105

<400> SEQUENCE: 50
gcacaagaat ggatcacaat t                                              21

<210> SEQ ID NO 51
<211> LENGTH: 21
<212> TYPE: DNA
<213> ORGANISM: Artificial Sequence
<220> FEATURE:
<223> OTHER INFORMATION: CT-111

<400> SEQUENCE: 51
ttgtgatcca ttcttgtgct t                                              21

<210> SEQ ID NO 52
<211> LENGTH: 21
<212> TYPE: DNA
<213> ORGANISM: Artificial Sequence
<220> FEATURE:
<223> OTHER INFORMATION: CT-155
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
```

-continued

```
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 52
utgtgaucca utctugugcu t                                              21

<210> SEQ ID NO 53
<211> LENGTH: 21
<212> TYPE: DNA
<213> ORGANISM: Artificial Sequence
<220> FEATURE:
<223> OTHER INFORMATION: CT-156
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
```

```
<223> OTHER INFORMATION: cm
<220> FEATURE:
<221> NAME/KEY: modified_base
<222> LOCATION: (20)..(20)
<223> OTHER INFORMATION: um

<400> SEQUENCE: 53
utgtgaucca utctugugcu t                                              21

<210> SEQ ID NO 54
<211> LENGTH: 21
<212> TYPE: DNA
<213> ORGANISM: Artificial Sequence
<220> FEATURE:
<223> OTHER INFORMATION: CT-157
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 54
utgtgaucca utctugugct u                                              21

<210> SEQ ID NO 55
<211> LENGTH: 21
<212> TYPE: DNA
<213> ORGANISM: Artificial Sequence
<220> FEATURE:
<223> OTHER INFORMATION: CT-158
<220> FEATURE:
<221> NAME/KEY: modified_base
<222> LOCATION: (1)..(1)
<223> OTHER INFORMATION: um
<220> FEATURE:
<221> NAME/KEY: modified_base
```

```
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 55
utgtgaucca utctugugcu u                                           21

<210> SEQ ID NO 56
<211> LENGTH: 21
<212> TYPE: DNA
<213> ORGANISM: Artificial Sequence
<220> FEATURE:
<223> OTHER INFORMATION: CT-159
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
```

```
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: um

<400> SEQUENCE: 56
utgtgaucca utctugugcu u                                             21

<210> SEQ ID NO 57
<211> LENGTH: 21
<212> TYPE: DNA
<213> ORGANISM: Artificial Sequence
<220> FEATURE:
<223> OTHER INFORMATION: CT-160
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 57
utgtgaucca utctugugct u                                             21

<210> SEQ ID NO 58
<211> LENGTH: 21
```

```
<212> TYPE: DNA
<213> ORGANISM: Artificial Sequence
<220> FEATURE:
<223> OTHER INFORMATION: CT-161
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm

<400> SEQUENCE: 58
utgtgaucca utctugugcu u                                              21

<210> SEQ ID NO 59
<211> LENGTH: 21
<212> TYPE: DNA
<213> ORGANISM: Artificial Sequence
<220> FEATURE:
<223> OTHER INFORMATION: CT-162
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
```

```
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: um

<400> SEQUENCE: 59
utgtgaucca utctugugcu u                                              21

<210> SEQ ID NO 60
<211> LENGTH: 18
<212> TYPE: DNA
<213> ORGANISM: Artificial Sequence
<220> FEATURE:
<223> OTHER INFORMATION: CT-169
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 60
gcacaagaau ggaucaca                                                  18

<210> SEQ ID NO 61
<211> LENGTH: 17
<212> TYPE: DNA
<213> ORGANISM: Artificial Sequence
```

```
<220> FEATURE:
<223> OTHER INFORMATION: CT-170
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine

<400> SEQUENCE: 61
gcacaagaau ggaucac                                                    17

<210> SEQ ID NO 62
<211> LENGTH: 16
<212> TYPE: DNA
<213> ORGANISM: Artificial Sequence
<220> FEATURE:
<223> OTHER INFORMATION: CT-171
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
```

-continued

```
<400> SEQUENCE: 62
gcacaagaau ggauca                                                    16

<210> SEQ ID NO 63
<211> LENGTH: 18
<212> TYPE: DNA
<213> ORGANISM: Artificial Sequence
<220> FEATURE:
<223> OTHER INFORMATION: CT-172
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O-methyladenosine

<400> SEQUENCE: 63
cacaagaaug gaucacaa                                                  18

<210> SEQ ID NO 64
<211> LENGTH: 17
<212> TYPE: DNA
<213> ORGANISM: Artificial Sequence
<220> FEATURE:
<223> OTHER INFORMATION: CT-173
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (10)..(10)
<223> OTHER INFORMATION: gm
```

```
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methyladenosine

<400> SEQUENCE: 64
acaagaaugg aucacaa                                                  17

<210> SEQ ID NO 65
<211> LENGTH: 16
<212> TYPE: DNA
<213> ORGANISM: Artificial Sequence
<220> FEATURE:
<223> OTHER INFORMATION: CT-174
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O-methyladenosine

<400> SEQUENCE: 65
caagaaugga ucacaa                                                   16

<210> SEQ ID NO 66
<211> LENGTH: 17
<212> TYPE: DNA
<213> ORGANISM: Artificial Sequence
<220> FEATURE:
<223> OTHER INFORMATION: CT-175
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
```

```
<223> OTHER INFORMATION: 2'-O-methyladenosine
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (17)..(17)
<223> OTHER INFORMATION: 2'-O-methyladenosine

<400> SEQUENCE: 66
cacaagaaug gaucaca                                               17

<210> SEQ ID NO 67
<211> LENGTH: 16
<212> TYPE: DNA
<213> ORGANISM: Artificial Sequence
<220> FEATURE:
<223> OTHER INFORMATION: CT-176
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: 2'-O-methyladenosine

<400> SEQUENCE: 67
cacaagaaug gaucac                                                16

<210> SEQ ID NO 68
<211> LENGTH: 16
<212> TYPE: DNA
<213> ORGANISM: Artificial Sequence
```

```
<220> FEATURE:
<223> OTHER INFORMATION: CT-177
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methyladenosine

<400> SEQUENCE: 68
acaagaaugg aucaca                                                     16

<210> SEQ ID NO 69
<211> LENGTH: 21
<212> TYPE: DNA
<213> ORGANISM: Artificial Sequence
<220> FEATURE:
<223> OTHER INFORMATION: CT-204
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
```

```
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 69
utgtgaucca utctugugca u                                              21

<210> SEQ ID NO 70
<211> LENGTH: 21
<212> TYPE: DNA
<213> ORGANISM: Artificial Sequence
<220> FEATURE:
<223> OTHER INFORMATION: CT-205
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 70
utgtgaucca utctugugcg u                                              21

<210> SEQ ID NO 71
<211> LENGTH: 21
<212> TYPE: DNA
<213> ORGANISM: Artificial Sequence
<220> FEATURE:
<223> OTHER INFORMATION: CT-206
```

```
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 71
utgtgaucca utctugugcc u                                           21

<210> SEQ ID NO 72
<211> LENGTH: 21
<212> TYPE: DNA
<213> ORGANISM: Artificial Sequence
<220> FEATURE:
<223> OTHER INFORMATION: CT-207
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
```

```
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: 2'-O-methyladenosine

<400> SEQUENCE: 72
utgtgaucca utctugugct a                                              21

<210> SEQ ID NO 73
<211> LENGTH: 21
<212> TYPE: DNA
<213> ORGANISM: Artificial
<220> FEATURE:
<223> OTHER INFORMATION: CT-208
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 73
```
utgtgaucca utctugugct g                21

<210> SEQ ID NO 74
<211> LENGTH: 21
<212> TYPE: DNA
<213> ORGANISM: Artificial Sequence
<220> FEATURE:
<223> OTHER INFORMATION: CT-209
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: cm

<400> SEQUENCE: 74
utgtgaucca utctugugct c                21

<210> SEQ ID NO 75
<211> LENGTH: 21
<212> TYPE: DNA
<213> ORGANISM: Artificial Sequence
<220> FEATURE:
<223> OTHER INFORMATION: CT-221
<220> FEATURE:
<221> NAME/KEY: modified_base
<222> LOCATION: (1)..(1)
<223> OTHER INFORMATION: 2'-O-methyladenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:

```
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 75
atgtgaucca utctugugct u                                              21

<210> SEQ ID NO 76
<211> LENGTH: 21
<212> TYPE: DNA
<213> ORGANISM: Artificial Sequence
<220> FEATURE:
<223> OTHER INFORMATION: CT-222
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
```

```
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 76
gtgtgaucca utctugugct u                                              21

<210> SEQ ID NO 77
<211> LENGTH: 21
<212> TYPE: DNA
<213> ORGANISM: Artificial Sequence
<220> FEATURE:
<223> OTHER INFORMATION: CT-223
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 77
ctgtgaucca utctugugct u                                              21

<210> SEQ ID NO 78
<211> LENGTH: 20
<212> TYPE: DNA
<213> ORGANISM: Artificial Sequence
<220> FEATURE:
<223> OTHER INFORMATION: CT-202
<220> FEATURE:
<221> NAME/KEY: modified_base
<222> LOCATION: (1)..(1)
```

```
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (20)..(20)
<223> OTHER INFORMATION: um

<400> SEQUENCE: 78
utgtgaucca utctugugtu                                                   20

<210> SEQ ID NO 79
<211> LENGTH: 20
<212> TYPE: DNA
<213> ORGANISM: Artificial Sequence
<220> FEATURE:
<223> OTHER INFORMATION: CT-203
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (14)..(14)
<223> OTHER INFORMATION: um
<220> FEATURE:
<221> NAME/KEY: modified_base
```

```
<222> LOCATION: (16)..(16)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (20)..(20)
<223> OTHER INFORMATION: um

<400> SEQUENCE: 79
tgtgauccau tctugugctu                                                      20

<210> SEQ ID NO 80
<211> LENGTH: 21
<212> TYPE: DNA
<213> ORGANISM: Artificial Sequence
<220> FEATURE:
<223> OTHER INFORMATION: CT-210
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (21)..(21)
<223> OTHER INFORMATION: um

<400> SEQUENCE: 80
gcacaagaat ggatcacaat u                                                    21

<210> SEQ ID NO 81
<211> LENGTH: 19
<212> TYPE: DNA
<213> ORGANISM: Artificial Sequence
<220> FEATURE:
<223> OTHER INFORMATION: CT-211
<220> FEATURE:
```

```
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: gm

<400> SEQUENCE: 81
tugugatcca tucutgtgc                                                 19

<210> SEQ ID NO 82
<211> LENGTH: 18
<212> TYPE: DNA
<213> ORGANISM: Artificial Sequence
<220> FEATURE:
<223> OTHER INFORMATION: CT-212
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: gm
```

```
<220> FEATURE:
<221> NAME/KEY: modified_base
<222> LOCATION: (18)..(18)
<223> OTHER INFORMATION: gm

<400> SEQUENCE: 82
tugugatcca tucutgtg                                                 18

<210> SEQ ID NO 83
<211> LENGTH: 21
<212> TYPE: DNA
<213> ORGANISM: Artificial Sequence
<220> FEATURE:
<223> OTHER INFORMATION: CT-243
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 83
atgtgaucca utctugugct u                                             21

<210> SEQ ID NO 84
<211> LENGTH: 21
<212> TYPE: DNA
<213> ORGANISM: Artificial Sequence
<220> FEATURE:
<223> OTHER INFORMATION: CT-244
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
```

```
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 84
gtgtgaucca utctugugct u                                              21

<210> SEQ ID NO 85
<211> LENGTH: 21
<212> TYPE: DNA
<213> ORGANISM: Artificial Sequence
<220> FEATURE:
<223> OTHER INFORMATION: CT-245
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
```

```
<222> LOCATION: (21)..(21)
<223> OTHER INFORMATION: um

<400> SEQUENCE: 85
ctgtgaucca utctugugct u                                              21

<210> SEQ ID NO 86
<211> LENGTH: 21
<212> TYPE: DNA
<213> ORGANISM: Artificial Sequence
<220> FEATURE:
<223> OTHER INFORMATION: CT-246
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 86
ttgtgaucca utctugugct u                                              21

<210> SEQ ID NO 87
<211> LENGTH: 21
<212> TYPE: DNA
<213> ORGANISM: Artificial Sequence
<220> FEATURE:
<223> OTHER INFORMATION: CT-247
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
```

```
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: 2'-O-methyladenosine

<400> SEQUENCE: 87
utgtgaucca utctugugcg a                                          21

<210> SEQ ID NO 88
<211> LENGTH: 21
<212> TYPE: DNA
<213> ORGANISM: Artificial Sequence
<220> FEATURE:
<223> OTHER INFORMATION: CT-248
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
```

-continued

```
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 88
utgtgaucca utctugugcg g                                              21

<210> SEQ ID NO 89
<211> LENGTH: 21
<212> TYPE: DNA
<213> ORGANISM: Artificial Sequence
<220> FEATURE:
<223> OTHER INFORMATION: CT-249
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: cm

<400> SEQUENCE: 89
utgtgaucca utctugugcg c                                              21

<210> SEQ ID NO 90
<211> LENGTH: 21
<212> TYPE: DNA
<213> ORGANISM: Artificial Sequence
<220> FEATURE:
<223> OTHER INFORMATION: CT-253
<220> FEATURE:
<221> NAME/KEY: modified_base
<222> LOCATION: (3)..(3)
```

```
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 90
ttgtgaucca utctugugcg u                                              21

<210> SEQ ID NO 91
<211> LENGTH: 21
<212> TYPE: DNA
<213> ORGANISM: Artificial
<220> FEATURE:
<223> OTHER INFORMATION: CT-254
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
```

-continued

```
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: 2'-O-Methyladenosine

<400> SEQUENCE: 91
ttgtgaucca utctugugcg a                                              21

<210> SEQ ID NO 92
<211> LENGTH: 21
<212> TYPE: DNA
<213> ORGANISM: Artificial Sequence
<220> FEATURE:
<223> OTHER INFORMATION: CT-255
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 92
ttgtgaucca utctugugcg g                                              21

<210> SEQ ID NO 93
<211> LENGTH: 21
<212> TYPE: DNA
<213> ORGANISM: Artificial Sequence
<220> FEATURE:
<223> OTHER INFORMATION: CT-256
<220> FEATURE:
<221> NAME/KEY: modified_base
<222> LOCATION: (3)..(3)
<223> OTHER INFORMATION: gm
<220> FEATURE:
```

```
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: cm

<400> SEQUENCE: 93
ttgtgaucca utctugugcg c                                      21

<210> SEQ ID NO 94
<211> LENGTH: 21
<212> TYPE: DNA
<213> ORGANISM: Artificial Sequence
<220> FEATURE:
<223> OTHER INFORMATION: CT-257
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
```

```
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: 2'-O-methyladenosine

<400> SEQUENCE: 94
ttgtgaucca utctugugca a                                              21

<210> SEQ ID NO 95
<211> LENGTH: 21
<212> TYPE: DNA
<213> ORGANISM: Artificial Sequence
<220> FEATURE:
<223> OTHER INFORMATION: CT-258
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 95
ttgtgaucca utctugugca g                                              21

<210> SEQ ID NO 96
<211> LENGTH: 21
<212> TYPE: DNA
<213> ORGANISM: Artificial Sequence
<220> FEATURE:
<223> OTHER INFORMATION: CT-264
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
```

```
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 96
utgtgaucca utctugugct u                                              21

<210> SEQ ID NO 97
<211> LENGTH: 21
<212> TYPE: DNA
<213> ORGANISM: Artificial Sequence
<220> FEATURE:
<223> OTHER INFORMATION: CT-265
<220> FEATURE:
<221> NAME/KEY: modified_base
<222> LOCATION: (1)..(1)
<223> OTHER INFORMATION: 2'-deoxy-5-methylcytidine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
```

-continued

```
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 97
ctgtgaucca utctugugct u                                          21

<210> SEQ ID NO 98
<211> LENGTH: 21
<212> TYPE: DNA
<213> ORGANISM: Artificial Sequence
<220> FEATURE:
<223> OTHER INFORMATION: CT-266
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 98
ctgtgaucca utctugugcg g                                          21

<210> SEQ ID NO 99
<211> LENGTH: 21
<212> TYPE: DNA
<213> ORGANISM: Artificial Sequence
<220> FEATURE:
<223> OTHER INFORMATION: CT-267
<220> FEATURE:
<221> NAME/KEY: modified_base
<222> LOCATION: (1)..(1)
<223> OTHER INFORMATION: 2'-deoxy-5-methylcytidine
<220> FEATURE:
```

```
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 99
ctgtgaucca utctugugcg g                                         21

<210> SEQ ID NO 100
<211> LENGTH: 19
<212> TYPE: RNA
<213> ORGANISM: Artificial Sequence
<220> FEATURE:
<223> OTHER INFORMATION: CT-125

<400> SEQUENCE: 100
gcacaagaau ggaucacaa                                            19

<210> SEQ ID NO 101
<211> LENGTH: 19
<212> TYPE: RNA
<213> ORGANISM: Artificial Sequence
<220> FEATURE:
<223> OTHER INFORMATION: CT-126

<400> SEQUENCE: 101
uugugaucca uucuugugc                                            19

<210> SEQ ID NO 102
<211> LENGTH: 18
<212> TYPE: DNA
<213> ORGANISM: Artificial Sequence
<220> FEATURE:
<223> OTHER INFORMATION: CT-288
<220> FEATURE:
<221> NAME/KEY: modified_base
<222> LOCATION: (1)..(1)
<223> OTHER INFORMATION: gm
```

```
<220> FEATURE:
<221> NAME/KEY: modified_base
<222> LOCATION: (3)..(3)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methyladenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: 2'-O-methyladenosine
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: cm

<400> SEQUENCE: 102
gcacaagaat ggatcaca                                                   18

<210> SEQ ID NO 103
<211> LENGTH: 21
<212> TYPE: DNA
<213> ORGANISM: Artificial Sequence
<220> FEATURE:
<223> OTHER INFORMATION: CT-289
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: 2'-O-methyladenosine
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
```

```
<223> OTHER INFORMATION: gm
<220> FEATURE:
<221> NAME/KEY: modified_base
<222> LOCATION: (21)..(21)
<223> OTHER INFORMATION: um

<400> SEQUENCE: 103
tugugatcca tucutgtgct u                                              21

<210> SEQ ID NO 104
<211> LENGTH: 18
<212> TYPE: DNA
<213> ORGANISM: Artificial Sequence
<220> FEATURE:
<223> OTHER INFORMATION: CT-278
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: gm
<220> FEATURE:
<221> NAME/KEY: modified_base
<222> LOCATION: (10)..(10)
<223> OTHER INFORMATION: 2'-O--methyladenosine
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 104
ggacaaggaa gctgcaga                                                  18

<210> SEQ ID NO 105
<211> LENGTH: 21
<212> TYPE: DNA
<213> ORGANISM: Artificial Sequence
<220> FEATURE:
<223> OTHER INFORMATION: CT-279
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: gm
<220> FEATURE:
<221> NAME/KEY: modified_base
```

```
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 105
utctgcagct ucctugucct u                                              21

<210> SEQ ID NO 106
<211> LENGTH: 21
<212> TYPE: DNA
<213> ORGANISM: Artificial Sequence
<220> FEATURE:
<223> OTHER INFORMATION: CT-280
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
```

```
<221> NAME/KEY: modified_base
<222> LOCATION: (21)..(21)
<223> OTHER INFORMATION: um

<400> SEQUENCE: 106
ttctgcagct ucctugucct u                                              21

<210> SEQ ID NO 107
<211> LENGTH: 21
<212> TYPE: DNA
<213> ORGANISM: Artificial Sequence
<220> FEATURE:
<223> OTHER INFORMATION: CT-281
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 107
ttctgcagct ucctugucca g                                              21

<210> SEQ ID NO 108
<211> LENGTH: 19
<212> TYPE: DNA
<213> ORGANISM: Artificial Sequence
<220> FEATURE:
<223> OTHER INFORMATION: DD-016
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
```

```
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: um

<400> SEQUENCE: 108
gccucagatu cgtagaaua                                                   19

<210> SEQ ID NO 109
<211> LENGTH: 21
<212> TYPE: DNA
<213> ORGANISM: Artificial Sequence
<220> FEATURE:
<223> OTHER INFORMATION: DD-017
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
```

<223> OTHER INFORMATION: um

<400> SEQUENCE: 109
uautctacga atctgaggct u                                                      21

<210> SEQ ID NO 110
<211> LENGTH: 18
<212> TYPE: DNA
<213> ORGANISM: Artificial Sequence
<220> FEATURE:
<223> OTHER INFORMATION: DD-022
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: um

<400> SEQUENCE: 110
gccucagatu cgtagaau                                                          18

<210> SEQ ID NO 111
<211> LENGTH: 21
<212> TYPE: DNA
<213> ORGANISM: Artificial Sequence
<220> FEATURE:
<223> OTHER INFORMATION: DD-023
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base

```
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 111
tautctacga atctgaggct u                                               21

<210> SEQ ID NO 112
<211> LENGTH: 21
<212> TYPE: DNA
<213> ORGANISM: Artificial Sequence
<220> FEATURE:
<223> OTHER INFORMATION: DD-024
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: 2'-O-methyladenosine
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: 2'-O-methyladenosine
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: gm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm

<400> SEQUENCE: 112
tautctacga atctgaggca g                                               21
```

```
<210> SEQ ID NO 113
<211> LENGTH: 18
<212> TYPE: DNA
<213> ORGANISM: Artificial Sequence
<220> FEATURE:
<223> OTHER INFORMATION: CT-169S
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (6)..(6)
<223> OTHER INFORMATION: 2'-O-methyladenosine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (16)..(16)
<223> OTHER INFORMATION: 2'-O-methyladenosine
<220> FEATURE:
<221> NAME/KEY: modified_base
<222> LOCATION: (18)..(18)
<223> OTHER INFORMATION: 2'-O-methyladenosine

<400> SEQUENCE: 113
gcacaagaau ggaucaca                                                 18

<210> SEQ ID NO 114
<211> LENGTH: 21
<212> TYPE: DNA
<213> ORGANISM: Artificial Sequence
<220> FEATURE:
<223> OTHER INFORMATION: CT-157S
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: um
```

```
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: um

<400> SEQUENCE: 114
utgtgaucca utcugugcu u                                               21

<210> SEQ ID NO 115
<211> LENGTH: 21
<212> TYPE: DNA
<213> ORGANISM: Artificial Sequence
<220> FEATURE:
<223> OTHER INFORMATION: CT-165

<400> SEQUENCE: 115
ggacaaggaa gcugcagaat t                                              21

<210> SEQ ID NO 116
<211> LENGTH: 21
<212> TYPE: DNA
<213> ORGANISM: Artificial Sequence
<220> FEATURE:
<223> OTHER INFORMATION: CT-166

<400> SEQUENCE: 116
uucugcagcu uccuugucct t                                              21

<210> SEQ ID NO 117
<211> LENGTH: 21
<212> TYPE: DNA
<213> ORGANISM: Artificial Sequence
<220> FEATURE:
<223> OTHER INFORMATION: DDX3 siRNA #5 sense

<400> SEQUENCE: 117
gccucagauu cguagaauat t                                              21

<210> SEQ ID NO 118
<211> LENGTH: 21
<212> TYPE: DNA
<213> ORGANISM: Artificial Sequence
<220> FEATURE:
<223> OTHER INFORMATION: DDX3 siRNA #5 antisense

<400> SEQUENCE: 118
uauucuacga aucugaggct c                                              21
```

DOUBLE-STRANDED POLYNUCLEOTIDE

CROSS-REFERENCE TO RELATED APPLICATIONS

This patent application is a National Stage application

SEQUENCE LISTING

A Sequence Listing in computer readable form (CRF) is submitted with this application. The CRF file is named 218147US-seqlist.txt, was created Dec. 21, 2010, and contains 104 kilobytes. The entire content of the CRF file is incorporated herein by reference.

TECHNICAL FIELD

The present invention relates to a novel double-stranded polynucleotide that is resistant to RNase and has an RNA interference effect, use of the double-stranded polynucleotide, a method for inhibiting gene expression using the double-stranded polynucleotide, a pharmaceutical composition comprising the double-stranded polynucleotide, etc.

BACKGROUND ART

A method for inhibiting the expression of a target gene in cells, tissues, or individuals includes an approach by which double-stranded RNA is introduced into the cells, tissues, or individuals. By this introduction of double-stranded RNA, mRNA having homology to the sequence is degraded such that the expression of the target gene is inhibited. This effect is called "RNA interference" or "RNAi". RNA interference was originally reported in *C. elegans* (see e.g., Non Patent Reference 1) and then also reported in plants (see e.g., Non Patent Reference 2).

Double-stranded RNA consisting of 21-nucleotide sense and antisense strands having a 2-nucleotide overhang at the 3'-end (small interfering RNA: siRNA) has been reported to have an RNA interference effect in cultured cells of vertebrates (see e.g., Non Patent Reference 3).

siRNA is useful for the identification of gene functions, screening of cell strains suitable for useful substance production, regulation of genes involved in disease, etc., but, however, it is disadvantageously degraded easily by RNase (see e.g., Non Patent Reference 4). RNA synthesis is more difficult than DNA synthesis and therefore reportedly entails a 5 to 10-times higher cost (see e.g., Non Patent Reference 5). Exemplary reasons for this include the need for a protective group for the 2'-hydroxy group, the need to deprotect the protective group, and poor RNA synthesis yields attributed to a reduction in condensation yield due to the steric hindrance of the protective group (see e.g., Non Patent Reference 6).

Thus, there has been demand for a polynucleotide to be developed which is highly resistant to RNase, can be produced at low cost, and retains RNAi activity.

To obtain siRNA having resistance to RNase, a method has been researched in which all or some of the RNA nucleotides constituting an siRNA are substituted with 2'-deoxyribonucleotides (DNAs) (see e.g., Patent Reference 1 and Non Patent References 7, 8, 9, 10, and 11). However, siRNA having both resistance to RNase and an RNA interference effect equivalent to that of natural siRNA has not been obtained yet.

An oligonucleotide having a phosphorothioate (PS) bond in which the non-bridged oxygen atom of the phosphate group in the phosphodiester bond has been substituted with a sulfur atom is known to be resistant to nuclease (see e.g., Non Patent Reference 12). siRNA having PS bonds substituting the phosphodiester bonds has been reported to exhibit RNA interference equivalent to that of unmodified siRNA (see e.g., Non Patent References 9, 13, and 14). However, the increased number of PS bonds in an oligonucleotide causes thermodynamic instability of double-stranded RNA and nonspecific binding with proteins and is therefore not thought to be preferable (see e.g., Non Patent Reference 15).

An attempt has also been made to obtain stable siRNA by substituting natural RNA with modified RNA. Since the 2'-OH group of RNA is essential for the RNase degradation reaction, this 2'-OH group is alkylated such that it does not serve as a substrate for RNase. A large number of such 2'-O-alkyl nucleoside derivatives have been reported. 2'-O-methyl nucleotides are naturally occurring modified nucleotides also found in tRNA and have been studied since the early stages of antisense research (see e.g., Non Patent Reference 16).

It has been reported that RNAi is completely lost by substituting either or both of the sense and antisense strands of siRNA with 2'-O-methyl nucleotides (see e.g., Non Patent References 7, 17, and 18) or that only weak RNAi is observed when substituting all ribonucleotides in the sense or antisense strand of siRNA with 2'-O-methyl nucleotides, and that RNAi is completely lost by substituting both the strands therewith (see e.g., Non Patent Reference 9).

There is a report that when all RNAs in a sense strand are substituted with 2'-O-methyl nucleotides, RNAi equivalent to that of unmodified siRNA is obtained, but this is influenced by the sequence of siRNA used in the experiment (see e.g., Non Patent Reference 19).

It has been reported that when four 2'-O-methyl nucleotides are introduced to the end of an siRNA, its RNAi is retained (see e.g., Non Patent Reference 14) and that when 2'-O-methyl nucleotides are alternately introduced to both the ends of the sense and antisense strands of siRNA, RNAi equivalent to that of unmodified siRNA is obtained (see e.g., Non Patent Reference 18). Moreover, it has been reported that the introduction of 3 consecutive 2'-O-methyl nucleotides does not cause any reduction in activity for a sense strand but does cause a reduction in activity for an antisense strand, and in particular, its introduction to the 5'-end of the antisense strand significantly reduces activity (see e.g., Non Patent Reference 20).

Moreover, siRNA comprising 2'-deoxyribonucleotides in the vicinity of the 3' and 5'-ends of the sense strand and 2'-O-methyl nucleotides in the central portion thereof has been reported but has not been compared in RNAi activity with unmodified siRNA (see e.g., Non Patent Reference 21).

An oligonucleotide having an artificially synthesized modified RNA 2'-deoxy-2'-fluoronucleotide (2'-F) preferentially forms the same N-type conformation as that of ribonucleotides and has higher affinity for RNA (see e.g., Non Patent Reference 22). However, those having phosphodiester bonds have no resistance to nuclease and therefore, in order to have nuclease resistance, they must be substituted with phosphorothioate bonds therefor (see e.g., Non Patent Reference 22).

It has been reported that when a pyrimidine nucleotide in siRNA is substituted with 2'-F, the resulting siRNA exhibits RNAi equivalent to that of unmodified siRNA (see e.g., Non Patent References 9 and 14). The introduction of 3 consecutive 2'-F moieties to an antisense strand hardly reduces its activity (see e.g., Non Patent Reference 20). Moreover, it has been reported that when either a pyrimidine nucleotide or a purine nucleotide in sense and/or antisense strands is substituted by 2'-F and both the modified strands are combined, the resulting siRNA exhibits RNAi equivalent to that of unmodified siRNA (see e.g., Non Patent Reference 23).

However, among these, those exhibiting an RNA interference effect contain a ribonucleotide and are thus degraded by RNase. It has been reported that when a pyrimidine nucleotide in siRNA was substituted by 2'-F, the enhancement of RNAi or its prolonged effect was not observed in animal models (see e.g., Non Patent Reference 24). Moreover, it has been reported that nonnatural nucleosides 2'-deoxy-2'-fluorocytidine and 2'-deoxy-2'-fluorouridine, which allegedly exhibit no toxicity when administered to rats or woodchucks, serve as substrates for DNA polymerase or RNA polymerase through intracellular triphosphorylation and are incorporated into DNA, RNA, and mitochondrial DNA in various organs (see e.g., Non Patent References 25 and 26). A triphosphate form of 2'-deoxy-2'-fluoronucleoside is incorporated as a substrate for DNA polymerase α or γ into DNA, whereas a triphosphate form of 2'-O-methyl nucleoside has been confirmed in vitro not to serve as a substrate for DNA polymerase α or γ (see e.g., Non Patent Reference 27). The genetic toxicity of the 2'-deoxy-2'-fluoronucleoside is of concern (see e.g., Non Patent Reference 28).

It has been reported that when all nucleotides in siRNA are substituted with 2'-F, its RNAi is merely slightly lower than that of unmodified siRNA and that such siRNA is resistant to RNase (see e.g., Non Patent Reference 29).

It has been reported that when 2'-O-methyl nucleotides and 2'-F are alternately introduced into the sense and antisense strands of siRNA, the obtained siRNA has RNAi equivalent to or higher than that of unmodified siRNA and is relatively stably maintained in serum (see e.g., Non Patent Reference 30). However, cytotoxicity or side effects caused by the introduction of a large number of nonnatural nucleic acids is of concern.

ENAs (2'-O,4'-C-ethylene-bridged nucleic acids) are modified nucleic acids having stability to nuclease (see e.g., Non Patent References 31 and 32). It has been reported that when ENAs are introduced to replace 2 nucleotides in the 3'-terminal overhang site of either or both of the sense and antisense strands of siRNA, the RNAi activity is reduced (see e.g., Non Patent Reference 33).

It has been reported that the introduction of chemically synthesized siRNA into cells phosphorylates the 5'-ends of both sense and antisense strands (see e.g., Non Patent Reference 34). In human cells, RNA kinase hClp1 has been reported to be responsible for the 5'-phosphorylation of siRNA (see e.g., Non Patent Reference 35). When siRNA having a phosphorylated 5'-end and siRNA having an unphosphorylated 5'-end were separately introduced into cells and their RNAi activity compared, no difference in activity was seen therebetween, indicating that siRNA having an unphosphorylated 5'-end is easily subject to phosphorylation in cells (see e.g., Non Patent Reference 14).

The X-ray analysis of a complex of an antisense strand with Argonaute protein (Ago) known to participate in RNAi activity has showed that the 5'-terminal phosphate group of the antisense strand and its neighboring nucleotides are strongly bound by the PIWI domain of Ago (see e.g., Non Patent Reference 36).

As regards the chain length of siRNA, 21 nucleotides are routinely used with each of the sense and antisense strands having a 2-nucleotide overhang at the 3'-end. When an antisense strand is set to being 21 nucleotides in length and the chain length of a sense strand is varied from the 3' or 5'-end, siRNA having a 21-nucleotides sense strand has been shown to have the strongest RNAi activity (see e.g., Non Patent References 7 and 37). Moreover, it has been reported that when a sense strand is 3'-terminally truncated to 17 or 18 nucleotides in chain length, the resulting siRNA exhibits RNAi activity equivalent to that of siRNA having a 21-nucleotide sense strand (see e.g., Non Patent Reference 38).

siRNA consisting of 21 nucleotides has been shown to have the strongest RNAi activity when the length of the 3'-terminal overhang is 2 nucleotides (see e.g., Non Patent Reference 7). It has been reported that when RNAi activity was examined using siRNA having the sequence AA, CC, GG, UU, or UG (wild-type) or TdG or TT (T and dG are 2'-deoxyribonucleotides) as the 3'-terminal overhang, all the sequences had RNAi activity (see e.g., Non Patent Reference 7). Moreover, it has been reported that siRNA having a UU sequence as the 3'-terminal overhang exhibits higher RNAi activity than that of siRNA having a TT sequence (see e.g., Non Patent Reference 10).

Double-stranded RNA such as polyI:polyC has been known as an interferon inducer for a long time, and TLR3 (Toll-like receptor 3) is involved in the mechanism. siRNA is also known to be recognized by TLR3 and its family members TLR7 and TLR8 are known to induce interferon or cytokines. Particularly, siRNA having a GU, UGUGU, or GUCCUUCAA sequence has been reported to tend to cause an immune response (see e.g., Non Patent References 39, 40, and 41). Moreover, the introduction of DNAs or chemically modified nucleotides such as 2'-OMeRNAs into siRNA has been shown to inhibit such immune response (see e.g., Non Patent References 41, 42, and 43).

The present inventors have conducted diligent studies to obtain a polynucleotide that is resistant to RNase, can be synthesized at low cost, and has an RNA interference effect, and have consequently completed the present invention by finding that a double-stranded polynucleotide comprising an oligonucleotide unit of DNAs and 2'-O-methyl RNAs alternately combined can solve the problems described above.

REFERENCE

Patent Reference

Patent Reference 1: International Publication No. WO 2003/044188
Patent Reference 2: U.S. Patent Publication No. US2007/0265220

Non Patent Reference

Non Patent Reference 1: Nature, 1998, Vol. 391, p. 806-811
Non Patent Reference 2: Science, 1999, Vol. 286, p. 950-952
Non Patent Reference 3: Nature, 2001, Vol. 411, p. 494-498
Non Patent Reference 4: Clinical Chemistry, 2002, Vol. 48, p. 1647-1653
Non Patent Reference 5: Sekine, M. and Taira K., ed., "RNAi Method and Antisense Method", Kodansha Ltd., published on Jun. 20, 2005, paragraph 2.4 RNAi Therapy—Application of siRNA to Therapeutic Drugs for Cancer, p. 76-87
Non Patent Reference 6: Current Opinion in Drug Discovery & Development, 2008, Vol. 11, p. 203-216
Non Patent Reference 7: EMBO Journal, 2001, Vol. 20, p. 6877-6888
Non Patent Reference 8: Nucleic Acids Research, 2002, Vol. 30, p. 1757-1766
Non Patent Reference 9: RNA, Vol. 9, 2003, p. 1034-1048
Non Patent Reference 10: FEBS Letters, 2002, Vol. 521, p. 195-199
Non Patent Reference 11: Nucleic Acids Research, 2008, Vol. 36, p. 2136-2151
Non Patent Reference 12: Nucleic Acid Drug Development, 2000, Vol. 10, p. 117-121
Non Patent Reference 13: Nucleic Acids Research, 2003, Vol. 31, p. 589-595
Non Patent Reference 14: Antisense Nucleic Acid Drug Development, 2003, Vol. 13, p. 83-105
Non Patent Reference 15: Antisense Nucleic Acid Drug Development, 2000, Vol. 10, p. 117-121
Non Patent Reference 16: Nucleic Acids Research, 1987, Vol. 15, p. 6131-6148
Non Patent Reference 17: Biochemistry, 2003, Vol. 42, p. 7967-7975
Non Patent Reference 18: Nucleic Acids Research, 2003, Vol. 31, p. 2705-2716
Non Patent Reference 19: RNA, 2006, Vol. 12, p. 163-176
Non Patent Reference 20: Journal of Medical Chemistry, 2005, Vol. 48, p. 4247-4253
Non Patent Reference 21: Nucleosides, Nucleotides, and Nucleic Acids, 2006, Vol. 25, p. 889-907
Non Patent Reference 22: Journal of Medical Chemistry, 1993, Vol. 36, p. 831-841
Non Patent Reference 23: Chemistry & Biodiversity, 2007, Vol. 4, p. 858-873
Non Patent Reference 24: RNA, 2004, Vol. 10, p. 766-771
Non Patent Reference 25: Toxicologic Pathology, 1999, Vol. 27, p. 607-617
Non Patent Reference 26: Chemical Research in Toxicology, 2002, Vol. 15, p. 922-926
Non Patent Reference 27: Biochemical Pharmacology, 2000, Vol. 59, p. 1045-1052
Non Patent Reference 28: Oligonucleotides, 2006, Vol. 16, p. 337-351
Non Patent Reference 29: Chemical Biology & Drug Design, 2007, Vol. 70, p. 113-122
Non Patent Reference 30: Journal of Medicinal Chemistry., 2005, Vol. 48, p. 901-904
Non Patent Reference 31: Bioorganic & Medicinal Chemistry Letters., 2002, Vol. 12, p. 73-76
Non Patent Reference 32: Bioorganic & Medicinal Chemistry, 2003, Vol. 11, p. 2211-2226
Non Patent Reference 33: Antisense and Nucleic Acid Drug Development, 2002, Vol. 12, p. 301-309
Non Patent Reference 34: Cell, 2001, Vol. 107, p. 309-321
Non Patent Reference 35: Nature, 2007, Vol. 447, p. 222-226
Non Patent Reference 36: Nature, 2005, Vol. 434, p. 663-666
Non Patent Reference 37: RNA, 2008, Vol. 14, p. 1714-1719
Non Patent Reference 38: Nucleic Acids Research, 2008, Vol. 36, p. 5812-5821
Non Patent Reference 39: Science, 2003, Vol. 303, p. 1526-1529
Non Patent Reference 40: Nature Biotechnology, 2005, Vol. 23, p. 457-462
Non Patent Reference 41: Nature Medicine, 2005, Vol. 11, p. 263-270
Non Patent Reference 42: Journal of Molecular Biology, 2005, Vol. 348, p. 1079-1090
Non Patent Reference 43: Nature Biotechnology, 2005, Vol. 23, p. 1002-1007

SUMMARY OF THE INVENTION

Problems to be Solved by the Invention

An aspect of the present invention is to provide a double-stranded polynucleotide that is resistant to RNase and has an RNA interference effect.

A further aspect of the present invention is to provide a method for inhibiting gene expression using the double-stranded polynucleotide.

A further aspect of the present invention is to provide a pharmaceutical composition comprising the double-stranded polynucleotide.

Means for Solving the Problems

Accordingly, the present invention includes:

(1) a double-stranded polynucleotide or a salt thereof, comprising a polynucleotide represented by formula (I) and a polynucleotide represented by formula (II):

$$5'\text{-}X\text{-}(\alpha\text{-}\beta)_q\text{-}\alpha_p\text{-}\lambda_m\text{-}3' \qquad (I)$$

$$5'\text{-}\delta_s\text{-}(\alpha\text{-}\beta)_r\text{-}Y\text{-}\upsilon_n\text{-}3' \qquad (II),$$

wherein
α and β each independently represent a DNA or a 2'-OMeRNA, wherein if α represents a DNA, then β represents a 2'-OMeRNA, and wherein if α represents a 2'-OMeRNA, then β represents a DNA, δ and λ, each independently represent a DNA or a 2'-OMeRNA, and each occurrence of a δ and each occurrence of a λ independently represents a DNA or a 2'-OMeRNA, υ represents a nucleotide selected from a DNA, an RNA, and a 2'-OMeRNA, and each occurrence of a υ independently represents a DNA, an RNA, or a 2'-OMeRNA, X and Y each independently represent an oligonucleotide, wherein each nucleotide in said oligonucleotide is independently selected from a DNA nucleotide, an RNA nucleotide, and a modified nucleic acid, p represents an integer of 0 or 1, m is 0 when p is 0 and represents any integer of 0 to 5 when p is 1, q represents any integer of 3 to 9, the total number of nucleotides in $(\alpha\text{-}\beta)_q$ and X is 17 or 18, s represents an integer of 0 or 1, n represents any integer of 0 to 5, r represents any integer of 3 to 9, the total number of nucleotides in $(\alpha\text{-}\beta)_r$ and Y is 17 or 18, $X\text{-}(\alpha\text{-}\beta)_q\text{-}\alpha_p$ in the polynucleotide represented by the formula (I) having a nucleotide sequence identical to a target gene; and
the nucleotide sequences of $X\text{-}(\alpha\text{-}\beta)_q$ in the formula (I) and $(\alpha\text{-}\beta)_r\text{-}Y$ in the formula (II) are complementary to each other;

(2) the double-stranded polynucleotide or a salt thereof according to (1), wherein in the polynucleotide represented by the formula (I), q is 3, and X is any one selected from the group consisting of $(\gamma\text{-}\beta)_6$, $(\alpha\text{-}\beta)\text{-}(\gamma\text{-}\beta)_5$, $(\alpha\text{-}\beta)_2\text{-}(\gamma\text{-}\beta)_4$, $(\alpha\text{-}\beta)_3$, $(\alpha\text{-}\beta)_4\text{-}(\gamma\text{-}\beta)_2$, $(\alpha\text{-}\beta)_5\text{-}(\gamma\text{-}\beta)$, $(\alpha\text{-}\beta)_6$, $\beta_{12}$, $(\alpha\text{-}\beta)\text{-}\beta_{10}$, $(\alpha\text{-}\beta)_2\text{-}\beta_8\text{-}(\alpha\text{-}\beta)_3\text{-}\beta_6$, $(\alpha\text{-}\beta)_4\text{-}\beta_4$, $(\alpha\text{-}\beta)_5\text{-}\beta_2$, $\beta\text{-}(\gamma\text{-}\beta)_5$, $\beta\text{-}(\alpha\text{-}\beta)\text{-}(\gamma\text{-}\beta)_4$, $\beta\text{-}(\alpha\text{-}\beta)_2$, $(\gamma\text{-}\beta)_3$, $\beta(\alpha\text{-}\beta)_3\text{-}(\gamma\text{-}\beta)_2$, $\beta\text{-}(\alpha\text{-}\beta)_4\text{-}(\gamma\text{-}=)$, $\beta_{11}$, $\beta\text{-}(\alpha\text{-}\beta)\text{-}\beta_8$, $\beta\text{-}(\alpha\text{-}\beta)_2\text{-}\beta_6$, $\beta\text{-}(\alpha\text{-}\beta)_3\text{-}\beta_4$, $\beta\text{-}(\alpha\text{-}\beta)_4\text{-}\beta_2$, and $\beta\text{-}(\alpha\text{-}\beta)_5$, wherein γ represents an RNA;

(3) the double-stranded polynucleotide or a salt thereof according to (1) or (2), wherein in the polynucleotide represented by the formula (II), r is 3, and Y is any one selected from the group consisting of $(\gamma-\beta)_6$, $(\gamma-\beta)_5-(\alpha-\beta)$, $(\gamma-\beta)_4-(\alpha-\beta)_2$, $(\gamma-\beta3)_3-(\alpha-\beta)_3$, $(\gamma-\beta)_2-(\alpha-\beta)_4$, $(\gamma-\beta)-(\alpha-\beta)_5$, $(\alpha-\beta)_6$, $\alpha_6-(\alpha-\beta)_3$, $\alpha_4-(\alpha-\beta)_4$, $\alpha_2-(\alpha-\beta)_5$, $(\gamma-\beta)_5-\alpha$, $(\gamma-\beta)_4-(\alpha-\beta)-\alpha$, $(\gamma-\beta)_3-(\alpha-\beta)_2-\alpha$, $(\gamma-\beta)_2-(\alpha-\beta)_3-\alpha$, $(\gamma-\beta)-(\alpha-\beta)_4-\alpha$, $\alpha_6-(\alpha-\beta)_2-\alpha$, $\alpha_4-(\alpha-\beta)_3-\alpha$, $\beta_2-(\alpha-\beta)_4-\alpha$, and $(\alpha-\beta)_5-\alpha$, wherein $\gamma$ represents an RNA;

(4) the double-stranded polynucleotide or a salt thereof according to (1) or (2), wherein in the polynucleotide represented by the formula (I), q is 3, and X is any one selected from the group consisting of $(\gamma-\beta)_6$, $(\alpha-\beta)-(\gamma-\beta)_5$, $(\alpha-\beta)_2-(\gamma-\beta)_4$, $(\alpha-\beta)_3-(\gamma-\beta)_3$, $(\alpha-\beta)_4-(\gamma-\beta)_2$, $(\alpha-\beta)_5-(\gamma-\beta)$, $(\alpha-\beta)_6$, $\beta_{12}$, $(\alpha-\beta)-\beta_{10}$, $(\alpha-\beta)_2\beta_8$, $(\alpha-\beta)_3-\beta_6$, $(\alpha-\beta)_4-\beta_4$, $(\alpha-\beta)_5\beta_2$, $\beta-(\gamma-\beta)_5$, $\beta(\alpha-\beta)-(\gamma-\beta)_4$, $\beta(\alpha-\beta)_2-(\gamma-\beta)_3$, $\beta-(\alpha-\beta)_3-(\gamma\beta)_2$, $\beta-(\alpha-\beta)_4-(\gamma-\beta)$, $\beta_{11}$, $\beta-(\alpha-\beta)\beta_8$, $\beta-(\alpha-\beta)_2-\beta_6$, $\beta-(\alpha-\beta)_3-\beta_4$, $\beta-(\alpha-\beta)_4-\beta_2$, and $\beta-(\alpha-\beta)_5$; and in the polynucleotide represented by the formula (II), r is 3, and Y is any one selected from the group consisting of $(\gamma-\beta)_6$, $(\gamma-\beta)_5-(\alpha-\beta)$, $(\gamma-\beta)_4-(\alpha-\beta)_2$, $(\gamma-\beta)_3-(\alpha-\beta)_3$, $(\gamma-\beta)_2-(\alpha-\beta)_4$, $(\gamma-\beta)-(\alpha-\beta)_5$, $(\alpha-\beta)_6$, $\alpha_6-(\alpha-\beta)_3$, $\alpha_4-(\alpha-\beta)_4$, $\alpha_2-(\alpha-\beta)_5$, $(\gamma-\beta)_5$, $(\gamma-\beta)_5-\alpha$, $(\gamma-\beta)_4-(\alpha-\beta)-\alpha$, $(\gamma-\beta)_3-(\alpha-\beta)_2-\alpha$, $(\gamma-\beta)_2-(\alpha-\beta)_3-\alpha$, $(\gamma-\beta)-(\alpha-\beta)_4-\alpha$, $\alpha_6-(\alpha-\beta)_2-\alpha$, $\alpha_4-(\alpha-\beta)_3-\alpha$, $\alpha_2-(\alpha-\beta)_4-\alpha$, and $(\alpha-\beta)_5-\alpha$, wherein $\gamma$ represents an RNA;

(5) the double-stranded polynucleotide or a salt thereof according to (1), wherein in the polynucleotide represented by the formula (I), q is 4, and X is any one selected from the group consisting of $(\gamma-\beta)_5$, $(\alpha-\beta)-(\gamma-\beta)_4$, $(\alpha-\beta)_2-(\gamma-\beta)_3$, $(\alpha-\beta)_3-(\gamma-\beta)_2$, $(\alpha-\beta)_4-(\gamma-\beta)$, $(\alpha-\beta)_5$, $\beta_{10}$, $(\alpha-\beta)-\beta_8$, $(\alpha-\beta)_2-\beta_6$, $(\alpha-\beta)_3-\beta_4$, $(\alpha-\beta)_4-\beta_2$, $\beta-(\gamma-\beta)_4$, $\beta-(\alpha-\beta)-(\gamma-\beta)_3$, $\beta-(\alpha-\beta)_2-(\gamma-\beta)_2$, $\beta-(\alpha-\beta)_3-(\gamma-\beta)$, $\beta_9$, $\beta-(\alpha-\beta)-\beta_6$, $\beta-(\alpha-\beta)_2-\beta_4$, $\beta-(\alpha-\beta)_3-\beta_2$, and $\beta-(\alpha-\beta)_4$,' wherein $\gamma$ represents an RNA;

(6) the double-stranded polynucleotide or a salt thereof according to (1) or (5), wherein in the polynucleotide represented by the formula (II), r is 4, and Y is any one selected from the group consisting of $(\gamma-\beta)_5$, $(\gamma-\beta)_4-(\alpha-\beta)$, $(\gamma-\beta)_3-(\alpha-\beta)_2$, $(\gamma-\beta)_2-(\alpha-\beta)_3$, $(\gamma-\beta)-(\alpha-\beta)_4$, $(\alpha-\beta)_5$, $\beta_6-(\alpha-\beta)_2$, $\beta_4-(\alpha-\beta)_3$, $\beta_2-(\alpha-\beta)_4$, $(\gamma-\beta)_4-\alpha$, $(\alpha-\beta)_4-\alpha$, $(\gamma-\beta)_3-(\alpha-\beta)-\alpha$, $(\gamma-\beta)_2-\alpha(\alpha-\beta)_2-\alpha$, $(\gamma-\beta)-(\alpha-\beta)_3-\alpha$, $\alpha_6-(\alpha-\beta)-\alpha$, $\alpha_4-(\alpha-\beta)_2-\alpha$, $\alpha_2-(\alpha-\beta)_3-\alpha$ and $(\alpha-\beta)_4-\alpha$, wherein $\gamma$ represents an RNA;

(7) the double-stranded polynucleotide or a salt thereof according to (1), wherein in the polynucleotide represented by the formula (I), q is 4, and X is any one selected from the group consisting of $(\gamma-\beta)_5$, $(\alpha-\beta)-(\gamma-\beta)_4$, $(\alpha-\beta)_2-(\gamma-\beta)_3$, $(\alpha-\beta)_3-(\gamma-\beta)_2$, $(\alpha-\beta)_4-(\gamma-\beta)$, $(\alpha-\beta)_5$, $\beta_{10}$, $(\alpha-\beta)-\beta_8$, $(\alpha-\beta)_2-\beta_6$, $(\alpha-\beta)_3-\beta_4$, $(\alpha-\beta)_4-\beta_2$, $\beta-(\gamma-\beta)_4$, $\beta-(\alpha-\beta)-(\gamma-\beta)_3$, $\beta-(\alpha-\beta)_2-(\gamma-\beta)_2$, $\beta-(\alpha-\beta)_3-(\gamma-\beta)$, $\beta_9$, $\beta-(\alpha-\beta)-\beta_6$, $\beta-(\alpha-\beta)_2-\beta_4$, $\beta-(\alpha-\beta)_3-\beta_2$, and $\beta-(\alpha-\beta)_4$; and in the polynucleotide represented by the formula (II), r is 4, and Y is any one selected from the group consisting of $(\gamma-\beta)_5$, $(\gamma-\beta)_4-(\alpha-\beta)$, $(\gamma-\beta)_3-(\alpha-\beta)_2$, $(\gamma-\beta)_2-(\alpha-\beta)_3$, $(\gamma-\beta)-(\alpha-\beta)_4$, $(\alpha-\beta)_5$, $\alpha_6-(\alpha-\beta)_2$, $\alpha_4-(\alpha-\beta)_3$, $\alpha_2-(\alpha-\beta)_4$, $(\gamma-\beta)_4-\alpha$, $(\alpha-\beta)_4-\alpha$, $(\gamma-\beta)_3-(\alpha-\beta)-\alpha$, $(\gamma-\beta)_2-(\alpha-\beta)_2-\alpha$, $(\gamma-\beta)-(\alpha-\beta)_3-\alpha$, $\alpha_6-(\alpha-\beta)-\alpha$, $\alpha_4-(\alpha-\beta)_2-\alpha$, $\alpha_2-(\alpha-\beta)_3-\alpha$, and $(\alpha-\beta)_4-\alpha$, wherein $\gamma$ represents an RNA;

(8) the double-stranded polynucleotide or a salt thereof according to (1), wherein in the polynucleotide represented by the formula (I), q is 5, and X is any one selected from the group consisting of $(\gamma-\beta)_4$, $(\alpha-\beta)-(\gamma-\beta)_3$, $(\alpha-\beta)_2-(\gamma-\beta)_2$, $(\alpha-\beta)_3-(\gamma-\beta)$, $(\alpha-\beta)_4$, $\beta_8$, $(\alpha-\beta)-\beta_6$, $(\alpha-\beta)_2-\beta_4$, $(\alpha-\beta)_3-\beta_2$, $\beta-(\gamma-\beta)_3$, $\beta-(\alpha-\beta)-(\gamma-\beta)_2$, $\beta-(\alpha-\beta)_2-(\gamma-\beta)$, $\beta_7$, $\beta-(\alpha-\beta)_4$, $\beta-(\alpha-\beta)_2\beta_2$, and $\beta-(\alpha-\beta)_3$, wherein $\gamma$ represents an RNA;

(9) the double-stranded polynucleotide or a salt thereof according to (1) or (8), wherein in the polynucleotide represented by the formula (II), r is 5, and Y is any one selected from the group consisting of $(\gamma-\beta)_4$, $(\gamma-\beta)_3-(\alpha-\beta)$, $(\gamma-\beta)_2-(\alpha-\beta)_2$, $(\gamma-\beta)-(\alpha-\beta)_3$, $(\alpha-\beta)_4$, $\beta_6-(\alpha-\beta)$, $\beta_4-(\alpha-\beta)_2$, $\beta_2-(\alpha-\beta)_3$, $(\gamma-\beta)_3-\alpha$, $(\gamma-\beta)_2-(\alpha-\beta)-\alpha$, $(\gamma-\beta)-(\alpha-\beta)_2-\alpha$, $\alpha_7$, $\alpha_4-(\alpha-\beta)-\alpha$, $\alpha_2-(\alpha-\beta)_2-\alpha$, and $(\alpha-\beta)_3-\alpha$, wherein $\gamma$ represents an RNA;

(10) the double-stranded polynucleotide or a salt thereof according to (1), wherein in the polynucleotide represented by the formula (I), q is 5, and X is any one selected from the group consisting of $(\gamma-\beta)_4$, $(\alpha-\beta)-(\gamma-\beta)_3$, $(\alpha-\beta)_2-(\gamma-\beta)_2$, $(\alpha-\beta)_3-(\gamma-\beta)$, $(\alpha-\beta)_4$, $(\alpha-\beta)-\beta_6$, $(\alpha-\beta)_2-\beta_4$, $(\alpha-\beta)_3-\beta_2$, $\beta-(\gamma-\beta)_3$, $\beta-(\alpha-\beta)-(\gamma-\beta)_2$, $\beta-(\alpha-\beta)_2-(\gamma-\beta)$, $\beta_7$, $\beta-(\alpha-\beta)_4$, $\beta-(\alpha-\beta)_2-\beta_2$, and $\beta-(\alpha-\beta)_3$; and in the polynucleotide represented by the formula (II), r is 5, and Y is any one selected from the group consisting of $(\gamma-\beta)_4$, $(\gamma-\beta)_3-(\alpha-\beta)$, $(\gamma-\beta)_2-(\alpha-\beta)_2$, $(\gamma-\beta)-(\alpha-\beta)_3$, $(\alpha-\beta)_4$, $\alpha_6-(\alpha-\beta)$, $\alpha_4-(\alpha-\beta)_2$, $\alpha_2-(\alpha-\beta)_3$, $(\gamma-\beta)_3-\alpha$, $(\gamma-\beta)_2-(\alpha-\beta)-\alpha$, $(\gamma-\beta)-(\alpha-\beta)_2-\alpha$, $\alpha_7$, $\alpha_4-(\alpha-\beta)-\alpha$, $\alpha_2-(\alpha-\beta)_2-\alpha$, and $(\alpha-\beta)_3-\alpha$, wherein $\gamma$ represents an RNA;

(11) a double-stranded polynucleotide or a salt thereof, comprising polynucleotides represented by formulas (I) and (III):

$$5'\text{-}X\text{-}(\alpha\text{-}\beta)_q\text{-}\alpha_p\text{-}\lambda_m\text{-}3' \quad (I)$$

$$5'\text{-}\delta_s\text{-}(\beta\text{-}\alpha)_r\text{-}Y\text{-}\upsilon_n\text{-}3' \quad (III),$$

wherein $\alpha$ and $\beta$ each independently represent a DNA or a 2'-OMeRNA, wherein if $\alpha$ represents a DNA, then $\beta$ represents a 2'-OMeRNA, and wherein if $\alpha$ represents a 2'-OMeRNA, then $\beta$ represents a DNA, $\delta$ and $\lambda$ each independently represent a DNA or a 2'-OMeRNA, and each occurrence of a $\delta$ and each occurrence of a $\lambda$ independently represents a DNA or a T-OMeRNA, $\upsilon$ represents a nucleotide selected from a DNA, an RNA, and a 2'-OMeRNA, and each occurrence of a u independently represents a DNA, an RNA, or a T-OMeRNA, X and Y each independently represent an oligonucleotide, wherein each nucleotide in said oligonucleotide is independently selected from a DNA nucleotide, an RNA nucleotide, and a modified nucleic acid, p represents an integer of 0 or 1, m is 0 when p is 0 and represents any integer of 0 to 5 when p is 1, q represents any integer of 3 to 9, the total number of nucleotides in $(\alpha-\beta)_q$ and X is 17 or 18, s represents an integer of 0 or 1, n represents any integer of 0 to 5, r represents any integer of 3 to 9, the total number of nucleotides in $(\beta-\alpha)_r$ and Y is 17 or 18, $X-(\alpha-\beta)_q-\alpha_p$ in the polynucleotide represented by the formula (I) having a nucleotide sequence identical to a target gene; and the nucleotide sequences of $X-(\alpha-\beta)_q$ in the formula (I) and $(\beta-\alpha)_r-Y$ in the formula (III) are complementary to each other;

(12) the double-stranded polynucleotide or a salt thereof according to (11), wherein in the polynucleotide represented by the formula (I), q is 3, and X is any one selected from the group consisting of $(\gamma-\beta)_6$, $(\alpha-\beta)-(\gamma-\beta)_5$, $(\alpha-\beta)_2-(\gamma-\beta)_4$, $(\alpha-\beta)_3-(\gamma-\beta)_3$, $(\alpha-\beta)_4-(\gamma-\beta)_2$, $(\alpha-\beta)_5-(\gamma-\beta)$, $(\alpha-\beta)_6$, $\beta_{12}$, $(\alpha-\beta)-\beta_{10}$, $(\alpha-\beta)_2\beta_8$, $(\alpha-\beta)_3-\beta_6$, $(\alpha-\beta)_4-\beta_4$, $(\alpha-\beta)_5-\beta_2$, $\beta-(\gamma-\beta)_5$, $\beta-(\alpha-\beta)-(\gamma-\beta)_4$, $\beta-(\alpha-\beta)_2-(\gamma-\beta)_3$, $\beta-(\alpha-\beta)_3-(\gamma-\beta)_2$, $\beta-(\alpha-\beta)_4-(\gamma-\beta)$, $\beta_{11}$, $\beta-(\alpha-\beta)\beta_8$, $\beta-(\alpha-\beta)_2-\beta_6$, $\beta-(\alpha-\beta)_3-\beta_4$, $\beta-(\alpha-\beta)_4-\beta_2$, and $\beta-(\alpha-\beta)_5$, wherein $\gamma$ represents an RNA;

(13) the double-stranded polynucleotide or a salt thereof according to (11), wherein in the polynucleotide represented by the formula (III), r is 3, and Y is any one selected from the group consisting of $(\beta-\gamma)_6$, $(\beta-\gamma)_5-(\beta-\alpha)$, $(\beta-\gamma)_4-(\beta-\alpha)_2$, $(\beta-\gamma)_3-(\beta-\alpha)_3$, $(\beta-\gamma)_2-(\beta-\alpha)_4$, $(\beta-\gamma)-(\beta-\alpha)_5$, $(\beta-\alpha)_6$, $\beta_6-(\beta-\alpha)_3$, $\beta_4-(\beta-\alpha)_4$, $\beta-(\beta-\gamma)_5-\beta$, $(\beta-\gamma)_4-(\beta-\alpha)-\beta$, $(\beta-\gamma)_3-(\beta-\alpha)_2-\beta$, $(\beta-\gamma)_2-(\beta-\alpha)_3-\beta$, $(\beta-\gamma)-(\beta-\alpha)_4-\beta$, $\beta_6-(\beta-\alpha)_2-\beta$, $\beta_4-(\beta-\alpha)_3-\beta$, $\beta_2-(\beta-\alpha)_4-\beta$, and $(\beta-\alpha)_5-\beta$, wherein $\gamma$ represents an RNA;

(14) the double-stranded polynucleotide or a salt thereof according to (11), wherein in the polynucleotide represented by the formula (I), q is 3, and X is any one selected from the group consisting of $(\gamma-\beta)_6$, $(\alpha-\beta)-(\gamma-\beta)_5$, $(\alpha-\beta)_2-(\gamma-\beta)_4$, $(\alpha-\beta)_3-(\gamma-\beta)_3$, $(\alpha-\beta)_4-(\gamma-\beta)_2$, $(\alpha-\beta)_5-(\gamma-\beta)$, $(\alpha-\beta)_6$, $\beta_{12}$, $(\alpha-\beta)-\beta_{10}$, $(\alpha-\beta)_2-\beta_8$, $(\alpha-\beta)_3-\beta_6$, $(\alpha-\beta)_4-\beta_4$, $(\alpha-\beta)_5-\beta_2$, $\beta-(\gamma-\beta)_5$, $\beta-(\alpha-\beta)-(\gamma-\beta)_4$, $\beta-(\alpha-\beta)_2-(\gamma-\beta)_3$, $\beta-(\alpha-\beta)_3-(\gamma-\beta)_2$, $\beta-(\alpha-\beta)_4-(\gamma-\beta)$, $\beta_{11}$, $\beta-(\alpha-\beta)-\beta_8$, $\beta-(\alpha-\beta)_2-\beta_6$, $\beta-(\alpha-\beta)_3-\beta_4$, $\beta-(\alpha-\beta)_4-\beta_2$, and $\beta-(\alpha-\beta)_5$; and in the polynucleotide represented by the formula (III), r is 3, and Y is any one selected from the group consisting of $(\beta-\gamma)_6$, $(\beta-\gamma)_5-(\beta-\alpha)$, $(\beta-\gamma)_4-(\beta-\alpha)_2$, $(\beta-\gamma)_3-(\beta-\alpha)_3$, $(\beta-\gamma)_2-(\beta-\alpha)_4$, $(\beta-\gamma)-(\beta-\alpha)_5$, $(\beta-\alpha)_6$, $\beta_6-(\beta-\alpha)_3$, $\beta_4-(\beta-\alpha)_4$, $\beta_2-(\beta-\alpha)_5$, $(\beta-\gamma)_5-\beta$, $(\beta-\gamma)_4-(\beta-\alpha)-\beta$, $(\beta-\gamma)_3-(\beta-\alpha)_2-\beta$, $(\beta-\gamma)_2-(\beta-\alpha)_3-\beta$, $(\beta-\gamma)-(\beta-\alpha)_4-\beta$, $\beta_6-(\beta-\alpha)_2-\beta$, $\beta_4-(\beta-\alpha)_3-\beta$, $\beta_2-(\beta-\alpha)_4-\beta$, and $(\beta-\alpha)_5-\beta$, wherein $\gamma$ represents an RNA;

(15) the double-stranded polynucleotide or a salt thereof according to (11), wherein in the polynucleotide represented by the formula (I), q is 4, and X is any one selected from the group consisting of $(\gamma-\beta)_5$, $(\alpha-\beta)-(\gamma-\beta)_4$, $(\alpha-\beta)_2-(\gamma-\beta)_3$, $(\alpha-\beta)_3-(\gamma-\beta)_2$, $(\alpha-\beta)_4-(\gamma-\beta)$, $(\alpha-\beta)_5$, $\beta_{10}$, $(\alpha-\beta)-\beta_8$, $(\alpha-\beta)_2-\beta_6$, $(\alpha-\beta)_3-\beta_4$, $(\alpha-\beta)_4-\beta_2$, $\beta-(\gamma-\beta)_4$, $\beta-(\alpha-\beta)-(\gamma-\beta)_3$, $\beta-(\alpha-\beta)_2-(\gamma-\beta)_2$, $\beta-(\alpha-\beta)_3-(\gamma-\beta)$, $\beta_9$, $\beta-(\alpha-\beta)-\beta_6$, $\beta-(\alpha-\beta)_2-\beta_4$, $\beta-(\alpha-\beta)_3-\beta_2$, and $\beta-(\alpha-\beta)_4$, wherein $\gamma$ represents an RNA;

(16) the double-stranded polynucleotide or a salt thereof according to (11), wherein in the polynucleotide represented by the formula (III), r is 4, and Y is any one selected from the group consisting of $(\beta-\gamma)_5$, $(\beta-\gamma)_4-(\beta-\alpha)$, $(\beta-\gamma)_3-(\beta-\alpha)_2$, $(\beta-\gamma)_2-(\beta-\alpha)_3$, $(\beta-\gamma)-(\beta-\alpha)_4$, $(\beta-\alpha)_5$, $\beta_6-(\beta-\alpha)_2$, $\beta_4-(\beta-\alpha)_3$, $\beta_2-(\beta-\alpha)_4$, $(\beta-\gamma)_4-\beta$, $(\beta-\alpha)_4-\beta$, $(\gamma-\beta)_3-(\beta\alpha)-\beta$, $(\gamma-\beta)_2-(\beta-\alpha)_2\beta$, $(\beta-\gamma)-(\beta-\alpha)_3-\beta$, $\beta_6-(\beta-\alpha)-\beta$, $\beta_4-(\beta-\alpha)_2-\beta$, $\beta_2-(\beta-\alpha_3-\beta$ and $(\beta-\alpha)_4-\beta$, wherein $\gamma$ represents an RNA;

(17) the double-stranded polynucleotide or a salt thereof according to (11), wherein in the polynucleotide represented by the formula (I), q is 4, and X is any one selected from the group consisting of $(\gamma-\beta)_5$, $(\alpha-\beta)-(\gamma-\beta)_4$, $(\alpha-\beta)_2-(\gamma-\beta)_3$, $(\alpha-\beta)_3-(\gamma-\beta)_2$, $(\alpha-\beta)_4-(\gamma-\beta)$, $(\alpha-\beta)_5$, $\beta_{10}$, $(\alpha-\beta)-\beta_8$, $(\alpha-\beta)_2-\beta_6$, $(\alpha-\beta)_3-\beta_4$, $(\alpha-\beta)_4-\beta_2$, $\beta-(\gamma-\beta)_4$, $\beta-(\alpha-\beta)-(\gamma-\beta)_3$, $\beta-(\alpha-\beta)_2-(\gamma-\beta)_2$, $\beta-(\alpha-\beta)_3-(\gamma-\beta)$, $\beta_9$, $\beta-(\alpha-\beta)-\beta_6$, $\beta-(\alpha-\beta)_2-\beta_4$, $\beta-(\alpha-\beta)_3-\beta_2$, and $\beta-(\alpha-\beta)_4$; and in the polynucleotide represented by the formula (III), r is 4, and Y is any one selected from the group consisting of $(\beta-\gamma)_5$, $(\beta-\gamma)_4-(\beta-\alpha)$, $(\beta-\gamma)_3-(\beta-\alpha)_2$, $(\beta-\gamma)_2-(\beta-\alpha)_3$, $(\beta-\gamma)-(\beta-\alpha)_4$, $(\beta-\alpha)_5$, $\beta_6-(\beta-\alpha)_2$, $\beta_4-(\beta-\alpha)_3$, $\beta_2-(\beta-\alpha)_4$, $(\beta-\gamma)_4-\beta$, $(\beta-\alpha)_4-\beta$, $(\gamma-\beta)_3-(\beta-\alpha)-\beta$, $(\gamma-\beta)_2-(\beta-\alpha)_2-\beta$, $(\beta-\gamma)-(\beta-\alpha)_3-\beta$, $\beta_6-(\beta-\alpha)-\beta$, $\beta_4-(\beta-\alpha)_2-\beta$, $\beta_2-(\beta-\alpha)_3-\beta$ and $(\beta-\alpha)_4-\beta$, wherein $\gamma$ represents an RNA;

(18) the double-stranded polynucleotide or a salt thereof according to (11), wherein in the polynucleotide represented by the formula (I), q is 5, and X is any one selected from the group consisting of $(\gamma-\beta)_4$, $(\alpha-\beta)-(\gamma-\beta)_3$, $(\alpha-\beta)_2-(\gamma-\beta)_2$, $(\alpha-\beta)_3-(\gamma-\beta)$, $(\alpha-\beta)_4$, $\beta_8$, $(\alpha-\beta)-\beta_6$, $(\alpha-\beta)_2-\beta_4$, $(\alpha-\beta)_3-\beta_2$, $\beta-(\gamma-\beta)_3$, $\beta-(\alpha-\beta)-(\gamma-\beta)_2$, $\beta-(\alpha-\beta)_2-(\gamma-\beta)$, $\beta_7$, $\beta-(\alpha-\beta)-\beta_4$, $\beta-(\alpha-\beta)_2-\beta_2$, and $\beta-(\alpha-\beta)_3$, wherein $\gamma$ represents an RNA;

(19) the double-stranded polynucleotide or a salt thereof according to (11), wherein in the polynucleotide represented by the formula (III), r is 5, and Y is any one selected from the group consisting of $(\beta-\gamma)_4$, $(\beta-\gamma)_3-(\beta-\alpha)$, $(\beta-\gamma)_2-(\beta-\alpha)_2$, $(\beta-\gamma)-(\beta-\alpha)_2$, $(\beta-\alpha)_4$, $\beta_6-(\beta-\alpha)$, $\beta_4-(\beta-\alpha)_2$, $\beta_2-(\beta-\alpha)_3$, $(\gamma-\beta)_3-\beta$, $(\beta-\gamma)_2-(\beta-\alpha)-\beta$, $(\beta-\gamma)-(\beta-\alpha)_2-\beta$, $\beta_7$, $\beta_4-(\beta-\alpha)-\beta$, $\beta_2-(\beta-\alpha)_2-\beta$, and $(\beta-\alpha)_3-\beta$, wherein $\gamma$ represents an RNA;

(20) the double-stranded polynucleotide or a salt thereof according to (11), wherein in the polynucleotide represented by the formula (I), q is 5, and X is any one selected from the group consisting of $(\gamma-\beta)_4$, $(\alpha-\beta)-(\gamma-\beta)_3$, $(\alpha-\beta)_2-(\gamma-\beta)_2$, $(\alpha-\beta)_3-(\gamma-\beta)$, $(\alpha-\beta)_4$, $(\alpha-\beta)-\beta_6$, $(\alpha-\beta)_2-\beta_4$, $(\alpha-\beta)_3-\beta_2$, $\beta-(\gamma-\beta)_3$, $\beta-(\alpha-\beta)-(\gamma-\beta)_2$, $\beta-(\alpha-\beta)_2-(\gamma-\beta)$, $\beta_7$, $\beta-(\alpha-\beta)-\beta_4$, $\beta-(\alpha-\beta)_2-\beta_2$, and $\beta-(\alpha-\beta)_3$; and in the polynucleotide represented by the formula (III), r is 5, and Y is any one selected from the group consisting of $(\beta-\gamma)_4$, $(\beta-\gamma)_3-(\beta-\alpha)$, $(\beta-\gamma)_2-(\beta-\alpha)_2$, $(\beta-\gamma)-(\beta-\alpha)_3$, $(\beta-\alpha)_4$, $\beta_6-(\beta-\alpha)$, $\beta_4-(\beta-\alpha)_2$, $\beta_2-(\beta-\alpha)_3$, $(\gamma-\beta)_3-\beta$, $(\beta-\gamma)_2-(\beta-\alpha)-\beta$, $(\beta-\alpha)_2-\beta$, $\delta_7$, $\beta_4-(\beta-\alpha)-\beta$, $\beta_2-(\beta-\alpha)_2-\beta$, and $(\beta-\alpha)_3-\beta$, wherein $\gamma$ represents an RNA;

(21) the double-stranded polynucleotide or a salt thereof according to (1) or (11), wherein in the polynucleotides represented by the formulas (I), (II), and (III), q is 9, the number of nucleotides in X is 0, p and m are 0, r is 9, and the number of nucleotides in Y is 0;

(22) a double-stranded polynucleotide or a salt thereof, comprising polynucleotides represented by formulas (IV) and (V):

$$5'-(\alpha-\beta)_9-\alpha_p-\lambda_m-3' \quad (IV)$$

$$5'-\delta_s-(\alpha-\beta)_9-\upsilon_n-3' \quad (V),$$

wherein $\alpha$ and $\beta$ each independently represent a DNA or a 2'-OMeRNA, wherein if $\alpha$ represents a DNA, then $\beta$ represents a 2'-OMeRNA, and wherein if $\alpha$ represents a 2'-OMeRNA, then $\beta$ represents a DNA, $\delta$ and $\lambda$ each independently represent a DNA or a 2'-OMeRNA, and each occurrence of a $\delta$ and each occurrence of a $\lambda$ independently represents a DNA or a 2'-OMeRNA, $\upsilon$ represents a nucleotide selected from a DNA, an RNA, and a 2'-OMeRNA, and each occurrence of a $\upsilon$ independently represents a DNA, an RNA, or a 2'-OMeRNA, p represents an integer of 0 or 1, m is 0 when p is 0 and represents any integer of 0 to 5 when p is 1, s represents an integer of 0 or 1, n represents any integer of 0 to 5, $(\alpha-\beta)_9-\alpha_p$ in the polynucleotide represented by the formula (IV) having a nucleotide sequence identical to a target gene; and the nucleotide sequences of $(\alpha-\beta)_9$ in the formula (IV) and $(\alpha-\beta)_9$ in the formula (V) are complementary to each other;

(23) a double-stranded polynucleotide or a salt thereof, comprising polynucleotides represented by formulas (VI) and (VII):

$$5'-\beta-(\alpha-\beta)_8-\alpha_p\lambda_m-3' \quad (VI)$$

$$5'-\delta_s-(\alpha-\beta)_8-(\alpha-\beta)-\upsilon_n-3' \quad (VII),$$

wherein $\alpha$ and $\beta$ each independently represent a DNA or a 2'-OMeRNA, wherein if $\alpha$ represents a DNA, then $\beta$ represents a 2'-OMeRNA, and wherein if $\alpha$ represents a 2'-OMeRNA, then $\beta$ represents a DNA, $\delta$ and $\lambda$ each independently represent a DNA or a 2'-OMeRNA, and each occurrence of a $\delta$ and each occurrence of a $\lambda$, independently represents a DNA or a 2'-OMeRNA, $\upsilon$ represents a nucleotide selected from a DNA, an RNA, and a 2'-OMeRNA and each occurrence of a $\upsilon$ independently represents a DNA, an RNA, or a 2'-OMeRNA, p represents an integer of 0 or 1, m is 0 when p is 0 and represents any integer of 0 to 5 when p is 1, s represents an integer of 0 or 1, n represents any integer of 0 to 5, $\beta-(\alpha-\beta)_8-\alpha_p$ in the polynucleotide represented by the formula (VI) having a nucleotide sequence identical to a target gene; and the nucleotide sequences of $(\alpha-\beta)_8$ in the formula (VI) and $(\alpha-\beta)_8$ in the formula (VII) are complementary to each other;

(24) the double-stranded polynucleotide or a salt thereof according to any one of (1) to (23), wherein $\alpha$ is a DNA, and $\beta$ is a 2'-OMeRNA;

(25) the double-stranded polynucleotide or a salt thereof according to any one of (1) to (24), wherein λ and υ each independently comprise a DNA selected from a thymine base, an adenine base, and a guanine base; or a 2'-OMeRNA selected from a uracil base, an adenine base, and a guanine base;

(26) the double-stranded polynucleotide or a salt thereof according to any one of (1) to (25), wherein m is 0, and n is 2;

(27) the double-stranded polynucleotide or a salt thereof according to any one of (1) to (26), wherein p and m are 0, s is 1, and n is 2;

(28) the double-stranded polynucleotide or a salt thereof according to any one of (1) to (27), wherein any or all of 1 to 4 2'-OMeRNA residues are substituted by an ENA or a 2',4'-BNA/LNA;

(29) the double-stranded polynucleotide or a salt thereof according to any one of (1) to (28), wherein any or all of 1 to 4 DNA residues are substituted by an RNA, an ENA or a 2',4'-BNA/LNA;

(30) the double-stranded polynucleotide or a salt thereof according to any one of (1) to (29), wherein the nucleotides are bonded to each other via a phosphodiester or phosphorothioate bond;

(31) the double-stranded polynucleotide or a salt thereof according to any one of (1) to (30), wherein at least one of the polynucleotides has a phosphorylated 5'-end;

(32) the double-stranded polynucleotide or a salt thereof according to any one of (1) to (31), wherein the antisense strand has a phosphorylated 5'-end;

(33) a pharmaceutical composition comprising a double-stranded polynucleotide or a salt thereof according to any one of (1) to (32) as an active ingredient; and

(34) a method for inhibiting the expression of a target gene, comprising administering a double-stranded polynucleotide or a salt thereof selected from (1) to (32) to a mammal.

Advantages of Invention

The present invention has provided a novel double-stranded polynucleotide that is resistant to RNase and has an RNA interference effect. The present invention allows functional analysis of various genes using the polynucleotide and provides a pharmaceutical composition comprising the double-stranded polynucleotide.

DESCRIPTION OF EMBODIMENTS

Description of Terms

Figure 1:
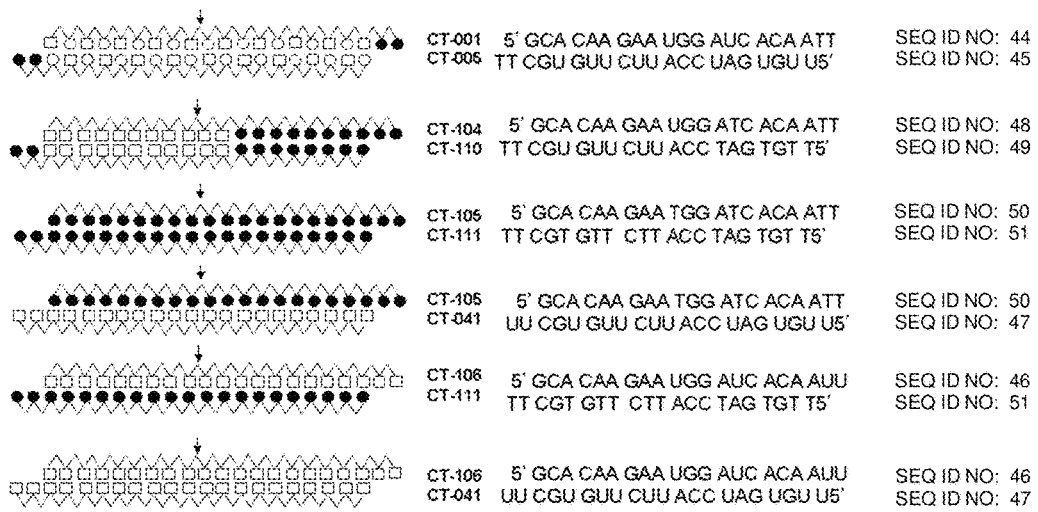
FIG. 1 is a diagram showing double-stranded polynucleotides against the human β-catenin gene (hereinafter, examples of combinations of polynucleotides as sense and antisense strands will be shown in each diagram; for symbols, the open square (□) represents an RNA, the filled circle (•) represents a DNA, the open circle (○) represents a 2'-O-methyl RNA, the open rhombus (◇) represents an ENA, and the filled rhombus (◆) represents a 2',4'-BNA/LNA. In the diagram, s represents a phosphorothioate bond, p represents a phosphate group, and the arrow represents a predicted cleavage site by Argonaute2. The same holds true for the diagrams shown below).

In the present specification, the "target gene" is not particularly limited as long as it can be translated to produce mRNA and/or protein in cells, tissues, or individuals to which or to whom this gene is introduced (hereinafter, they may be referred to as "recipients"). Specifically, the target gene may be endogenous to the recipients for introduction or may be exogenous and introduced thereto by an approach such as gene transfer. It may also be a gene present on the chromosome or an extrachromosomal gene. Examples of the exogenous gene include, but are not limited to, viruses, bacteria, fungi, and those derived from protozoans, which can infect the recipients. The function of a gene may be known or unknown.

Examples of such a target gene can include, but are not limited to, the human β-catenin gene and the DDX3 (DEAD (Asp-Glu-Ala-Asp) box polypeptide 3, X-linked) gene.

In the present specification, the "natural nucleoside" refers to a 2'-deoxynucleoside such as 2'-deoxyadenosine, 2'-deoxyguanosine, 2'-deoxycytidine, 2'-deoxy-5-methylcytidine, and thymidine or a ribonucleoside such as adenosine, guanosine, cytidine, 5-methylcytidine, and uridine. Moreover, the "oligonucleotide" refers to an oligonucleotide composed of a compound in which the sugar moiety of the nucleoside forms an ester with phosphoric acid.

In the present specification, 2'-deoxyadenosine may be referred to as $A^t$; 2'-deoxyguanosine may be referred to as $G^t$; T-deoxycytidine may be referred to as $C^t$; 2'-deoxy-5-methylcytidine may be referred to as $5meC^t$; thymidine may be referred to as $T^t$; T-deoxyuridine may be referred to as $U^t$; adenosine may be referred to as $A^{rt}$; guanosine may be referred to as $AG^{rt}$; cytidine may be referred to as $C^{rt}$; 5-methylcytidine may be referred to as $5meC^{rt}$; and uridine may be referred to as $U^{rt}$. Moreover, in the present specification, 2'-deoxyadenosine nucleotide may be referred to as $A^p$; 2'-deoxyguanosine nucleotide may be referred to as $G^p$; 2'-deoxycytidine nucleotide may be referred to as $C^p$; 2'-deoxy-5-methylcytidine nucleotide may be referred to as $5meC^p$; a thymidine nucleotide may be referred to as $T^p$; a 2'-deoxyuridine nucleotide may be referred to as $U^p$; an adenosine nucleotide may be referred to as $A^{rp}$; a guanosine nucleotide may be referred to as $G^{rp}$; a cytidine nucleotide may be referred to as $C^{rp}$; a 5-methylcytidine nucleotide may be referred to as $5meC^{rp}$; and a uracil nucleotide may be referred to as $U^{rp}$.

In the present specification, where there are phosphorothioate ester forms instead of phosphoester forms of a nucleotide, a counterpart of $A^p$ may be referred to as $A^s$; a counterpart of $G^p$ may be referred to as $G^s$; a counterpart of $C^p$ may be referred to as $C^s$; a counterpart of $5meC^p$ may be referred to as $5meC^s$; a counterpart of $T^p$ may be referred to as $T^s$; a counterpart of $U^p$ may be referred to as $U^s$; a counterpart of $A^{rp}$ may be referred to as $A^{rs}$; a counterpart of $G^{rp}$ may be referred to as $G^{rs}$; a counterpart of $C^{rp}$ may be referred to as $C^{rs}$; a counterpart of $5meC^{rp}$ may be referred to as $5meC^{rs}$; and a counterpart of $U^{rp}$ may be referred to as $U^{rs}$.

In the present specification, the term "nucleoside with modified sugar" refers to a nucleoside whose sugar moiety has been modified.

Particularly, as examples of 2'-O-methyl modification, a counterpart of $A^{rt}$ may be referred to as $A^{m1t}$; a counterpart of $G^{rt}$ may be referred to as $G^{m1t}$; a counterpart of $C^{rt}$ may be referred to as $C^{m1t}$; a counterpart of $5meC^{rt}$ may be referred to as $5meC^{m1t}$; a counterpart of $U^{rt}$ may be referred to as $U^{m1t}$; a counterpart of $A^{rp}$ may be referred to as $A^{m1p}$; a counterpart of $G^{rp}$ may be referred to as $G^{m1p}$; a counterpart of $C^{rp}$ may be referred to as $C^{m1p}$; a counterpart of $5meC^{rp}$ may be referred to as $5meC^{m1p}$; a counterpart of $U^{rp}$ may be referred to as $U^{m1p}$; a counterpart of $A^{rs}$ may be referred to as $A^{m1s}$; a counterpart of $G^{rs}$ may be referred to as $G^{m1s}$; a counterpart of $C^{rs}$ may be referred to as $C^{m1s}$; a counterpart of $5meC^{rs}$ may be referred to as $5meC^{m1s}$; and a counterpart of $U^{rs}$ may be referred to as $U^{m1s}$.

In the present specification, the 2'-O,4'-C-ethylene nucleotide unit and the "ENA unit" refer to those nucleosides and nucleotides having an ENA and also refer to nucleosides and nucleotides having an ENA unit: a counterpart of $A^t$ may be referred to as $A^{2t}$; a counterpart of $A^p$ may be referred to as $A^{c2p}$; a counterpart of $A^s$ may be referred to as $A^{e2s}$; a counterpart of $G^t$ may be referred to as $G^{2t}$; a counterpart of GP may be referred to as $G^{e2p}$; a counterpart of $G^s$ may be referred to as $G^{e2s}$; a counterpart of $5meC^t$ may be referred to as $C^{2t}$; a counterpart of $5meC^p$ may be referred to as $C^{e2p}$; a counterpart of $5meC^s$ may be referred to as $C^{e2s}$; a counterpart of $T^t$ may be referred to as $T^{2t}$; a counterpart of $T^p$ may be referred to as $T^{e2p}$; and a counterpart of $T^s$ may be referred to as $T^{e2s}$.

In the present specification, the 2'-O,4'-C-methylene nucleotide unit and the "2',4'-BNA/LNA unit" refer to those nucleosides and nucleotides having a 2',4'-BNA/LNA and also refer to nucleosides and nucleotides having a 2',4'-BNA/LNA unit: a counterpart of $A^t$ may be referred to as $A^{1t}$; a counterpart of $A^p$ may be referred to as $A^{e1p}$; a counterpart of $A^s$ may be referred to as $A^{e1s}$; a counterpart of $G^t$ may be referred to as $G^{1t}$; a counterpart of GP may be referred to as $G^{e1p}$; a counterpart of $G^s$ may be referred to as $G^{e1s}$; a counterpart of $5meC^t$ may be referred to as $C^{1t}$; a counterpart of $5meC^p$ may be referred to as $C^{e1p}$; a counterpart of $5meC^s$ may be referred to as $C^{e1s}$; a counterpart of $T^t$ may be referred to as $T^{1t}$; a counterpart of $T^p$ may be referred to as $T^{e1p}$; and a counterpart of $T^s$ may be referred to as $T^{e1s}$.

Hereinafter, the structural formula of each nucleotide will be shown.

[Formula 1]

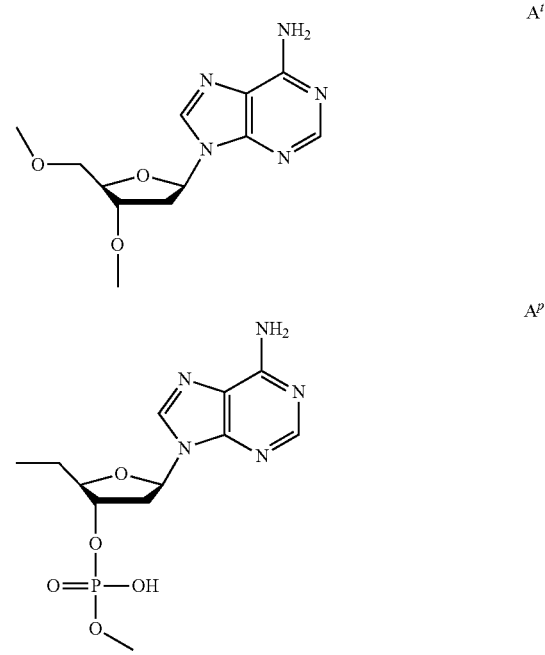

-continued
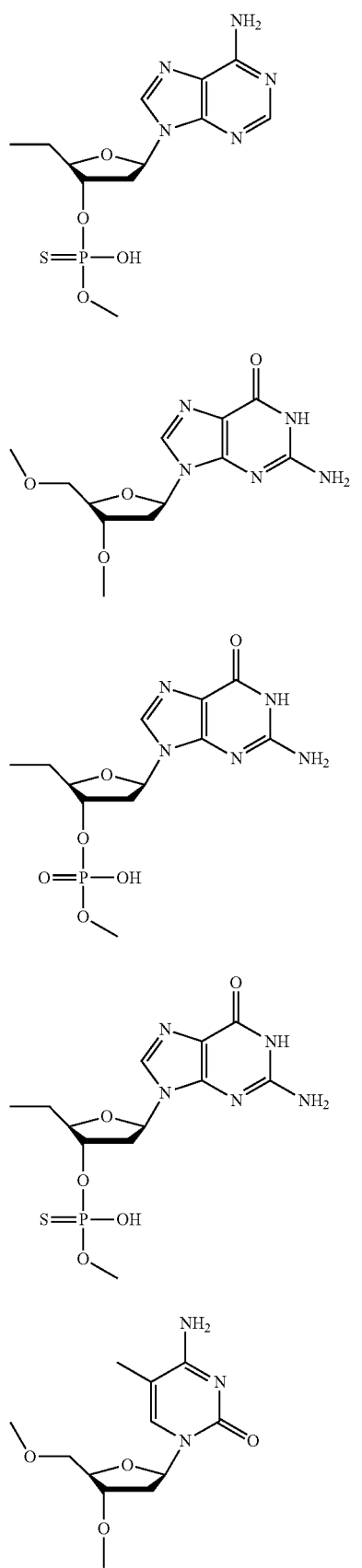
A^s
G^t
G^p
G^s
5meC^t
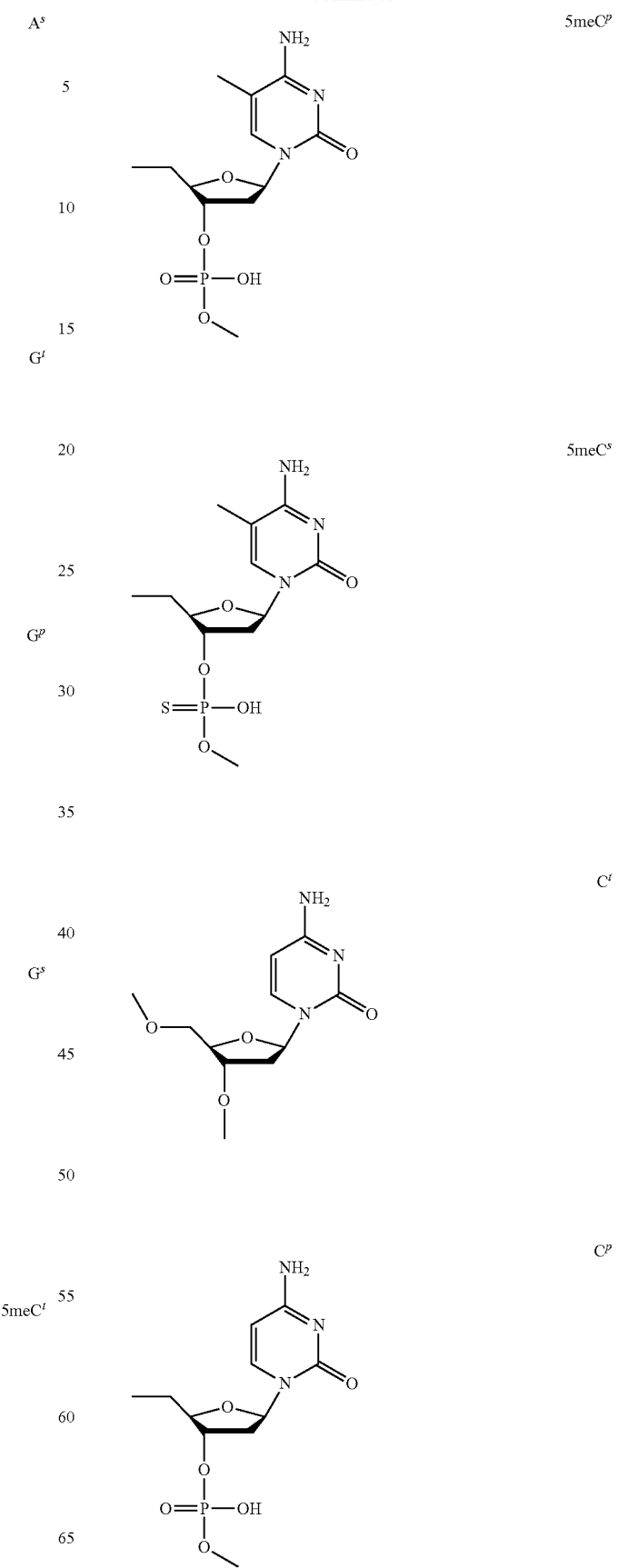
5meC^p
5meC^s
C^t
C^p

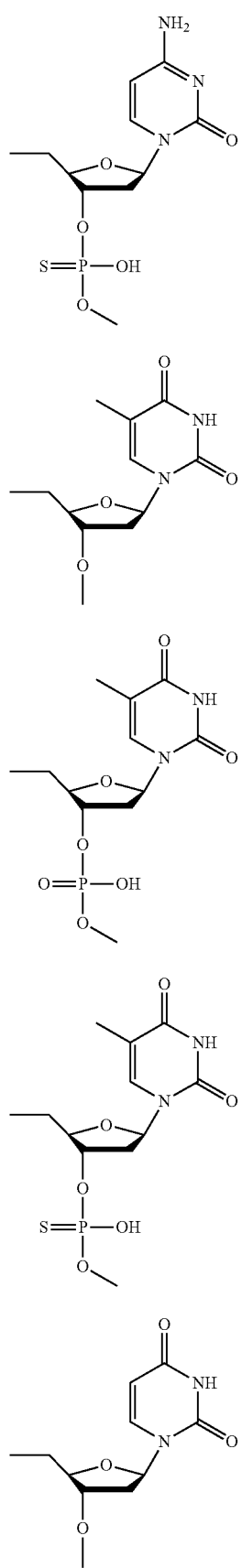
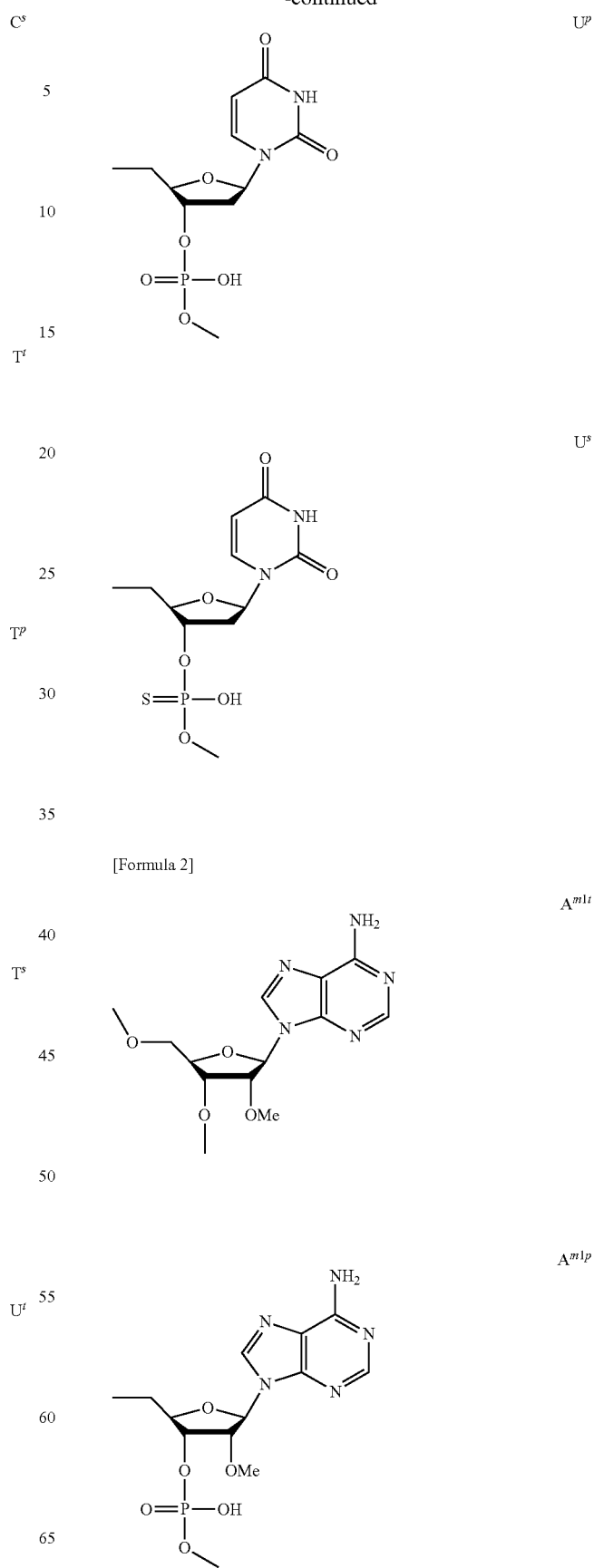
[Formula 2]

23
-continued
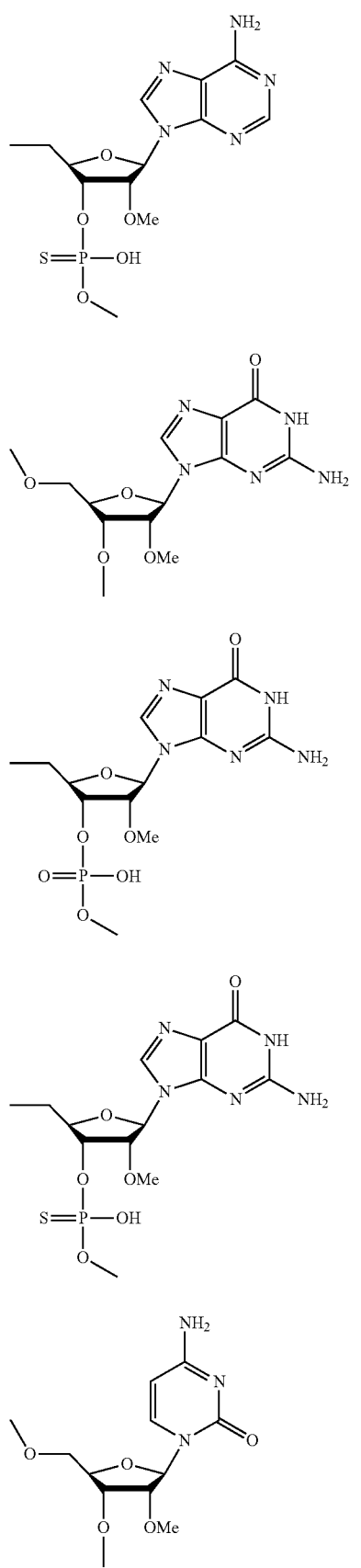
24
-continued
A<sup>m1s</sup>
G<sup>m1t</sup>
G<sup>m1p</sup>
G<sup>m1s</sup>
C<sup>m1t</sup>
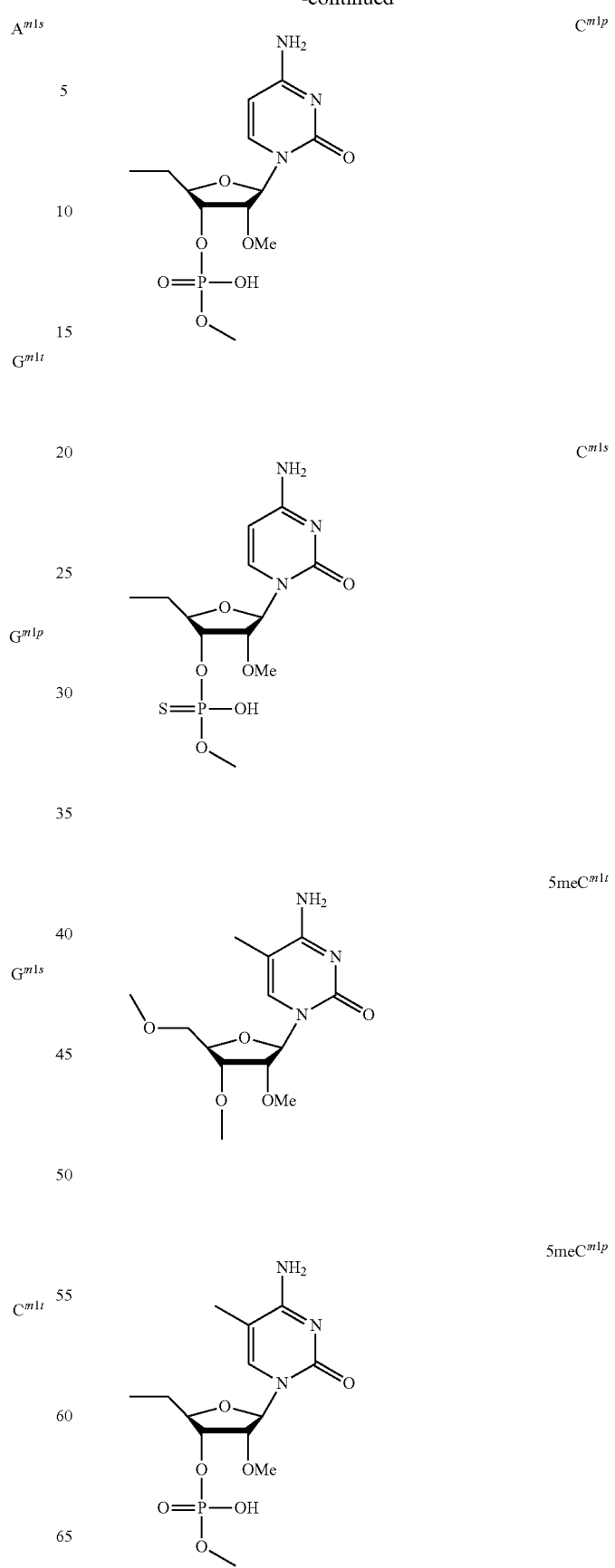
C<sup>m1p</sup>
C<sup>m1s</sup>
5meC<sup>m1t</sup>
5meC<sup>m1p</sup>

25
-continued
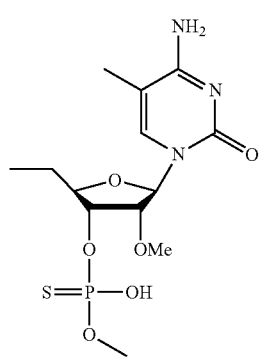
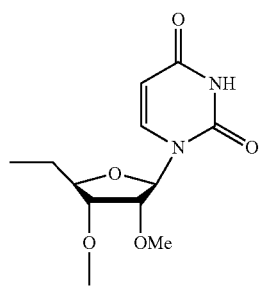
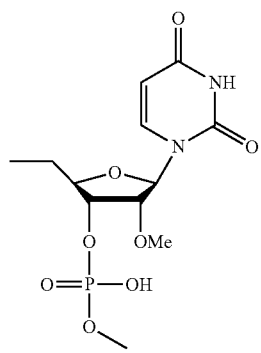
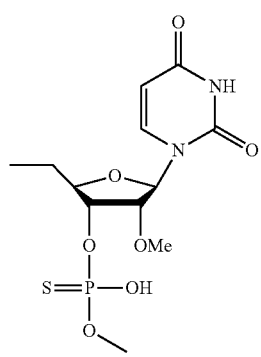
26
-continued
5meC$^{m1s}$
[Formula 3]
A$^{2t}$
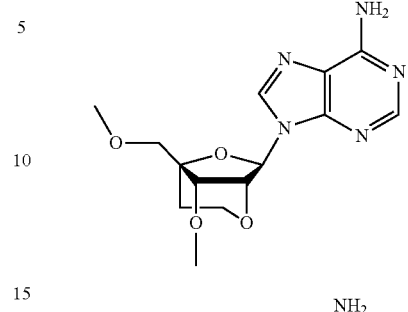
U$^{m1t}$
A$^{e2p}$
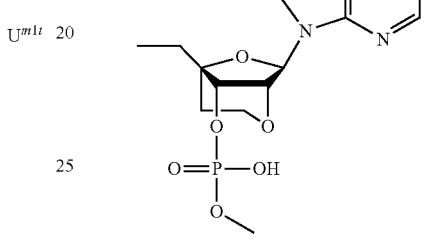
A$^{e2s}$
U$^{m1p}$
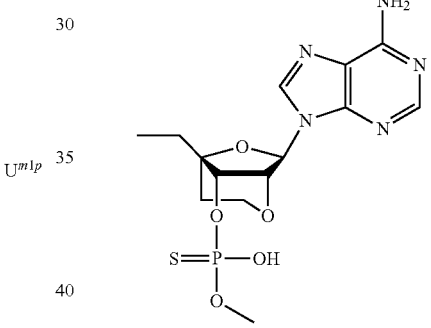
G$^{2t}$
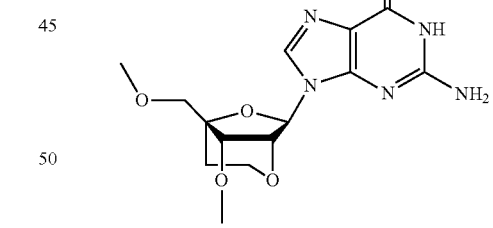
U$^{m1s}$
G$^{e2p}$
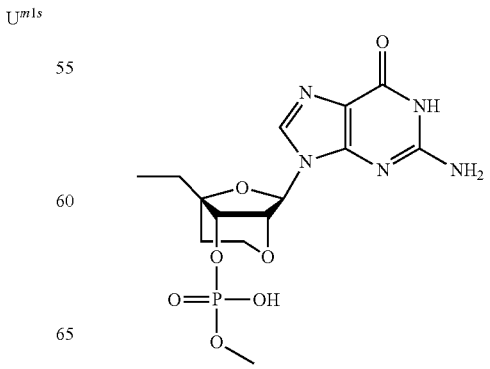

G^{e2s}
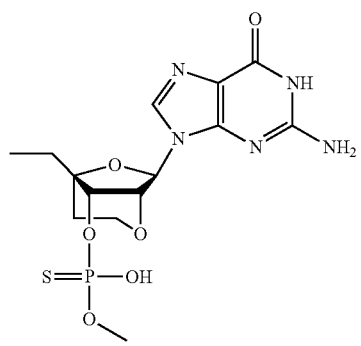
C^{2t}
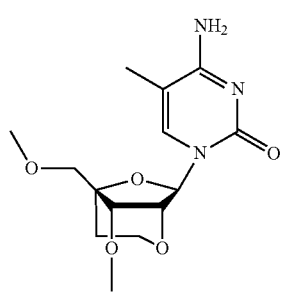
C^{e2p}
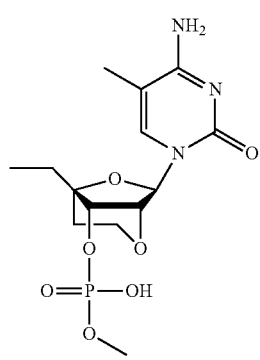
C^{e2s}
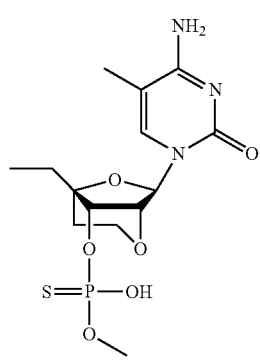
T^{2t}
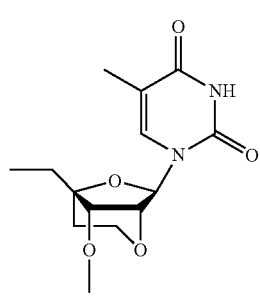
T^{e2p}
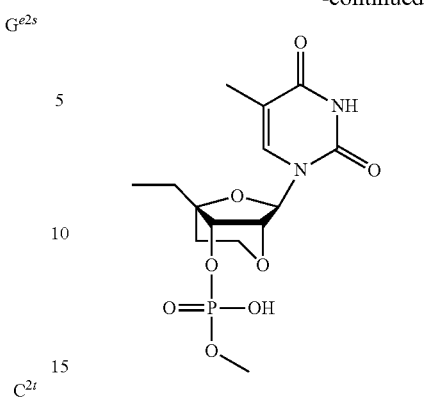
T^{e2s}
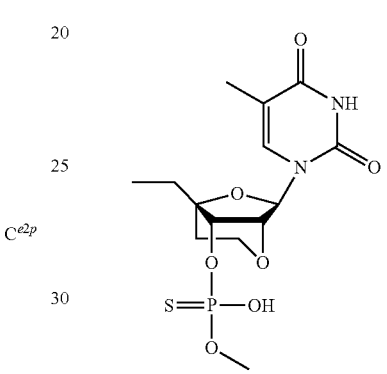
[Formula 4]
A^{1t}
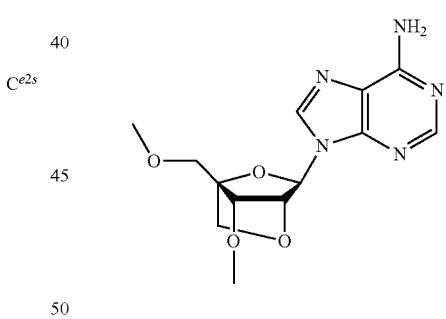
A^{e1p}
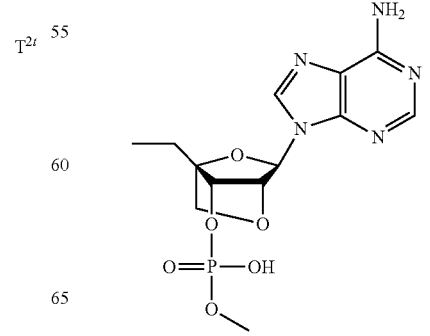

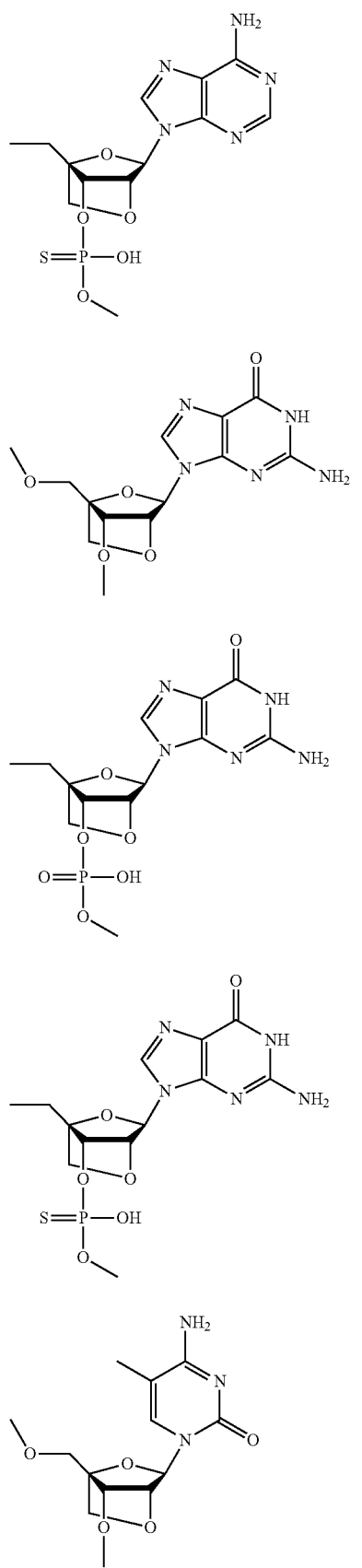
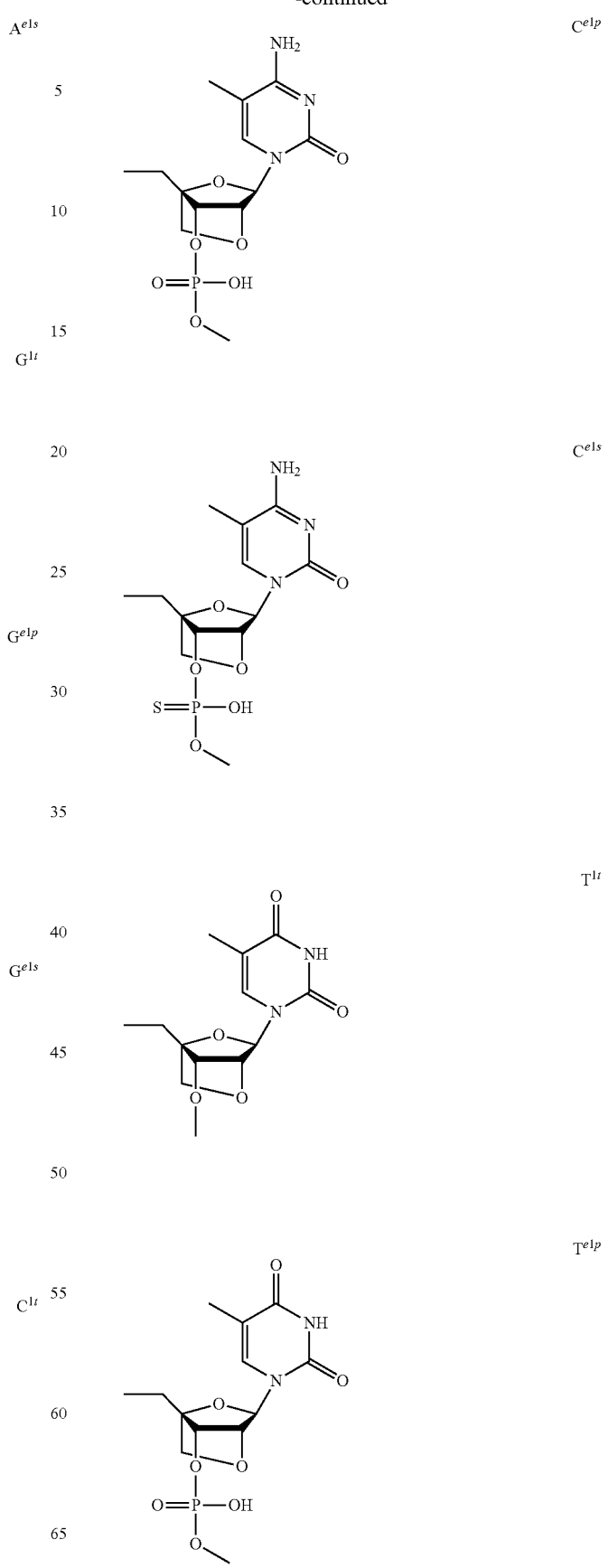

31
-continued
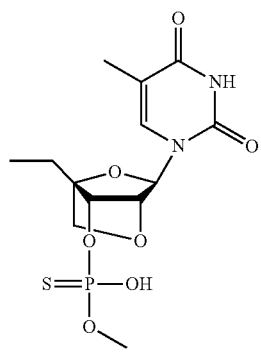
[Formula 5]
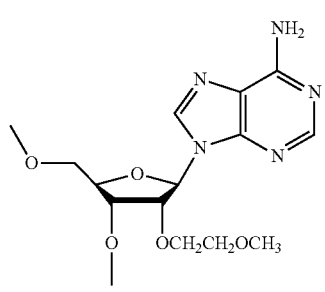
A$^{m2t}$
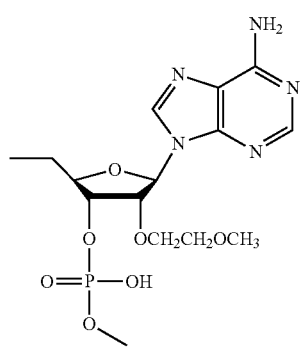
A$^{m2p}$
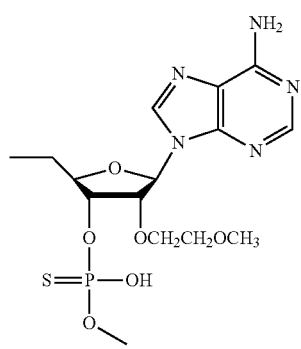
A$^{m2s}$
32
-continued
T$^{els}$
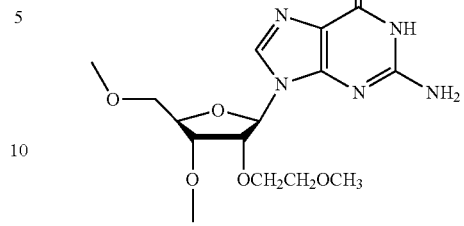
G$^{m2t}$
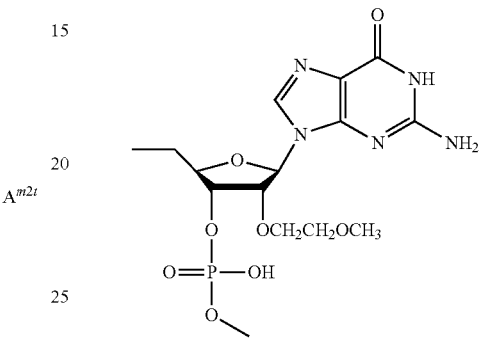
G$^{m2p}$
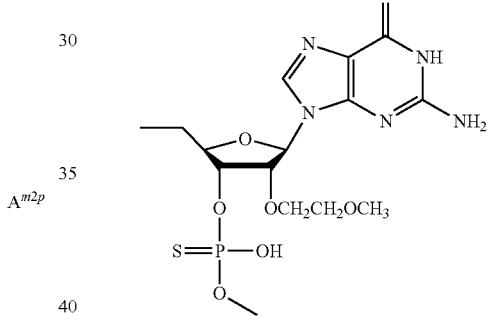
G$^{m2s}$
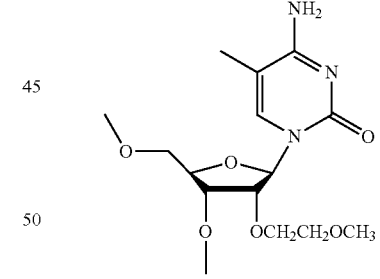
5meC$^{m2t}$
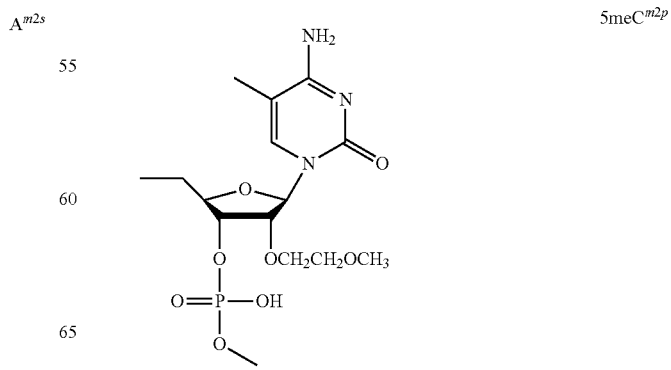
5meC$^{m2p}$ 33
-continued
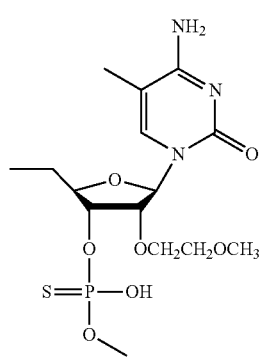
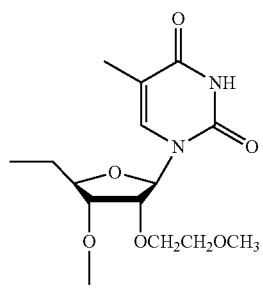
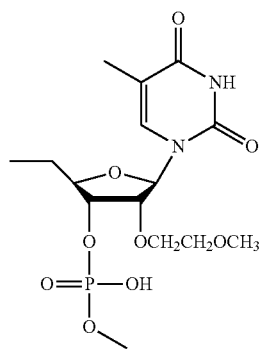
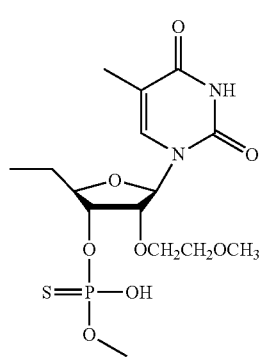
34
-continued
5meC^{m2s}
[Formula 6]
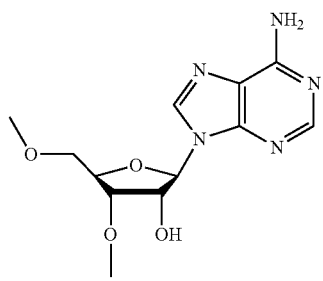 A^{rt}
T^{m2t}
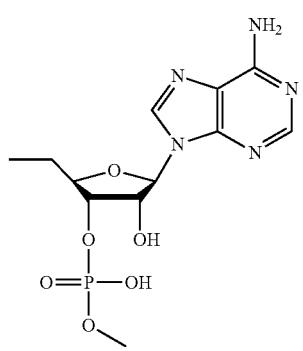 A^{rp}
T^{m2p}
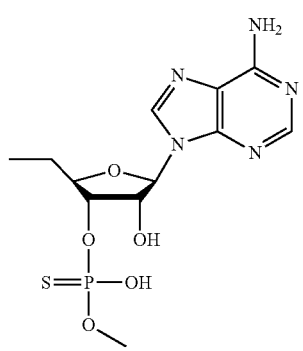 A^{rs}
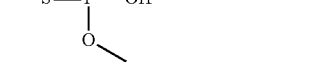 G^{rt}
T^{m2s}
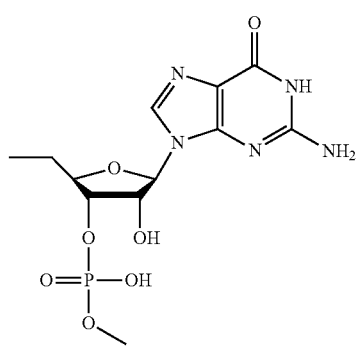 G^{rp}

G<sup>rs</sup>

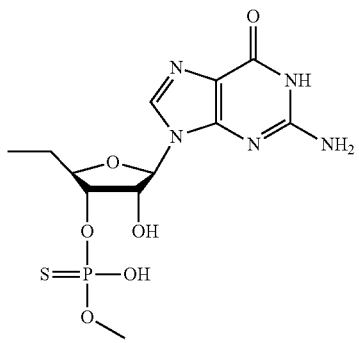

C<sup>rt</sup>

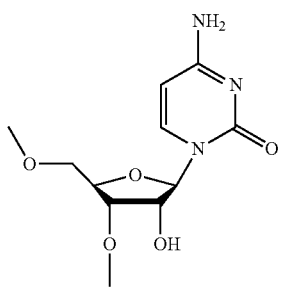

C<sup>rp</sup>

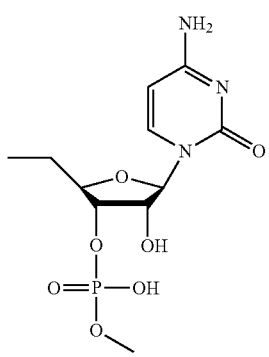

C<sup>rs</sup>

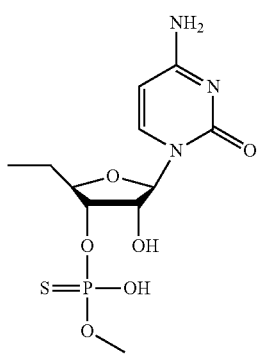

U<sup>rt</sup>

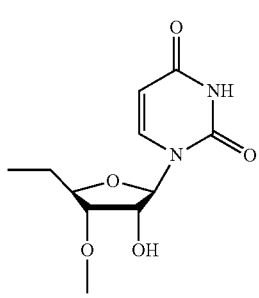

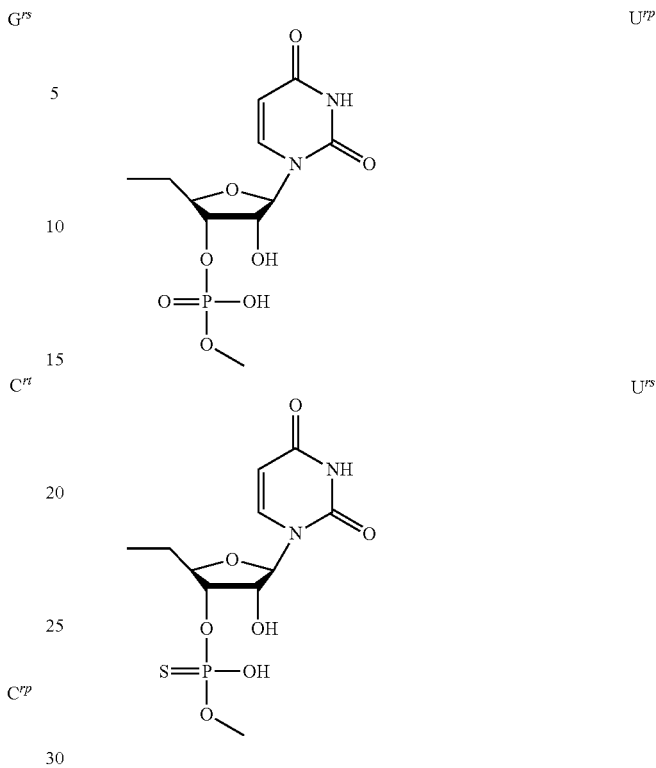

In the present specification, the term "complementary nucleotides" refers to nucleotides whose base moieties are complementary to each other and refers specifically to nucleotides complementary to each other by way of adenine and thymine, guanine and cytosine, guanine and 5-methylcytosine, and adenine and uracil as base moieties.

In the present specification, the "complementary nucleotide sequence" includes a nucleotide sequence consisting of nucleotides, all of which are complementary to a target nucleotide sequence, and also includes a nucleotide sequence forming base pairs with a target oligonucleotide and/or polynucleotide, albeit with one or more nucleotides that are not complementary.

In the present specification, the "double-stranded polynucleotide" is a polynucleotide assuming a duplex by Watson-Crick base pairs formed between complementary nucleotides, though not all the nucleotides in the polynucleotide may form Watson-Crick base pairs.

In the present specification, of the double-stranded polynucleotide, a strand comprising a nucleotide sequence identical to a target gene is called a passenger strand or sense strand, whereas a strand comprising a nucleotide sequence complementary to the target gene is called a guide strand or antisense strand.

In the present specification, the phrase "having a nucleotide sequence identical to a target gene" refers to having a sequence identical to at least a partial nucleotide sequence of the target gene. It includes a completely identical sequence and also includes a substantially identical sequence as long as the resulting double-stranded polynucleotide has an RNA interference effect. Moreover, when the target gene is known to have SNPs or the like, a sequence having these variations is also included as an identical nucleotide sequence.

A polynucleotide having a sequence identical or substantially identical to at least a partial nucleotide sequence of the target gene is a polynucleotide having a sequence identical or substantially identical to any 18-nucleotide or more sequence in the nucleotide sequence of the target gene. In this context, the "substantially identical sequence" refers to a sequence having 70% or higher, preferably 80% or higher, more preferably 90% or higher homology, to the nucleotide sequence of the target gene. The homology of the nucleotide sequence can be calculated using gene analysis software known in the art such as BLAST (registered trademark).

In the item <223> for each sequence in the Sequence Listing attached to the present specification, "cm" represents 2'-O-methylcytidine; "um" represents 2'-O-methyluridine; and "gm" represents 2'-O-methylguanosine.

Double-Stranded Polynucleotide

The chain length of the double-stranded polynucleotide according to the present invention may be any length from 18 nucleotides to the full length of the open reading frame (ORF) of the target gene as long as it has an RNA interference effect. The sense strand is preferably 18 to 21 nucleotides, more preferably 18 or 19 nucleotides, in chain length. The antisense strand is preferably 19 to 21 nucleotides, more preferably 21 nucleotides, in chain length. The double-stranded polynucleotide does not have to be a duplex as a whole and includes those partially overhanging at the 5' and/or 3'-ends. The overhanging end has 1 to 5 nucleotides, preferably 1 to 3 nucleotides, more preferably 2 nucleotides. Moreover, the most preferable examples thereof include those having a structure in which the 3'-end of the polynucleotide which is the antisense strand overhangs by 2 nucleotides (overhang structure).

2-1.

An example of the double-stranded polynucleotide can include a double-stranded polynucleotide comprising a sense strand comprising a polynucleotide represented by the following formula (I) and an antisense strand comprising a polynucleotide represented by the following formula (II):

$$5'\text{-}X\text{-}(\alpha\text{-}\beta)_q\text{-}\alpha_p\text{-}\lambda_m\text{-}3' \quad (I)$$

$$5'\text{-}\delta_s\text{-}(\alpha\text{-}\beta)_r\text{-}Y\text{-}\upsilon_n\text{-}3' \quad (II),$$

wherein
$\alpha$ and $\beta$ each independently represent a DNA or a 2'-OMeRNA, wherein if $\alpha$ represents a DNA, then $\beta$ represents a T-OMeRNA, and wherein if $\alpha$ represents a 2'-OMeRNA, then $\beta$ represents a DNA. $\delta$ and $\lambda$ each independently represent a DNA or a 2'-OMeRNA, and each occurrence of a $\delta$ and each occurrence of a $\lambda$ independently represents a DNA or a 2'-OMeRNA, (e.g. where s is 2, then $\delta$ can be DNA-DNA, DNA-2'-OMeRNA, T-OMeRNA-DNA, or 2'-OMeRNA-2'-OMeRNA. Likewise, e.g. where m is 2, then $\lambda$ can be DNA-DNA, DNA-2'-OMeRNA, 2'-OMeRNA-DNA, or 2'-OMeRNA-2'-OMeRNA), $\upsilon$ represents a nucleotide selected from a DNA, an RNA, and a 2'-OMeRNA, and each occurrence of a $\upsilon$ independently represents a DNA, an RNA, or a 2'-OMeRNA (e.g., for $\upsilon_n$, if n is 2, $\upsilon_2$ can be DNA-DNA, RNA-RNA and 2'-OMeRNA-2'OMeRNA, and also can be DNA-2'-OMeRNA, DNA-RNA, RNA-2'-OMeRNA, 2'-OMeRNA-DNA, RNA-DNA and 2'-OMeRNA-RNA), X and Y each independently represent an oligonucleotide, wherein each nucleotide in said oligonucleotide is independently selected from a DNA nucleotide, an RNA nucleotide, and a modified nucleic acid,
p represents an integer of 0 or 1, m is 0 when p is 0 and represents any integer of 0 to 5 when p is 1, q represents any integer of 3 to 9, the total number of nucleotides in $(\alpha\text{-}\beta)_q$ and X is 17 or 18, s represents an integer of 0 or 1, n represents any integer of 0 to 5, r represents any integer of 3 to 9, the total number of nucleotides in $(\alpha\text{-}\beta)_r$ and Y is 17 or 18, $X\text{-}(\alpha\text{-}\beta)_q\text{-}\alpha_p$ in the polynucleotide represented by the formula (I) having a nucleotide sequence identical to a target gene; and the nucleotide sequences of $X\text{-}(\alpha\text{-}\beta)_q$ in the formula (I) and $(\alpha\text{-}\beta)_r\text{-}Y$ in the formula (II) are complementary to each other.

In this context, p, q, r, s, m, and n are numbers representing the number of nucleotides. For example, $(\alpha\text{-}\beta)_2$ means $(\alpha\text{-}\beta)\text{-}(\alpha\text{-}\beta)$. This means that when p in $\alpha_p$ is 0, this nucleotide is absent. $\alpha_p$ represents $\alpha$ when p is 1 and represents $\alpha\text{-}\alpha$ when p is 2.

2-2.

An example of the double-stranded polynucleotide represented by the formulas (I) and (II) can include a double-stranded polynucleotide wherein both q and r are 9, and the number of nucleotides in X and Y is 0.

2-3.

Another example of the double-stranded polynucleotide can include a double-stranded polynucleotide comprising a sense strand which is a polynucleotide wherein in the polynucleotide represented by the formula (I):

q is 3, and X is any one selected from the group consisting of $(\gamma\text{-}\beta)_6$, $(\alpha\text{-}\beta)\text{-}(\gamma\text{-}\beta)_5$, $(\alpha\text{-}\beta)_2\text{-}(\gamma\text{-}\beta)_4$, $(\alpha\text{-}\beta)_3\text{-}(\gamma\text{-}\beta)_3$, $(\alpha\text{-}\beta)_4\text{-}(\gamma\text{-}\beta)_2$, $(\alpha\text{-}\beta)_5\text{-}(\gamma\text{-}\beta)$, $(\alpha\text{-}\beta)_6$, $\beta_{12}$, $(\alpha\text{-}\beta)\text{-}\beta_{10}$, $(\alpha\text{-}\beta)_2\text{-}\beta_8$, $(\alpha\text{-}\beta)_3\text{-}\beta_6$, $(\alpha\text{-}\beta)_4\text{-}\beta_4$, $(\alpha\text{-}\beta)_5\text{-}\beta_2$, $\beta\text{-}(\gamma\text{-}\beta)_5$, $\beta\text{-}(\alpha\text{-}\beta)\text{-}(\gamma\text{-}\beta)_4$, $\beta\text{-}(\alpha\text{-}\beta)_2\text{-}(\gamma\text{-}\beta)_3$, $\beta\text{-}(\alpha\text{-}\beta)_3\text{-}(\gamma\text{-}\beta)_2$, $\beta\text{-}(\alpha\text{-}\beta)_4\text{-}(\gamma\text{-}\beta)$, $\beta_{11}$, $\beta\text{-}(\alpha\text{-}\beta)\text{-}\beta_8$, $\beta\text{-}(\alpha\text{-}\beta)_2\text{-}\beta_6$, $\beta\text{-}(\alpha\text{-}\beta)_3\text{-}\beta_4$, $\beta\text{-}(\alpha\text{-}\beta)_4\text{-}\beta_2$, and $\beta\text{-}(\alpha\text{-}\beta)_5$;

q is 4, and X is any one selected from the group consisting of $(\gamma\text{-}\beta)_5$, $(\alpha\text{-}\beta)\text{-}(\gamma\text{-}\beta)_4$, $(\alpha\text{-}\beta)_2\text{-}(\gamma\text{-}\beta)_3$, $(\alpha\text{-}\beta)_3\text{-}(\gamma\text{-}\beta)_2$, $(\alpha\text{-}\beta)_4\text{-}(\gamma\text{-}\beta)$, $(\alpha\text{-}\beta)_5$, $\beta_{10}$, $(\alpha\text{-}\beta)\text{-}\beta_8$, $(\alpha\text{-}\beta)_2\text{-}\beta_6$, $(\alpha\text{-}\beta)_3\text{-}\beta_4$, $(\alpha\text{-}\beta)_4\text{-}\beta_2$, $\beta\text{-}(\gamma\text{-}\beta)_4$, $\beta\text{-}(\alpha\text{-}\beta)_4$, $\beta\text{-}(\alpha\text{-}\beta)\text{-}(\gamma\text{-}\beta)_3$, $\beta(\alpha\text{-}\beta)_2\text{-}(\gamma\text{-}\beta)_2$, $\beta\text{-}(\alpha\text{-}\beta)_3\text{-}(\gamma\text{-}\beta)$, $\beta_9$, $\beta\text{-}(\alpha\text{-}\beta)\beta_6$, $\beta\text{-}(\alpha\text{-}\beta)_2\text{-}\beta_4$, $\beta\text{-}(\alpha\text{-}\beta)_3\text{-}\beta_2$, and $\beta\text{-}(\alpha\text{-}\beta)_4$;

or q is 5, and X is any one selected from the group consisting of $(\gamma\text{-}\beta)_4$, $(\alpha\text{-}\beta)\text{-}(\gamma\text{-}\beta)_3$, $(\alpha\text{-}\beta)_2\text{-}(\gamma\text{-}\beta)_2$, $(\alpha\text{-}\beta)_3\text{-}(\gamma\text{-}\beta)$, $(\alpha\text{-}\beta)_4$, $\beta_8$, $(\alpha\text{-}\beta)\text{-}\beta_6$, $(\alpha\text{-}\beta)_2\text{-}\beta_4$, $(\alpha\text{-}\beta)_3\text{-}\beta_2$, $\beta\text{-}(\gamma\text{-}\beta)_3$, $\beta\text{-}(\alpha\text{-}\beta)\text{-}(\gamma\text{-}\beta)_2$, $\beta\text{-}(\alpha\text{-}\beta)_2\text{-}(\gamma\text{-}\beta)$, $\beta_7$, $\beta\text{-}(\alpha\text{-}\beta)\beta_4$, $\beta\text{-}(\alpha\text{-}\beta)_2\text{-}\beta_2$, and $\beta\text{-}(\alpha\text{-}\beta)_3$, wherein $\gamma$ represents an RNA, and an antisense strand which is a polynucleotide wherein in the polynucleotide represented by the formula (II):

r is 3, and Y is any one selected from the group consisting of $(\gamma\text{-}\beta)_6$, $(\gamma\text{-}\beta)_5\text{-}(\alpha\text{-}\beta)$, $(\gamma\text{-}\beta)_4\text{-}(\alpha\text{-}\beta)_2$, $(\gamma\text{-}\beta)_3\text{-}(\alpha\text{-}\beta)_3$, $(\gamma\text{-}\beta)_2\text{-}(\alpha\text{-}\beta)_4$, $(\gamma\text{-}\beta)\text{-}(\alpha\text{-}\beta)_5$, $(\alpha\text{-}\beta)_6$, $\alpha_6\text{-}(\alpha\text{-}\beta)_3$, $\alpha_4\text{-}(\alpha\text{-}\beta)_4$, $\alpha_2\text{-}(\alpha\text{-}\beta)_5$, $(\gamma\text{-}\beta)_5\text{-}\alpha$, $(\gamma\text{-}\beta)_4\text{-}(\alpha\text{-}\beta)\text{-}\alpha$, $(\gamma\text{-}\beta)_3\text{-}(\alpha\text{-}\beta)_2\text{-}\alpha$, $(\gamma\text{-}\beta)_2\text{-}(\alpha\text{-}\beta)_3\text{-}\alpha$, $(\gamma\text{-}\beta)\text{-}(\alpha\text{-}\beta)_4\text{-}\alpha$, $\alpha_6\text{-}(\alpha\text{-}\beta)_2\text{-}\alpha$, $\alpha_4\text{-}(\alpha\text{-}\beta)_3\text{-}\alpha$, $\beta_2\text{-}(\alpha\text{-}\beta)_4\text{-}\alpha$, and $(\alpha\text{-}\beta)_5\text{-}\alpha$; r is 4, and Y is any one selected from the group consisting of $(\gamma\text{-}\beta)_5$, $(\gamma\text{-}\beta)_4\text{-}(\alpha\text{-}\beta)$, $(\gamma\text{-}\beta)_3\text{-}(\alpha\text{-}\beta)_2$, $(\gamma\text{-}\beta)_2\text{-}(\alpha\text{-}\beta)_3$, $(\gamma\text{-}\beta)\text{-}(\alpha\text{-}\beta)_4$, $(\alpha\text{-}\beta)_5$, $\beta_6\text{-}(\alpha\text{-}\beta)_2$, $\beta_4\text{-}(\alpha\text{-}\beta)_3$, $\beta_2\text{-}(\alpha\text{-}\beta)_4$, $(\gamma\text{-}\beta)_4\text{-}\alpha$, $(\alpha\text{-}\beta)_4\text{-}\alpha$, $(\gamma\text{-}\beta)_3\text{-}(\alpha\text{-}\beta)\text{-}\alpha$, $(\gamma\text{-}\beta)_2\text{-}(\alpha\text{-}\beta)_2\text{-}\alpha$, $(\gamma\text{-}\beta)\text{-}(\alpha\text{-}\beta)_3\text{-}\alpha$, $\alpha_6\text{-}(\alpha\text{-}\beta)\text{-}\alpha$, $\alpha_4\text{-}(\alpha\text{-}\beta)_2\text{-}\alpha$, $\alpha_2\text{-}(\alpha\text{-}\beta)_3\text{-}\alpha$ and $(\alpha\text{-}\beta)_4\text{-}\alpha$; or r is 5, and Y is any one selected from the group consisting of $(\gamma\text{-}\beta)_4$, $(\gamma\text{-}\beta)_3\text{-}(\alpha\text{-}\beta)$, $(\gamma\text{-}\beta)_2\text{-}(\alpha\text{-}\beta)_2$, $(\gamma\text{-}\beta)\text{-}(\alpha\text{-}\beta)_3$, $(\alpha\text{-}\beta)_4$, $\beta_6\text{-}(\alpha\text{-}\beta)$, $\beta_4\text{-}(\alpha\text{-}\beta)_2$, $\beta_2\text{-}(\alpha\text{-}\beta)_3$, $(\gamma\text{-}\beta)_3\text{-}\alpha$, $(\gamma\text{-}\beta)_2\text{-}(\alpha\text{-}\beta)\text{-}\alpha$, $(\gamma\text{-}\beta)\text{-}(\alpha\text{-}\beta)_2\text{-}\alpha$, $\alpha_7$, $\alpha_4\text{-}(\alpha\text{-}\beta)\text{-}\alpha$, $\alpha_2\text{-}(\alpha\text{-}\beta)_2\text{-}\alpha$, and $(\alpha\text{-}\beta)_3\text{-}\alpha$, wherein $\gamma$ represents an RNA.

2-4.

Another example of the double-stranded polynucleotide can include a double-stranded polynucleotide comprising a sense strand comprising a polynucleotide represented by the following formula (I) and an antisense strand comprising a polynucleotide represented by the following formula (III):

$$5'\text{-}X\text{-}(\alpha\text{-}\beta)_q\text{-}\alpha_p\text{-}\lambda_m\text{-}3' \quad (I)$$

$$5'\text{-}\delta_s\text{-}(\beta\text{-}\alpha)_r\text{-}Y\text{-}\upsilon_n\text{-}3' \quad (III),$$

wherein

α and β each independently represent a DNA or a 2'-OMeRNA, wherein if α represents a DNA, then β represents a 2'-OMeRNA, and wherein if α represents a 2'-OMeRNA, then β represents a DNA, δ and λ each independently represent a DNA or a 2'-OMeRNA, and each occurrence of a δ and each occurrence of a λ independently represents a DNA or a 2'-OMeRNA, υ represents a nucleotide selected from a DNA, an RNA, and a 2'-OMeRNA, and each occurrence of a υ independently represents a DNA, an RNA, or a 2'-OMeRNA, X and Y each independently represent an oligonucleotide, wherein each nucleotide in said oligonucleotide is independently selected from a DNA nucleotide, an RNA nucleotide, and a modified nucleic acid, p represents an integer of 0 or 1, m is 0 when p is 0 and represents any integer of 0 to 5 when p is 1, q represents any integer of 3 to 9, the total number of nucleotides in $(\alpha\text{-}\beta)_q$ and X is 17 or 18, s represents an integer of 0 or 1, n represents any integer of 0 to 5, r represents any integer of 3 to 9, the total number of nucleotides in $(\beta\text{-}\alpha)_r$ and Y is 17 or 18, $X\text{-}(\alpha\text{-}\beta)_q\text{-}\alpha_p$ in the polynucleotide represented by the formula (I) having a nucleotide sequence identical to a target gene; and the nucleotide sequences of $X\text{-}(\alpha\text{-}\beta)_q$ in the formula (I) and $(\beta\text{-}\alpha)_r\text{-}Y$ in the formula (III) are complementary to each other.

2-5.

An example of the double-stranded polynucleotide represented by the formulas (I) and (III) can include a double-stranded polynucleotide wherein both q and r are 9, and the number of nucleotides in X and Y is 0.

2-6.

Another example of the double-stranded polynucleotide can include a double-stranded polynucleotide comprising a sense strand which is a polynucleotide wherein in the polynucleotide represented by the formula (I);

q is 3, and X is any one selected from the group consisting of $(\gamma\text{-}\beta)_6$, $(\alpha\text{-}\beta)\text{-}(\gamma\text{-}\beta)_5$, $(\alpha\text{-}\beta)_2\text{-}(\gamma\text{-}\beta)_4$, $(\alpha\text{-}\beta)_3\text{-}(\gamma\text{-}\beta)_3$, $(\alpha\text{-}\beta)_4\text{-}(\gamma\text{-}\beta)_2$, $(\alpha\text{-}\beta)_5\text{-}(\gamma\text{-}\beta)$, $(\alpha\text{-}\beta)_6$, $\beta_{12}$, $(\alpha\text{-}\beta)\text{-}\beta_{10}$, $(\alpha\text{-}\beta)_2\text{-}\beta_8$, $(\alpha\text{-}\beta)_3\text{-}\beta_6$, $(\alpha\text{-}\beta)_4\text{-}\beta_4$, $(\alpha\text{-}\beta)_5\text{-}\beta_2$, $\beta\text{-}(\gamma\text{-}\beta)_5$, $\beta\text{-}(\alpha\text{-}\beta)_4\text{-}(\gamma\text{-}\beta)$, $\beta_{11}$, $\beta\text{-}(\alpha\text{-}\beta)\text{-}\beta^8$, $\beta\text{-}(\alpha\text{-}\beta)_2\text{-}\beta_6$, $\beta\text{-}(\alpha\text{-}\beta)_3\text{-}\beta_4$, $\beta\text{-}(\alpha\text{-}\beta)_4\text{-}\beta_2$, and $\beta\text{-}(\alpha\text{-}\beta)_5$; q is 4, and X is any one selected from the group consisting of $(\gamma\text{-}\beta)_5$, $(\alpha\text{-}\beta)\text{-}(\gamma\text{-}\beta)_4$, $(\alpha\text{-}\beta)_2\text{-}(\gamma\text{-}\beta)_3$, $(\alpha\text{-}\beta)_3\text{-}(\gamma\text{-}\beta)_2$, $(\alpha\text{-}\beta)_4\text{-}(\gamma\text{-}\beta)$, $(\alpha\text{-}\beta)_5$, $\beta_{10}$, $(\alpha\text{-}\beta)\text{-}\beta_8$, $(\alpha\text{-}\beta)_2\text{-}\beta_6$, $(\alpha\text{-}\beta)_3\text{-}\beta_4$, $(\alpha\text{-}\beta)_4\text{-}\beta_2$, $\beta\text{-}(\gamma\text{-}\beta)_4$, $\beta\text{-}(\alpha\text{-}\beta)\text{-}(\gamma\text{-}\beta)_3$, $\beta\text{-}(\alpha\text{-}\beta)_2\text{-}(\gamma\text{-}\beta)_2$, $\beta\text{-}(\alpha\text{-}\beta)_3\text{-}(\gamma\text{-}\beta)$, $\beta_9$, $\beta\text{-}(\alpha\text{-}\beta)\text{-}\beta_6$, $\beta\text{-}(\alpha\text{-}\beta)_2\text{-}\beta_4$, $\beta\text{-}(\alpha\text{-}\beta)_3\text{-}\beta_2$, and $\beta\text{-}(\alpha\text{-}\beta)_4$; or q is 5, and X is any one selected from the group consisting of $(\gamma\text{-}\beta)_4$, $(\alpha\text{-}\beta)\text{-}(\gamma\text{-}\beta)_3$, $(\alpha\text{-}\beta)_2\text{-}(\gamma\text{-}\beta)_2$, $(\alpha\text{-}\beta)_3\text{-}(\gamma\text{-}\beta)$, $(\alpha\text{-}\beta)_4$, $\beta_8$, $(\alpha\text{-}\beta)\text{-}\beta_6$, $(\alpha\text{-}\beta)_2\text{-}\beta_4$, $(\alpha\text{-}\beta)_3\text{-}\beta_2$, $\beta\text{-}(\gamma\text{-}\beta)_3$, $\beta\text{-}(\alpha\text{-}\beta)\text{-}(\gamma\text{-}\beta)_2$, $\beta\text{-}(\alpha\text{-}\beta)_2\text{-}(\gamma\text{-}\beta)$, $\beta_7$, $\beta\text{-}(\alpha\text{-}\beta)\text{-}\beta_4$, $\beta\text{-}(\alpha\text{-}\beta)_2\text{-}\beta_2$, and $\beta\text{-}(\alpha\text{-}\beta)_3$, wherein γ represents an RNA, and an antisense strand which is a polynucleotide wherein in the polynucleotide represented by the formula (III):

r is 3, and Y is any one selected from the group consisting of $(\beta\text{-}\gamma)_6$, $(\beta\text{-}\gamma)_5\text{-}(\beta\text{-}\alpha)$, $(\beta\text{-}\gamma)_4\text{-}(\beta\text{-}\alpha)_2$, $(\beta\text{-}\gamma)_3\text{-}(\beta\text{-}\alpha)_3$, $(\beta\text{-}\gamma)_2\text{-}(\beta\text{-}\alpha)_4$, $(\beta\text{-}\gamma)\text{-}(\beta\text{-}\alpha)_5$, $(\beta\text{-}\alpha)_6$, $\beta_6\text{-}(\beta\text{-}\alpha)_3$, $\beta_4\text{-}(\beta\text{-}\alpha)_4$, $\beta_2\text{-}(\beta\text{-}\alpha)_5$, $(\beta\text{-}\gamma)_5\text{-}\beta$, $(\beta\text{-}\gamma)_4\text{-}(\beta\text{-}\alpha)\text{-}\beta$, $(\beta\text{-}\gamma)_3\text{-}(\beta\text{-}\alpha)_2\text{-}\beta$, $(\beta\text{-}\gamma)_2\text{-}(\beta\text{-}\alpha)_3\text{-}\beta$, $(\beta\text{-}\gamma)\text{-}(\beta\text{-}\alpha)_4\text{-}\beta$, $\beta_6\text{-}(\beta\text{-}\alpha)_2\beta$, $\beta_4\text{-}(3\text{-}\alpha)_3\text{-}\beta$, $\beta_2\text{-}(\beta\text{-}\alpha)_4\text{-}\beta$, and $(\beta\text{-}\alpha)_5\text{-}\beta$; r is 4, and Y is any one selected from the group consisting of $(\beta\text{-}\gamma)_5$, $(\beta\text{-}\gamma)_4\text{-}(\beta\text{-}\alpha)$, $(\beta\text{-}\gamma)_3\text{-}(\beta\text{-}\alpha)_2$, $(\beta\text{-}\gamma)_2\text{-}(\beta\text{-}\alpha)_3$, $(\beta\text{-}\gamma)\text{-}(\beta\text{-}\alpha)_4$, $(\beta\text{-}\alpha)_5$, $\beta_6\text{-}(\beta\text{-}\alpha)_2$, $\beta_4\text{-}(\beta\text{-}\alpha)_3$, $\beta_2\text{-}(\beta\text{-}\alpha)_4$, $(\beta\text{-}\gamma)_4\text{-}\beta$, $(\beta\text{-}\alpha)_4\text{-}\beta$, $(\gamma\text{-}\beta)_3\text{-}(\beta\text{-}\alpha)\text{-}\beta$, $(\gamma\text{-}\beta)_2\text{-}(\beta\text{-}\alpha)_2\text{-}\beta$, $(\beta\text{-}\gamma)\text{-}(\beta\text{-}\alpha)_3\text{-}\beta$, $\beta_6\text{-}(\beta\text{-}\alpha)\text{-}\beta$, $\beta_4\text{-}(\beta\text{-}\alpha)_2\text{-}\beta$, $\beta_2\text{-}(\beta\text{-}\alpha)_3\text{-}\beta$, and $(\beta\text{-}\alpha)_4\text{-}\beta$; or r is 5, and Y is any one selected from the group consisting of $(\beta\text{-}\gamma)_4$, $(\beta\text{-}\gamma)_3\text{-}(\beta\text{-}\alpha)$, $(\beta\text{-}\gamma)_2\text{-}(\beta\text{-}\alpha)_2$, $(\beta\text{-}\gamma)\text{-}(\beta\text{-}\alpha)_3$, $(\beta\text{-}\alpha)_4$, $\beta_6\text{-}(\beta\text{-}\alpha)$, $\beta_4\text{-}(\beta\text{-}\alpha)_2$, $\beta_2\text{-}(\beta\text{-}\alpha)_3$, $(\gamma\text{-}\beta)_3\text{-}\beta$, $(\beta\text{-}\gamma)_2\text{-}(\beta\text{-}\alpha)\text{-}\beta$, $(\gamma\text{-}\gamma)\text{-}(\beta\text{-}\alpha)_2\text{-}\beta$, $\beta_7$, $\beta_4\text{-}(\beta\text{-}\alpha)\text{-}\beta$, $\beta_2\text{-}(\beta\text{-}\alpha)_2\text{-}\beta$, and $(\beta\text{-}\alpha)_3\text{-}\beta$, wherein y represents an RNA.

2-7.

Another example of the double-stranded polynucleotide can include a double-stranded polynucleotide comprising a sense strand comprising a polynucleotide represented by the following formula (IV) and an antisense strand comprising a polynucleotide represented by the following formula (V):

$$5'\text{-}(\alpha\text{-}\beta)_9\text{-}\alpha_p\text{-}\lambda_m\text{-}3' \qquad (IV)$$

$$5'\text{-}\delta_s\text{-}(\alpha\text{-}\beta)_9\text{-}\upsilon_n\text{-}3' \qquad (V),$$

wherein

α and β each independently represent a DNA or a 2'-OMeRNA, wherein if α represents a DNA, then β represents a 2'-OMeRNA, and wherein if α represents a 2'-OMeRNA, then β represents a DNA, δ and λ each independently represent a DNA or a 2'-OMeRNA, and each occurrence of a δ and each occurrence of a λ independently represents a DNA or a 2'-OMeRNA, υ represents a nucleotide selected from a DNA, an RNA, and a 2'-OMeRNA, and each occurrence of a υ independently represents a DNA, an RNA, or a 2'-OMeRNA, p represents an integer of 0 or 1, m is 0 when p is 0 and represents any integer of 0 to 5 when p is 1, s represents an integer of 0 or 1, n represents any integer of 0 to 5, $(\alpha\text{-}\beta)_9\text{-}\alpha_p$ in the polynucleotide represented by the formula (IV) having a nucleotide sequence identical to a target gene; and the nucleotide sequences of $(\alpha\text{-}\beta)_9$ in the formula (IV) and $(\alpha\text{-}\beta)_9$ in the formula (V) are complementary to each other.

2-8.

Another example of the double-stranded polynucleotide can include a double-stranded polynucleotide comprising a sense strand comprising a polynucleotide represented by the following formula (VI) and an antisense strand comprising a polynucleotide represented by the following formula (VII):

$$5'\text{-}\beta\text{-}(\alpha\text{-}\beta)_8\text{-}\alpha_p\text{-}\lambda_m\text{-}3' \qquad (VI)$$

$$5'\text{-}\delta_s\text{-}(\alpha\text{-}\beta)_8\text{-}(\alpha\text{-}\beta)\text{-}\upsilon_n\text{-}3' \qquad (VII),$$

wherein

α and β each independently represent a DNA or a 2'-OMeRNA, wherein if α represents a DNA, then β represents a 2'-OMeRNA, and wherein if α represents a 2'-OMeRNA, then β represents a DNA, δ and λ each independently represent a DNA or a 2'-OMeRNA, and each occurrence of a δ and each occurrence of a λ independently represents a DNA or a 2'-OMeRNA, υ represents a nucleotide selected from a DNA, an RNA, and a 2'-OMeRNA and each occurrence of a υ independently represents a DNA, an RNA, or a 2'-OMeRNA, p represents an integer of 0 or 1, m is 0 when p is 0 and represents any integer of 0 to 5 when p is 1, s represents an integer of 0 or 1, n represents any integer of 0 to 5, $\beta\text{-}(\alpha\text{-}\beta)_8\text{-}\alpha_p$ in the polynucleotide represented by the formula (VI) having a nucleotide sequence identical to a target gene; and the nucleotide sequences of $(\alpha\text{-}\beta)_8$ in the formula (VI) and $(\alpha\text{-}\beta)_8$ in the formula (VII) are complementary to each other.

2-9.

Another example of the double-stranded polynucleotide can include a double-stranded polynucleotide represented by the following formulas (VIII) and (IX):

$$5'\text{-}X\text{-}(\alpha\text{-}\beta)_q\text{-}\alpha\text{-}\alpha_m\text{-}3' \qquad (VIII)$$

$$5'\text{-}\beta\text{-}(\alpha\text{-}\beta)_r\text{-}Y\text{-}\alpha_n\text{-}3' \qquad (IX),$$

wherein

α represents a DNA, β represents a 2'-OMeRNA, and X and Y each independently represent an oligonucleotide, wherein each nucleotide in said oligonucleotide is independently selected from a DNA nucleotide, an RNA nucleotide, and a modified nucleic acid;

q represents any integer from 3 to 9, the total number of nucleotides in $(\alpha\text{-}\beta)_q$ and X is 18, r represents any integer from 3 to 9, the total number of nucleotides in $(\alpha\text{-}\beta)_r$ and Y is 18, and n and m each independently represent an integer from 0 to 5;

$X\text{-}(\alpha\text{-}\beta)_q\text{-}\alpha$ in the polynucleotide represented by the formula (VIII) has a nucleotide sequence identical to a target gene; and the nucleotide sequences of $X\text{-}(\alpha\text{-}\beta)_q\text{-}\alpha$ in the formula (VIII) and $\beta\text{-}(\alpha\text{-}\beta)_r\text{-}Y$ in the formula (IX) are complementary to each other.

In the polynucleotides represented by the formulas (VIII) and (IX), the numbers represented by n and m are preferably 2.

Moreover, examples of nucleotides as preferable α in $\alpha_m$ and $\alpha_n$ can include thymidine for all of them.

An example of the double-stranded polynucleotide represented by the formulas (VIII) and (IX) can include a double-stranded polynucleotide wherein both q and r are 9, and the number of nucleotides in X and Y is 0.

Another example of the double-stranded polynucleotide can include a double-stranded polynucleotide wherein in the formula (VIII), q is 3, and X is any one selected from the group consisting of $(\gamma\text{-}\beta)_6$, $(\alpha\text{-}\beta)\text{-}(\gamma\text{-}\beta)_5$, $(\alpha\text{-}\beta)_2\text{-}(\gamma\text{-}\beta)_4$, $(\alpha\text{-}\beta)_3\text{-}(\gamma\text{-}\beta)_3$, $(\alpha\text{-}\beta)_4\text{-}(\gamma\text{-}\beta)_2$, $(\alpha\text{-}\beta)_5\text{-}(\gamma\text{-}\beta)$, $(\alpha\text{-}\beta)_3\text{-}\beta_6$, $(\alpha\text{-}\beta)_4\text{-}\beta_4$, and $(\alpha\text{-}\beta)_5\text{-}\beta_2$ wherein α represents a DNA, β represents a 2'-OMeRNA, and γ represents an RNA.

Another example of the double-stranded polynucleotide can include a double-stranded polynucleotide or a salt thereof, wherein in the formula (IX), r is 3, and Y is any one selected from the group consisting of $(\gamma\text{-}\beta)_6$, $(\gamma\text{-}\beta)_5\text{-}(\alpha\text{-}\beta)$, $(\gamma\text{-}\beta)_4\text{-}(\alpha\text{-}\beta)_2$, $(\gamma\text{-}\beta)_3\text{-}(\alpha\text{-}\beta)_3$, $(\gamma\text{-}\beta)_2\text{-}(\alpha\text{-}\beta)_4$, $(\gamma\text{-}\beta)\text{-}(\alpha\text{-}\beta)_5$, $\alpha_6\text{-}(\alpha\text{-}\beta)_3$, $\alpha_4\text{-}(\alpha\text{-}\beta)_4$, and $\alpha_2\text{-}(\alpha\text{-}\beta)_5$ wherein α represents a DNA, β represents a 2'-OMeRNA, and γ represents an RNA.

A further example of the double-stranded polynucleotide can include a double-stranded polynucleotide wherein in the formula (VIII), q is 3, and X is any one selected from the group consisting of $(\gamma\text{-}\beta)_6$, $(\alpha\text{-}\beta)\text{-}(\gamma\text{-}\beta)_5$, $(\alpha\text{-}\beta)_2\text{-}(\gamma\text{-}\beta)_4$, $(\alpha\text{-}\beta)_3\text{-}(\gamma\text{-}\beta)_3$, $(\alpha\text{-}\beta)_4\text{-}(\gamma\text{-}\beta)_2$, $(\alpha\text{-}\beta)_5\text{-}(\gamma\text{-}\beta)$, $(\alpha\text{-}\beta)_3\text{-}\beta_6$, $(\alpha\text{-}\beta)_4\text{-}\beta_4$, and $(\alpha\text{-}\beta)_5\text{-}\beta_2$; and in the formula (IX), r is 3, and Y is any one selected from the group consisting of $(\gamma\text{-}\beta)_6$, $(\gamma\text{-}\beta)_5\text{-}(\alpha\text{-}\beta)$, $(\gamma\text{-}\beta)_4\text{-}(\alpha\text{-}\beta)_2$, $(\gamma\text{-}\beta)_3\text{-}(\alpha\text{-}\beta)_3$, $(\gamma\text{-}\beta)_2\text{-}(\alpha\text{-}\beta)_4$, $(\gamma\text{-}\beta)\text{-}(\alpha\text{-}\beta)_5$, $\alpha_6\text{-}(\alpha\text{-}\beta)$, $\alpha_4\text{-}(\alpha\text{-}\beta)_4$, and $\alpha_2\text{-}(\alpha\text{-}\beta)_5$ wherein α represents a DNA, β represents a 2'-OMeRNA, and γ represents an RNA.

Another example of the double-stranded polynucleotide can include a double-stranded polynucleotide wherein in the formula (VIII), q is 4, and X is any one selected from the group consisting of $(\gamma\text{-}\beta)_5$, $(\alpha\text{-}\beta)\text{-}(\gamma\text{-}\beta)_4$, $(\alpha\text{-}\beta)_2\text{-}(\beta\text{-}\beta)_3$, $(\alpha\text{-}\beta)_3\text{-}(\gamma\text{-}\beta)_2$, $(\alpha\text{-}\beta)_4\text{-}(\gamma\text{-}\beta)$ $(\alpha\text{-}\beta)_2\text{-}\beta_6$, $(\alpha\text{-}\beta)_3\text{-}\beta_4$, and $(\alpha\text{-}\beta)_4\text{-}\beta_2$ wherein α represents a DNA, β represents a 2'-OMeRNA, and γ represents an RNA.

Another example of the double-stranded polynucleotide can include a double-stranded polynucleotide wherein in the formula (IX), r is 4, and Y is any one selected from the group consisting of $(\gamma\text{-}\beta)_5$, $(\gamma\text{-}\beta)_4\text{-}(\alpha\text{-}\beta)$, $(\gamma\text{-}\beta)_3\text{-}(\alpha\text{-}\beta)_2$, $(\gamma\text{-}\beta)_2\text{-}(\alpha\text{-}\beta)_3$, $(\gamma\text{-}\beta)\text{-}(\alpha\text{-}\beta)_4$, $\alpha_6\text{-}(\alpha\text{-}\beta)_2$, $\alpha_4\text{-}(\alpha\text{-}\beta)_3$, and $\alpha_2\text{-}(\alpha\text{-}\beta)_4$ wherein α represents a DNA, β represents a 2'-OMeRNA, and γ represents an RNA.

A further example of the double-stranded polynucleotide can include a double-stranded polynucleotide wherein in the formula (VIII), q is 4, and X is any one selected from the group consisting of $(\gamma\text{-}\beta)_5$, $(\alpha\text{-}\beta)\text{-}(\gamma\text{-}\beta)_4$, $(\alpha\text{-}\beta)_2\text{-}(\gamma\text{-}\beta)_3$, $(\alpha\text{-}\beta)_3\text{-}(\gamma\text{-}\beta)_2$, $(\alpha\text{-}\beta)_4\text{-}(\gamma\text{-}\beta)$, $(\alpha\text{-}\beta)_2\text{-}\beta_6$, $(\alpha\text{-}\beta)_3\text{-}\beta_4$, and $(\alpha\text{-}\beta)_4\text{-}\beta_2$; and in the formula (IX), r is 4, and Y is any one selected from the group consisting of $(\gamma\text{-}\beta)_5$, $(\gamma\text{-}\beta)_4\text{-}(\alpha\text{-}\beta)$, $(\gamma\text{-}\beta)_3\text{-}(\alpha\text{-}\beta)_2$, $(\gamma\text{-}\beta)_2\text{-}(\alpha\text{-}\beta)_3$, $(\gamma\text{-}\beta)\text{-}(\alpha\text{-}\beta)_4$, $\beta_6\text{-}(\alpha\text{-}\beta)_2$, $\beta_4\text{-}(\alpha\text{-}\beta)_3$, and $\beta_2\text{-}(\alpha\text{-}\beta)_4$ wherein α represents a DNA, β represents a 2'-OMeRNA, and γ represents an RNA.

Another example of the double-stranded polynucleotide can include a double-stranded polynucleotide wherein in the formula (VIII), q is 5, and X is any one selected from the group consisting of $(\gamma\text{-}\beta)_4$, $(\alpha\text{-}\beta)\text{-}(\gamma\text{-}\beta)_3$, $(\alpha\text{-}\beta)_2\text{-}(\gamma\text{-}\beta)_2$, $(\alpha\text{-}\beta)_3\text{-}(\gamma\text{-}\beta)$, $(\alpha\text{-}\beta)\text{-}\beta_6$, $(\alpha\text{-}\beta)_2\text{-}\beta_4$, and $(\alpha\text{-}\beta)_3\text{-}\beta_2$ wherein α represents a DNA, β represents a 2'-OMeRNA, and γ represents an RNA.

Another example of the double-stranded polynucleotide can include a double-stranded polynucleotide wherein in the formula (IX), r is 5, and Y is any one selected from the group consisting of $(\gamma\text{-}\beta)_4$, $(\beta\text{-}\beta)_3\text{-}(\alpha\text{-}\beta)$, $(\gamma\text{-}\beta)_2\text{-}(\alpha\text{-}\beta)_2$, $(\gamma\text{-}\beta)\text{-}(\alpha\text{-}\beta)_3$, $\alpha_6\text{-}(\alpha\text{-}\beta)$ $\alpha_4\text{-}(\alpha\text{-}\beta)_2$, and $\alpha_2\text{-}(\alpha\text{-}\beta)_3$ wherein α represents a DNA, β represents a 2'-OMeRNA, and γ represents an RNA.

A further example of the double-stranded polynucleotide can include a double-stranded polynucleotide wherein in the formula (VIII), q is 5, and X is any one selected from the group consisting of $(\gamma\text{-}\beta)_4$, $(\alpha\text{-}\beta)\text{-}(\gamma\text{-}\beta)_3$, $(\alpha\text{-}\beta)_2\text{-}(\alpha\text{-}\beta)_2$, $(\alpha\text{-}\beta)_3\text{-}(\gamma\text{-}\beta)$, $(\alpha\text{-}\beta)\text{-}\beta_6$, $(\alpha\text{-}\beta)_2\text{-}\beta_4$, and $(\alpha\text{-}\beta)_3\text{-}\beta_2$; and in the formula (IX), r is 5, and Y is any one selected from the group consisting of $(\gamma\text{-}\beta)_4$, $(\gamma\text{-}\beta)_3\text{-}(\alpha\text{-}\beta)$, $(\gamma\text{-}\beta)_2\text{-}(\alpha\text{-}\beta)_2$, $(\gamma\text{-}\beta)\text{-}(\alpha\text{-}\beta)_3$, $\beta_6\text{-}(\alpha\text{-}\beta)$, $\beta_4\text{-}(\alpha\text{-}\beta)_2$, and $\beta_2\text{-}(\alpha\text{-}\beta)_3$ wherein α represents a DNA, β represents a 2'-OMeRNA, and γ represents an RNA.

The nucleotide with a modified sugar encompasses all manner of sugar modification known in the technical field to which the present invention belongs. The nucleotide with a modified sugar can retain every heterocyclic base site and internucleoside bond and further includes nucleotides with a modified sugar different from the sugar modifications described above. The group of nucleotides with modified sugars includes 2'-modified nucleotides, 4'-thio-modified nucleotides, 4'-thio-2'-modified nucleotides, and bicyclic nucleotides each with a modified sugar.

The 2'-modified nucleotides are, for example, halo, allyl, amino, azide, O-allyl, O—$C_1$-$C_{10}$ alkyl, $OCF_3$, O—$(CH_2)_2$—O—$CH_3$, 2'-O$(CH_2)_2SCH_3$, O—$(CH_2)_2$—O—N$(R_m)(R_n)$, and O—$CH_2$—C(=O)—N$(R_m)(R_n)$, wherein $R_m$ and $R_n$ are each individually H, an amino protective group, or substituted or unsubstituted $C_1$-$C_{10}$ alkyl. A preferable 2'-modification is —F, —$OCH_3$, or —O—$(CH_2)_2$—O—$CH_3$, more preferably —$OCH_3$.

Examples of the 4'-thio-modified nucleosides can include β-D-ribonucleosides in which the 4'-oxygen atom has been substituted by a sulfur atom (Hoshika, S. et al. FEBS Lett. 579, p. 3115-3118, (2005); Dande, P. et al. J. Med. Chem. 49, p. 1624-1634 (2006); and Hoshika, S. et al. ChemBioChem. 8, p. 2133-2138, (2007)).

Examples of the 4'-thio-2'-modified nucleosides can include 4'-thio-2'-modified nucleosides retaining 2'-H or 2'-O-methyl (Matsugami, et al. Nucleic Acids Res. 36, 1805 (2008)).

Examples of the bicyclic nucleosides with a modified sugar can include nucleosides retaining the second ring formed by bridging two atoms of the ribose ring. Examples of such nucleosides can include: 2',4'-BNAs/LNAs (bridged nucleic acids/locked nucleic acids) in which the 2'-oxygen atom and the 4'-carbon atom are bridged by a methylene chain (Obika, S. et al. Tetrahedron Lett., 38, p. 8735-(1997); Obika, S. et al., Tetrahedron Lett., 39, p. 5401-(1998); A. A. Koshkin, A. A. et al. Tetrahedron, 54, p. 3607 (1998); and Obika, S. Bioorg. Med. Chem., 9, p. 1001 (2001); and ENAs (2'-O,4'-C-ethylene-bridged nucleic acids) bridged by an ethylene chain longer by one carbon than the methylene chain of the 2',4'-BNA/LNA (Morita, K. et al. Bioorg. Med. Chem. Lett., 12, p. 73 (2002); and Morita, K. et al. Bioorg. Med. Chem., 11, p. 2211 (2003).).

When arbitrary 1 to 4 2'-OMeRNA residues in the double-stranded polynucleotide are substituted by nucleotides with a modified sugar, more preferable nucleotides with a modified sugar are each independently an ENA or a 2',4'-BNA/LNA counterparts of the nucleotides with the modified sugar.

The double-stranded polynucleotide also includes a double-stranded polynucleotide in which 1 to 4 DNA residues in the polynucleotide are each independently substituted by an RNA, an ENA, or a 2',4'-BNA/LNA.

The double-stranded polynucleotide also includes those comprising the antisense strand represented by the formula (II), (III), (V), (VII), or (IX) further having a phosphorylated 5'-end.

The double-stranded polynucleotide also includes those having phosphorothioate bonds instead of phosphoester bonds. The number of phosphorothioate bonds is preferably 0 to 5. Moreover, the phosphorothioate bonds are preferably positioned in the vicinity of the 5' and 3'-ends of each polynucleotide.

The method for preparing each polynucleotide constituting the double-stranded polynucleotide is not particularly limited, and a known chemical synthesis method can be used, for example, a phosphotriester, phosphoramidite, or H-phosphonate method. For example, it can be synthesized using a commercially available nucleic acid synthesizer and commercially available reagents used in DNA/RNA synthesis.

The polynucleotide having a phosphorylated 5'-end can also be synthesized by a known synthesis method and can be synthesized, for example, using Phosphalink (manufactured by Applied Biosystems).

In the chemical synthesis, single-stranded polynucleotides having complementarity to each other can be synthesized separately and associated by an appropriate method to form a duplex. A specific example of the association method includes a method by which the synthesized single-stranded polynucleotides are mixed at a molar ratio of preferably at least 3:7, more preferably approximately 4:6, most preferably equimolar ratio (5:5), then heated to a dissociation temperature of the duplex, and then gradually cooled. The associated double-stranded polynucleotide is purified, if necessary, by a method usually used and known per se in the art. For example, a method can be used as the purification method, by which the association is confirmed using an agarose gel or the like, and residual single-stranded polynucleotides are removed, for example, by degradation with an appropriate enzyme.

The double-stranded polynucleotide also includes: a double-stranded polynucleotide comprising a cholesterol, lipid, or vitamin E unit introduced therein (see e.g., Lorenz, C. et al. Bioorg. Med. Chem. Lett., 14, p. 4975-4977 (2004); Soutschek, J., et al. Nature, 432, p. 173-178, (2004); Wolfrum, C. et al. Nature Biotech. 25, p. 1149-1157, (2007); Kubo, T. et al. Oligonucleotides, 17, p. 1-20, (2007); Kubo, T., et al. Biochem. Biophys. Res. Comm. 365, p. 54-61, (2008); and Nishina, K., et al., Mol. Ther. 16, p. 734-740, (2008)); and a double-stranded polynucleotide bound at the end with an aptamer, a protein-binding nucleic acid molecule.

The double-stranded polynucleotide also includes a double-stranded polynucleotide bound to a monoclonal antibody (or an appropriate binding site thereof) or a protein (or an appropriate oligopeptide fragment thereof) (see e.g., Song, et al. Nature Biotech. 23, p. 709-717 (2005); Xia et al. Pharm. Res. 24, p. 2309-2316 (2007); and Kumar, et al. Nature, 448, p. 39-43 (2007)).

Moreover, the double-stranded polynucleotide also includes a positively charged complex of a double-stranded polynucleotide supplemented with a cationic polymer (see, as successful examples achieving distribution in organs and cells, Leng et al. J. Gen. Med. 7, p. 977-986 (2005); Baigude et al. 2, p. 237-241, ACS Chem. Biol. (2007); and Yadava et al. Oligonucleotide 17, p. 213-222 (2007)).

The double-stranded polynucleotide includes every pharmaceutically acceptable salt or ester of the double-stranded polynucleotide, or salts of such esters.

Preferable examples of the pharmaceutically acceptable salt of the double-stranded polynucleotide can include: alkali metal salts such as a sodium salt, a potassium salt, and a lithium salt, alkaline earth metal salts such as a calcium salt and a magnesium salt, and metal salts such as an aluminum salt, an iron salt, a zinc salt, a copper salt, a nickel salt, and a cobalt salt; amine salts including inorganic salts such as an ammonium salt and organic salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt, a tris(hydroxymethyl)aminomethane salt; inorganic acid salts such as a hydrohalide (e.g., a hydrofluoride, a hydrochloride, a hydrobromide, and a hydroiodide), a nitrate, a perchlorate, a sulfate, and a phosphate; organic acid salts such as lower alkanesulfonates (e.g., a methanesulfonate, a trifluoromethanesulfonate, and an ethanesulfonate), arylsulfonates (e.g., a benzenesulfonate and a p-toluenesulfonate), an acetate, a malate, a fumarate, a succinate, a citrate, a tartrate, an oxalate, and a maleate; and amino acid salts such as a glycine salt, a lysine salt, an arginine salt, an ornithine salt, a glutamate, and an aspartate.

A composition comprising the double-stranded polynucleotide is mixed, encapsulated, or conjugated with another molecule, molecular structure, or mixture of compounds, for example, as a liposome, a receptor-targeting molecule, an oral, rectal, or local formulation, or other formulations for assisting in uptake, distribution, and/or absorption.

When the double-stranded polynucleotide is used as a preventive or therapeutic drug for disease, the polynucleotide or a pharmacologically acceptable salt thereof can be administered either by itself or after mixing with an appropriate pharmacologically acceptable excipient, diluent, or the like, as an oral formulation such as tablets, capsules, granules, powders, or syrups or as a parenteral formulation such as injections, suppositories, patches, or external preparations.

These preparations are produced by a well-known method using additives such as excipients (examples thereof can include organic excipients including: sugar derivatives such as lactose, saccharose, glucose, mannitol, and sorbitol; starch derivatives such as corn starch, potato starch, a starch, and dextrin; cellulose derivatives such as crystalline cellulose; gum arabic; dextran; and pullulan, and inorganic excipients including: silicate derivatives such as light anhydrous silicic acid, synthetic aluminum silicate, calcium silicate, and magnesium aluminometasilicate; a phosphate such as calcium hydrogen phosphate; a carbonate such as calcium carbonate; and a sulfate such as calcium sulfate), lubricants (examples thereof can include: metal salts of stearic acid such as stearic acid, calcium stearate, and magnesium stearate; talc; colloidal silica; waxes such as beeswax and spermaceti; boric acid; adipic acid; a sulfate such as sodium sulfate; glycol; fumaric acid; sodium benzoate; DL leucine; a lauryl sulfate such as sodium lauryl sulfate and magnesium lauryl sulfate; silicic acids such as anhydrous silicic acid and silicic hydrate; and the starch derivatives described above), binders (examples thereof can include hydroxypropylcellulose, hydroxypropylmethylcellulose, polyvinylpyrrolidone, macrogol, and the same compounds as the excipients), disintegrants (examples thereof can include: cellulose derivatives such as low substituted hydroxypropylcellulose, carboxymethylcellulose, carboxymethylcellulose calcium, and internally bridged carboxymethylcellulose sodium; and chemically modified starches/celluloses such as carboxymethyl starch, carboxymethyl starch sodium, and bridged polyvinylpyrrolidone), emulsifying agents (examples thereof can include: colloidal clay such as bentonite and veegum; a metal hydroxide such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester), stabilizers (examples thereof can include: p-oxybenzoic acid esters such as methylparaben and propylparaben; alcohols such as chlorobutanol, benzyl alcohol, and phenylethyl alcohol; benzalkonium chloride; phenols such as phenol and cresols; thimerosal; dehydroacetic acid; and sorbic acid), corrigents (examples thereof can include sweeteners, acidulants, and flavors that are usually used), and diluents.

Introduction of Double-Stranded Polynucleotide to Cells, Tissues, or Individuals, and Regulation of Expression of Target Gene Recipients to which or to whom the double-stranded polynucleotide thus prepared is introduced are not particularly limited as long as the target gene can be intracellularly transcribed into RNA or translated into a protein therein. The recipients mean cells, tissues, or individuals.

The cells for which the double-stranded polynucleotide is used may be any of germline cells, somatic cells, totipotent cells, pluripotent cells, cleaved cells, non-cleaved cells, parenchymal cells, epithelial cells, immortalized cells, transformed cells, nerve cells, and immunocytes.

The tissues include 1-cell embryos or constitutive cells, or polyploid embryos, embryonic tissues, or the like. Moreover, examples of the above differentiated cells include adipocytes, fibroblasts, myocytes, cardiomyocytes, endothelial cells, nerve cells, glial cells, blood cells, megakaryocytes, lymphocytes, macrophages, neutrophils, eosinophils, basophiles, mast cells, leukocytes, granulocytes, keratinocytes, chondrocytes, osteoblasts, osteoclasts, hepatocytes, and endocrine or exocrine cells. For example, CHO-K1 cells (RIKEN Cell bank), *Drosophila* S2 cells (Schneider, 1. et al., J. Embryol. Exp. Morph., 27, p. 353-365 (1972)), human HeLa cells (ATCC: CCL-2), and human HEK293 cells (ATCC: CRL-1573) are preferably used as such cells.

Furthermore, specific examples of the individuals used as recipients of the double-stranded polynucleotide include plants, animals, protozoans, viruses, bacteria, and those belonging to the *Eumycetes*. The plants may be monocots, dicots, or gymnosperms. The animals may be vertebrates or invertebrate. The vertebrates are preferably mammals including mice, rats, monkeys, dogs, and humans.

When the recipients are cells or tissues, a calcium phosphate method, electroporation, a lipofection method, viral infection, immersion in a double-stranded polynucleotide solution, or transformation, or the like is used as a method for introducing the double-stranded polynucleotide into the recipients. Moreover, examples of a method for introduction into embryos include microinjection, electroporation, and viral infection. When the recipients are plants, a method involving injection or perfusion into the cavities or interstitial cells or the like of the plants or spraying thereonto is used. Moreover, for animal individuals, a method involving systemic introduction through, for example, oral, local, hypodermic, intramuscular, intravenous, parenteral, transvaginal, rectal, nasal, ocular, or transmucosal administration, or electroporation, viral infection, or the like is used. A method by which the double-stranded polynucleotide is directly mixed with a diet for the organisms can also be used as an oral introduction method.

In addition to these approaches, a colloidal dispersion system can be used as a method for introducing the double-stranded polynucleotide into patients.

The colloidal dispersion system is expected to have the effect of enhancing the in-vivo stability of the compound or the effect of efficiently transporting the compound to particular organs, tissues, or cells.

The colloidal dispersion system used is not limited as long as it is usually applicable. Examples thereof can include polymer complexes, nanocapsules, microspheres, beads, and water-in-oil emulsifying agents, micelles, mixed micelles, and lipid-based dispersion systems including liposomes. Preferably, the colloidal dispersion system is a plurality of liposomes or artificial membrane vesicles having the effect of efficiently transporting the compound to particular organs, tissues, or cells (Mannino et al., Biotechniques, 1988, 6, p. 682-; Blume and Cevc, Biochem. et Biophys. Acta, 1990, 1029, p. 91-; Lappalainen et al., Antiviral Res., 1994, 23, p. 119-; and Chonn and Cullis, Current Op. Biotech., 1995, 6, p. 698-).

Unilamellar liposomes of 0.2 to 0.4 µm in size range are capable of encapsulating a considerable amount of an aqueous buffer containing macromolecules, and the contents are encapsulated in this aqueous inner membrane and transported in a biologically active form to brain cells (Fraley et al., Trends Biochem. Sci., 1981, 6, p. 77-).

The liposome composition is usually a complex of lipid, particularly phospholipid, specifically phospholipid having a high phase transition temperature, with one or more steroids, particularly cholesterols.

Examples of the lipid useful for liposome production include phosphatidyl compounds such as phosphatidyl glycerol, phosphatidyl choline, phosphatidyl serine, sphingolipid, phosphatidyl ethanolamine, cerebroside, and ganglioside.

Diacyl phosphatidyl glycerol is particularly useful, wherein the lipid moiety contains 14 to 18 carbon atoms and is saturated (devoid of any internal double bonds in the chain of 14 to 18 carbon atoms) and, in particular, contains 16 to 18 carbon atoms.

Typical phospholipids encompass phosphatidyl choline, dipalmitoyl phosphatidyl choline, and distearoyl phosphatidyl choline.

Targeting by the colloidal dispersion system including liposomes may be passive or active.

Such passive targeting is achieved by use of the fundamental tendency of liposomes to be distributed to reticuloendothelial cells in organs containing sinusoids.

On the other hand, examples of the active targeting can include liposome modification approaches involving binding particular ligands such as viral coat protein (Morishita et al., Proc. Natl. Acad. Sci. (U.S.A.), 1993, 90, p. 8474-), monoclonal antibodies (or appropriate binding sites thereof), sugars, glycolipids, or proteins (or appropriate oligopeptide fragments thereof) to liposomes or changing liposome composition to achieve distribution to organs and cell types other than naturally occurring sites of localization.

The surface of the colloidal dispersion system may be modified in various ways for targeting purposes.

In the liposomal targeted delivery system, a lipid group can be incorporated into the lipid bilayer of the liposome to maintain target ligands through tight association with the lipid bilayer.

Various linking groups may be used for linking the lipid chain to the target ligands.

The target ligands binding to particular cell surface molecules predominantly found on cells desired to receive the delivery of the double-stranded polynucleotide can be, for example, (1) hormones, growth factors, or appropriate oligopeptide fragments thereof, binding to particular cell receptors predominantly expressed by the cells desired to receive the delivery, or (2) polyclonal or monoclonal antibodies or appropriate fragments thereof (e.g., Fab or F(ab')2) specifically binding to antigenic epitopes predominantly found on the target cells.

Two or more bioactive agents can also be compounded within the single liposome and administered.

A medicament for enhancing the intracellular stability of the contents and/or targeting may further be added to the colloidal dispersion system.

The amount of the double-stranded polynucleotide or pharmacologically acceptable salt thereof used differs depending on symptoms, ages, etc. 1 mg (preferably, 30 mg) as the lower limit to 2000 mg (preferably, 1500 mg) as the upper limit of the polynucleotide or the salt per dose for oral administration or 0.5 mg (preferably, 5 mg) as the lower limit to 500 mg (preferably, 250 mg) as the upper limit of the polynucleotide or the salt per dose for intravenous administration is preferably administered to an adult once to six times a day according to symptoms.

Pharmaceutical compositions and formulations for local administration include transdermal patches, ointments, lotions, creams, gels, troches, suppositories, sprays, liquids, and powders.

EXAMPLES

Hereinafter, the present invention will be described more specifically with reference to Examples, Reference Examples, and Test Examples. However, the present invention is not intended to be limited to them. In the Examples below, procedures of genetic engineering were performed by the methods described in "Molecular Cloning" [Sambrook, J., Fritsch, E. F. and Maniatis, T., published in 1989 by Cold Spring Harbor Laboratory Press] or according to the instructions of the commercially available reagents or kits used, unless otherwise specified.

Example 1

Synthesis of HO-$G^p$-$C^{m1p}$-$A^p$-$C^{m1p}$-$A^p$-$A^{m1p}$-$G^p$-$A^{m1p}$-$A^{rp}$-$U^{m1p}$-$G^{rp}$-$G^{m1p}$-$A^p$-$U^{m1p}$-$C^p$-$A^{m1p}$-$C^p$-$A^{m1p}$-$A^p$-$T^p$-$T^t$-H (SEQ ID NO: 1 of the Sequence Listing) (CT-095)

CT-095 was synthesized according to an RNA synthesis program on the scale of 0.2 μmol using an automatic nucleic acid synthesizer (manufactured by PerkinElmer Inc., ABI model 394 DNA/RNA synthesizer). Solvents, reagents, and phosphoramidites were used in each synthesis cycle at the same concentrations as in natural oligodeoxynucleotide synthesis.

When deoxynucleoside phosphoramidites were used, 5'-O-dimethoxytrityl-6-N-benzoyl-2'-deoxyadenosine-3'-O-(2-cyanoethyl N,N-diisopropyl)phosphoramidites, 5'-O-dimethoxytrityl-2-N-isobutyryl-2'-deoxyguanosine-3'-O-(2-cyanoethyl N,N-diisopropyl)phosphoramidites, 5'-O-dimethoxytrityl-4-N-benzoyl-2'-deoxycytidine-3'-O-(2-cyanoethyl N,N-diisopropyl)phosphoramidites, and 5'-O-dimethoxytritylthymidine-3'-O-(2-cyanoethyl N,N-diisopropyl)phosphoramidites were purchased from Proligo and appropriately adjusted for use.

When 2'-O-methyl nucleoside phosphoramidites were used, 5'-O-dimethoxytrityl-6-N-benzoyl-2'-O-methyladenosine-3'-O-(2-cyanoethyl N,N-diisopropyl)phosphoramidites, 5'-O-dimethoxytrityl-2-N-isobutyryl-2'-O-methylguanosine-3'-O-(2-cyanoethyl N,N-diisopropyl)phosphoramidites, 5'-O-dimethoxytrityl-4-N-acetyl-2'-O-methylcytidine-3'-O-(2-cyanoethyl N,N-diisopropyl)phosphoramidites, and 5'-O-dimethoxytrityl-2'-O-methyluridine-3'-O-(2-cyanoethyl N,N-diisopropyl)phosphoramidites were purchased from Glen Research Corp. and appropriately adjusted for use.

When ribonucleoside phosphoramidites were used, 5'-O-dimethoxytrityl-6-N-benzoyl-2'-O-(tert-butyldimethylsilyl)adenosine-3'-O-(2-cyanoethyl N,N-diisopropyl)phosphoramidites, 5'-O-dimethoxytrityl-2-N-dimethylformamidine-2'-O-(tert-butyldimethylsilyl)guanosine-3'-O-(2-cyanoethyl N,N-diisopropyl)phosphoramidites, 5'-O-dimethoxytrityl-4-N-acetyl-2'-O-(tert-butyldimethylsilyl)cytidine-3'-O-(2-cyanoethyl N,N-diisopropyl)phosphoramidites, and 5'-O-dimethoxytrityl-2'-O-(tert-butyldimethylsilyl)uridine-3'-O-(2-cyanoethyl N,N-diisopropyl)phosphoramidites were purchased from Proligo and appropriately adjusted for use.

When 2'-O,4'-C-ethylene nucleoside phosphoramidites were used, compounds of Example 14 (5'-O-dimethoxytrityl-2'-O,4'-C-ethylene-6-N-benzoyladenosine-3'-O-(2-cyanoethyl N,N-diisopropyl)phosphoramidites), Example 27 (5'-O-dimethoxytrityl-2'-O,4'-C-ethylene-2-N-isobutyrylguanosine-3'-O-(2-cyanoethyl N,N-diisopropyl)phosphoramidites), Example 22 (5'-O-dimethoxytrityl-2'-O,4'-C-ethylene-4-N-benzoyl-5-methylcytidine-3'-O-(2-cyanoethyl N,N-diisopropyl)phosphoramidites), and Example 9 (5'-O-dimethoxytrityl-2'-O,4'-C-ethylene-5-methyluridine-3'-O-(2-cyanoethyl N,N-diisopropyl)phosphoramidites) of Japanese Patent No. 3420984 were appropriately prepared for use.

The phosphoramidites were appropriately supplied to the automatic nucleic acid synthesizer to synthesize a polynucleotide having the desired sequence. 0.5 μmol of CPG (controlled pore glass; manufactured by Applied Biosystems or Glen Research Corp.) bound with the desired nucleosides was used as a solid-phase carrier to synthesize the title polynucleotide.

The protected polynucleotide analog having the sequence of interest was treated with 2 mL of an ammonia water: ethanol solution (3:1 v/v) at 55° C. for 16 hours to excise the oligomer from the support and to remove the cyanoethyl group acting as a protective group for the phosphate group and the protective group on the base of the nucleic acid. CPG was removed by filtration. After washing with ethanol, the filtrate and the wash were combined, and the solvent was distilled off under reduced pressure. To the residue, 0.3 mL of triethylamine trihydrofluoride was added, and the mixture was left at room temperature for 19 hours. 60 μL of H$_2$O and 3 mL of n-butanol were added thereto, and the mixture was left at −20° C. for 1 hour. Then, precipitates were collected by centrifugation. The obtained precipitates were dissolved in 200 μL of H$_2$O and purified by 20% polyacrylamide gel electrophoresis containing 7 M urea (1×TBE, 600 V, 4 hours). After the electrophoresis, bands were visualized using a UV lamp, and the bands of interest were excised using a knife. 1 mL of a solution containing 0.2 M NaCl and 10 mM EDTA (pH 7.2) was added thereto, and the mixture was left overnight to elute the polynucleotide from the gel slice. The oligonucleotide was precipitated by the addition of ethanol and collected by centrifugation. The molecular weight of the present polynucleotide was identified by negative ion ESI mass spectrometry (calculated value: 6721.46, measured value: 6721.14).

The nucleotide sequence of the present polynucleotide comprises a sequence of nucleotide Nos. 3139-3157 of the human β-catenin gene (GenBank accession No. NM_001904.3). The nucleotide sequence of the human β-catenin gene is also shown in SEQ ID NO: 2 of the Sequence Listing, and its amino acid sequence is shown in SEQ ID NO: 3 of the Sequence Listing.

Example 2

Synthesis of HO-U$^{m1p}$-T$^p$-G$^{m1p}$-T$^p$-G$^{m1p}$-A$^p$-U$^{m1p}$-C$^p$-C$^{m1p}$-A$^{rp}$-U$^{m1p}$-U$^{rp}$-C$^{m1p}$-T$^p$-U$^{m1p}$-G$^p$-U$^{m1p}$-G$^p$-C$^{m1p}$-T$^p$-T$^t$-H (SEQ ID NO: 4 of the Sequence Listing) (CT-096)

CT-096 was synthesized in the same way as for Example 1.

Molecular weight calculated value: 6632.29, measured value: 6632.17

Nucleotide sequence: comprising a sequence complementary to nucleotide Nos. 3139-3157 of the human β-catenin gene (GenBank accession No. NM_001904.3)

Example 3

Synthesis of HO-G$^p$-C$^{m1p}$-A$^p$-C$^{m1p}$-A$^p$-A$^{m1p}$-G$^{rp}$-A$^{m1p}$-A$^{rp}$-U$^{m1p}$-G$^{rp}$-G$^{m1p}$-A$^p$-U$^{m1p}$-C$^p$-A$^{m1p}$-C$^p$-A$^{m1p}$-A$^p$-T$^p$-T$^t$-H (SEQ ID NO: 5 of the Sequence Listing) (CT-097)

CT-097 was synthesized in the same way as for Example 1, and the molecular weight was measured.

Molecular weight calculated value: 6737.46, measured value: 6737.38

Nucleotide sequence: comprising a sequence of nucleotide Nos. 3139-3157 of the human β-catenin gene (GenBank accession No. NM_001904.3)

Example 4

Synthesis of HO-U$^{m1p}$-T$^p$-G$^{m1p}$-T$^p$-G$^{m1p}$-A$^p$-U$^{m1p}$-C$^p$-C$^{m1p}$-A$^{rp}$-U$^{m1p}$-U$^{rp}$-C$^{m1p}$-U$^{rp}$-U$^{m1p}$-G$^p$-U$^{m1p}$-G$^p$-C$^{m1p}$-T$^p$-T$^t$-H (SEQ ID NO: 6 of the Sequence Listing) (CT-098)

CT-098 was synthesized in the same way as for Example 1.

Molecular weight calculated value: 6634.26, measured value: 6634.90

Nucleotide sequence: comprising a sequence complementary to nucleotide Nos. 3139-3157 of the human β-catenin gene (GenBank accession No. NM_001904.3)

Example 5

Synthesis of HO-G$^{rp}$-C$^{m1p}$-A$^{rp}$-C$^{m1p}$-A$^{rp}$-A$^{m1p}$-G$^{rp}$-A$^{m1p}$-A$^{rp}$-U$^{m1p}$-G$^{rp}$-G$^{m1p}$-A$^p$-U$^{m1p}$-C$^p$-A$^{m1p}$-C$^p$-A$^{m1p}$-A$^p$-T$^p$-T$^t$-H (SEQ ID NO: 7 of the Sequence Listing) (CT-099)

CT-099 was synthesized in the same way as for Example 1.

Molecular weight calculated value: 6785.46, measured value: 6785.12

Nucleotide sequence: comprising a sequence of nucleotide Nos. 3139-3157 of the human β-catenin gene (GenBank accession No. NM_001904.3)

Example 6

Synthesis of HO-U$^{m1p}$-T$^p$-G$^{m1p}$-T$^p$-G$^{m1p}$-A$^p$-U$^{m1p}$-C$^p$-C$^{m1p}$-A$^{rp}$-U$^{m1p}$-U$^{rp}$-C$^{m1p}$-U$^{rp}$-U$^{m1p}$-G$^{rp}$-U$^{m1p}$-G$^{rp}$-C$^{m1p}$-T$^p$-T$^t$-H (SEQ ID NO: 8 of the Sequence Listing) (CT-100)

CT-100 was synthesized in the same way as for Example 1.

Molecular weight calculated value: 6666.26, measured value: 6665.71

Nucleotide sequence: comprising a sequence complementary to nucleotide Nos. 3139-3157 of the human β-catenin gene (GenBank accession No. NM_001904.3)

Example 7

Synthesis of HO-G$^p$-C$^{m1p}$-A$^p$-C$^{m1p}$-A$^p$-A$^{m1p}$-G$^p$-A$^{m1p}$-A$^p$-T$^{e2p}$-G$^p$-G$^{m1p}$-A$^p$-U$^{m1p}$-C$^p$-A$^{m1p}$-C$^p$-A$^{m1p}$-A$^p$-T$^p$-T$^t$-H (SEQ ID NO: 9 of the Sequence Listing) (CT-112)

CT-112 was synthesized in the same way as for Example 1. However, in the final step of the automatic nucleic acid synthesizer, acid treatment was not performed (the dimethoxytrityl group was bound to the oligonucleotide). The present polynucleotide was treated with an ammonia water: ethanol solution (3:1 v/v) and then purified by reverse-phase HPLC (LC-10VP manufactured by Shimadzu Corp., column (Merck, Chromolith Performance RP-18e (4.6×100 mm)), Solution A: 5% acetonitrile, 0.1 M aqueous triethylamine acetate solution (TEAA), pH 7.0, Solution B: acetonitrile, B %: 10%→60% (10 min, linear gradient); 60° C.; 2 ml/min; 260 nm) to gather peaks of the product of interest having the dimethoxytrityl group. Water was added thereto, and TEAA was distilled off under reduced pressure. An 80% aqueous acetic acid solution (2 mL) was added thereto, and the mixture was left for 20 minutes to deprotect the dimethoxytrityl group. The solvent was distilled off, and the residue was dissolved in 500 µl of water, washed with ethyl acetate, and freeze-dried to obtain the oligonucleotide of interest.

Molecular weight calculated value: 6715.50, measured value: 6714.92

Nucleotide sequence: comprising a sequence of nucleotide Nos. 3139-3157 of the human β-catenin gene (GenBank accession No. NM_001904.3)

Example 8

Synthesis of HO-$G^p$-$C^{m1p}$-$A^p$-$C^{m1p}$-$A^p$-$A^{m1p}$-$G^p$-$A^{m1p}$-$A^{e2p}$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 10 of the Sequence Listing) (CT-113)

CT-113 was synthesized in the same way as for Example 7.

Molecular weight calculated value: 6731.50, measured value: 6732.22

Nucleotide sequence: comprising a sequence of nucleotide Nos. 3139-3157 of the human β-catenin gene (GenBank accession No. NM_001904.3)

Example 9

Synthesis of HO-$G^p$-$C^{m1p}$-$A^p$-$C^{m1p}$-$A^p$-$A^{m1p}$-$G^p$-$A^{e2p}$-$A^p$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H A (SEQ ID NO: 11 of the Sequence Listing) (CT-114)

CT-114 was synthesized in the same way as for Example 7.

Molecular weight calculated value: 6701.47, measured value: 6701.06

Nucleotide sequence: comprising a sequence of nucleotide Nos. 3139-3157 of the human β-catenin gene (GenBank accession No. NM_001904.3)

(Example 10)

Synthesis of HO-$G^p$-$C^{m1p}$-$A^p$-$C^{e2p}$-$A^p$-$A^{m1p}$-$G^p$-$A^{e2P}$-$A^p$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 12 of the Sequence Listing) (CT-115)

CT-115 was synthesized in the same way as for Example 7.

Molecular weight calculated value: 6727.51, measured value: 6728.07

Nucleotide sequence: comprising a sequence of nucleotide Nos. 3139-3157 of the human β-catenin gene (GenBank accession No. NM_001904.3)

Example 11

Synthesis of HO-$U^{m1p}$-$T^p$-$G^{m1p}$-$T^p$-$G^{m1p}$-$A^p$-$U^{m1p}$-$C^p$-$C^{m1p}$-$A^{e2P}$-$U^{m1p}$-$T^p$-$C^{m1p}$-$T^p$-$U^{m1p}$-$G^p$-$U^{m1p}$-$G^p$-$C^{m1p}$-$T^p$-$T^r$-H (SEQ ID NO: 13 of the Sequence Listing) (CT-116)

CT-116 was synthesized in the same way as for Example 7.

Molecular weight calculated value: 6656.35, measured value: 6655.97

Nucleotide sequence: comprising a sequence complementary to nucleotide Nos. 3139-3157 of the human β-catenin gene (GenBank accession No. NM_001904.3)

Example 12

Synthesis of HO-$U^{m1p}$-$T^p$-$G^{m1p}$-r-$G^{m1p}$-$A^p$-$U^{m1p}$-$C^p$-$C^{m1p}$-$A^p$-$T^{e2p}$-$T^p$-$C^{m1p}$-$T^p$-$U^{m1p}$-$G^p$-$U^{m1p}$-$G^p$-$C^{m1p}$-$T^p$-$T^r$-H (SEQ ID NO: 14 of the Sequence Listing) (CT-117)

CT-117 was synthesized in the same way as for Example 7.

Molecular weight calculated value: 6640.35, measured value: 6640.88

Nucleotide sequence: comprising a sequence complementary to nucleotide Nos. 3139-3157 of the human β-catenin gene (GenBank accession No. NM_001904.3)

Example 13

Synthesis of HO-$U^{m1p}$-$T^p$-$G^{m1p}$-$T^p$-$G^{m1p}$-$A^p$-$U^{m1p}$-$C^p$-$C^{m1p}$-$A^p$-$T^{e2p}$-$T^p$-$C^{m1p}$-$T^p$-$T^{e2p}$-$G^p$-$U^{m1p}$-$G^p$-$C^{m1p}$-$T^p$-$T^r$-H (SEQ ID NO: 15 of the Sequence Listing) (CT-118)

CT-118 was synthesized in the same way as for Example 7.

Molecular weight calculated value: 6666.39, measured value: 6666.04

Nucleotide sequence: comprising a sequence complementary to nucleotide Nos. 3139-3157 of the human β-catenin gene (GenBank accession No. NM_001904.3)

Example 14

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 16 of the Sequence Listing) (CT-091)

CT-091 was synthesized in the same way as for Example 7.

Molecular weight calculated value: 6689.46, measured value: 6689.81

Nucleotide sequence: comprising a sequence of nucleotide Nos. 3139-3157 of the human β-catenin gene (GenBank accession No. NM_001904.3)

Example 15

Synthesis of HO-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$T^r$-H (SEQ ID NO: 17 of the Sequence Listing) (CT-092)

CT-092 was synthesized in the same way as for Example 7.

Molecular weight calculated value: 6614.31, measured value: 6614.80

Nucleotide sequence: comprising a sequence complementary to nucleotide Nos. 3139-3157 of the human β-catenin gene (GenBank accession No. NM_001904.3)

Example 16

Synthesis of HO-$G^p$-$C^{m1p}$-$A^p$-$C^{m1p}$-$A^p$-$A^{m1p}$-$G^p$-$A^{m1p}$-$A^{m1p}$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 18 of the Sequence Listing) (CT-101)

CT-101 was synthesized in the same way as for Example 7.

Molecular weight calculated value: 6719.49, measured value: 6719.67

Nucleotide sequence: comprising a sequence of nucleotide Nos. 3139-3157 of the human fβ-catenin gene (GenBank accession No. NM_001904.3)

Example 17

Synthesis of HO-$G^p$-$C^{m1p}$-$A^p$-$C^{m1p}$-$A^p$-$A^{m1p}$-$G^p$-$A^{m1p}$-$A^{rp}$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 19 of the Sequence Listing) (CT-102)

CT-102 was synthesized in the same way as for Example 1.

Molecular weight calculated value: 6705.46, measured value: 6705.58

Nucleotide sequence: comprising a sequence of nucleotide Nos. 3139-3157 of the human β-catenin gene (GenBank accession No. NM_001904.3)

Example 18

Synthesis of HO-$U^{m1p}$-$T^p$-$G^{m1p}$-$T^p$-$G^{m1p}$-$A^p$-$U^{m1p}$-$C^p$-$C^{m1p}$-$A^{m1p}$-$U^{m1p}$-$T^p$-$C^{m1p}$-$T^p$-$U^{m1p}$-$G^p$-$U^{m1p}$-$G^p$-$C^{m1p}$-$T^p$-$T^r$-H (SEQ ID NO: 20 of the Sequence Listing) (CT-107)

CT-107 was synthesized in the same way as for Example 7.

Molecular weight calculated value: 6644.34, measured value: 6644.47

Nucleotide sequence: comprising a sequence complementary to nucleotide Nos. 3139-3157 of the human β-catenin gene (GenBank accession No. NM_001904.3)

Example 19

Synthesis of HO-$U^{m1p}$-$T^p$-$G^{m1p}$-$T^p$-$G^{m1p}$-$A^p$-$U^{m1p}$-$C^p$-$C^{m1p}$-$A^{rp}$-$U^{m1p}$-$T^p$-$C^{m1p}$-$T^p$-$U^{m1p}$-$G^p$-$U^{m1p}$-$G^p$-$C^{m1p}$-$T^p$-$T^r$-H (SEQ ID NO: 21 of the Sequence Listing) (CT-108)

CT-108 was synthesized in the same way as for Example 1.

Molecular weight calculated value: 6630.31, measured value: 6630.48

Nucleotide sequence: comprising a sequence complementary to nucleotide Nos. 3139-3157 of the human β-catenin gene (GenBank accession No. NM_001904.3)

Example 20

Synthesis of HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-$A^r$-H (SEQ ID NO: 22 of the Sequence Listing) (CT-103)

CT-103 was synthesized in the same way as for Example 7.

Molecular weight calculated value: 6081.07, measured value: 6081.08

Nucleotide sequence: comprising a sequence of nucleotide Nos. 3139-3157 of the human β-catenin gene (GenBank accession No. NM_001904.3)

Example 21

Synthesis of HO-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1r}$-H (SEQ ID NO: 23 of the Sequence Listing) (CT-109)

CT-109 was synthesized in the same way as for Example 7.

Molecular weight calculated value: 6005.92, measured value: 6005.89

Nucleotide sequence: comprising a sequence complementary to nucleotide Nos. 3139-3157 of the human β-catenin gene (GenBank accession No. NM_001904.3)

Example 22

Synthesis of HO-$G^p$-$C^{m1p}$-$A^p$-$C^{m1p}$-$A^p$-$A^{m1p}$-$G^p$-$A^{m1p}$-$A^{m1p}$-$U^{m1p}$-$G^{m1p}$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 24 of the Sequence Listing) (CT-127)

CT-127 was synthesized in the same way as for Example 7.

Molecular weight calculated value: 6749.52, measured value: 6749.26

Nucleotide sequence: comprising a sequence of nucleotide Nos. 3139-3157 of the human β-catenin gene (GenBank accession No. NM_001904.3)

Example 23

Synthesis of HO-$G^p$-$C^{m1p}$-$A^p$-$C^{m1p}$-$A^p$-$A^{m1p}$-$G^{m1p}$-$A^{m1p}$-$A^{m1p}$-$U^{m1p}$-$G^{m1p}$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 25 of the Sequence Listing) (CT-128)

CT-128 was synthesized in the same way as for Example 7.

Molecular weight calculated value: 6779.54, measured value: 6779.31

Example 24

Synthesis of HO-$G^p$-$C^{m1p}$-$A^p$-$C^{m1p}$-$A^{m1p}$-$A^{m1p}$-$G^{m1p}$-$A^{m1p}$-$A^{m1p}$-$U^{m1p}$-$G^{m1p}$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 26 of the Sequence Listing) (CT-129)

CT-129 was synthesized in the same way as for Example 7.

Molecular weight calculated value: 6809.57, measured value: 6809.23

Nucleotide sequence: comprising a sequence of nucleotide Nos. 3139-3157 of the human β-catenin gene (GenBank accession No. NM_01904.3)

Example 25

Synthesis of HO-$G^p$-$C^{m1p}$-$A^p$-$C^{m1p}$-$A^p$-$A^{m1p}$-$G^{m1p}$-$A^{m1p}$-$A^{m1p}$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 27 of the Sequence Listing) (CT-130)

CT-130 was synthesized in the same way as for Example 7.

Molecular weight calculated value: 6749.52, measured value: 6749.21

Nucleotide sequence: comprising a sequence of nucleotide Nos. 3139-3157 of the human β-catenin gene (GenBank accession No. NM_001904.3)

Example 26

Synthesis of HO-$G^p$-$C^{m1p}$-$A^p$-$C^{m1p}$-$A^{m1p}$-$A^{m1p}$-$G^{m1p}$-$A^{m1p}$-$A^{m1p}$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 28 of the Sequence Listing) (CT-131)

CT-131 was synthesized in the same way as for Example 7.

Molecular weight calculated value: 6779.54, measured value: 6779.17

Nucleotide sequence: comprising a sequence of nucleotide Nos. 3139-3157 of the human β-catenin gene (GenBank accession No. NM_001904.3)

Example 27

Synthesis of HO-$G^p$-$C^{m1p}$-$A^p$-$C^{m1p}$-$A^p$-$A^{m1p}$-$G^p$-$A^{e2p}$-$A^p$-$T^{e2p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 29 of the Sequence Listing) (CT-132)

CT-132 was synthesized in the same way as for Example 7.

Molecular weight calculated value: 6727.51, measured value: 6728.00

Nucleotide sequence: comprising a sequence of nucleotide Nos. 3139-3157 of the human β-catenin gene (GenBank accession No. NM_001904.3)

Example 28

Synthesis of HO-$G^p$-$C^{m1p}$-$A^p$-$C^{m1p}$-$A^p$-$A^{e2p}$-$G^p$-$A^{e2p}$-$A^p$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 30 of the Sequence Listing) (CT-133)

CT-133 was synthesized in the same way as for Example 7.

Molecular weight calculated value: 6713.48, measured value: 6713.77

Nucleotide sequence: comprising a sequence of nucleotide Nos. 3139-3157 of the human β-catenin gene (GenBank accession No. NM_001904.3)

Example 29

Synthesis of HO-$G^p$-$C^{m1p}$-$A^p$-$C^{m1p}$-$A^p$-$A^{e2p}$-$G^p$-$A^{m1p}$-$A^p$-$T^{e2p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 31 of the Sequence Listing) (CT-134)

CT-134 was synthesized in the same way as for Example 7.

Molecular weight calculated value: 6727.51, measured value: 6728.04

Nucleotide sequence: comprising a sequence of nucleotide Nos. 3139-3157 of the human β-catenin gene (GenBank accession No. NM_001904.3)

Example 30

Synthesis of HO-$G^p$-$C^{m1p}$-$A^p$-$C^{m1p}$-$A^p$-$A^{e2p}$-$G^p$-$A^{e2p}$-$A^p$-$T^{e2p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 32 of the Sequence Listing) (CT-135)

CT-135 was synthesized in the same way as for Example 7.

Molecular weight calculated value: 6739.52, measured value: 6740.48

Nucleotide sequence: comprising a sequence of nucleotide Nos. 3139-3157 of the human β-catenin gene (GenBank accession No. NM_001904.3)

Example 31

Synthesis of HO-$G^p$-$C^{m1p}$-$A^p$-$C^{e2p}$-$A^p$-$A^{m1p}$-$G^p$-$A^{e2p}$-$A^p$-$T^{e2p}$-$G^p$-$G^{m1p}$-$A^p$-$U^{m1p}$-$C^p$-$A^{m1p}$-$C^p$-$A^{m1p}$-$A^p$-$T^p$-$T^r$-H (SEQ ID NO: 33 of the Sequence Listing) (CT-137)

CT-137 was synthesized in the same way as for Example 7.

Molecular weight calculated value: 6753.55, measured value: 6754.15

Nucleotide sequence: comprising a sequence of nucleotide Nos. 3139-3157 of the human β-catenin gene (GenBank accession No. NM_001904.3)

Example 32

Synthesis of HO-$G^p$-$C^{m1p}$-$A^p$-$C^{e2p}$-$A^p$-$A^{e2p}$-$G^p$-$A^{e2p}$-$A^p$-$U^{m1p}$-$G^p$-$G^{m1p}$-$A^p$-$U^{m1p}$-$C^p$-$A^{m1p}$-$C^p$-$A^{m1p}$-$A^p$-$T^p$-$T^t$-H (SEQ ID NO: 34 of the Sequence Listing) (CT-136)

CT-136 was synthesized in the same way as for Example 7.
Molecular weight calculated value: 6739.52, measured value: 6739.51
Nucleotide sequence: comprising a sequence of nucleotide Nos. 3139-3157 of the human β-catenin gene (GenBank accession No. NM_001904.3)

Example 33

Synthesis of HO-$G^p$-$C^{m1p}$-$A^p$-$C^{e2p}$-$A^p$-$A^{e2p}$-$G^p$-$A^{e2p}$-$A^p$-$T^{e2p}$-$G^p$-$G^{m1p}$-$A^p$-$U^{m1p}$-$C^p$-$A^{m1p}$-$C^p$-$A^{m1p}$-$A^p$-$T^p$-$T^t$-H (SEQ ID NO: 35 of the Sequence Listing) (CT-138)

CT-138 was synthesized in the same way as for Example 7.
Molecular weight calculated value: 6765.56, measured value: 6765.76
Nucleotide sequence: comprising a sequence of nucleotide Nos. 3139-3157 of the human β-catenin gene (GenBank accession No. NM_001904.3)

Example 34

Synthesis of HO-$G^{m1p}$-$C^p$-$A^{m1p}$-$C^p$-$A^{m1p}$-$A^p$-$G^{m1p}$-$A^p$-$A^{m1p}$-$T^p$-$G^{m1p}$-$G^p$-$A^{m1p}$-$T^p$-$C^{m1p}$-$A^p$-$C^{m1p}$(SEQ ID NO: 36 of the Sequence Listing) (CT-119)

CT-119 was synthesized in the same way as for Example 7.
Molecular weight calculated value: 6747.54, measured value: 6747.39
Nucleotide sequence: comprising a sequence of nucleotide Nos. 3139-3157 of the human ii-catenin gene (GenBank accession No. NM_001904.3)

Example 35

Synthesis of HO-$T^p$-$U^{m1p}$-$G^p$-$U^{m1p}$-$G^p$-$A^{m1p}$-$T^p$-$C^{m1p}$-$C^p$-$A^{m1p}$-$T^p$-$U^{m1p}$-$C^p$-$U^{m1p}$-$T^p$-$G^{m1p}$-$T^p$-$G^{m1p}$-$C^p$-$T^p$-$T^t$-H (SEQ ID NO: 37 of the Sequence Listing) (CT-120)

CT-120 was synthesized in the same way as for Example 7.
Molecular weight calculated value: 6598.32, measured value: 6598.26
Nucleotide sequence: comprising a sequence complementary to nucleotide Nos. 3139-3157 of the human β-catenin gene (GenBank accession No. NM_001904.3)

Example 36

Synthesis of HO-$G^s$-$C^{m1s}$-$A^p$-$C^{m1p}$-$A^p$-$A^{m1p}$-$G^{rp}$-$A^{m1p}$-$A^{rp}$-$U^{m1p}$-$G^{rp}$-$G^{m1p}$-$A^p$-$U^{m1p}$-$C^p$-$A^{m1p}$-$C^p$-$A^{m1s}$-$A^s$-$T^s$-$T^t$-H (SEQ ID NO: 38 of the Sequence Listing) (CT-097S)

CT-097S is synthesized in the same way as for Example 1. However, the moiety having a phosphorothioate bond can be synthesized by treatment with a 0.2 M phenylacetyl disulfide/pyridine-acetonitrile (1:1 v/v) solution for 3 minutes instead of oxidation with an iodine/tetrahydrofuran/pyridine/H$_2$O solution (Ravikumar, V. T. et al. Bioorg. Med. Chem. Lett. (2006) 16, p. 2513-2517). CT-097S is identified by negative ion mass spectrometry.
Nucleotide sequence: comprising a sequence of nucleotide Nos. 3139-3157 of the human β-catenin gene (GenBank accession No. NM_001904.3)

Example 37

Synthesis of HO-$U^{m1s}$-$T^s$-$G^{m1p}$-$T^p$-$G^{m1p}$-$A^p$-$U^{m1p}$-$C^p$-$C^{m1p}$-$A^{rp}$-$U^{m1p}$-$U^{rp}$-$C^{m1p}$-$U^{rp}$-$U^{m1p}$)-$G^p$-$U^{m1p}$-$G^s$-$C^{m1s}$-$T^s$-$T^t$-H (SEQ ID NO: 39 of the Sequence Listing) (CT-098S)

CT-098S is synthesized in the same way as for Example 36. CT-098S is identified by negative ion mass spectrometry.
Nucleotide sequence: comprising a sequence complementary to nucleotide Nos. 3139-3157 of (GenBank accession No. NM_001904.3)

Example 38

Synthesis of HO-$G^s$-$C^{m1s}$-$A^p$-$C^{m1p}$-$A^p$-$A^{m1p}$-$G^p$-$A^{e2p}$-$A^p$-$U^{m1p}$-$G^p$-$G^{m1p}$-$A^p$-$U^{m1p}$-$C^p$-$A^{m1p}$-$C^p$-$A^{m1s}$-$A^s$-$T^s$-$T^t$-H (SEQ ID NO: 40 of the Sequence Listing) (CT-139)

CT-139 was synthesized in the same way as for Example 7. However, the moiety having a phosphorothioate bond was treated with a 0.2 M phenylacetyl disulfide/pyridine-acetonitrile (1:1 v/v) solution for 3 minutes instead of oxidation with an iodine/tetrahydrofuran/pyridine/H$_2$O solution (Ravikumar, V. T. et al. Bioorg. Med. Chem. Lett. (2006) 16, p. 2513-2517). CT-139 was identified by negative ion ESI mass spectrometry.
Molecular weight calculated value: 6781.78, measured value: 6781.89
Nucleotide sequence: comprising a sequence of nucleotide Nos. 3139-3157 of the human β-catenin gene (GenBank accession No. NM_001904.3)

Example 39

Synthesis of HO-$U^{m1s}$-$T^s$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$)-$G^p$-$U^{m1p}$-$G^s$-$C^{m1s}$-$T^s$-$T^t$-H (SEQ ID NO: 41 of the Sequence Listing) (CT-141)

CT-141 was synthesized in the same way as for Example 38.
Molecular weight calculated value: 6829.82, measured value: 6830.13
Nucleotide sequence: comprising a sequence complementary to nucleotide Nos. 3139-3157 of the human β-catenin gene (GenBank accession No. NM_001904.3)

Example 40

Synthesis of HO-G$^s$-C$^{m1s}$-A$^p$-C$^{m1p}$-A$^p$-A$^{m1p}$-G$^{m1p}$-A$^{m1p}$-A$^{m1p}$-U$^{m1p}$-G$^p$-G$^{m1p}$-A$^p$-U$^{m1p}$-C$^p$-A$^{m1p}$-C$^p$-A$^{m1s}$-A$^s$-T$^s$-T$^t$-H (SEQ ID NO: 42 of the Sequence Listing) (CT-140)

CT-140 was synthesized in the same way as for Example 38.

Molecular weight calculated value: 6694.62, measured value: 6694.71

Nucleotide sequence: comprising a sequence of nucleotide Nos. 3139-3157 of the human β-catenin gene (GenBank accession No. NM_001904.3)

Example 41

Synthesis of HO-G$^p$-C$^{m1p}$-A$^p$-C$^{m1p}$-A$^p$-A$^{m1p}$-G$^p$-A$^{e1p}$-A$^p$-U$^{m1p}$-G$^p$-G$^{m1p}$-A$^p$-U$^{m1p}$-C$^p$-A$^{m1p}$-C$^p$-A$^{m1p}$-A$^p$-T$^p$-T$^t$-H (SEQ ID NO: 43 of the Sequence Listing) (CT-114L)

CT-114L is synthesized in the same way as for Example 7. However, the 2',4'-BNA/LNA moiety is synthesized using 5'-O-dimethoxytrityl-2'-O,4'-C-methylene-6-N-benzoyladenosine-3'-O-(2-cyanoethyl N,N-diisopropyl)phosphoramidites as described in the literature (A. A. Koshkin, A. A. et al. Tetrahedron, 54, p. 3607-(1998)). CT-114L is identified by negative ion ESI mass spectrometry.

Nucleotide sequence: comprising a sequence of nucleotide Nos. 3139-3157 of the human β-catenin gene (GenBank accession No. NM_001904.3)

Example 42)

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-T$^t$-H (SEQ ID NO: 17 of the Sequence Listing) (CT-149)

CT-149 was synthesized in the same way as for Example 7. However, the 5'-terminal phosphate group moiety was synthesized using PHOSPHALINK (manufactured by Applied Biosystems).

Molecular weight: calculated value: 6694.28, measured value: 6694.55

Nucleotide sequence: comprising a sequence complementary to nucleotide Nos. 3139-3157 of the human β-catenin gene (GenBank accession No. NM_001904.3)

Example 43

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^p$-T$^t$-H (SEQ ID NO: 52 of the Sequence Listing) (CT-155)

CT-155 was synthesized in the same way as for Example 42.

Molecular weight: calculated value: 6696.27, measured value: 6696.44

Nucleotide sequence: comprising a sequence complementary to nucleotide Nos. 3139-3157 of the human β-catenin gene (GenBank accession No. NM_001904.3)

Example 44

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$ C$^{m1p}$-T$^p$-U$^{m1p}$-G$^p$-U$^{m1p}$-G$^p$-C$^{m1p}$-U$^{m1p}$-T$^t$-H (SEQ ID NO: 53 of the Sequence Listing) (CT-156)

CT-156 was synthesized in the same way as for Example 42.

Molecular weight: calculated value: 6710.29, measured value: 6710.13

Nucleotide sequence: comprising a sequence complementary to nucleotide Nos. 3139-3157 of the human β-catenin gene (GenBank accession No. NM_001904.3)

Example 45)

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 54 of the Sequence Listing) (CT-157)

CT-157 was synthesized in the same way as for Example 42.

Molecular weight: calculated value: 6710.29, measured value: 6710.39

Nucleotide sequence: comprising a sequence complementary to nucleotide Nos. 3139-3157 of the human β-catenin gene (GenBank accession No. NM_001904.3)

Example 46

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^{p}$-U$^{m1t}$-H (SEQ ID NO: 55 of the Sequence Listing) (CT-158)

CT-158 was synthesized in the same way as for Example 42.

Molecular weight: calculated value: 6712.27, measured value: 6712.50

Nucleotide sequence: comprising a sequence complementary to nucleotide Nos. 3139-3157 of the human β-catenin gene (GenBank accession No. NM_001904.3)

Example 47

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^{m1p}$-U$^{m1t}$-H (SEQ ID NO: 56 of the Sequence Listing) (CT-159)

CT-159 was synthesized in the same way as for Example 42.

Molecular weight: calculated value: 6726.29, measured value: 6726.40

Nucleotide sequence: comprising a sequence complementary to nucleotide Nos. 3139-3157 of the human β-catenin gene (GenBank accession No. NM_001904.3)

Example 48

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{rt}$-H (SEQ ID NO: 57 of the Sequence Listing) (CT-160)

CT-160 was synthesized in the same way as for Example 42.

Molecular weight: calculated value: 6696.27, measured value: 6696.26

Nucleotide sequence: comprising a sequence complementary to nucleotide Nos. 3139-3157 of the human β-catenin gene (GenBank accession No. NM_001904.3)

Example 49

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^{\prime p}$-U$^{rt}$-H (SEQ ID NO: 58 of the Sequence Listing) (CT-161)

CT-161 was synthesized in the same way as for Example 42.

Molecular weight: calculated value: 6698.24, measured value: 6698.34

Nucleotide sequence: comprising a sequence complementary to nucleotide Nos. 3139-3157 of the human β-catenin gene (GenBank accession No. NM_001904.3)

Example 50

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^{m1p}$-U$^{rt}$-H (SEQ ID NO: 59 of the Sequence Listing) (CT-162)

CT-162 was synthesized in the same way as for Example 42.

Molecular weight: calculated value: 6712.27, measured value: 6712.30

Nucleotide sequence: comprising a sequence complementary to nucleotide Nos. 3139-3157 of the human β-catenin gene (GenBank accession No. NM_001904.3)

Example 51

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1t}$-H (SEQ ID NO: 60 of the Sequence Listing) (CT-169)

CT-169 was synthesized in the same way as for Example 7.

Molecular weight: calculated value: 5767.86, measured value: 5767.78

Nucleotide sequence: comprising a sequence of nucleotide Nos. 3139-3156 of the human β-catenin gene (GenBank accession No. NM_001904.3)

Example 52

Synthesis of HO-G$^p$-C$^{m1p}$-A$^p$-C$^{m1p}$-A$^p$-A$^{m1p}$-G$^p$-A$^{m1p}$-A$^p$-U$^{m1P}$-G$^p$-G$^{m1P}$-A$^p$-U$^{m1P}$-C$^p$-A$^{m1p}$-C$^p$-H (SEQ ID NO: 61 of the Sequence Listing) (CT-170)

CT-170 was synthesized in the same way as for Example 7.

Molecular weight: calculated value: 5424.62, measured value: 5424.47

Nucleotide sequence: comprising a sequence of nucleotide Nos. 3139-3155 of the human β-catenin gene (GenBank accession No. NM_001904.3)

Example 53

Synthesis of HO-G$^p$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1t}$-H (SEQ ID NO: 62 of the Sequence Listing) (CT-171)

CT-171 was synthesized in the same way as for Example 7.

Molecular weight: calculated value: 5135.44, measured value: 5134.53

Nucleotide sequence: comprising a sequence of nucleotide Nos. 3139-3154 of the human β-catenin gene (GenBank accession No. NM_001904.3)

Example 54

Synthesis of HO-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$)-C$^p$-A$^{m1p}$-A$^t$-H (SEQ ID NO: 63 of the Sequence Listing) (CT-172)

CT-172 was synthesized in the same way as for Example 7.

Molecular weight: calculated value: 5751.86, measured value: 5751.80

Nucleotide sequence: comprising a sequence of nucleotide Nos. 3140-3157 of the human β-catenin gene (GenBank accession No. NM_001904.3)

Example 55

Synthesis of HO-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^p$-A$^{m1p}$-C$^p$-A$^{m1p}$-A$^t$-H (SEQ ID NO: 64 of the Sequence Listing) (CT-173)

CT-173 was synthesized in the same way as for Example 7.

Molecular weight: calculated value: 5432.65, measured value: 5432.62

Nucleotide sequence: comprising a sequence of nucleotide Nos. 3141-3157 of the human β-catenin gene (GenBank accession No. NM_001904.3)

Example 56

Synthesis of HO-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$A^t$-H (SEQ ID NO: 65 of the Sequence Listing) (CT-174)

CT-174 was synthesized in the same way as for Example 7.

Molecular weight: calculated value: 5119.44, measured value: 5119.39

Nucleotide sequence: comprising a sequence of nucleotide Nos. 3142-3157 of the human (β-catenin gene (GenBank accession No. NM_001904.3)

Example 57

Synthesis of HO-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1t}$-H (SEQ ID NO: 66 of the Sequence Listing) (CT-175)

CT-175 was synthesized in the same way as for Example 7.

Molecular weight: calculated value: 5438.65, measured value: 5438.55

Nucleotide sequence: comprising a sequence of nucleotide Nos. 3140-3156 of the human β-catenin gene (GenBank accession No. NM_001904.3)

Example 58

Synthesis of HO-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^{pt}$-H (SEQ ID NO: 67 of the Sequence Listing) (CT-176)

CT-176 was synthesized in the same way as for Example 7.

Molecular weight: calculated value: 5095.42, measured value: 5095.25

Nucleotide sequence: comprising a sequence of nucleotide Nos. 3140-3155 of the human β-catenin gene (GenBank accession No. NM_0.001904.3)

Example 59

Synthesis of HO-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1t}$-H (SEQ ID NO: 68 of the Sequence Listing) (CT-177)

CT-177 was synthesized in the same way as for Example 7.

Molecular weight: calculated value: 5119.44, measured value: 5119.33

Nucleotide sequence: comprising a sequence of nucleotide Nos. 3141-3156 of the human β-catenin gene (GenBank accession No. NM_001904.3)

Example 60

Synthesis of HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$A^p$-$U^{m1t}$-H (SEQ ID NO: 69 of the Sequence Listing) (CT-204)

CT-204 was synthesized in the same way as for Example 42.

Molecular weight: calculated value: 6719.31, measured value: 6719.99

Nucleotide sequence: comprising a sequence complementary to nucleotide Nos. 3139-3157 of the human β-catenin gene (GenBank accession No. NM_001904.3)

Example 61

Synthesis of HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$G^p$-$U^{m1t}$-H (SEQ ID NO: 70 of the Sequence Listing) (CT-205)

CT-205 was synthesized in the same way as for Example 42.

Molecular weight: calculated value: 6735.31, measured value: 6735.79

Nucleotide sequence: comprising a sequence complementary to nucleotide Nos. 3139-3157 of the human β-catenin gene (GenBank accession No. NM_001904.3)

Example 62

Synthesis of HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$)-$T^p$-$U^{m1p}$-$G^p$-$U^{m1p}$-$G^p$-$C^{m1p}$-$C^p$-$U^{m1t}$-H (SEQ ID NO: 71 of the Sequence Listing) (CT-206)

CT-206 was synthesized in the same way as for Example 42.

Molecular weight: calculated value: 6695.28, measured value: 6696.00

Nucleotide sequence: comprising a sequence complementary to nucleotide Nos. 3139-3157 of the human β-catenin gene (GenBank accession No. NM_001904.3)

Example 63

Synthesis of HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$A^{m11}$-14 (SEQ ID NO: 72 of the Sequence Listing) (CT-207)

CT-207 was synthesized in the same way as for Example 42.

Molecular weight: calculated value: 6733.33, measured value: 6733.98

Nucleotide sequence: comprising a sequence complementary to nucleotide Nos. 3139-3157 of the human β-catenin gene (GenBank accession No. NM_001904.3)

Example 64

Synthesis of HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{1P}$-$T^p$-$G^{m1t}$-H (SEQ ID NO: 73 of the Sequence Listing) (CT-208)

CT-208 was synthesized in the same way as for Example 42.

Molecular weight: calculated value: 6749.33, measured value: 6750.11

Nucleotide sequence: comprising a sequence complementary to nucleotide Nos. 3139-3157 of the human β-catenin gene (GenBank accession No. NM_001904.3)

Example 65

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-C$^{m1t}$-H (SEQ ID NO: 74 of the Sequence Listing) (CT-209)

CT-209 was synthesized in the same way as for Example 42.
Molecular weight: calculated value: 6709.31, measured value: 6709.81
Nucleotide sequence: comprising a sequence complementary to nucleotide Nos. 3139-3157 of the human β-catenin gene (GenBank accession No. NM_001904.3)

Example 66

Synthesis of HO-P(=O)(OH)—O-A$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 75 of the Sequence Listing) (CT-221)

CT-221 was synthesized in the same way as for Example 42.
Molecular weight: calculated value: 6733.23, measured value: 6733.00
Nucleotide sequence: comprising a sequence complementary to nucleotide Nos. 3139-3156 of the human β-catenin gene (GenBank accession No. NM_001904.3)

Example 67

Synthesis of HO-P(=O)(OH)—O-G$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 76 of the Sequence Listing) (CT-222)

CT-222 was synthesized in the same way as for Example 42.
Molecular weight: calculated value: 6749.33, measured value: 6749.06
Nucleotide sequence: comprising a sequence complementary to nucleotide Nos. 3139-3156 of the human β-catenin gene (GenBank accession No. NM_001904.3)

Example 68

Synthesis of HO-P(=O)(OH)—O-C$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 77 of the Sequence Listing) (CT-223)

CT-223 was synthesized in the same way as for Example 42.
Molecular weight: calculated value: 6709.31, measured value: 6709.00
Nucleotide sequence: comprising a sequence complementary to nucleotide Nos. 3139-3156 of the human fβ-catenin gene (GenBank accession No. NM_001904.3)

Example 69)

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-T$^p$-U$^{m1t}$-H (SEQ ID NO: 78 of the Sequence Listing) (CT-202)

CT-202 was synthesized in the same way as for Example 42.
Molecular weight: calculated value: 6391.06, measured value: 6391.70
Nucleotide sequence: comprising a sequence complementary to nucleotide Nos. 3140-3157 of the human β-catenin gene (GenBank accession No. NM_001904.3)

Example 70

Synthesis of HO-P(=O)(OH)—O-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 79 of the Sequence Listing) (CT-203)

CT-203 was synthesized in the same way as for Example 42.
Molecular weight: calculated value: 6390.10, measured value: 6390.72
Nucleotide sequence: comprising a sequence complementary to nucleotide Nos. 3139-3156 of the human β-catenin gene (GenBank accession No. NM_001904.3)

Example 71

Synthesis of HO-P(=O)(OH)—O-G$^{m1p}$-C$^p$-A$^{m1p}$-C$^p$-A$^{m1p}$-A$^p$-G$^{m1p}$-A$^p$-A$^{m1p}$-T$^p$-G$^{m1p}$-G$^p$-A$^{m1p}$-T$^p$-C$^{m1p}$-A$^p$-C$^{m1p}$-A$^p$-A$^{m1p}$-T$^p$-U$^{m1t}$-H (SEQ ID NO: 80 of the Sequence Listing) (CT-210)

CT-210 was synthesized in the same way as for Example 42.
Molecular weight: calculated value: 6843.52, measured value: 6844.23
Nucleotide sequence: comprising a sequence of nucleotide Nos. 3139-3157 of the human β-catenin gene (GenBank accession No. NM_001904.3)

Example 72

Synthesis of HO-T$^p$-U$^{m1p}$-G$^p$-U$^{m1p}$-G$^p$-A$^{m1p}$-T$^p$-C$^{m1p}$-C$^p$-A$^{m1p}$-T$^p$-U$^{m1p}$-C$^p$-U$^{m1p}$-T$^p$-G$^{m1p}$-T$^p$-G$^{m1p}$-C$^t$-H (SEQ ID NO: 81 of the Sequence Listing) (CT-211)

CT-211 was synthesized in the same way as for Example 42.
Molecular weight: calculated value: 5989.92, measured value: 5990.31
Nucleotide sequence: comprising a sequence complementary to nucleotide Nos. 3139-3157 of the human β-catenin gene (GenBank accession No. NM_001904.3)

Example 73

Synthesis of HO-T$^p$-U$^{m1p}$-G$^p$-U$^{m1p}$-G$^p$-A$^{m1p}$-T$^p$-C$^{m1p}$-C$^p$-A$^{m1p}$-T$^p$-U$^{m1p}$-C$^p$-U$^{m1p}$-T$^p$-G$^{m1p}$-T$^p$-G$^{m1t}$-H (SEQ ID NO: 82 the Sequence Listing) (CT-212)

CT-212 was synthesized in the same way as for Example 7.
Molecular weight: calculated value: 5700.74, measured value: 5701.15
Nucleotide sequence: comprising a sequence complementary to nucleotide Nos. 3140-3157 of the human β-catenin gene (GenBank accession No. NM_001904.3)

Example 74

Synthesis of HO-P(=O)(OH)—O-A$^p$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 83 of the Sequence Listing) (CT-243)

CT-243 was synthesized in the same way as for Example 42.
Molecular weight: calculated value: 6703.31, measured value: 6703.35
Nucleotide sequence: comprising a sequence complementary to nucleotide Nos. 3139-3156 of the human β-catenin gene (GenBank accession No. NM_001904.3)

Example 75

Synthesis of HO-P(=O)(OH)—O-G$^p$-T$^p$-G$^{m1p}$-T$^p$-U$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 84 of the Sequence Listing) (CT-244)

CT-244 was synthesized in the same way as for Example 42.
Molecular weight: calculated value: 6719.13, measured value: 6719.46
Nucleotide sequence: comprising a sequence complementary to nucleotide Nos. 3139-3156 of the human iβ-catenin gene (GenBank accession No. NM_001904.3)

Example 76

Synthesis of HO-P(=O)(OH)—O-C$^p$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 85 of the Sequence Listing) (CT-245)

CT-245 was synthesized in the same way as for Example 42.
Molecular weight: calculated value: 6679.28, measured value: 6679.43
Nucleotide sequence: comprising a sequence complementary to nucleotide Nos. 3139-3156 of the human β-catenin gene (GenBank accession No. NM_001904.3)

Example 77

Synthesis of HO-P(=O)(OH)—O-T$^p$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 86 of the Sequence Listing) (CT-246)

CT-246 was synthesized in the same way as for Example 42.
Molecular weight: calculated value: 6694.29, measured value: 6694.49
Nucleotide sequence: comprising a sequence complementary to nucleotide Nos. 3139-3157 of the human β-catenin gene (GenBank accession No. NM_001904.3)

Example 78

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-G$^p$-A$^{m1t}$-H (SEQ ID NO: 87 of the Sequence Listing) (CT-247)

CT-247 was synthesized in the same way as for Example 42.
Molecular weight: calculated value: 6758.35, measured value: 6758.46
Nucleotide sequence: comprising a sequence complementary to nucleotide Nos. 3139-3157 of the human β-catenin gene (GenBank accession No. NM_001904.3)

Example 79)

Synthesis of HO-P(=O)(OH)—O-U$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-G$^p$-G$^{m1t}$-H (SEQ ID NO: 88 of the Sequence Listing) (CT-248)

CT-248 was synthesized in the same way as for Example 42.
Molecular weight: calculated value: 6774.35, measured value: 6774.55
Nucleotide sequence: comprising a sequence complementary to nucleotide Nos. 3139-3157 of the human β-catenin gene (GenBank accession No. NM_001904.3)

Example 80

Synthesis of HO-P(=O)(OH)—O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-G$^p$-C$^{m1t}$-H (SEQ ID NO: 89 of the Sequence Listing) (CT-249)

CT-249 was synthesized in the same way as for Example 42.
Molecular weight: calculated value: 6734.32, measured value: 6734.35
Nucleotide sequence: comprising a sequence complementary to nucleotide Nos. 3139-3157 of the human β-catenin gene (GenBank accession No. NM_001904.3)

Example 81

Synthesis of HO-P(=O)(OH)—O-T$^p$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-G$^p$-U$^{m1t}$-H (SEQ ID NO: 90 of the Sequence Listing) (CT-253)

CT-253 was synthesized in the same way as for Example 42.
Molecular weight: calculated value: 6719.31, measured value: 6719.44
Nucleotide sequence: comprising a sequence complementary to nucleotide Nos. 3139-3157 of the human β-catenin gene (GenBank accession No. NM_001904.3)

Example 82

Synthesis of HO-P(=O)(OH)—O-T$^p$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-G$^p$-A$^{m1t}$-H (SEQ ID NO: 91 of the Sequence Listing) (CT-254)

CT-254 was synthesized in the same way as for Example 42.
Molecular weight: calculated value: 6742.35, measured value: 6742.45
Nucleotide sequence: comprising a sequence complementary to nucleotide Nos. 3139-3157 of the human β-catenin gene (GenBank accession No. NM_001904.3)

Example 83

Synthesis of HO-P(=O)(OH)—O-$T^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$G^p$-$G^{m1t}$-H (SEQ ID NO: 92 of the Sequence Listing) (CT-255)

CT-255 was synthesized in the same way as for Example 42.
Molecular weight: calculated value: 6758.35, measured value: 6758.66
Nucleotide sequence: comprising a sequence complementary to nucleotide Nos. 3139-3157 of the human β-catenin gene (GenBank accession No. NM_001904.3)

Example 84

Synthesis of HO-P(=O)(OH)—O-$T^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$G^p$-$C^{m1t}$-H (SEQ ID NO: 93 of the Sequence Listing) (CT-256)

CT-256 was synthesized in the same way as for Example 42.
Molecular weight: calculated value: 6718.32, measured value: 6718.59
Nucleotide sequence: comprising a sequence complementary to nucleotide Nos. 3139-3157 of the human β-catenin gene (GenBank accession No. NM_001904.3)

Example 85

Synthesis of HO-P(=O)(OH)—O-$T^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$A^p$-$A^{m1t}$-H (SEQ ID NO: 94 of the Sequence Listing) (CT-257)

CT-257 was synthesized in the same way as for Example 42.
Molecular weight: calculated value: 6726.35, measured value: 6726.52
Nucleotide sequence: comprising a sequence complementary to nucleotide Nos. 3139-3157 of the human β-catenin gene (GenBank accession No. NM_001904.3)

Example 86

Synthesis of HO-P(=O)(OH)—O-$T^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$A^p$-$G^{m1t}$-H (SEQ ID NO: 95 of the Sequence Listing) (CT-258)

CT-258 was synthesized in the same way as for Example 42.
Molecular weight: calculated value: 6742.35, measured value: 6742.54
Nucleotide sequence: comprising a sequence complementary to nucleotide Nos. 3139-3157 of the human β-catenin gene (GenBank accession No. NM_001904.3)

Example 87

Synthesis of HO-P(=O)(OH)—O-$U^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (SEQ ID NO: 96 of the Sequence Listing) (CT-264)

CT-264 was synthesized in the same way as for Example 42. However, the $U^p$ moiety was synthesized using DMT-deoxyuridine-β-cyanoethyl phosphoramidite (DMT-dUridine Amidite, manufactured by Sigma-Aldrich Corp.).
Molecular weight: calculated value: 6680.27, measured value: 6680.29
Nucleotide sequence: comprising a sequence complementary to nucleotide Nos. 3139-3157 of the human β-catenin gene (GenBank accession No. NM_001904.3)

Example 88

Synthesis of HO-P(=O)(OH)—O-5me$C^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$T^p$-$U^{m1t}$-H (SEQ ID NO: 97 of the Sequence Listing) (CT-265)

CT-265 was synthesized in the same way as for Example 42. However, the 5Me$C^p$ moiety was synthesized using DMT-5-methyl-deoxycytidine(ac)-3-cyanoethyl phosphoramidite (5-Methyl-dC(ac) Amidite, manufactured by Sigma-Aldrich Corp.).
Molecular weight: calculated value: 6693.31, measured value: 6693.23
Nucleotide sequence: comprising a sequence complementary to nucleotide Nos. 3139-3156 of the human β-catenin gene (GenBank accession No. NM_001904.3)

Example 89

Synthesis of HO-P(=O)(OH)—O-$C^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$G^p$-$G^{m1t}$-H (SEQ ID NO: 98 of the Sequence Listing) (CT-266)

CT-266 was synthesized in the same way as for Example 42.
Molecular weight: calculated value: 6743.34, measured value: 6743.78
Nucleotide sequence: comprising a sequence complementary to nucleotide Nos. 3139-3156 of the human β-catenin gene (GenBank accession No. NM_001904.3)

Example 90

Synthesis of HO-P(=O)(OH)—O-5me$C^p$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$G^p$-$G^{m1t}$-H (SEQ ID NO: 99 of the Sequence Listing) (CT-267)

CT-267 was synthesized in the same way as for Example 88.
Molecular weight: calculated value: 6757.36, measured value: 6757.52
Nucleotide sequence: comprising a sequence complementary to nucleotide Nos. 3139-3156 of the human β-catenin gene (GenBank accession No. NM_001904.3)

Example 91

Synthesis of HO-$G^{m1p}$-$C^p$-$A^{m1p}$-$C^p$-$A^{m1p}$-$A^p$-$G^{m1p}$-$A^p$-$A^{m1p}$-$T^p$-$G^{m1p}$-$G^p$-$A^{m1p}$-$T^p$-$C^{m1p}$-$A^p$-$C^{m1p}$-$A^t$-H (SEQ ID NO: 102 of the Sequence Listing) (CT-288)

CT-288 was synthesized in the same way as for Example 7.
Molecular weight: calculated value: 5795.91, measured value: 5795.76

Nucleotide sequence: comprising a sequence of nucleotide Nos. 3139-3156 of the human β-catenin gene (GenBank accession No. NM_001904.3)

Example 92

Synthesis of HO-P(=O)(OH)—O-T$^p$-U$^{m1p}$-G$^p$-U$^{m1p}$-G$^p$-A$^{m1p}$-T$^p$-C$^{m1p}$-C$^p$-A$^{m1p}$-T$^p$-U$^{m1p}$-C$^p$-U$^{m1p}$-T$^p$-G$^{m1p}$-T$^p$-G$^{m1p}$-C$^p$-T$^p$-U$^{m1t}$-H (SEQ ID NO: 103 of the Sequence Listing) (CT-289)

CT-289 was synthesized in the same way as for Example 42.

Molecular weight: calculated value: 6694.29, measured value: 6694.09

Nucleotide sequence: comprising a sequence complementary to nucleotide Nos. 3139-3157 of the human β-catenin gene (GenBank accession No. NM_001904.3)

Example 93

Synthesis of HO-G$^p$-G$^{m1p}$-A$^p$-C$^{m1p}$-A$^p$-A$^{m1p}$-G$^p$-G$^{m1p}$-A$^p$-A$^{m1p}$-G$^p$-C$^{m1p}$-T$^p$-G$^{m1p}$-C$^p$-A$^{m1p}$-G$^p$-A$^{m1t}$-H (SEQ ID NO: 104 of the Sequence Listing) (CT-278)

CT-278 was synthesized in the same way as for Example 7.

Molecular weight: calculated value: 5876.95, measured value: 5877.25

Nucleotide sequence: comprising a sequence of nucleotide Nos. 2137-2154 of the human β-catenin gene (GenBank accession No. NM_001904.3)

Example 94

Synthesis of HO-P(=O)(OH)—O-U$^{m1p}$-T$^p$-C$^{m1p}$-T$^p$-G$^{m1p}$-C$^p$-A$^{m1p}$-G$^p$-C$^{m1p}$-T$^p$-U$^{m1p}$-C$^p$-C$^{m1p}$-T$^p$-U$^{m1p}$-G$^p$-U$^{m1p}$-C$^p$-C$^{m1p}$-T$^p$-U$^{m1t}$-H (SEQ ID NO: 105 of the Sequence Listing) (CT-279)

CT-279 was synthesized in the same way as for Example 42.

Molecular weight: calculated value: 6645.26, measured value: 6645.44

Nucleotide sequence: comprising a sequence complementary to nucleotide Nos. 2137-2155 of the human β-catenin gene (GenBank accession No. NM_001904.3)

Example 95

Synthesis of HO-P(=O)(OH)—O-T$^p$-T$^p$-C$^{m1p}$-T$^p$-G$^{m1p}$-C$^p$-A$^{m1p}$-G$^p$-C$^{m1p}$-T$^p$-U$^{m1p}$-C$^p$-C$^{m1p}$-T$^p$-U$^{m1p}$-G$^p$-U$^{m1p}$-C$^p$-C$^{m1p}$-T$^p$-U$^{m1p}$-H (SEQ ID NO: 106 of the Sequence Listing) (CT-280)

CT-280 was synthesized in the same way as for Example 42.

Molecular weight: calculated value: 6629.26, measured value: 6629.51

Nucleotide sequence: comprising a sequence complementary to nucleotide Nos. 2137-2155 of the human β-catenin gene (GenBank accession No. NM_001904.3)

Example 96

Synthesis of HO-P(=O)(OH)—O-T$^p$-T$^p$-C$^{m1p}$-T$^p$-G$^{m1p}$-C$^p$-A$^{m1p}$-G$^p$-C$^{m1p}$-T$^p$-U$^{m1p}$-C$^p$-C$^{m1p}$-T$^p$-U$^{m1p}$-G$^p$-U$^{m1p}$-C$^p$-C$^{m1p}$-A$^p$-G$^{m1p}$-H (SEQ ID NO: 107 of the Sequence Listing) (CT-281)

CT-281 was synthesized in the same way as for Example 42.

Molecular weight: calculated value: 6677.31, measured value: 6677.65

Nucleotide sequence: comprising a sequence complementary to nucleotide Nos. 2137-2155 of the human β-catenin gene (GenBank accession No. NM_001904.3)

Example 97

Synthesis of HO-G$^p$-C$^{m1p}$-C$^p$-U$^{m1p}$-C$^p$-A$^{m1p}$-G$^p$-A$^{m1p}$-T$^p$-U$^{m1p}$-C$^p$-G$^{m1p}$-T$^p$-A$^{m1p}$-G$^p$-A$^{m1p}$-A$^p$-U$^{m1p}$-A$^t$-H (SEQ ID NO: 108 of the Sequence Listing) (DD-016)

DD-016 was synthesized in the same way as for Example 7.

Molecular weight: calculated value: 6040.00, measured value: 6040.44

Nucleotide sequence: comprising a sequence of nucleotide Nos. 1929-1947 of the DDX3 (DEAD (Asp-Glu-Ala-Asp) box polypeptide 3, X-linked) gene (GenBank accession No. NM_001356.3)

Example 98

Synthesis of HO-P(=O)(OH)—O-U$^{m1p}$-A$^p$-U$^{m1p}$-T$^p$-C$^{m1p}$-T$^p$-A$^{m1p}$-C$^p$-G$^{m1p}$-A$^p$-A$^{m1p}$-T$^p$-C$^{m1p}$-T$^p$-G$^{m1p}$-A$^p$-G$^{m1p}$-G$^p$-C$^{m1p}$-T$^p$-U$^{m1p}$-H (SEQ ID NO: 109 of the Sequence Listing) (DD-017)

DD-017 was synthesized in the same way as for Example 42.

Molecular weight: calculated value: 6779.41, measured value: 6780.29

Nucleotide sequence: comprising a sequence complementary to nucleotide Nos. 1929-1947 of the DDX3 gene (GenBank accession No. NM_001356.3)

Example 99

Synthesis of HO-G$^p$-C$^{m1p}$-C$^p$-U$^{m1p}$-C$^p$-A$^{m1p}$-G$^p$-A$^{m1p}$-T$^p$-U$^{m1p}$-C$^p$-G$^{m1p}$-T$^p$-A$^{m1p}$-G$^p$-A$^{m1p}$-A$^p$-U$^{m1t}$-H (SEQ ID NO: 110 of the Sequence Listing) (DD-022)

DD-022 was synthesized in the same way as for Example 7.

Molecular weight: calculated value: 5726.79, measured value: 5726.89

Nucleotide sequence: comprising a sequence of nucleotide Nos. 1929-1946 of the DDX3 gene (GenBank accession No. NM_001356.3)

Example 100

Synthesis of HO-P(=O)(OH)—O-T$^p$-A$^p$-U$^{m1p}$-T$^p$-C$^{m1p}$-T$^p$-A$^{m1p}$-C$^p$-G$^{m1p}$-A$^p$-A$^{m1p}$-T$^p$-C$^{m1p}$-T$^p$-G$^{m1p}$-A$^p$-G$^{m1p}$-G$^p$-C$^{m1p}$-T$^p$-U$^{m1p}$-H (SEQ ID NO: 111 of the Sequence Listing) (DD-023)

DD-023 was synthesized in the same way as for Example 42.
Molecular weight: calculated value: 6763.42, measured value: 6763.69
Nucleotide sequence: comprising a sequence complementary to nucleotide Nos. 1929-1947 of the DDX3 gene (GenBank accession No. NM_001356.3)

Example 101

Synthesis of HO-P(=O)(OH)—O-T$^p$-A$^p$-U$^{m1p}$-T$^p$-C$^{m1p}$-T$^p$-A$^{m1p}$-C$^p$-G$^{m1p}$-A$^p$-A$^{m1p}$-T$^p$-C$^{m1p}$-T$^p$-G$^{m1p}$-A$^p$-G$^{m1p}$-G$^p$-C$^{m1p}$-A$^p$-G$^{m1t}$-H (SEQ ID NO: 112 of the Sequence Listing) (DD-024)

DD-024 was synthesized in the same way as for Example 42.
Molecular weight: calculated value: 6811.47, measured value: 6811.66
Nucleotide sequence: comprising a sequence complementary to nucleotide Nos. 1929-1947 of the DDX3 gene (GenBank accession No. NM_001356.3)

Example 102

Synthesis of HO-G$^s$-C$^{m1p}$-A$^p$-C$^{m1p}$-A$^p$-A$^{m1p}$-G$^p$-A$^{m1p}$-A$^p$-U$^{m1p}$-G$^p$-G$^{m1p}$-A$^p$-U$^{m1p}$-C$^s$-A$^{m1s}$-C$^s$-A$^{m1p}$-H (SEQ ID NO: 113 of the Sequence Listing) (CT-169S)

CT-169S is synthesized in the same way as for Example 36. CT-169S is identified by negative ion mass spectrometry.
Nucleotide sequence: comprising a sequence of nucleotide Nos. 3139-3156 of the human β-catenin gene (GenBank accession No. NM_001904.3)

Example 103

Synthesis of HO-P(=O)(OH)—O-U$^{m1s}$-T$^s$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^s$-C$^{m1s}$-T$^s$-U$^{m1t}$-H (SEQ ID NO: 114 of the Sequence Listing) (CT-157S)

CT-157S is synthesized in the same way as for Example 42. However, the moiety having a phosphorothioate bond is treated with a 0.2 M phenylacetyl disulfide/pyridine-acetonitrile (1:1 v/v) solution for 3 minutes instead of oxidation with an iodine/tetrahydrofuran/pyridine/H$_2$O solution (Ravikumar, V. T. et al. Bioorg. Med. Chem. Lett. (2006) 16, p. 2513-2517). CT-157S is identified by negative ion mass spectrometry.
Nucleotide sequence: comprising a sequence complementary to nucleotide Nos. 3139-3157 of the human β-catenin gene (GenBank accession No. NM_001904.3)

Reference Example 1

Synthesis of HO-C$^p$-C$^{m1p}$-A$^{rp}$-C$^{m1p}$-A$^{rp}$-A$^{m1p}$-G$^{rp}$-A$^{m1p}$-A$^{rp}$-U$^{m1p}$-G$^{rp}$-G$^{m1p}$-A$^{rp}$-U$^{m1p}$-C$^{rp}$-A$^{m1p}$-C$^{rp}$-A$^{m1p}$-A$^{rp}$-T$^p$-T$^t$-H (SEQ ID NO: 44 of the Sequence Listing) (CT-001)

CT-001 was synthesized in the same way as for Example 1.
Molecular weight: calculated value: 6849.46, measured value: 6850.8
Nucleotide sequence: comprising a sequence of nucleotide Nos. 3139-3157 of the human β-catenin gene (GenBank accession No. NM_001904.3)

Reference Example 2

Synthesis of HO-U$^{m1p}$-U$^{rp}$-G$^{m1p}$-U$^{rp}$-G$^{m1p}$-A$^{rp}$-U$^{m1p}$-C$^{rp}$-C$^{m1p}$-A$^{rp}$-U$^{m1p}$-U$^{rp}$-C$^{m1p}$-U$^{rp}$-U$^{m1p}$-G$^{rp}$-U$^{m1p}$-G$^{rp}$-C$^{m1p}$-T$^p$-T$^t$-H (SEQ ID NO: 45 of the Sequence Listing) (CT-005)

CT-005 was synthesized in the same way as for Example 1.
Molecular weight: calculated value: 6702.20, measured value: 6702.2
Nucleotide sequence: comprising a sequence complementary to nucleotide Nos. 3139-3157 of the human β-catenin gene (GenBank accession No. NM_001904.3)

Reference Example 3

Synthesis of HO-G$^{rp}$-C$^{rp}$-A$^{rp}$-C$^{rp}$-A$^{rp}$-A$^{rp}$-G$^{rp}$-A$^{rp}$-A$^{rp}$-U$^{rp}$-U$^{rp}$-G$^{rp}$-A$^{rp}$-U$^{rp}$-C$^{rp}$-A$^{rp}$-C$^{rp}$-A$^{rp}$-A$^{rp}$-U$^{rp}$-U$^{rt}$-H (SEQ ID NO: 46 of the Sequence Listing) (CT-106)

CT-106 was synthesized in the same way as for Example 1.
Molecular weight: calculated value: 6727.16, measured value: 6726.73
Nucleotide sequence: comprising a sequence of nucleotide Nos. 3139-3157 of the human β-catenin gene (GenBank accession No. NM_001904.3)

Reference Example 4

Synthesis of HO-U$^{rp}$-U$^{rp}$-G$^{rp}$-U$^{rp}$-G$^{rp}$-A$^{rp}$-U$^{rp}$-C$^{rp}$-C$^{rp}$-A$^{rp}$-U$^{rp}$-U$^{rp}$-C$^{rp}$-U$^{rp}$-U$^{rp}$-G$^{rp}$-A$^{rp}$-G$^{rp}$-C$^{rp}$-U$^{rp}$-U$^{rt}$-H (SEQ ID NO: 47 of the Sequence Listing) (CT-041)

CT-041 was synthesized in the same way as for Example 1.
Molecular weight: calculated value: 6565.88, measured value: 6565.34
Nucleotide sequence: comprising a sequence complementary to nucleotide Nos. 3139-3157 of the human β-catenin gene (GenBank accession No. NM_001904.3)

Reference Example 5)

Synthesis of HO-G$^{rp}$-C$^{rp}$-A$^{rp}$-C$^{rp}$-A$^{rp}$-A$^{rp}$-G$^{rp}$-A$^{rp}$-A$^{rp}$-U$^{rp}$-G$^{rp}$-G$^p$-A$^p$-T$^p$-C$^p$-A$^p$-C$^p$-A$^p$-A$^p$-T$^p$-T$^t$-H (SEQ ID NO: 48 of the Sequence Listing) (CT-104)

CT-104 was synthesized in the same way as for Example 1.

Molecular weight: calculated value: 6609.25, measured value: 6608.98

Nucleotide sequence: comprising a sequence of nucleotide Nos. 3139-3157 of the human β-catenin gene (GenBank accession No. NM_001904.3)

Reference Example 6

Synthesis of HO-T$^p$-T$^p$-G$^p$-T$^p$-G$^p$-A$^p$-T$^p$-C$^p$-C$^{\prime p}$-A$^{\prime p}$-U$^{\prime p}$-U$^{\prime p}$-C$^{\prime p}$-U$^{\prime p}$-U$^{\prime p}$-G$^{\prime p}$-U$^{\prime p}$-G$^{\prime p}$-C$^{\prime p}$-T$^p$-T$^t$-H (SEQ ID NO: 49 of the Sequence Listing) (CT-110)

CT-110 was synthesized in the same way as for Example 1.

Molecular weight: calculated value: 6490.05, measured value: 6489.61

Nucleotide sequence: comprising a sequence complementary to nucleotide Nos. 3139-3157 of the human β-catenin gene (GenBank accession No. NM_001904.3)

Reference Example 7

Synthesis of HO-G$^p$-C$^p$-A$^p$-C$^p$-A$^p$-A$^p$-G$^p$-A$^p$-A$^p$-T$^p$-G$^p$-G$^p$-A$^p$-T$^p$-C$^p$-A$^p$-C$^p$-A$^p$-A$^p$-T$^p$-T$^t$-H (SEQ ID NO: 50 of the Sequence Listing) (CT-105)

CT-105 was synthesized in the same way as for Example 7.

Molecular weight: calculated value: 6447.28, measured value: 6447.58

Nucleotide sequence: comprising a sequence of nucleotide Nos. 3139-3157 of the human fβ-catenin gene (GenBank accession No. NM_001904.3)

Reference Example 8

Synthesis of HO-T$^p$-T$^p$-G$^p$-T$^p$-G$^p$-A$^p$-T$^p$-C$^p$-C$^p$-A$^p$-T$^p$-T$^p$-C$^p$-T$^p$-G$^p$-T$^p$-G$^p$-C$^p$-T$^p$-T$^t$-H (SEQ ID NO: 51 of the Sequence Listing) (CT-111)

CT-111 was synthesized in the same way as for Example 7.

Molecular weight: calculated value: 6384.19, measured value: 6384.05

Nucleotide sequence: comprising a sequence complementary to nucleotide Nos. 3139-3157 of the human β-catenin gene (GenBank accession No. NM_001904.3)

Reference Example 9

Synthesis of HO-G$^{\prime p}$-C$^{\prime p}$-A$^{\prime p}$-C$^{\prime p}$-A$^{\prime p}$-A$^{\prime p}$-G$^{\prime p}$-A$^{\prime p}$-A$^{\prime p}$-U$^{\prime p}$-C$^p$-G$^{\prime p}$-A$^{1F}$-U$^{\prime p}$-C$^p$-A$^{\prime p}$-C$^p$-A$^{\prime p}$-A$^{\prime t}$-H (SEQ ID NO: 100 of the Sequence Listing) (CT-125)

CT-125 was synthesized in the same way as for Example 1.

Molecular weight: calculated value: 6114.82, measured value: 6114.59

Nucleotide sequence: comprising a sequence of nucleotide Nos. 3139-3157 of the human β-catenin gene (GenBank accession No. NM_001904.3)

Reference Example 10

Synthesis of HO-U$^{\prime p}$-U$^{\prime p}$-G$^{\prime p}$-U$^{\prime p}$-G$^{\prime p}$-A$^{\prime p}$-U$^{\prime p}$-C$^{\prime p}$-C$^{\prime p}$-A$^{\prime p}$-U$^{\prime p}$-U$^{\prime p}$-C$^{\prime p}$-U$^{\prime p}$-U$^{\prime p}$-G$^{\prime p}$-U$^{\prime p}$-G$^{\prime p}$-C$^{\prime t}$-H (SEQ ID NO: 101 of the Sequence Listing) (CT-126)

CT-126 was synthesized in the same way as for Example 1.

Molecular weight: calculated value: 5953.54, measured value: 5953.38).

Nucleotide sequence: comprising a sequence complementary to nucleotide Nos. 3139-3157 of the human β-catenin gene (GenBank accession No. NM_001904.3)

Reference Example 11

Synthesis of HO-G$^{\prime p}$-G$^{\prime p}$-A$^{\prime p}$-C$^{\prime p}$-A$^{\prime p}$-A$^{\prime p}$-G$^{\prime p}$-G$^{\prime p}$-A$^{\prime p}$-A$^{\prime p}$-G$^{\prime p}$-C$^{\prime p}$-U$^{\prime p}$-G$^{\prime p}$-C$^{\prime p}$-A$^{\prime p}$-G$^{\prime p}$-A$^{\prime p}$-A$^{\prime p}$-T$^p$-T$^t$-H (SEQ ID NO: 115 of the Sequence Listing) (CT-165)

CT-165 was synthesized in the same way as for Example 1.

Molecular weight: calculated value: 6818.28, measured value: 6818.27

Nucleotide sequence: comprising a sequence of nucleotide Nos. 2137-2155 of the human β-catenin gene (GenBank accession No. NM_001904.3)

Reference Example 12

Synthesis of HO-U$^{\prime p}$-U$^{\prime p}$-C$^{\prime p}$-U$^{\prime p}$-G$^{\prime p}$-C$^{\prime p}$-A$^{\prime p}$-G$^{\prime p}$-C$^{\prime p}$-U$^{\prime p}$-U$^{\prime p}$-C$^p$-C$^{\prime p}$-U$^{\prime p}$-U$^{\prime p}$-G$^{\prime p}$-U$^{\prime p}$-C$^{\prime p}$-C$^{\prime p}$-T$^p$-T$^t$-H (SEQ ID NO: 116 of the Sequence Listing) (CT-166)

CT-166 was synthesized in the same way as for Example 1.

Molecular weight: calculated value: 6496.90, measured value: 6496.99

Nucleotide sequence: comprising a sequence complementary to nucleotide Nos. 2137-2155 of the human β-catenin gene (GenBank accession No. NM_001904.3)

Example 104

Annealing for Formation of Double-Stranded Polynucleotide

The polynucleotides synthesized in the above Examples and Reference Examples were placed in the combinations shown in Tables 1 and 2 into one tube at concentrations of 300 pmol of each sense and antisense strand and dried under reduced pressure. 30 μL of an siRNA suspension buffer (QIAGEN) was added thereto, and the mixture was heated at 65° C. for 1 minute and then left at room temperature for 5 minutes for annealing of the sense and antisense strands to obtain a 10 μM double-stranded polynucleotide solution.

Reference Example 13

Double-stranded RNA was purchased from Ambion (Silencer Pre-designed siRNA, Gene Symbol: DDX3X, Locus ID: 1654 [Ambion] siRNA ID #145804) and used. Hereinafter, this RNA is referred to as DDX3 siRNA#5 (SEQ ID NOS: 117 and 118 of the

SEQUENCE LISTING

TABLE 1

| | | | |
|---|---|---|---|
| CT-105 | CT-041 | CT-115 | CT-092 |
| CT-106 | CT-111 | CT-135 | CT-092 |
| CT-106 | CT-041 | CT-137 | CT-092 |
| CT-091 | CT-092 | CT-119 | CT-120 |
| CT-101 | CT-092 | CT-119 | CT-092 |
| CT-102 | CT-092 | CT-091 | CT-120 |
| CT-091 | CT-107 | CT-091 | CT-116 |
| CT-091 | CT-108 | CT-091 | CT-117 |
| CT-103 | CT-109 | CT-091 | CT-118 |
| CT-095 | CT-096 | CT-113 | CT-092 |
| CT-097 | CT-098 | CT-114 | CT-092 |
| CT-099 | CT-100 | CT-115 | CT-092 |
| CT-097 | CT-092 | CT-115 | CT-118 |
| CT-091 | CT-098 | CT-136 | CT-092 |
| CT-127 | CT-092 | CT-138 | CT-092 |
| CT-128 | CT-092 | CT-001 | CT-092 |
| CT-129 | CT-092 | CT-139 | CT-141 |
| CT-101 | CT-092 | CT-140 | CT-141 |
| CT-130 | CT-092 | CT-097S | CT-098S |
| CT-131 | CT-092 | CT-114L | CT-092 |
| CT-112 | CT-092 | CT-091 | CT-149 |
| CT-114 | CT-092 | | |

TABLE 2

Double-stranded polynucleotide

| Sense strand | Antisense strand | Sense strand | Antisense strand |
|---|---|---|---|
| CT-125 | CT-126 | CT-103 | CT-157 |
| CT-103 | CT-092 | CT-103 | CT-221 |
| CT-091 | CT-109 | CT-103 | CT-222 |
| CT-103 | CT-109 | CT-103 | CT-223 |
| CT-103 | CT-149 | CT-169 | CT-157 |
| CT-106 | CT-041 | CT-169 | CT-221 |
| CT-103 | CT-149 | CT-169 | CT-222 |
| CT-103 | CT-155 | CT-169 | CT-223 |
| CT-103 | CT-156 | CT-172 | CT-202 |
| CT-103 | CT-157 | CT-169 | CT-203 |
| CT-103 | CT-158 | CT-210 | CT-211 |
| CT-103 | CT-159 | CT-210 | CT-212 |
| CT-103 | CT-160 | CT-169 | CT-243 |
| CT-103 | CT-161 | CT-169 | CT-244 |
| CT-103 | CT-162 | CT-169 | CT-245 |
| CT-169 | CT-149 | CT-169 | CT-246 |
| CT-170 | CT-149 | CT-169 | CT-205 |
| CT-171 | CT-149 | CT-169 | CT-247 |
| CT-172 | CT-149 | CT-169 | CT-248 |
| CT-173 | CT-149 | CT-169 | CT-249 |
| CT-174 | CT-149 | CT-169 | CT-254 |
| CT-175 | CT-149 | CT-169 | CT-255 |
| CT-176 | CT-149 | CT-169 | CT-256 |
| CT-177 | CT-149 | CT-169 | CT-257 |
| CT-103 | CT-204 | CT-169 | CT-258 |
| CT-103 | CT-205 | CT-169 | CT-253 |
| CT-103 | CT-206 | CT-169 | CT-264 |
| CT-103 | CT-207 | CT-169 | CT-265 |
| CT-103 | CT-208 | CT-169 | CT-266 |
| CT-103 | CT-209 | CT-169 | CT-267 |

TABLE 3

Double-stranded polynucleotide

| Sense strand | Antisense strand | Sense strand | Antisense strand |
|---|---|---|---|
| CT-169 | CT-157 | CT-278 | CT-281 |
| CT-288 | CT-289 | DDX3 | siRNA #5 |

TABLE 3-continued

Double-stranded polynucleotide

| Sense strand | Antisense strand | Sense strand | Antisense strand |
|---|---|---|---|
| CT-288 | CT-157 | DD-016 | DD-017 |
| CT-169 | CT-289 | DD-022 | DD-017 |
| CT-165 | CT-166 | DD-022 | DD-023 |
| CT-278 | CT-279 | DD-022 | DD-024 |
| CT-278 | CT-280 | CT-169S | CT-157S |

Test Example 1

(1) Transfection

A human colon cancer SW480 cell strain (derived from human adenocarcinoma of the large intestine) was cultured in an RPMI1640 medium (Invitrogen Corp.) containing 10% fetal bovine serum. The culture solution of SW480 was seeded at a concentration of 100000 cells/well onto a 12-well plate and cultured overnight. Next, a lipofection reagent, HiPerFect Transfection Reagent (QIAGEN), at a final concentration of 0.5% and a double-stranded polynucleotide solution at a final concentration of 30, 3, 0.3, or 0.03 nM (or 30, 3, 1, 0.3, 0.1, or 0.03 nM) were added to each well, and the culture was further continued for 3 days. Then, the medium was removed, and the cells were washed with PBS (phosphate buffered saline) and then lysed by the direct addition of 100 pt of Laemmli Sample Buffer containing 5% 2-mercaptoethanol. The cell lysate was collected into a tube and then heated at 100° C. for 5 minutes to effect protein denaturation. The structures and nucleotide sequences of the double-stranded polynucleotides are shown in FIGS. 1, 2, 4, 6, 7, 8, 9, 13, 14, 16, 18, 20, and 21.

(2) Western Blot Analysis

Each sample (1 μg in terms of protein amount) was separated by polyacrylamide gel electrophoresis (5-20% gradient gel) and electrically transferred to a nitrocellulose membrane. The membrane was blocked with a 5% skim milk solution. Then, β-catenin proteins were detected using rabbit anti-β-catenin antibodies (Cell Signaling Technology, Inc.) as primary antibodies and HRP-labeled anti-rabbit IgG antibodies (GE Healthcare Life Sciences) as secondary antibodies. β-actin proteins were detected as a negative control using anti-β-actin monoclonal antibodies (GE Healthcare Life Sciences) and HRP-labeled anti-mouse IgG antibodies (GE Healthcare Life Sciences). Each protein detection was performed by visualization based on High Performance Chemiluminescence Film (GE Healthcare Life Sciences) photosensitized with chemiluminescence generated with Western Lightning (PerkinElmer Life Sciences) as a substrate.

(3) Results of Western Blot Analysis (a) Gene Expression Inhibitory Activities of Double-Stranded Polynucleotides Synthesized as Reference Examples The experiment was carried out on a double-stranded polynucleotide consisting of the combination CT-106/CT-041 in which all nucleotides in the double-stranded polynucleotide consisted of RNAs (hereinafter, each double-stranded polynucleotide may be indicated only in the combination of sense and antisense strands, i.e., for example, the double-stranded polynucleotide consisting of the combination CT-106/CT-041 may be simply referred to as "CT-106/CT-041"), and on double-stranded polynucleotides CT-104/CT-110, CT-105/CT-111, CT-105/CT-041, and CT-106/CT-111 in which some or all of RNAs constituting the double-stranded polynucleotide were substituted by DNAs. The structures of these double-stranded polynucleotides are shown in FIG. 1.

Figure 3:
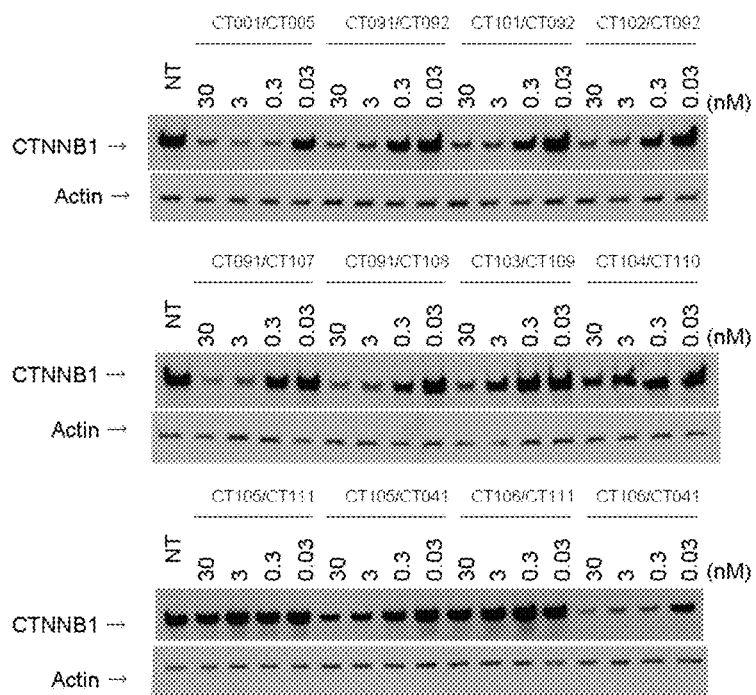
FIG. 3 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene. In the diagram, the notation "CT001/CT005" means "CT-001/CT-005"; thus, the "hyphen: -" in the notations of double-stranded polynucleotides may be omitted. The same holds true for the diagrams shown below.
Figure 4:
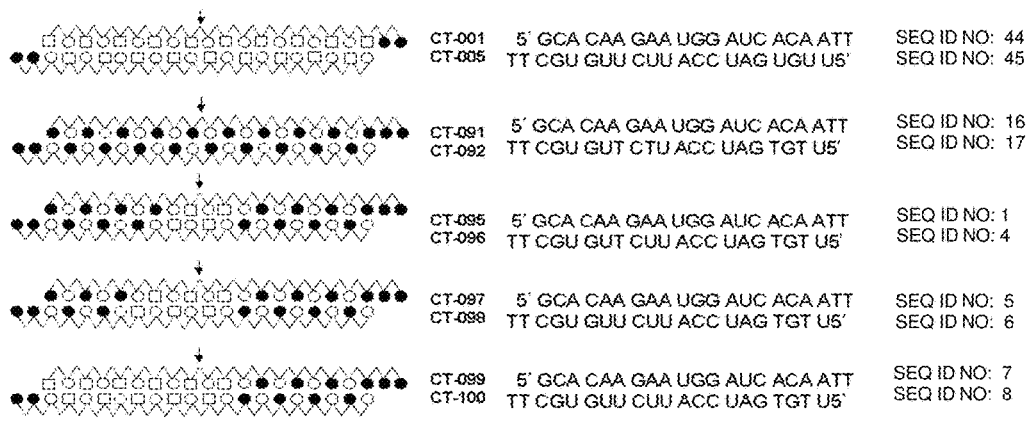
FIG. 4 is a diagram showing double-stranded polynucleotides against the human β-catenin gene.

As shown in FIG. 3, CT-106/CT-041 strongly inhibited the expression of the human β-catenin gene. On the other hand, CT-104/CT-110, CT-105/CT-111, CT-105/CT-041, and CT-106/CT-111 displayed little or no inhibition of the expression of the β-catenin gene. These results demonstrated that strong inhibitory effect on gene expression is lost by substituting DNAs for either or both of the sense and antisense strands of a double-stranded polynucleotide, the 3' sequence of the sense strand, or the 5' sequence of the antisense strand. This result was mostly consistent with the previously reported results (EMBO J., 20, p. 6877-6888 (2001); Nucleic Acids Res. 30, p. 1757-1766 (2002); and RNA, 9, p. 1034-1048, (2003)).

(b) Analysis of Gene Inhibitory Activities of Double-Stranded Polynucleotides-1-

CT-001/CT-005 comprising RNAs alternated with 2'-O-methyl RNAs, and DNAs in the overhang moiety (see FIG. 2) inhibited the expression of the human β-catenin gene at a level equivalent to CT-106/CT-041 in which all nucleotides consisted of RNAs (FIG. 3). In the subsequent experiments, CT-001/CT-005 was used as a control.

Double-stranded polynucleotides CT-091/CT-092, CT-095/CT-096, CT-097/CT-098, and CT-099/CT-100 in which RNAs in CT-001/CT-005 were partially (from the end) or wholly substituted by DNAs (for their structures, see FIG. 4) were examined for their gene expression inhibitory activities.

Figure 5:
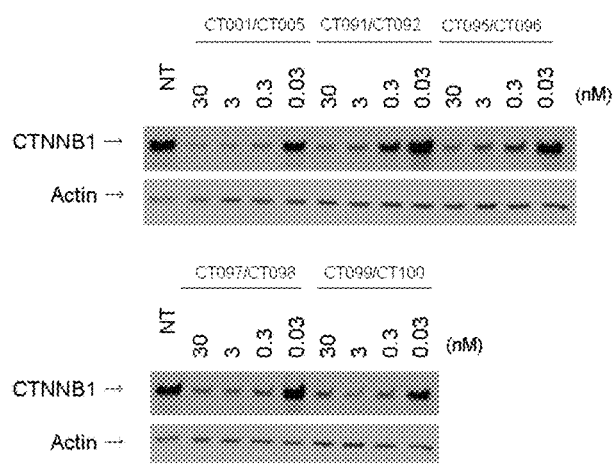
FIG. 5 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 6:
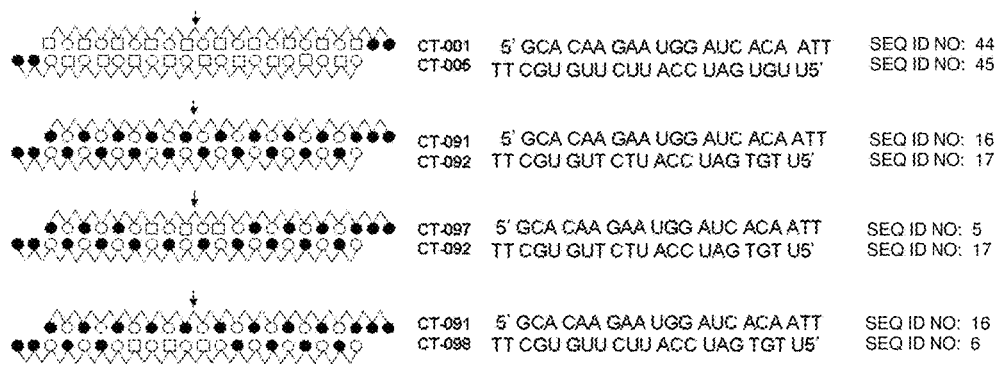
FIG. 6 is a diagram showing double-stranded polynucleotides against the human β-catenin gene.

As shown in FIG. 5, CT-091/CT-092, CT-095/CT-096, CT-097/CT-098, and CT-099/CT-100 strongly inhibited the expression of the human β-catenin gene. Particularly, CT-095/CT-096, CT-097/CT-098, and CT-099/CT-100 inhibited the gene expression at a level equivalent to CT-001/CT-005. This shows that a double-stranded polynucleotide comprising alternately located 2' methyl RNAs or DNAs and partially having RNAs (or having no RNA in some cases) has strong gene expression inhibitory activity.

(c) Analysis of Gene Inhibitory Activities of Double-Stranded Polynucleotides-2-

Figure 10:
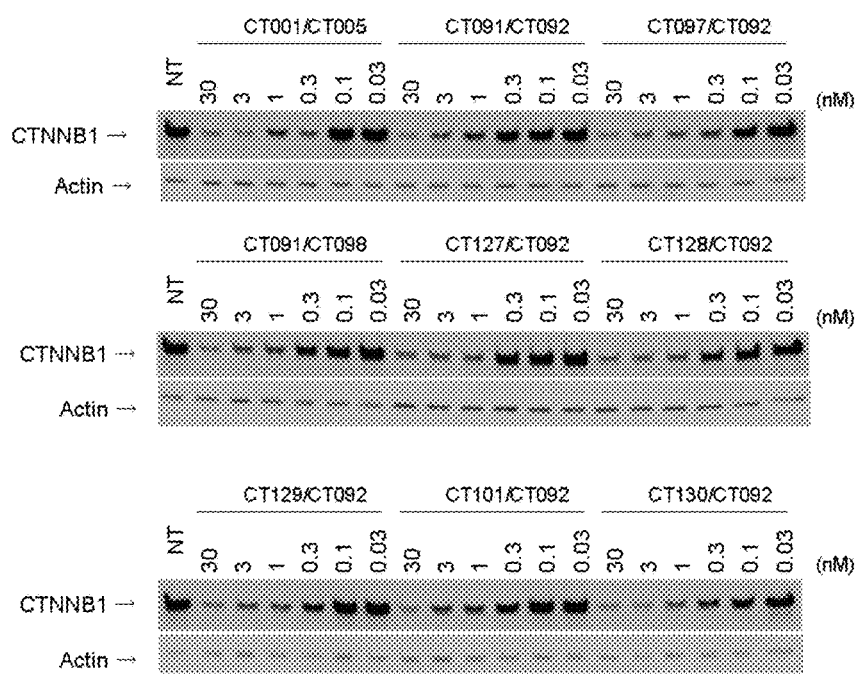
FIG. 10 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

Results of experiment on double-stranded polynucleotides CT-091/CT-092, CT-097/CT-092, and CT-091/CT-098 (see FIG. 6) are shown in FIG. 10.

Both the double-stranded polynucleotides CT-097/CT-092 and CT-091/CT-098 strongly inhibited the expression of the β-catenin gene. Particularly CT-097/CT-092 inhibited the gene expression more strongly than the double-stranded polynucleotide CT-091/CT-098 and comparably to CT-001/CT-005. These results demonstrated that as seen in CT-097/CT-092, strong gene expression inhibitory activity can be retained even if a site other than the central portion of the sense strand of a double-stranded polynucleotide is substituted by 2'-O-methyl RNAs or DNAs.

(d) Analysis of Gene Inhibitory Activities of Double-Stranded Polynucleotides-3-

Figure 7:
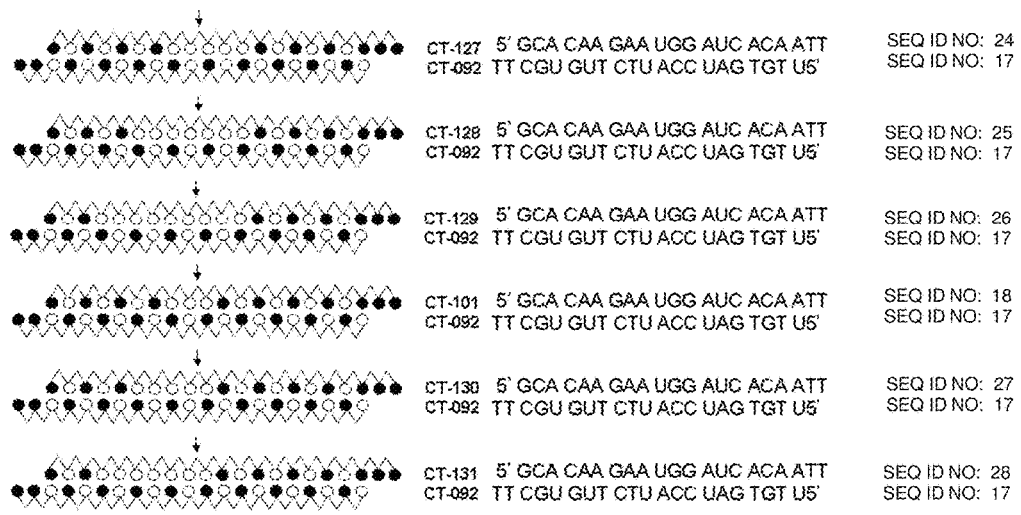
FIG. 7 is a diagram showing double-stranded polynucleotides against the human β-catenin gene.
Figure 8:
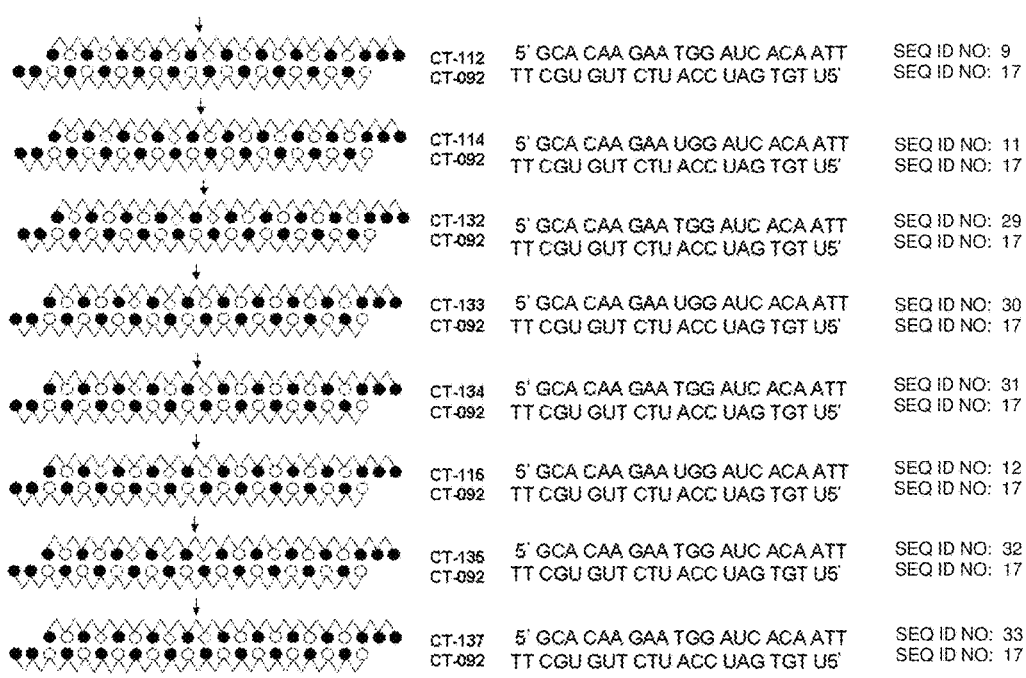
FIG. 8 is a diagram showing double-stranded polynucleotides against the human β-catenin gene.
Figure 9:
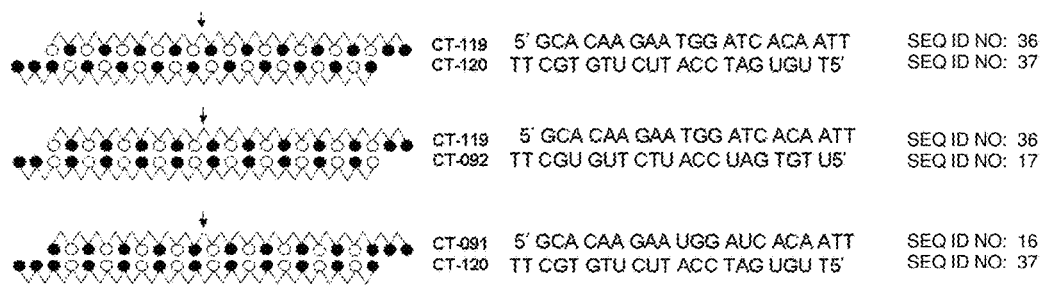
FIG. 9 is a diagram showing double-stranded polynucleotides against the human β-catenin gene.
Figure 11:
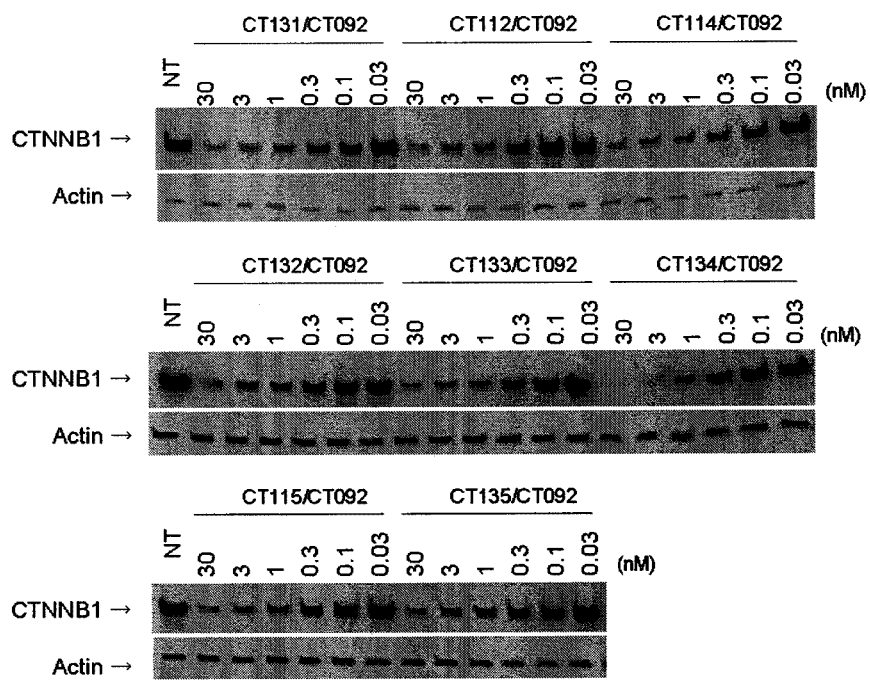
FIG. 11 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human (β-catenin gene.

Results are shown in FIGS. 10 and 11 as to double-stranded polynucleotides CT-127/CT-092, CT-128/CT-092, CT-129/CT-092, CT-101/CT-092, CT-130/CT-092, and CT-131/CT-092 in which a site other than the central portion of the sense strand of the double-stranded polynucleotide comprised 2'-O-methyl RNAs or DNAs and the central portion of the sense strand was substituted by 2'-O-methyl RNAs (see FIG. 7).

The double-stranded polynucleotides CT-127/CT-092, CT-128/CT-092, CT-129/CT-092, CT-101/CT-092, CT-130/ CT-092, and CT-131/CT-092 strongly inhibited the expression of the β-catenin gene. Particularly, CT-130/CT-092 exhibited gene expression inhibitory activity stronger than that of the double-stranded polynucleotide CT-091/CT-092 and comparable to that of CT-001/CT-005.

(e) Analysis of Gene Inhibitory Activities of Double-Stranded Polynucleotides-4-

Figure 12:
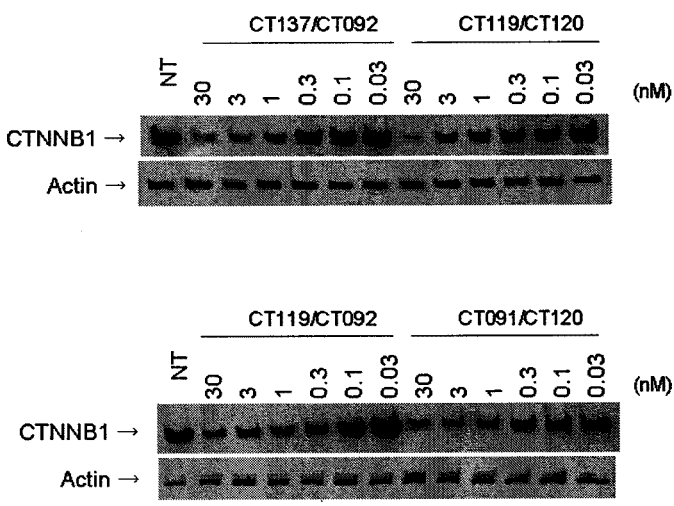
FIG. 12 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 13:
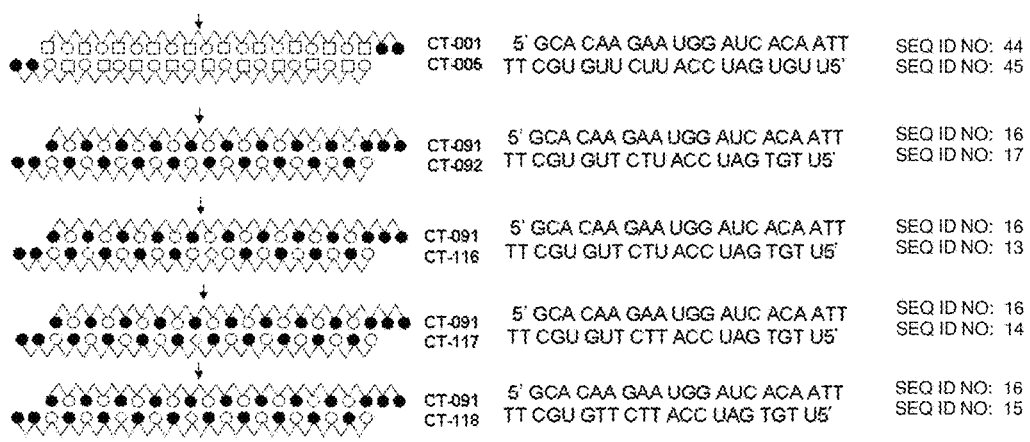
FIG. 13 is a diagram showing double-stranded polynucleotides against the human β-catenin gene.
Figure 14:
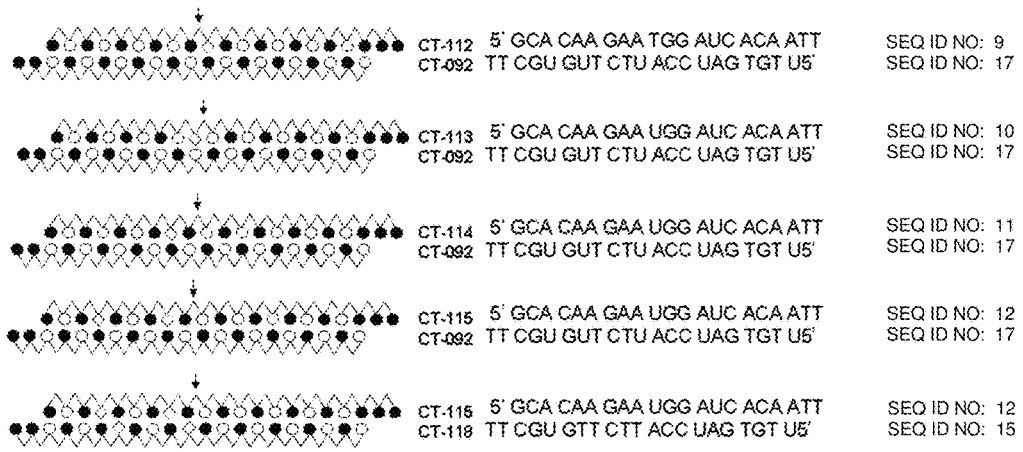
FIG. 14 is a diagram showing double-stranded polynucleotides against the human β-catenin gene.
Figure 17:
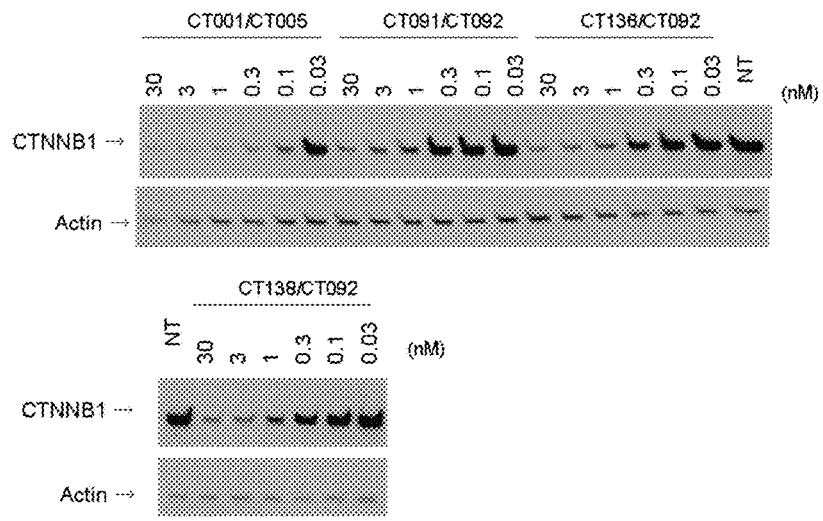
FIG. 17 is a diagram showing the results of western blot analysis of the inhibitory activities of double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 18:
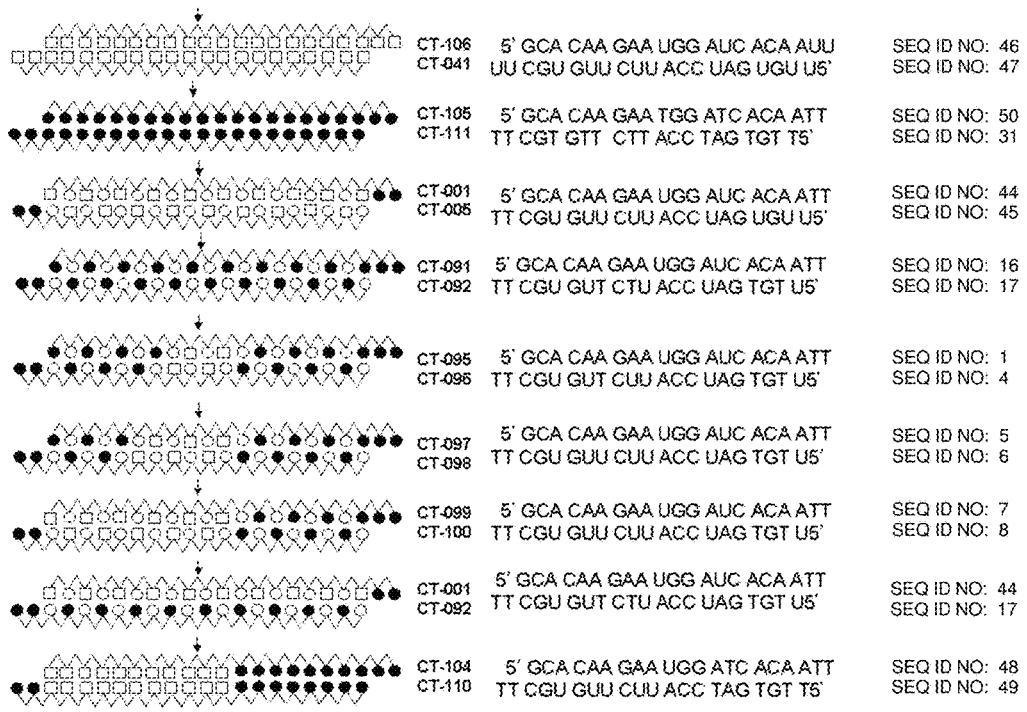
FIG. 18 is a diagram showing double-stranded polynucleotides against the human β-catenin gene used in an RNase degradation reaction.

Results are shown in FIGS. 11, 12, and 17 as to double-stranded polynucleotides CT-112/CT-092, CT-114/CT-092, CT-132/CT-092, CT-133/CT-092, CT-134/CT-092, CT-115/CT-092, CT-135/CT-092, and CT-137/CT-092 (see FIG. 8), CT-136/CT-092 and CT-138/CT-092 (see FIG. 16) in which a site other than the central portion of the sense strand of the double-stranded polynucleotide comprised 2'-O-methyl RNAs or DNAs and ENAs were introduced in the central portion of the sense strand.

The double-stranded polynucleotides CT-114/CT-092, CT-132/CT-092, CT-133/CT-092, CT-134/CT-092, CT-115/CT-092, CT-135/CT-092, CT-137/CT-092, CT-136/CT-092, and CT-138/CT-092 strongly inhibited the expression of the β-catenin gene. Particularly, CT-114/CT-092 inhibited the expression of the (β-catenin gene more strongly than the double-stranded polynucleotide CT-091/CT-092 shown in FIG. 10 and comparably to the double-stranded polynucleotide CT-001/CT-005 shown in FIG. 10.

(f) Analysis of Gene Inhibitory Activities of Double-Stranded Polynucleotides-5-

Figure 15:
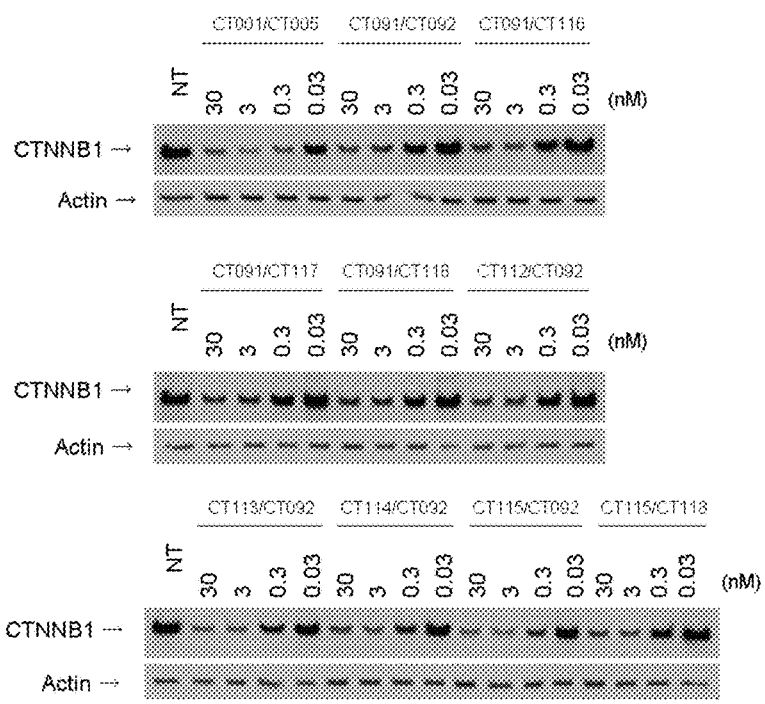
FIG. 15 is a diagram showing the results of western blot analysis of the inhibitory activities of double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 16:
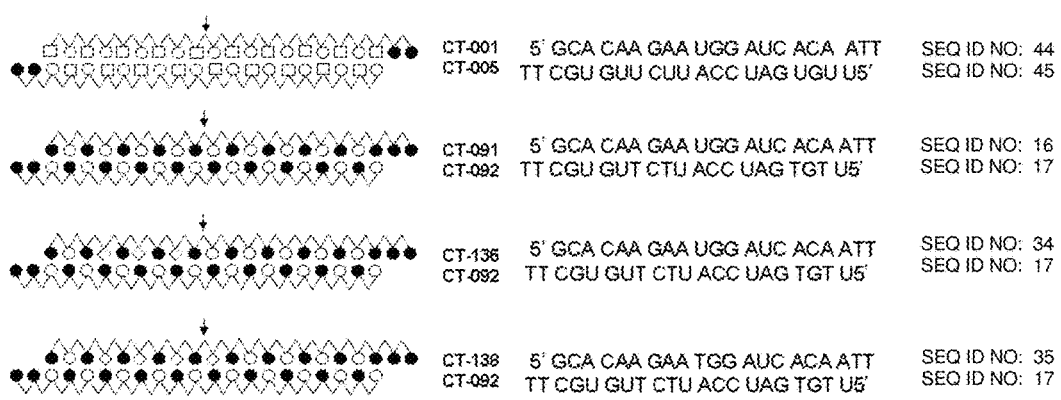
FIG. 16 is a diagram showing double-stranded polynucleotides against the human β-catenin gene.

Double-stranded polynucleotides CT-102/CT-092, CT-091/CT-107, and CT-091/CT-108 (see FIG. 2), CT-091/CT-116, CT-091/CT-117, and CT-091/CT-118 (see FIG. 13), CT-113/CT-092 and CT-115/CT-118 (see FIG. 14), in which a portion of the double-stranded polynucleotide CT-091/CT-092 was substituted by RNAs, ENAs, or 2'-O-methyl RNAs, were analyzed for their inhibitory activities on the expression of the human β-catenin gene, and the results are shown in FIGS. 3 and 15. All the double-stranded polynucleotides exhibited inhibitory activity on the expression of the human β-catenin gene equivalent to that of CT-091/CT-092.

Figure 2:
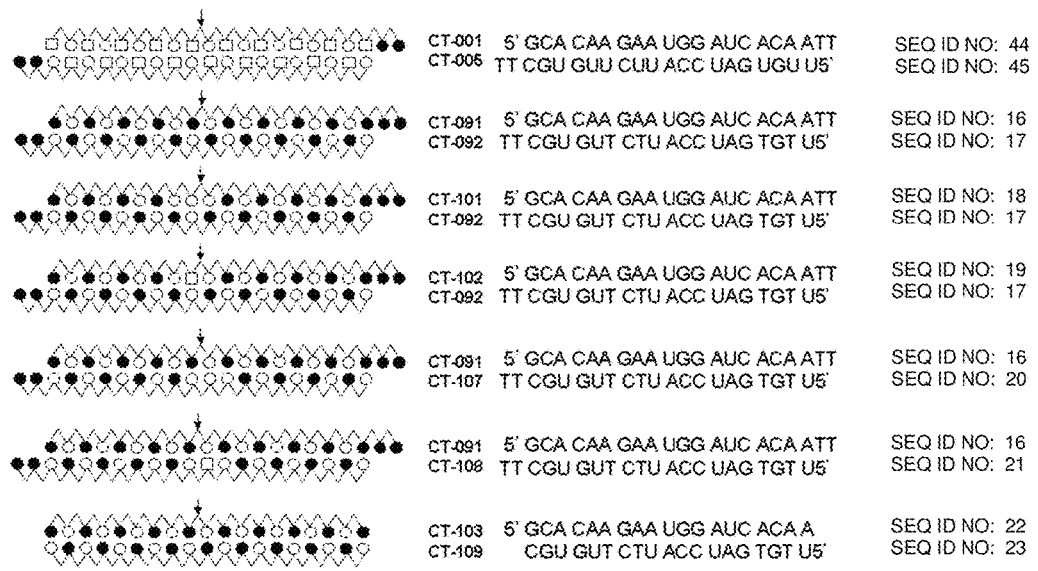
FIG. 2 is a diagram showing double-stranded polynucleotides against the human β-catenin gene.

(g) Comparison in Activity Based on Presence or Absence of Overhang Moiety of Double-Stranded Polynucleotide The intensity of gene expression inhibitory activity was compared between a double-stranded polynucleotide CT-091/CT-092 and its overhang moiety-free double-stranded polynucleotide CT-103/CT-109 (see FIG. 2). As shown in FIG. 3, CT-091/CT-092 having an overhang moiety inhibited the expression of the human β-catenin gene more strongly than overhang-free CT-103/CT-109. This shows that an overhang is important for designing a double-stranded polynucleotide.

(h) Analysis of Gene Inhibitory Activities of Double-Stranded Polynucleotides-6-

The inhibitory activities of CT-119/CT-120, in which the sequences of DNAs and 2'-O-methyl RNAs of the double-stranded polynucleotide CT-091/CT-092 were altered, and CT-119/CT-092 and CT-091/CT-120, in which the combinations of the sense and antisense strands of CT-091/CT-092 and CT-119/CT-120 were altered (see FIG. 9), on the expression of the human β-catenin gene are shown in FIG. 12. CT-119/CT-120, CT-119/CT-092, and CT-091/CT-120 inhibited the expression of the β-catenin gene, whereas CT-091/CT-092 (see FIG. 10) inhibited the gene expression more strongly.

Test Example 2

The intensity of gene expression inhibitory activity was compared among double-stranded polynucleotides as follows in the same way as in Test Example 1.

Figure 22:
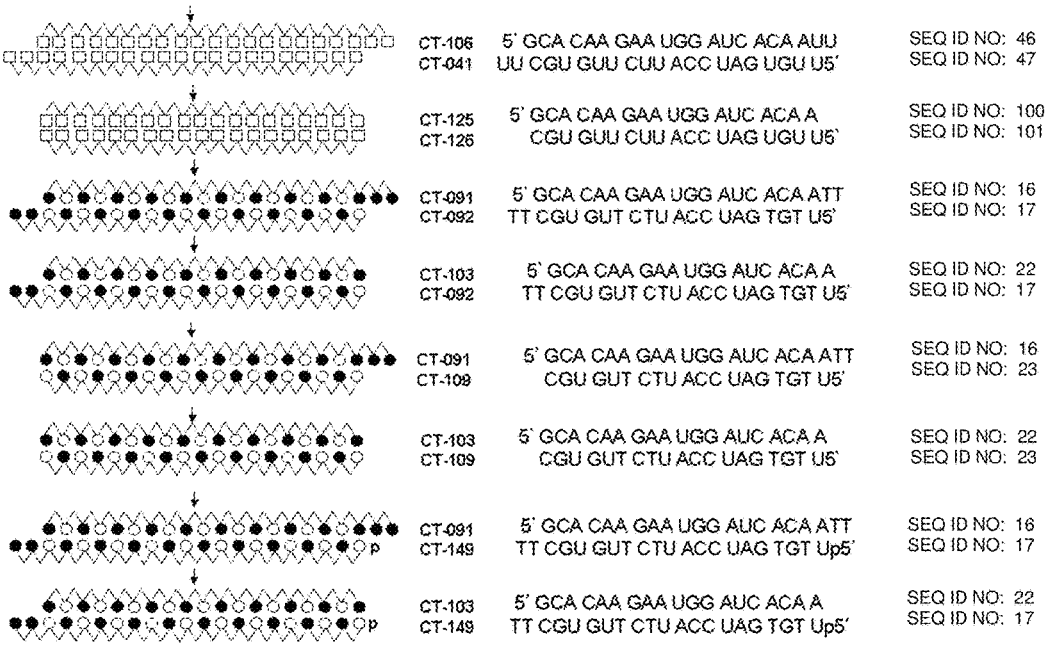
FIG. 22 is a diagram showing double-stranded polynucleotides against the human β-catenin gene.

(a) Comparison in Activity Based on Presence or Absence of Overhang Moiety and 5'-Phosphate Group of Double-Stranded Polynucleotide The intensity of gene expression inhibitory activity was compared in the same way as in Test Example 1 among a double-stranded polynucleotide CT-091/CT-092, a double-stranded polynucleotide CT-103/CT-109 having no overhang moiety at the 3'-ends of both the strands, CT-103/CT-092 having a 3'-terminal overhang moiety only in the antisense strand, CT-091/CT-109 having a 3'-terminal overhang moiety only in the sense strand, a double-stranded polynucleotide CT-091/CT-149 having an overhang moiety in both the strands and having a phosphate group at the 5'-end of the antisense strand, and a double-stranded polynucleotide CT-091/CT-149 having a 3'-terminal overhang moiety and a 5'-terminal phosphate group in the antisense strand (see FIG. 22).

Figure 23:
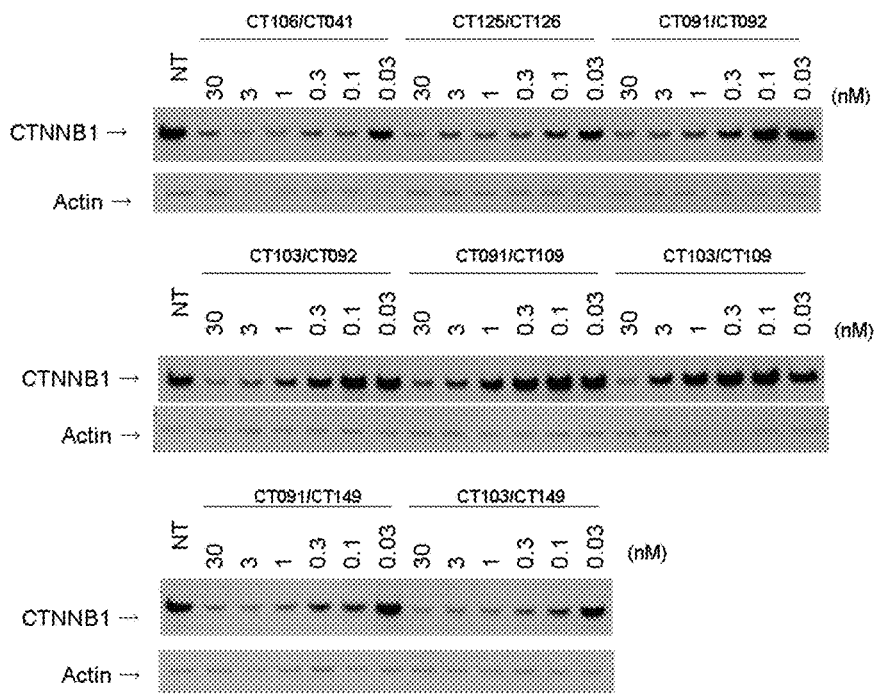
FIG. 23 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 23, CT-091/CT-092 and CT-103/CT-092 having an overhang moiety at the 3'-end of the antisense strand inhibited the expression of the human β-catenin gene more strongly than CT-103/CT-109 and CT-091/CT-109 having no overhang at the 3'-end of the antisense strand. Moreover, the double-stranded polynucleotide CT-091/CT-149 having a phosphate group at the 5'-end of the antisense strand inhibited the expression of the human β-catenin gene more strongly than the double-stranded polynucleotide CT-091/CT-092 having no 5'-terminal phosphate group. CT-103/CT-149 having a phosphate group at the 5'-end of the antisense strand inhibited the expression of the human β-catenin gene more strongly than the double-stranded polynucleotide CT-103/CT-092 having no 5'-terminal phosphate group. This shows that the 5'-terminal phosphate group and 3'-terminal overhang of an antisense strand are important for designing a double-stranded polynucleotide.

Figure 24:
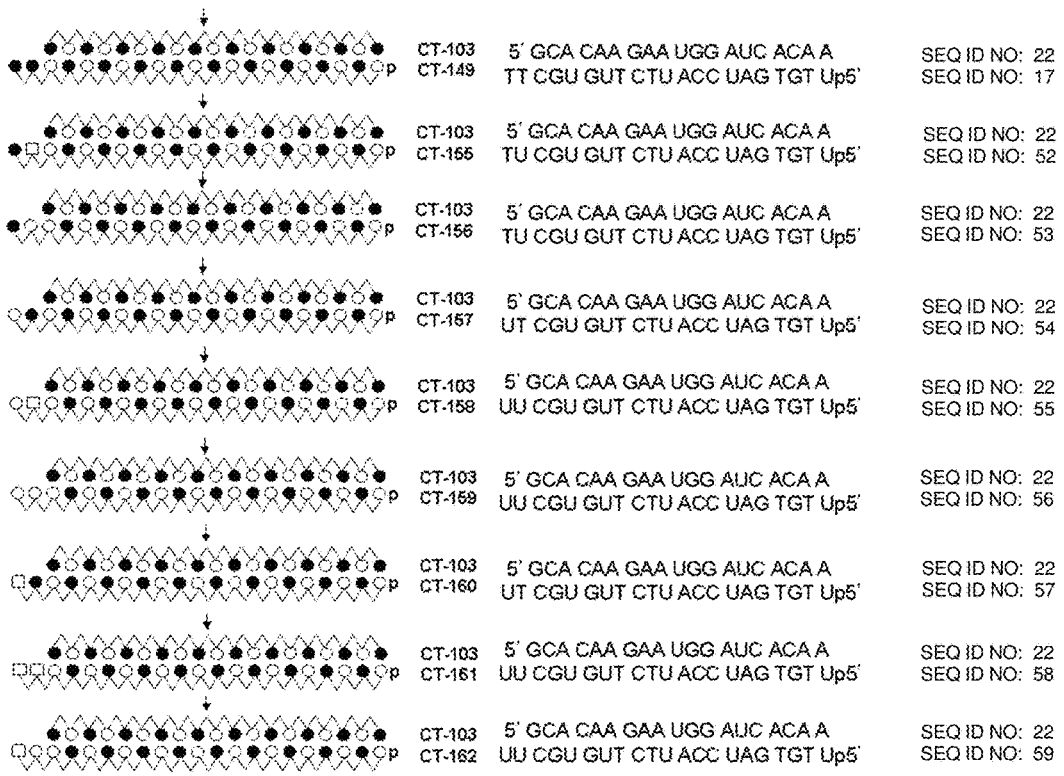
FIG. 24 is a diagram showing double-stranded polynucleotides against the human β-catenin gene.

(b) Comparison in Activity Based on Difference in Nucleotides in 3'-Overhang Moiety of Antisense Strand of Double-Stranded Polynucleotide A double-stranded polynucleotide CT-103/CT-149 having a 5'-terminal phosphate group in the antisense strand has a TT dimer sequence of DNAs in the 3'-overhang moiety of the antisense strand (CT-149). The intensity of gene expression inhibitory activity was compared among double-stranded polynucleotides CT-103/CT-155, CT-103/CT-156, CT-103/CT-157, CT-103/CT-158, CT-103/CT-159, CT-103/CT-160, CT-103/CT-161, and, CT-103/CT-162 in which the thymidine dimer of DNAs in the 3'-overhang moiety of the antisense strand (CT-149) was converted into a dimer of uridine, thymidine, and 2'-O-methyluridine in various possible combinations (see FIG. 24).

Figure 25:
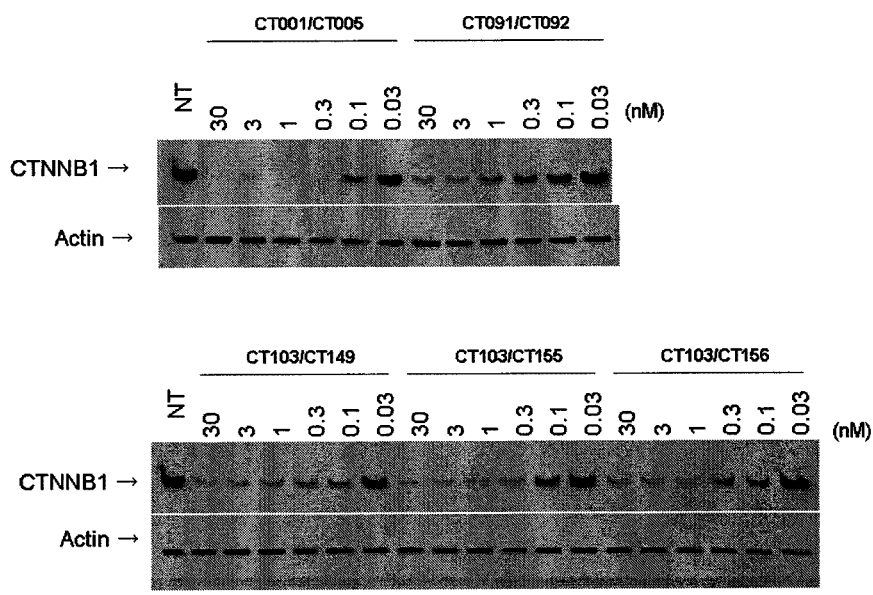
FIG. 25 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 26:
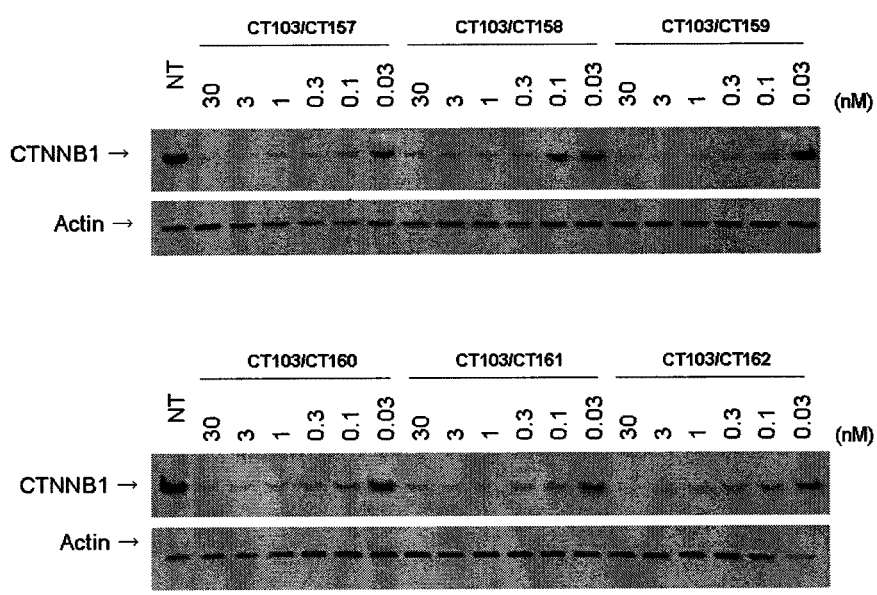
FIG. 26 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIGS. 25 and 26, CT-103/CT-155, CT-103/CT-156, CT-103/CT-157, CT-103/CT-158, CT-103/CT-159, CT-103/CT-160, CT-103/CT-161, and CT-103/CT-162 strongly inhibited the expression of the human β-catenin gene. Particularly CT-103/CT-157, CT-103/CT-158, CT-103/CT-159, CT-103/CT-160, CT-103/CT-161, and CT-103/CT-162 having 3'-terminal uridine or 2'-O-methyluridine more strongly inhibited the expression of the human β-catenin gene.

Figure 27:
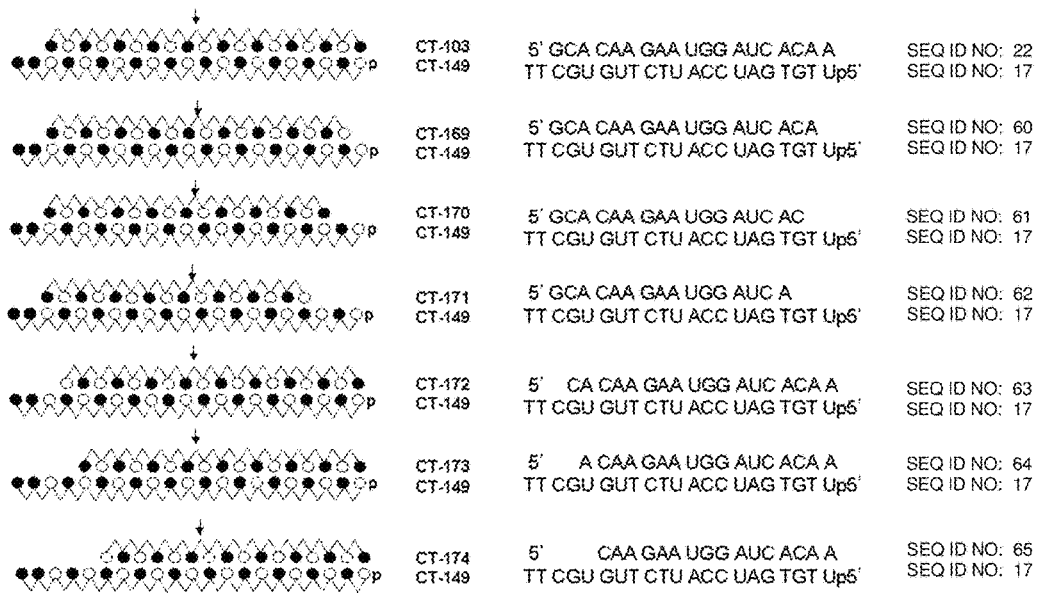
FIG. 27 is a diagram showing double-stranded polynucleotides against the human β-catenin gene.
Figure 29:
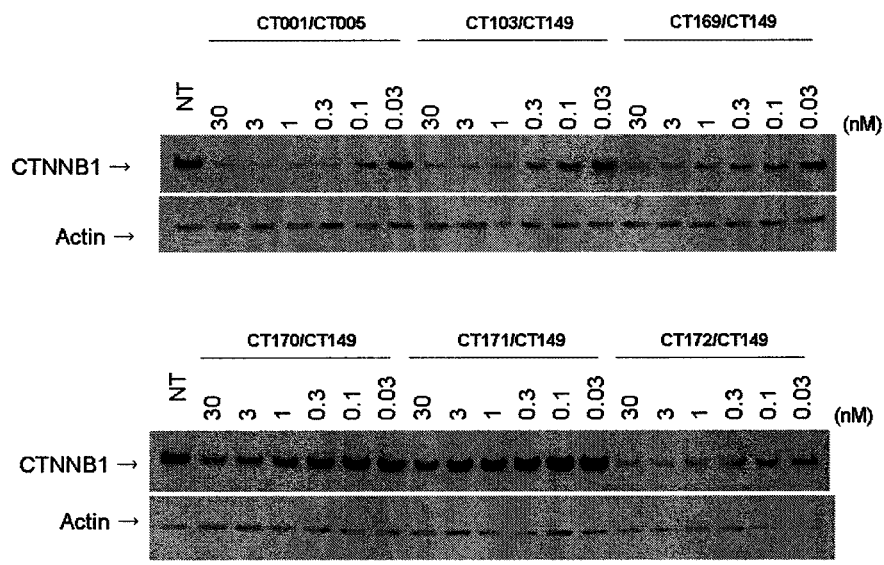
FIG. 29 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

(c) Comparison in Activity Among Double-Stranded Polynucleotides Having 3'- or 5'-Terminally Truncated Sense Strand The intensity of gene expression inhibitory activity was compared among double-stranded polynucleotides CT-169/CT-149, CT-170/CT-149, and CT-171/CT-149 in which 1 to 3 nucleotides were deleted from the 3'-end of the sense strand of the double-stranded polynucleotide CT-103/CT-149 (see FIG. 27). As shown in FIG. 29, the double-stranded polynucleotide CT-169/CT-149 in which 1 nucleotide was deleted from the 3'-end of the sense strand strongly inhibited the expression of the human β-catenin gene, as with CT-103/CT-149. However, the double-stranded polynucleotides CT-170/CT-149 and CT-171/CT-149 in which 2 or 3 nucleotides were deleted from the 3'-end of the sense strand had reduced inhibitory activity on the expression of the human β-catenin gene, compared with CT-103/CT-149.

Figure 30:
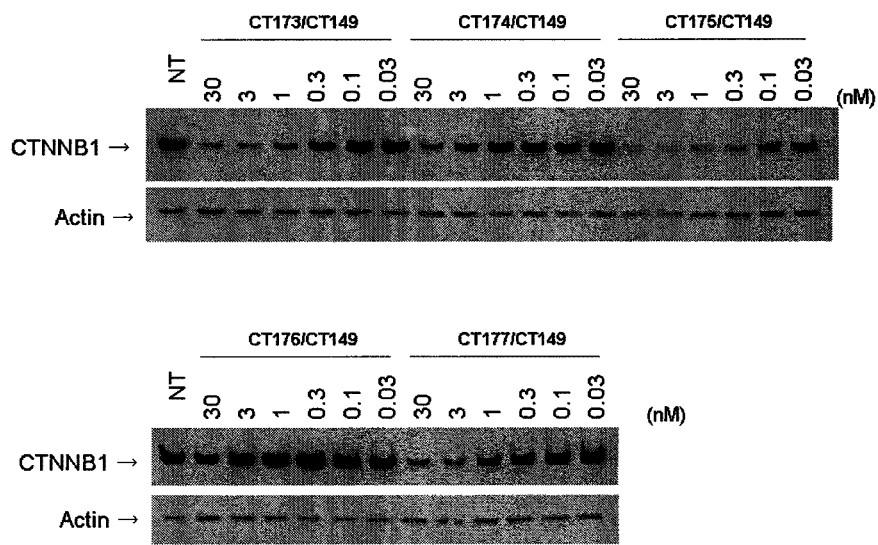
FIG. 30 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

The intensity of gene expression inhibitory activity was compared among double-stranded polynucleotides CT-172/CT-149, CT-173/CT-149, and CT-174/CT-149 in which 1 to 3 nucleotides were deleted from the 5'-end of the sense strand of the double-stranded polynucleotide CT-103/CT-149 (see FIG. 27). As shown in FIGS. 29 and 30, the double-stranded polynucleotide CT-172/CT-149 in which 1 nucleotide was deleted from the 5'-end of the sense strand strongly inhibited the expression of the human β-catenin gene, as with CT-103/CT-149. However, the double-stranded polynucleotides CT-173/CT-149 and CT-174/CT-149 in which 2 or 3 nucleotides were deleted from the 5'-end of the sense strand had reduced inhibitory activity on the expression of the human β-catenin gene, compared with CT-103/CT-149.

Figure 28:
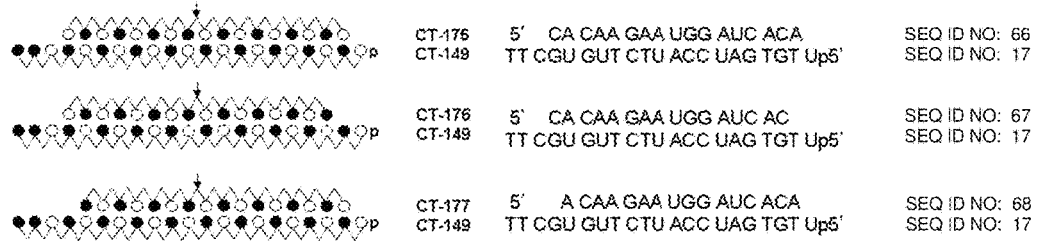
FIG. 28 is a diagram showing double-stranded polynucleotides against the human β-catenin gene.

The intensity of gene expression inhibitory activity was compared among double-stranded polynucleotides CT-175/CT-149, CT-176/CT-149, and CT-177/CT-149 in which 1 or 2 nucleotides were deleted from the 3' and 5'-ends of the sense strand of the double-stranded polynucleotide CT-103/CT-149 (see FIG. 28). As shown in FIGS. 29 and 30, the double-stranded polynucleotide CT-175/CT-149 in which 1 nucleotide was deleted from each of the 3' and 5'-ends of the sense strand strongly inhibited the expression of the human β-catenin gene, as with CT-103/CT-149. However, the double-stranded polynucleotides CT-176/CT-149 and CT-177/CT-149 in which 1 or 2 nucleotides were deleted from the 3' and 5'-ends of the sense strand had reduced inhibitory activity on the expression of the human β-catenin gene, compared with CT-103/CT-149.

This demonstrated that even a double-stranded polynucleotide of 18 or 17 base pairs obtained by deleting 1 nucleotide from either or both of the 3' and 5'-ends of a sense strand in its design exhibits gene expression inhibitory activity.

Figure 31:
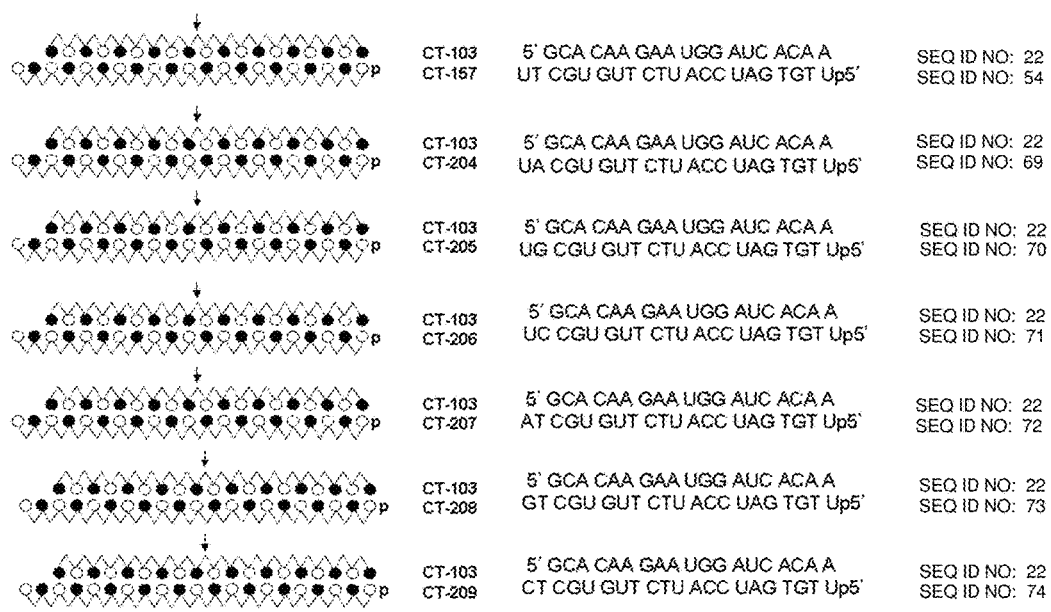
FIG. 31 is a diagram showing double-stranded polynucleotides against the human β-catenin gene.

(d) Comparison in Activity Based on Difference in Nucleotide Sequence of 3'-Overhang Moiety in Antisense Strand of Double-Stranded Polynucleotide A double-stranded polynucleotide CT-103/CT-157 having a 5'-terminal phosphate group in the antisense strand has a dimer sequence consisting of thymidine and 2'-O-methyluridine in the 3'-overhang moiety of the antisense strand (CT-157). The intensity of gene expression inhibitory activity was compared among double-stranded polynucleotides CT-103/CT-204, CT-103/CT-205, CT-103/CT-206, CT-103/CT-207, CT-103/CT-208, and CT-103/CT-209 in which the dimer sequence in the 3'-overhang moiety of the antisense strand (CT-157) was converted (see FIG. 31).

Figure 32:
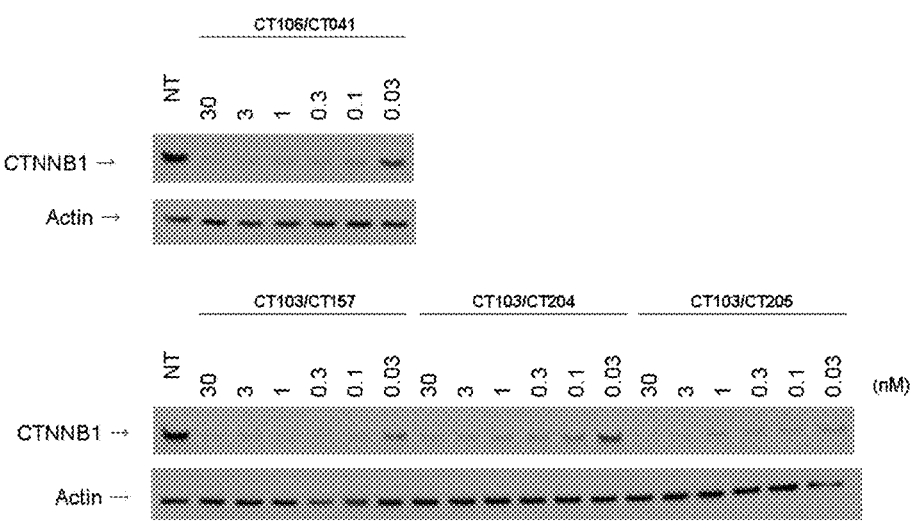
FIG. 32 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 33:
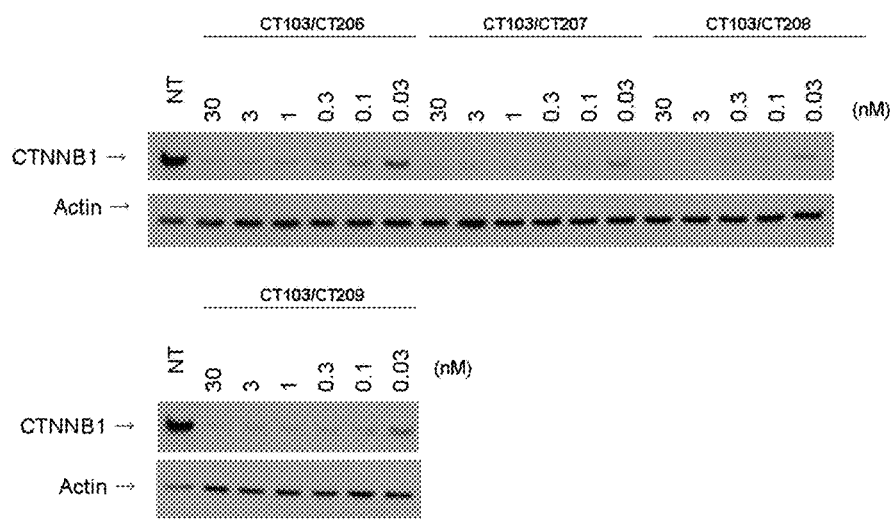
FIG. 33 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIGS. 32 and 33, CT-103/CT-204, CT-103/CT-205, CT-103/CT-206, CT-103/CT-207, CT-103/CT-208, and CT-103/CT-209 strongly inhibited the expression of the human β-catenin gene.

Figure 34:
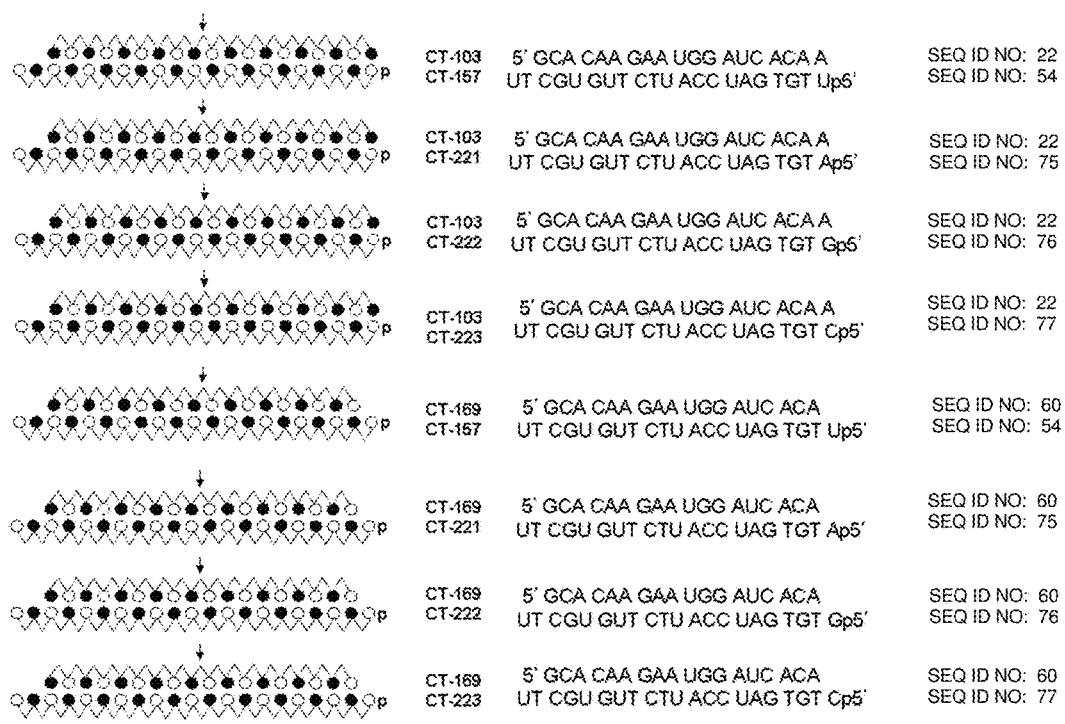
FIG. 34 is a diagram showing double-stranded polynucleotides against the human β-catenin gene.

(e) Comparison in Activity Based on Difference in 5'-Terminal Nucleotide Sequence of Antisense Strand of Double-Stranded Polynucleotide A double-stranded polynucleotide CT-103/CT-157 has 2'-O-methyluridine at the 5'-end of the antisense strand (CT-157). The intensity of gene expression inhibitory activity was compared among double-stranded polynucleotides CT-103/CT-221, CT-103/CT-222, and CT-103/CT-223 in which the base moiety of 5'-terminal 2'-O-methyluridine in the antisense strand (CT-157) was converted (see FIG. 34).

Figure 35:
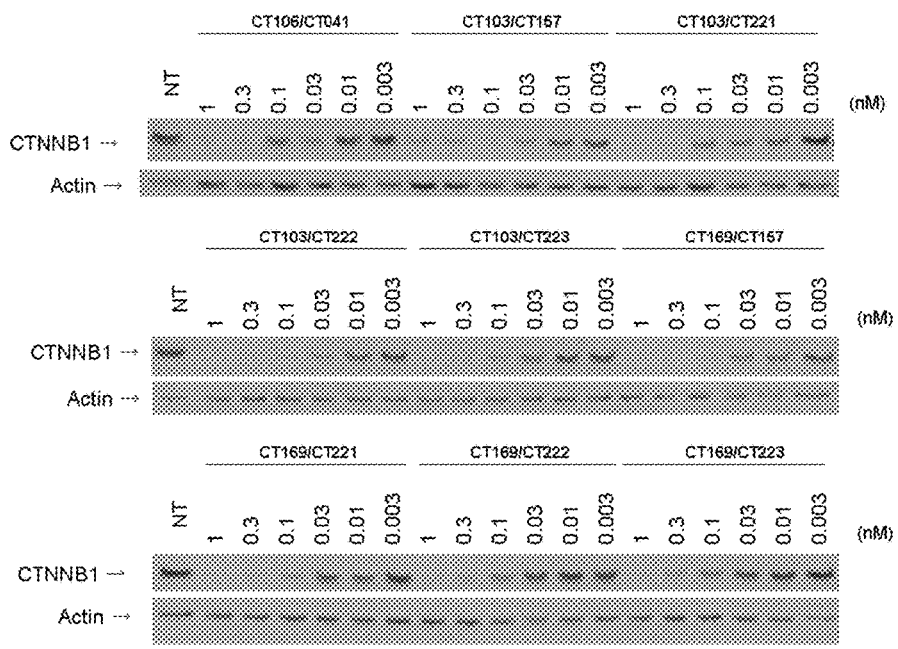
FIG. 35 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 35, CT-103/CT-221, CT-103/CT-222, and CT-103/CT-223 strongly inhibited the expression of the human β-catenin gene at a level equivalent to CT-103/CT-157.

Furthermore, CT-169/CT-157 in which 1 nucleotide was deleted from the 3'-end of the sense strand of the double-stranded polynucleotide CT-103/CT-157 (see FIG. 34) strongly inhibited the expression of the human β-catenin gene at a level equivalent to the double-stranded polynucleotide CT-103/CT-157 (see FIG. 35). The intensity of gene expression inhibitory activity was compared among double-stranded polynucleotides CT-169/CT-221, CT-169/CT-222, and CT-169/CT-223 in which the base moiety of 5'-terminal 2'-O-methyluridine in the antisense strand (CT-157) of the double-stranded polynucleotide CT-169/CT-157 was converted (see FIG. 34).

As shown in FIG. 35, CT-169/CT-221, CT-169/CT-222, and CT-169/CT-223 strongly inhibited the expression of the human β-catenin gene at a level equivalent to CT-169/CT-157.

Figure 36:
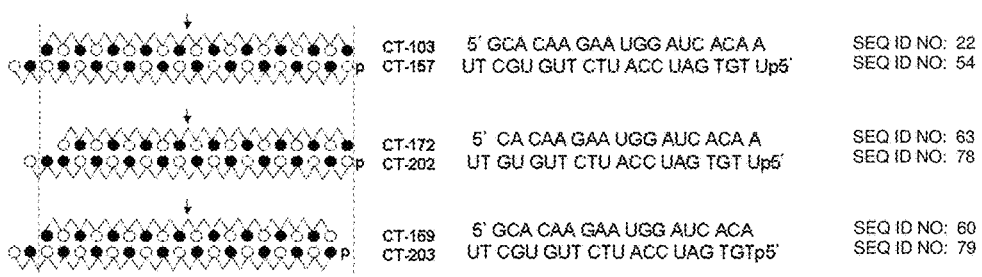
FIG. 36 is a diagram showing double-stranded polynucleotides against the human β-catenin gene.

(f) Gene Inhibitory Activities of Double-Stranded Polynucleotides Consisting of 18 Base Pairs A double-stranded polynucleotide CT-103/CT-157 having a 5'-terminal phosphate group in the antisense strand has a duplex structure of 19 base pairs. The intensity of gene expression inhibitory activity was compared between a double-stranded polynucleotide CT-172/CT-202 in which 1 base pair was deleted from the 5'-end of the sense strand and the 3'-end of the antisense, and a double-stranded polynucleotide CT-169/CT-203 in which 1 base pair was deleted from the 3'-end of the sense strand and the 5'-end of the antisense strand (see FIG. 36).

Figure 37:
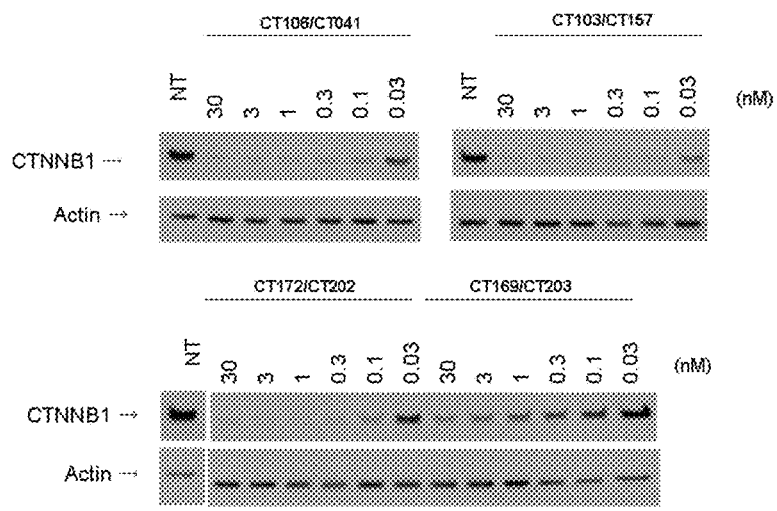
FIG. 37 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 37, CT-172/CT-202 and CT-169/CT-203 strongly inhibited the expression of the human β-catenin gene.

(g) Prevention of Off-Target of Asymmetric Double-Stranded Polynucleotide

Figure 38:
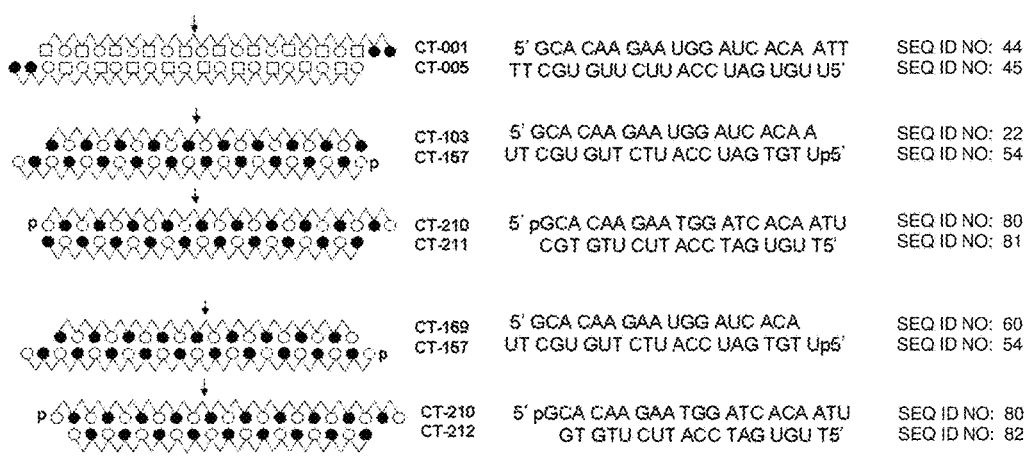
FIG. 38 is a diagram showing double-stranded polynucleotides against the human β-catenin gene.
Figure 39:
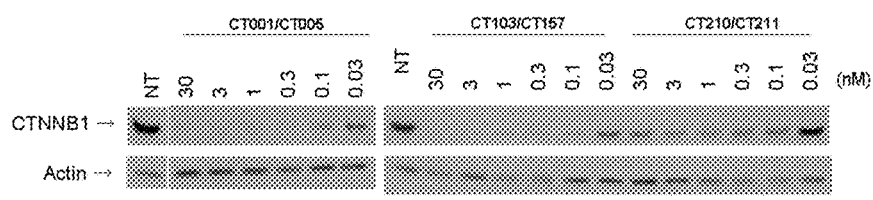
FIG. 39 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.
Figure 39:
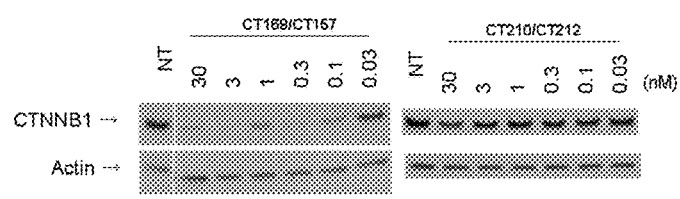

Focusing on the terminal structures of a double-stranded polynucleotide CT-103/CT-157 having a 5'-terminal phosphate group in the antisense strand, the sense and antisense strands are asymmetric. Specifically, in the double-stranded polynucleotide CT-103/CT-157, the antisense strand has a 5'-terminal phosphate group and a 3'-terminal overhang structure, while the sense strand has neither 5'-terminal phosphate group nor 3'-terminal overhang structure. Thus, a double-stranded polynucleotide CT-210/CT-211, in which the sense strand was allowed to have a 5'-terminal phosphate group and a 3'-terminal overhang structure and the antisense strand was allowed to have neither 5'-terminal phosphate group nor 3'-terminal overhang structure, was synthesized (see FIG. 38) to examine gene expression inhibitory activity depending on the antisense sequence having neither 5'-terminal phosphate group nor 3'-terminal overhang structure. As shown in FIG. 39, CT-210/CT-211 ended in slight reduction in activity compared with CT-103/CT-157.

In a double-stranded polynucleotide CT-169/CT-157, the antisense strand has a 5'-terminal phosphate group and a 3'-terminal overhang structure, while the sense strand has neither of them. Furthermore, it comprised 18 base pairs due to the deletion of 1 nucleotide from the 3'-end of the sense strand (CT-169). As in CT-103/CT-157, a double-stranded polynucleotide CT-210/CT-212, in which the sense strand was allowed to have a 5'-terminal phosphate group and a 3'-terminal overhang structure and the antisense strand was allowed to have neither 5'-terminal phosphate group nor 3'-terminal overhang structure, was synthesized (see FIG. 38) to compare, with CT-169/CT-157, gene expression inhibitory activity depending on the antisense sequence having neither 5'-terminal phosphate group nor 3'-terminal overhang structure.

As shown in FIG. 39, CT-210/CT-212 had significantly reduced activity compared with CT-169/CT-157. This shows that, among double-stranded polynucleotides having 18 base pairs consisting of a polynucleotide strand having a 5'-terminal phosphate group and a 3'-terminal overhang structure and a polynucleotide strand which is truncated by 1 nucleotide, a polynucleotide strand having a 5'-terminal phosphate group and a 3'-terminal overhang structure has gene expression inhibitory activity but a polynucleotide strand having neither a 5'-terminal phosphate group nor a 3'-terminal overhang structure does not have gene expression inhibitory activity.

Figure 40:
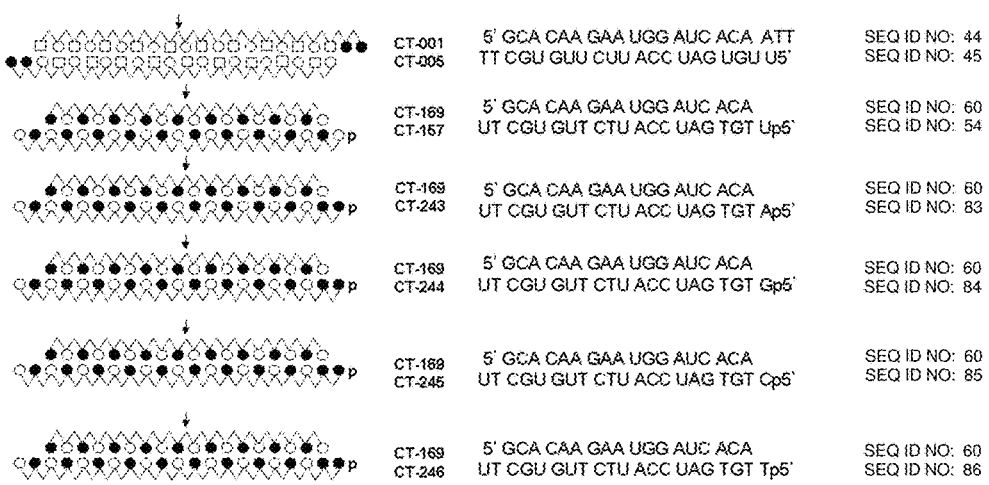
FIG. 40 is a diagram showing double-stranded polynucleotides against the human β-catenin gene.

(h) Comparison in Activity Based on Substitution of DNA for 5'-Terminal Nucleotide in Antisense Strand of Asymmetric Double-Stranded Polynucleotide An asymmetric double-stranded polynucleotide CT-169/CT-157 has 2'-O-methyluridine at the 5'-end of the antisense strand (CT-157). The intensity of gene expression inhibitory activity was compared among double-stranded polynucleotides CT-169/CT-243, CT-169/CT-244, CT-169/CT-245, and CT-169/CT-226 in which the 5'-terminal 2'-O-methyluridine in the antisense strand (CT-157) was substituted by a DNA (see FIG. 40).

Figure 41:
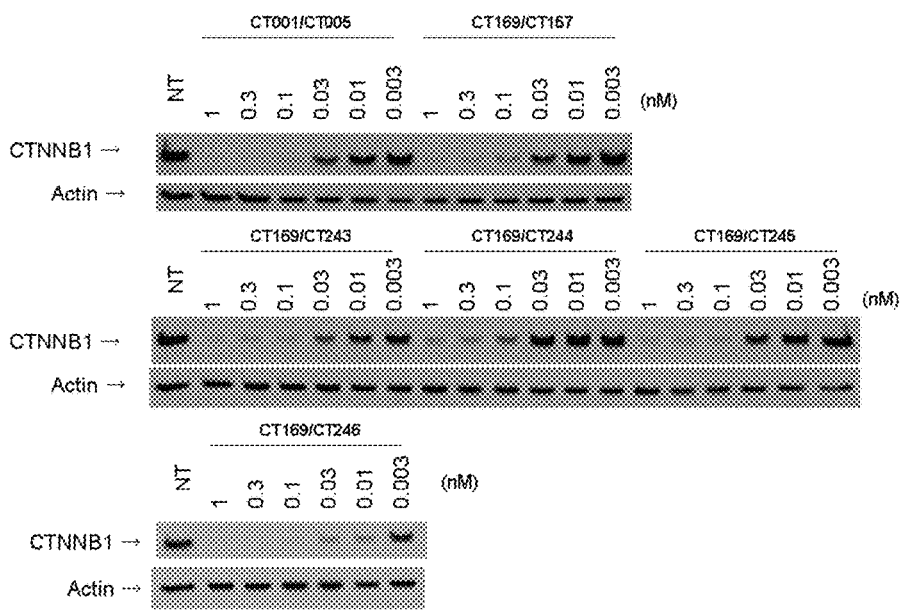
FIG. 41 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 41, CT-169/CT-243, CT-169/CT-244, and CT-169/CT-245 strongly inhibited the expression of the human β-catenin gene at a level equivalent to CT-169/CT-157 and CT-001/CT-005. Moreover, CT-169/CT-246 inhibited the expression of the human β-catenin gene more strongly than CT-169/CT-157 and CT-001/CT-005.

Figure 42:
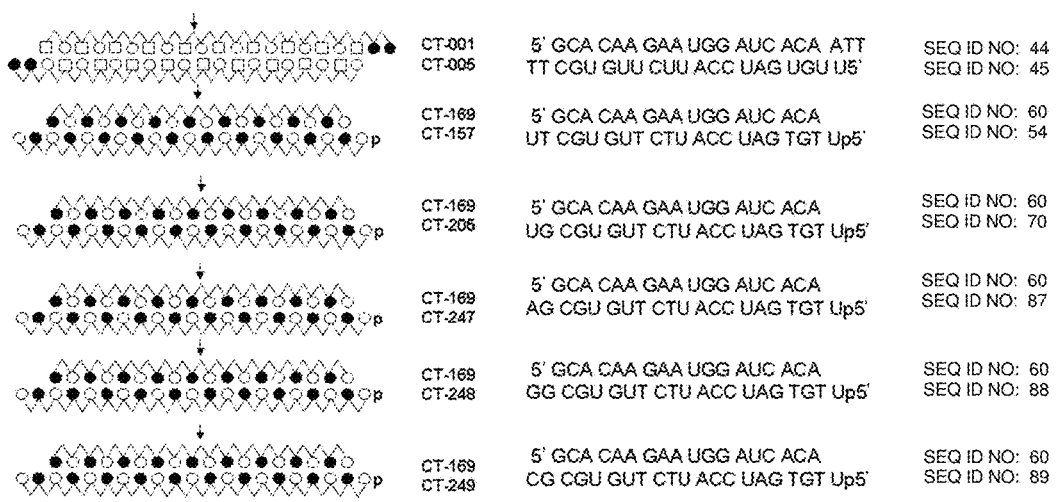
FIG. 42 is a diagram showing double-stranded polynucleotides against the human β-catenin gene.

(i) Comparison in Activity Based on Difference in Nucleotide Sequence of 3'-Overhang Moiety in Antisense Strand of Asymmetric Double-Stranded Polynucleotide An asymmetric double-stranded polynucleotide CT-169/CT-157 has a dimer sequence consisting of thymidine and 2'-O-methyluridine in the 3'-overhang moiety of the antisense strand. The intensity of gene expression inhibitory activity was compared among double-stranded polynucleotides CT-169/CT-205, CT-169/CT-247, CT-169/CT-248, and CT-169/CT-249 in which the dimer sequence of the 3'-overhang moiety in the antisense strand (CT-157) was converted (see FIG. 42).

Figure 43:
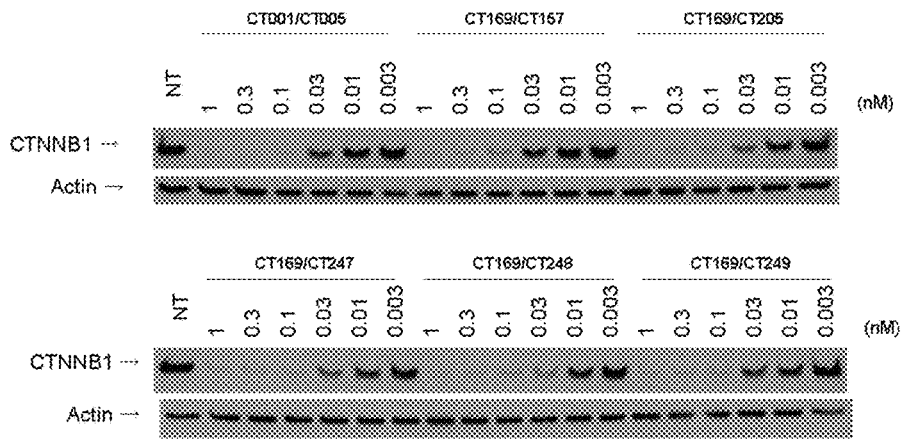
FIG. 43 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 43, CT-169/CT-205, CT-169/CT-247, and CT-169/CT-249 strongly inhibited the expression of the human β-catenin gene at a level equivalent to CT-169/CT-157 and CT-001/CT-005. Moreover, CT-169/CT-248 inhibited the expression of the human β-catenin gene more strongly than CT-169/CT-157 and CT-001/CT-005.

Figure 44:
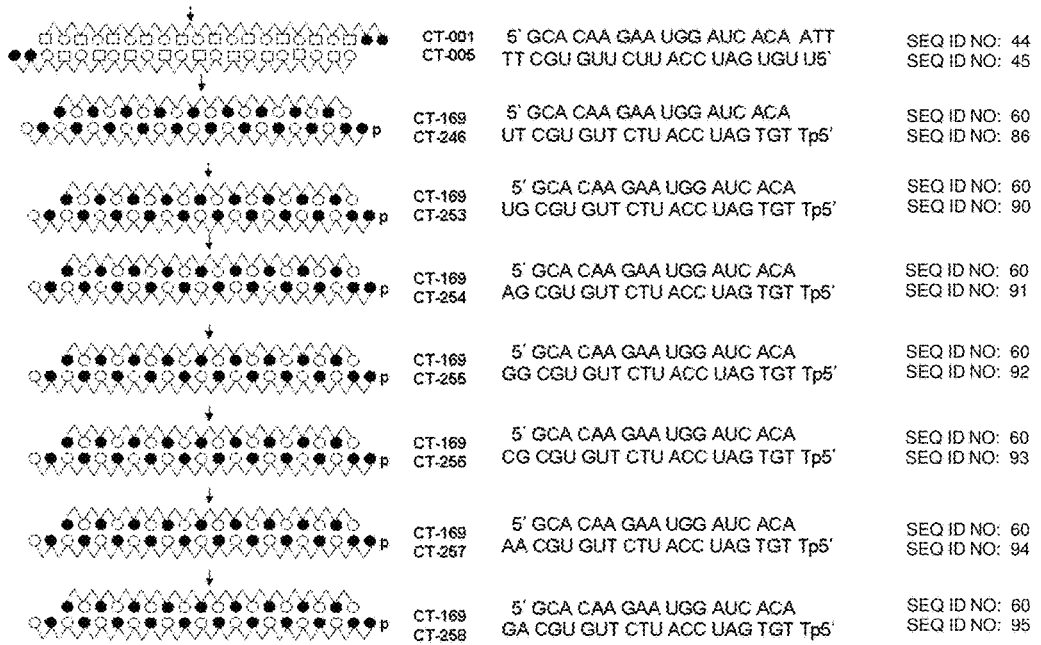
FIG. 44 is a diagram showing double-stranded polynucleotides against the human β-catenin gene.

(j) Comparison in Activity Based on Substitution of DNA for 5'-Terminal Nucleotide of Antisense Strand of Asymmetric Double-Stranded Polynucleotide and Difference in Nucleotide Sequence of 3'-Overhang Moiety An asymmetric double-stranded polynucleotide CT-169/CT-246 has thymidine at the 5'-end of the antisense strand (CT-246). The intensity of gene expression inhibitory activity was compared among double-stranded polynucleotides CT-169/CT-253, CT-169/CT-254, CT-169/CT-255, CT-169/CT-256, CT-169/CT-257, and CT-169/CT-258 in which the dimer sequence of the 3'-overhang moiety in the antisense strand (CT-246) was converted (see FIG. 44).

Figure 45:
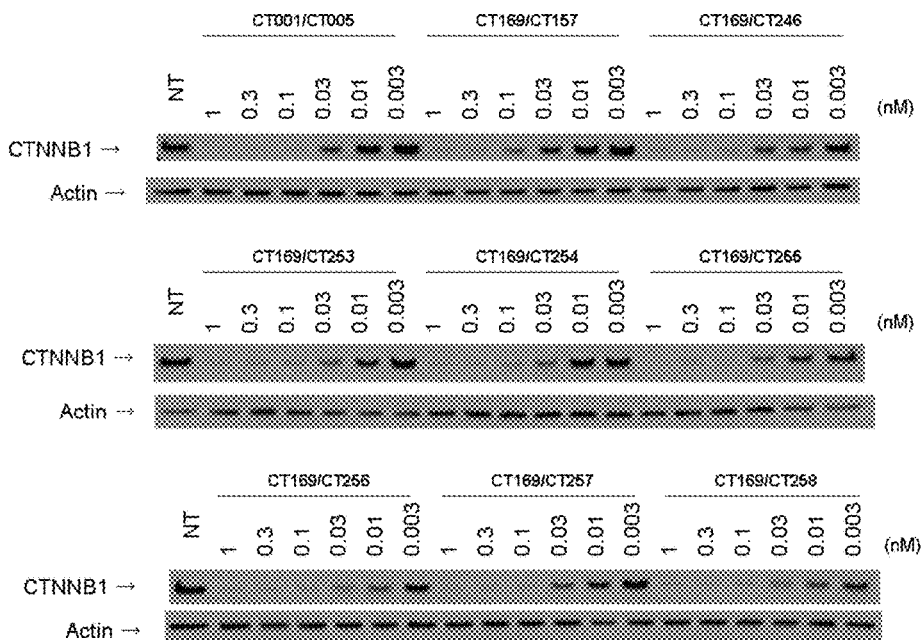
FIG. 45 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 45, CT-169/CT-253, CT-169/CT-254, CT-169/CT-255, CT-169/CT-256, CT-169/CT-257, and CT-169/CT-258 strongly inhibited the expression of the human β-catenin gene at a level equivalent to or higher than CT-001/CT-005.

Figure 46:
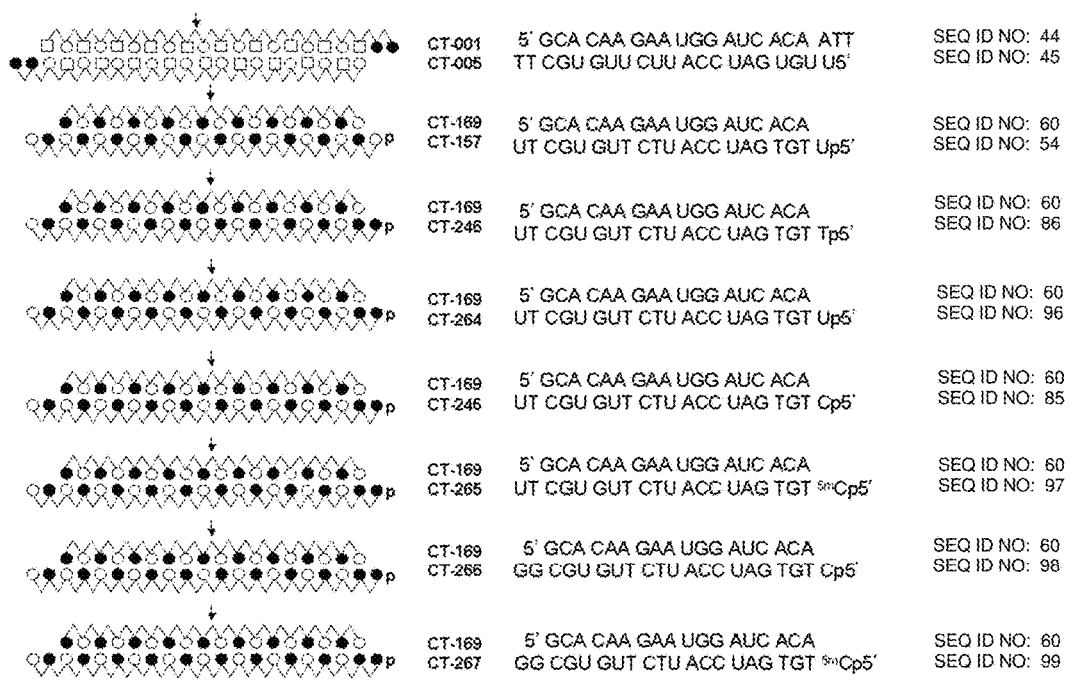
FIG. 46 is a diagram showing double-stranded polynucleotides against the human β-catenin gene.

Moreover, the intensity of gene expression inhibitory activity was compared among double-stranded polynucleotides CT-169/CT-264, CT-169/CT-265, CT-169/CT-266, and CT-169/CT-267 in which the DNA as a 5'-terminal nucleotide in the antisense strand (CT-246) was substituted by 2'-deoxyuridine, 2'-deoxycytidine, or 5-methyl-2'-deoxycytidine and the dimer sequence of the 3'-overhang moiety was converted (see FIG. 46).

Figure 47:
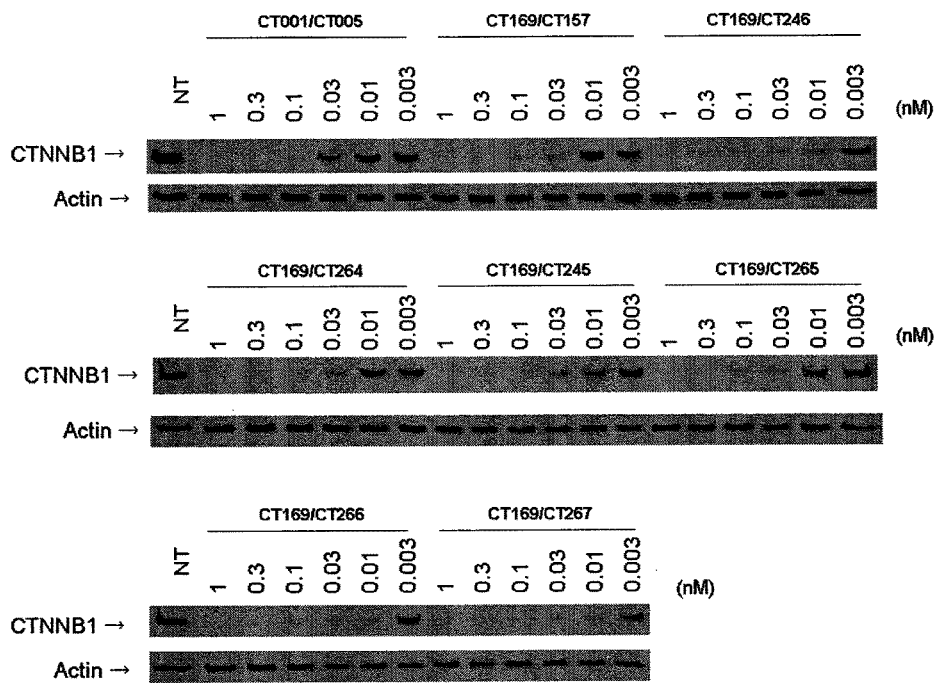
FIG. 47 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

As shown in FIG. 47, CT-169/CT-264, CT-169/CT-265, CT-169/CT-266, and CT-169/CT-267 strongly inhibited the expression of the human β-catenin gene at a level equivalent to or higher than CT-001/CT-005.

(Test Example 3) Test on IFN-α Production of Peripheral Mononuclear Cells Using siRNA (a) Without the Use of Transfection Reagent Peripheral mononuclear cells of healthy people were prepared by Ficoll-Paque density-gradient centrifugation. The prepared human peripheral mononuclear cells ($2 \times 10^5$ cells/well) were cultured for 24 hours in the presence of a double-stranded polynucleotide using a 96-well plate, and IFN-α in the collected supernatant was assayed using an ELISA kit (Human IFN-α ELISA Kit, Pestka Biomedical Laboratories, Inc.). Various double-stranded polynucleotides were used as a solution containing PolyI:C (Sigma-Aldrich Corp.): 2 μg/ml, imiquimod (Invivogen): $10^{-5}$ M, ssRNA40 (Invivogen): 2 μg/ml ssRNA41 (Invivogen): 2 μg/ml, ODN 2336 (Invivogen): $10^{-5}$ M, ODN 2336 control (Invivogen): $10^{-5}$ M, and one of unmodified double-stranded siRNA CT-106/041, double-stranded polynucleotide CT-103/157, or double-stranded polynucleotide CT-169/157: $10^{-7}$-$10^{-5}$ M.

Figure 48:
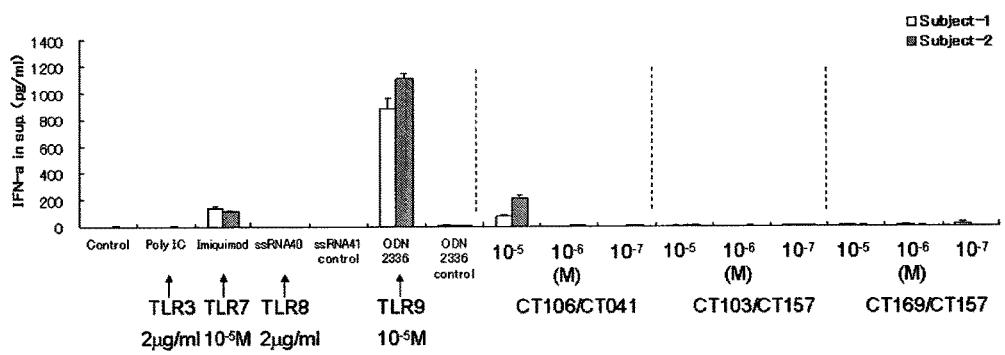
FIG. 48 is a diagram showing the change in IFN-α production caused by the administration of double-stranded polynucleotides without the use of a transfection reagent. The ordinate shows IFN-α production with the administration of a reagent known to act on Toll-like receptors (TLR) or the double-stranded polynucleotides. "Control" shows IFN-α production without the administration of a reagent known to act on Toll-like receptors (TLR) or the double-stranded polynucleotides. In the diagram, "TLR3" represents Toll-like receptor 3, "TLR7" represents Toll-like receptor 7, "TLR8" represents Toll-like receptor 8, and "TLR9" represents Toll-like receptor 9. The same holds true for FIG. 49.

As shown in FIG. 48, IFN-α production was observed for the unmodified siRNA CT-106/041 at $10^{-5}$ M and however, not observed for the double-stranded polynucleotides CT-103/157 and CT-169/157. This result shows that the double-stranded polynucleotides can reduce IFN-α production and provide a polynucleotide with fewer adverse reactions.

(b) With the Use of Transfection Reagent

Peripheral mononuclear cells of healthy people were prepared by Ficoll-Paque density-gradient centrifugation. The prepared human peripheral mononuclear cells ($1.1 \times 10^6$ cells/well) were cultured for 24 hours in the presence of a double-stranded polynucleotide using a 24-well plate, and IFN-α in the collected supernatant was assayed using an ELISA kit (Human IFN-α ELISA Kit, Pestka Biomedical Laboratories, Inc.). When a transfection reagent was used, the double-stranded polynucleotides (CT-103/157 and CT-169/157) and (CT-106/041) described in the Examples and Reference Examples were separately mixed in advance with Lipofectamine 2000 (Invitrogen Corporation), and each mixture was added to the cell culture solution. A solution containing PolyI:C (Sigma-Aldrich Corp.): 2 μg/ml, imiquimod (Invivogen): $10^{-5}$ M, ssRNA40 (Invivogen): 2 μg/ml, ssRNA41 (Invivogen): 2

ODN 2336 (Invivogen): $10^{-5}$ M, and ODN 2336 control (Invivogen): $10^{-5}$ M was used as a standard compound without the use of the transfection reagent. A solution of unmodified siRNA CT-106/041, double-stranded polynucleotide CT-103/157, or double-stranded polynucleotide CT-169/157: $10^{-7}$ M was tested using the transfection reagent.

Figure 49:
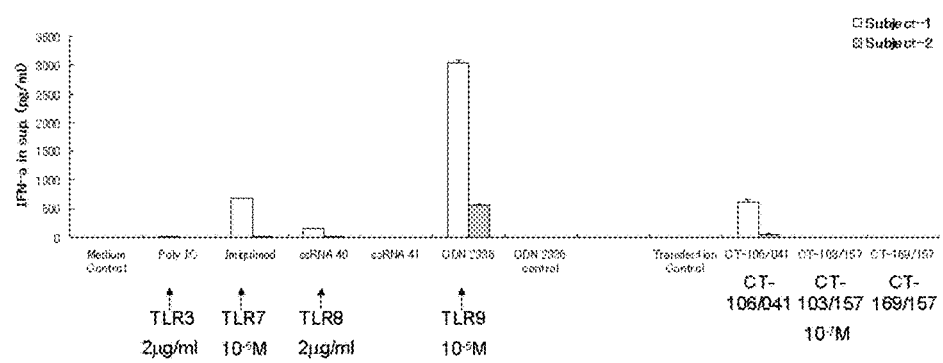
FIG. 49 is a diagram showing the change in IFN-α production caused by the administration of double-stranded polynucleotides with the use of a transfection reagent. The ordinate shows IFN-α production with the administration of a reagent known to act on Toll-like receptors (TLR) or the double-stranded polynucleotides. "Medium control" shows IFN-α production without the administration of a reagent known to act on Toll-like receptors (TLR) or the double-stranded polynucleotides. "Transfection control" shows IFN-α production with the addition of only the transfection reagent.

As shown in FIG. 49, IFN-α production was observed for the unmodified siRNA CT-106/041 but not observed for the double-stranded polynucleotides CT-103/157 and CT-169/157. This shows that the polynucleotides of the present Examples can potentially reduce IFN-α production and provide a polynucleotide with fewer adverse reactions.

(Test Example 4) Test on Resistance to RNase

50 μmol of each of double-stranded polynucleotides CT-106/CT-041, CT-105/CT-111, CT-001/CT-005, CT-091/CT-092, CT-095/CT-096, CT-097/CT-098, CT-099/CT-100, CT-001/CT-092, and CT-104/CT-110 (see FIG. 18) was brought to the total volume of 14.5 μL with RNase One buffer (10 mM Tris-HCl pH 7.5, 5 mM EDTA, 200 mM DTT, 200 mM sodium acetate, Promega) and treated at 37° C. by the addition of 5 U RNase One (0.5 μL, Promega).

A 4 μL aliquot was taken from each reaction solution after a lapse of 3 hours and 20 hours, supplemented with 1.0 μL of a loading solution (50% glycerol, 1 mM EDTA pH 8.0, 0.25% bromophenol blue, 0.25% xylene cyanol FF), and stored at −20° C. until analysis.

To analyze the degradation reaction of the double-stranded polynucleotide by RNase One, the sample was subjected to 20% polyacrylamide electrophoresis (1× Tris-Borate-EDTA, 200 V, 2 hours) and stained with SYBR Gold (Invitrogen Corp.). siRNA Ladder Markers manufactured by TAKARA BIO INC. were used as makers indicating the sizes of double-stranded nucleic acids. The stained gel was visualized with Molecular Imager FX Fluorescent Imager system (manufactured by Bio-Rad Laboratories Inc.).

Figure 19:
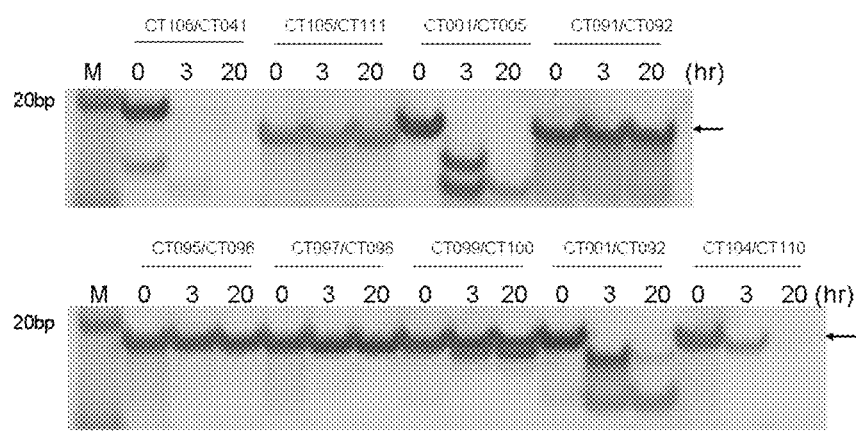
FIG. 19 is a diagram showing results of polyacrylamide electrophoresis analysis of an RNase degradation reaction of double-stranded polynucleotides. The arrow represents the positions of bands of the double-stranded polynucleotides.
Figure 20:
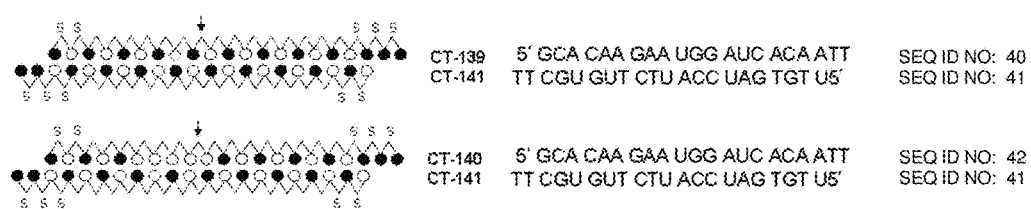
FIG. 20 is a diagram showing double-stranded polynucleotides against the human β-catenin gene.
Figure 21:
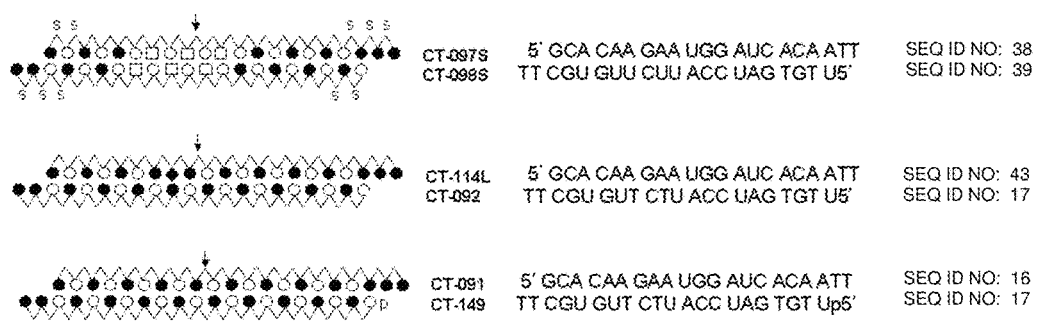
FIG. 21 is a diagram showing double-stranded polynucleotides against the human β-catenin gene.

CT-105/CT-111 in which all nucleotides constituting the double-stranded polynucleotide consisted of DNAs was not degraded by RNase (FIG. 19). However, CT-105/CT-111 does not inhibit β-catenin expression, as shown in Test Example 1.

CT-106/CT-041 in which all nucleotides constituting the double-stranded polynucleotide consisted of RNAs, and CT-001/005 in which the duplex region consisted of RNAs or 2'-O-methyl RNAs exhibited the inhibition of β-catenin expression, as shown in Test Example 1, and were easily degraded by RNase (see FIG. 19).

On the other hand, double-stranded RNA (CT-104/CT-110) having DNAs in the vicinity of the 3'-end of the sense strand and the 5'-end of the antisense strand, which was obtained by a modification method used in WO2003/044188, was also easily degraded by RNase. Furthermore, a double-stranded nucleic acid (CT-001/CT-092) having a sense strand comprising RNAs or 2'-O-methyl RNAs and an antisense strand comprising DNAs or 2'-O-methyl RNAs, which was obtained by a duplex region modification method used in WO2004/044136, was also easily degraded by RNase.

By contrast, CT-099/CT-100 corresponding to a form in which RNAs in CT-001/CT-005 were partially substituted by DNAs was only slightly degraded by RNase. CT-095/CT-096 and CT-097/CT-098 having further substitution by DNAs and CT-091/CT-092 having complete substitution of RNAs by DNAs were not degraded by RNase.

Test Example 5

The intensity of gene expression inhibitory activity was compared among double-stranded polynucleotides as follows in the same way as in Test Example 1.

Figure 50:
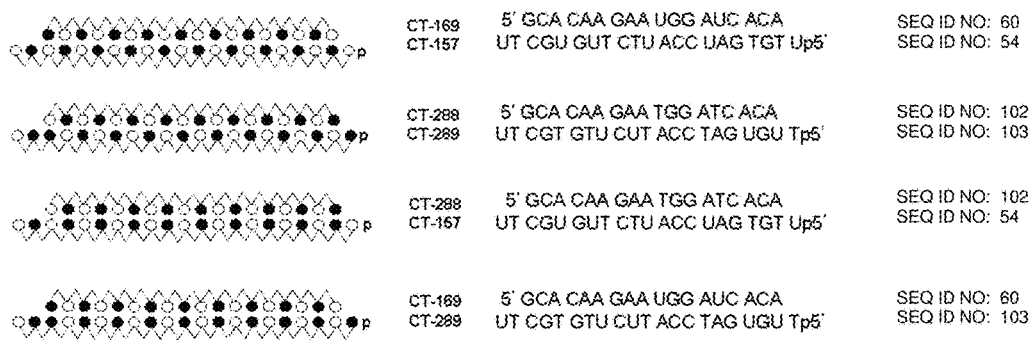
FIG. 50 is a diagram showing double-stranded polynucleotides against the human β-catenin gene.
Figure 51:
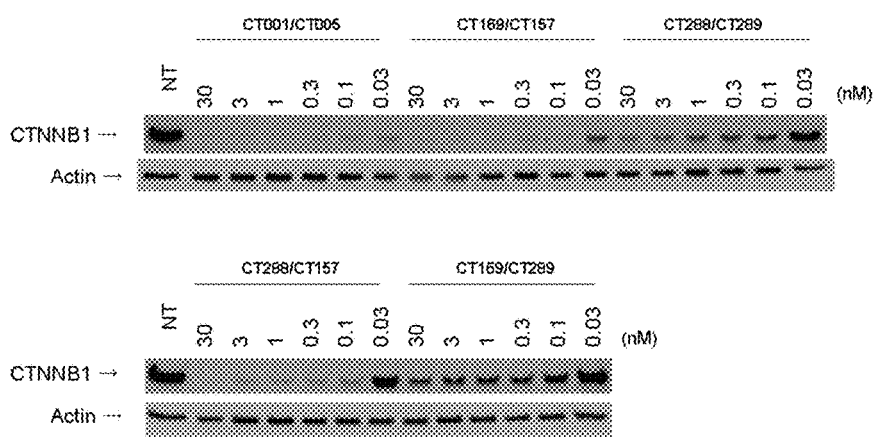
FIG. 51 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

(a) Comparison in Activity Based on Difference in DNA and 2'-O-Methyl RNA Modification Position in Asymmetric Double-Stranded Polynucleotide The inhibitory activities of a double-stranded polynucleotide CT-169/CT-157, CT-288/CT-289 in which the sequences of DNA and 2'-O-methyl RNA modifications were altered, and CT-288/CT-157 and CT-169/CT-289 in which the combinations of the sense and antisense strands in CT-169/CT-157 and CT-288/CT-289 were altered (see FIG. 50) on the expression of the human β-catenin gene are shown in FIG. 51. CT-169/CT-157 and CT-288/CT-157 inhibited the gene expression more strongly than CT-288/CT-289 and CT-169/CT-289.

Figure 52:
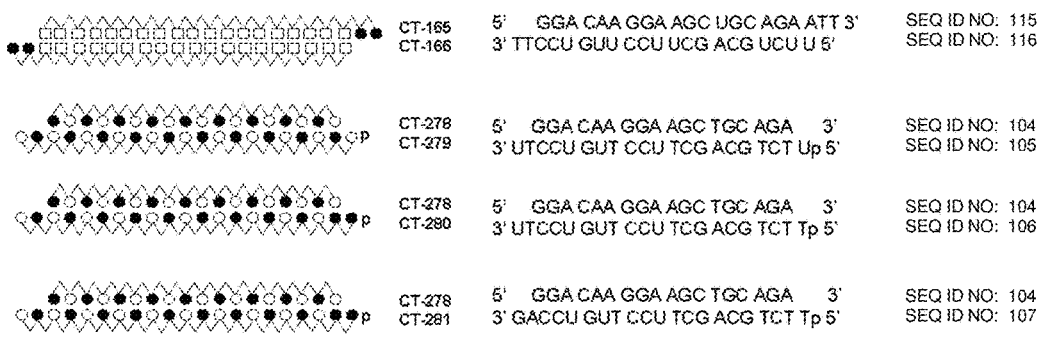
FIG. 52 is a diagram showing double-stranded polynucleotides against the human β-catenin gene.
Figure 53:
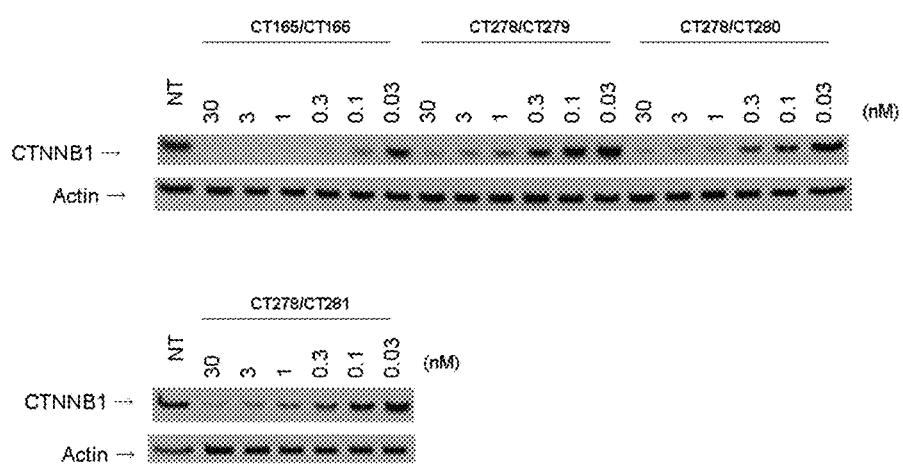
FIG. 53 is a diagram showing the results of western blot analysis of the intensities of inhibitory activities of various double-stranded polynucleotides on the expression of the human β-catenin gene. CTNNB1 represents the expression of human β-catenin proteins, and Actin represents the expression of β-actin proteins used as a control. The number represents the concentration of the double-stranded polynucleotide added. A lighter-colored band means stronger inhibitory activity on the expression of the human β-catenin gene.

(b) Gene Expression Inhibitory Activities of Double-Stranded Polynucleotides Targeting Different Sequences of Human β-Catenin Gene Sequences different from the target sequence used in Test Examples 1 and 2 were selected from within the human β-catenin gene to study the inhibitory activities of double-stranded polynucleotides on the expression of the human β-catenin gene. CT-165/CT-166 having TT in the 3'-terminal overhang moiety and all the other nucleotides consisting of RNAs (see FIG. 52) inhibited the expression of the human β-catenin gene, as shown in FIG. 53. Double-stranded polynucleotides CT-278/CT-279, CT-278/CT-280 and CT-278/CT-281 consisting of 2'-O-methyl RNAs or DNAs inhibited the expression of the human (β-catenin gene, as with CT-165/CT-166.

Test Example 6

The intensity of DDX3 gene expression inhibitory activity was compared among double-stranded polynucleotides as follows.

(1) Transfection

A human lung cancer NCI-H322 cell strain (derived from human bronchioloalveolar carcinoma) was adjusted to a concentration of 200000 cells/mL in an RPMI1640 medium (Invitrogen Corp.) containing 10% fetal bovine serum. Then, the solution was seeded at a concentration of 100 μL/well onto a 96-well flat-bottomed plate (manufactured by Corning Inc.) and cultured at 37° C. for 1 day under 5.0% $CO_2$ gas. A lipofection reagent Lipofectamine RNAiMAX (manufactured by Invitrogen Corp.) at a final concentration of 0.3 fit and a double-stranded polynucleotide solution at a final concentration of 5 nM were mixed in an RPMI1640 medium and left standing at room temperature for 20 minutes. The mixture was added to each well, and the culture was further continued for 3 days.

(2) Real-Time PCR

After the transfection, the culture supernatant was removed from each well, and mRNA was extracted using RNeasy Micro kit (manufactured by QIAGEN). The mRNA was quantified by real-time PCR as follows using a TaqMan probe for DDX3 (manufactured by Applied Biosystems), a TaqMan probe for β-actin (manufactured by Applied Biosystems) as an internal standard, and a real-time PCR kit (manufactured by QIAGEN) containing reagents necessary for PCR. 10 μL of QuantiTect Probe RT-PCR Master Mix, 4-8 μL at of RNase-Free Water, and 0.2 μL of QuantiTect RT Mix included in the real-time PCR kit were injected per well of a 96-well PCR plate (manufactured by Applied Biosystems). The solution was further brought to a total volume of 20 μL by the addition of 14 of the TaqMan probes and 4 μL, of the extracted mRNA solution and loaded in Mx3000P (manufactured by STRATAGENE), followed by PCR under the following conditions:

Reverse transcription reaction at 50° C. for 30 minutes
PCR initial activation at 95° C. for 15 minutes
PCR at 94° C. for 15 seconds
60° C. for 1 minute This PCR cycle was repeated 48 times. A calibration curve was prepared by the UV quantification of mRNA extracted from cells treated only with the lipofection reagent. Based on the calibration curve, DDX3 and β-actin in each transfectant were quantified, and a value determined by dividing the amount of DDX3 by the amount of β-actin was plotted in a graph. Real-time PCR was conducted on N=3, and SE is shown in the graph (the structures and nucleotide sequences of the double-stranded polynucleotides are shown in FIGS. 1, 2, 4, 6, 7, 8, 9, 13, 14, 16, 18, 20, and 21).

(3) Results of Real-Time PCR Analysis

Figure 54:
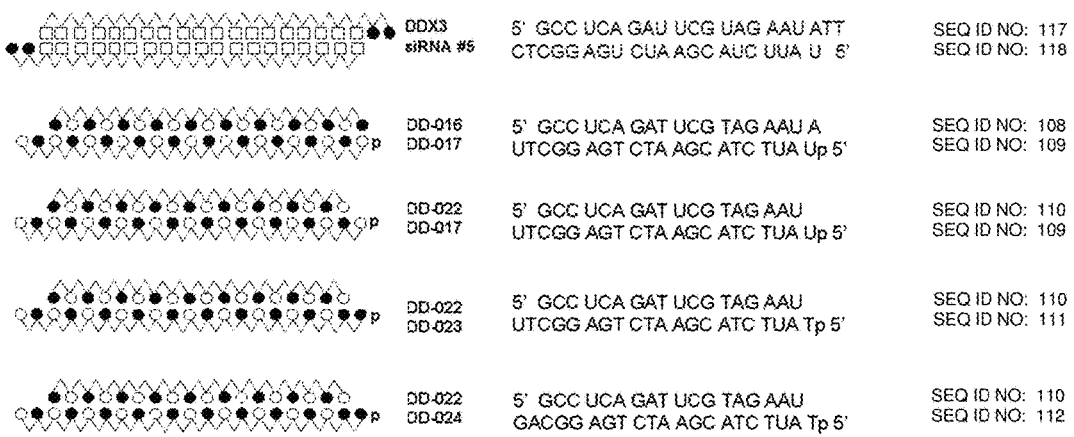
FIG. 54 is a diagram showing double-stranded polynucleotides against the DDX3 (DEAD (Asp-Glu-Ala-Asp) box polypeptide 3, X-linked) gene.
Figure 55:
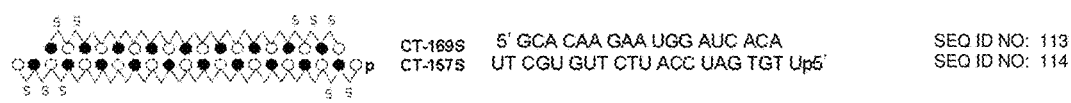
FIG. 55 is a diagram showing double-stranded polynucleotides against the human β-catenin gene.
Figure 56:
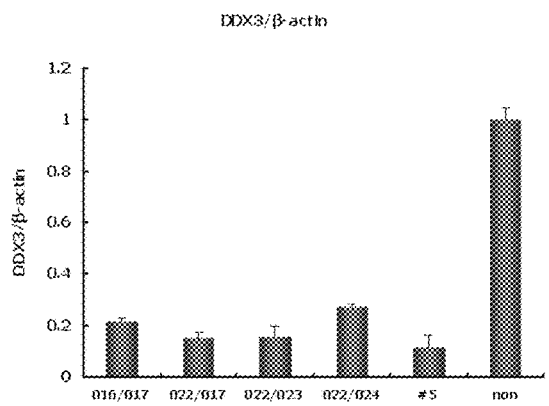
FIG. 56 is a diagram showing the intensities of inhibitory activities of DD-016/DD-017 (in the diagram, 016/017; the same holds true for the description below), DD-022/DD-017 (022/017), DD-022/DD-023 (022/023), and DD-022/DD-024 (022/024), and a natural double-stranded polynucleotide DDX3 siRNA#5 (#5) on the expression of the DDX3 gene. That derived from cells treated with only a lipofection reagent was used as a control and is indicated as "non" in the diagram.

A natural double-stranded polynucleotide against the human DDX3 gene (DDX3 siRNA#5) and double-stranded polynucleotides were studied by real-time PCR for their inhibitory activities on the expression of the human DDX3 gene. Double-stranded polynucleotides DD-016/DD-017, DD-022/DD-017, DD-022/DD-023, and DD-022/DD-024 comprising 2'-O-methyl RNAs or DNAs (see FIG. 54) inhibited the expression of the human DDX3 gene at a level equivalent to the natural double-stranded polynucleotide (DDX3 siRNA#5), as shown in FIG. 56.

INDUSTRIAL APPLICABILITY

The present invention could provide a double-stranded polynucleotide that is resistant to RNase, can be synthesized at low cost, and has a genetic interference effect.

The double-stranded polynucleotide can be used in the functional analysis of genes, pharmaceutical compositions, etc. However, the industrial field of the present double-stranded polynucleotide is not limited as long as it can be used therein.

The invention claimed is:

1. A double-stranded polynucleotide or a salt thereof, comprising polynucleotides represented by formulas (IV) and (V):

$$5'\text{-}(\alpha\text{-}\beta)_9\text{-}\alpha_p\text{-}\lambda_m\text{-}3' \quad (IV)$$

$$5'\text{-}\delta_s\text{-}(\alpha\text{-}\beta)_9\text{-}\upsilon_n\text{-}3' \quad (V),$$

wherein:
α and β are independently selected from a DNA and a 2'-OMeRNA, wherein if α is a DNA, then β is a 2'-OMeRNA, and if α is a 2'-OMeRNA, then β is a DNA;
each occurrence of δ is independently selected from a DNA and a 2'-OMeRNA;
each occurrence of λ is independently selected from a DNA and a 2'-OMeRNA;
each occurrence of υ is independently selected from a DNA and a 2'-OMeRNA;
p is an integer of 0 or 1;
m is 0 when p is 0 and is selected from any integer of 0 to 5 when p is 1;
s is an integer of 0 or 1;
n is selected from any integer of 0 to 5;
$(\alpha\text{-}\beta)_9\text{-}\alpha_p$ in the polynucleotide represented by formula (IV) has a nucleotide sequence identical to a target gene;
the nucleotide sequences of $(\alpha\text{-}\beta)_9$ in formula (IV) and $(\alpha\text{-}\beta)_9$ in formula (V) are complementary to each other.

2. A double-stranded polynucleotide or a salt thereof, comprising polynucleotides represented by formulas (VI) and (VII):

$$5'\text{-}\beta\text{-}(\alpha\text{-}\beta)_8\text{-}\alpha_p\text{-}\lambda_m\text{-}3' \quad (VI)$$

$$5'\text{-}\delta_s\text{-}(\alpha\text{-}\beta)_8\text{-}(\alpha\text{-}\beta)\text{-}\upsilon_n\text{-}3' \quad (VII),$$

wherein:
α and β are independently selected from a DNA and a 2'-OMeRNA, wherein if α is a DNA, then β is a 2'-OMeRNA, and wherein if α is a 2'-OMeRNA, then β is a DNA;
each occurrence of δ is independently selected from a DNA and a 2'-OMeRNA;
each occurrence of λ is independently selected from a DNA and a 2'-OMeRNA;
each occurrence of υ is independently selected from a DNA and a 2'-OMeRNA;
p is an integer of 0 or 1;
m is 0 when p is 0 and is selected from any integer of 0 to 5 when p is 1;
s is an integer of 0 or 1;
n is any integer of 0 to 5;
$\beta\text{-}(\alpha\text{-}\beta)_8\text{-}\alpha_p$ in the polynucleotide represented by formula (VI) has a nucleotide sequence identical to a target gene;
the nucleotide sequences of $(\alpha\text{-}\beta)_8$ in formula (VI) and $(\alpha\text{-}\beta)_8$ in formula (VII) are complementary to each other.

3. The double-stranded polynucleotide or salt thereof of claim 1 or claim 2, wherein:
the polynucleotide represented by formula IV or formula VI is:
HO-$G^p$-$C^{m1p}$-$A^p$-$C^{m1p}$-$A^p$-$A^{m1p}$-$G^p$-$A^{m1p}$-$A^p$-$U^{m1p}$-$C^p$-$A^{m1p}$-$C^p$-$A^{m1t}$-H (SEQ ID NO: 60);
the polynucleotide represented by formula VI or formula VII is:
HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}T^p$-$U^{m1t}$-H (SEQ ID NO: 54); and
$G^p$ is a 2'-deoxyguanosine nucleotide, $C^{m1p}$ is a cytidine nucleotide with a 2'-O-methyl modification, $A^p$ is a 2'-deoxyadenosine nucleotide, $A^{m1p}$ is an adenosine nucleotide with a 2'-O-methyl modification, $U^{m1p}$ is a uracil nucleotide with a 2'-O-methyl modification, $G^{m1p}$ is a guanosine nucleotide with a 2'-O-methyl modification, $C^p$ is a 2'-deoxycytidine nucleotide, $A^{m1t}$ is an adenosine with a 2'-O-methyl modification, $T^p$ is a thymidine nucleotide and $U^{m1t}$ is a uridine with a 2'-O-methyl modification.

4. The double-stranded polynucleotide or salt thereof of claim 1 or claim 2, wherein:
the polynucleotide represented by formula IV or formula VI is:
HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1p}$-$A^t$-H (SEQ ID NO: 22);
the polynucleotide represented by formula VI or formula VII is:
HO-P(=O)(OH)—O-$U^{m1p}$-$T^p$-$G^{m1p}$-$T^p$-$G^{m1p}$-$A^p$-$U^{m1p}$-$C^p$-$C^{m1p}$-$A^p$-$U^{m1p}$-$T^p$-$C^{m1p}$-$T^p$-$U^{m1p}$-$G^p$-$U^{m1p}$-$G^p$-$C^{m1p}$-$U^{m1t}$-H (SEQ ID NO: 54); and
$G^p$ is a 2'-deoxyguanosine nucleotide, $C^{m1p}$ is a cytidine nucleotide with a 2'-O-methyl modification, $A^p$ is a 2'-deoxyadenosine nucleotide, $A^{m1p}$ is an adenosine nucleotide with a 2'-O-methyl modification, $U^{m1p}$ is a uracil nucleotide with a 2'-O-methyl modification, $G^{m1p}$ is a guanosine nucleotide with a 2'-O-methyl modification, $C^p$ is a 2'-deoxycytidine nucleotide, $A^t$ is 2'-deoxyadenosine, $T^p$ is a thymidine nucleotide and $U^{m1t}$ is a uridine with a 2'-O-methyl modification.

5. A double-stranded polynucleotide or a salt thereof, comprising polynucleotides represented by formulas (I) and (III):

$$5'\text{-}X\text{-}(\alpha\text{-}\beta)_q\text{-}\alpha_p\text{-}\lambda_m\text{-}3' \quad (I)$$

$$5'\text{-}\delta_s\text{-}(\beta\text{-}\alpha)_r\text{-}Y\text{-}\upsilon_n\text{-}3' \quad (III),$$

wherein:
α and β are independently selected from a DNA and a 2'-OMeRNA, wherein if α is a DNA then β represents a 2'-OMeRNA, and if α is a 2'-OMeRNA, then β is a DNA;
each occurrence of δ is independently selected from a DNA and a 2'-OMeRNA;
each occurrence of λ is independently selected from a DNA and a 2'-OMeRNA;
each occurrence of υ is independently selected from a DNA and a 2'-OMeRNA;
X is 0;
Y is 0;
p is an integer of 0 or 1;
m is 0 when p is 0 and is selected from any integer of 0 to 5 when p is 1;
q is 9;
s is an integer of 0 or 1;
n is selected from any integer of 0 to 5;
r is 9;
$X\text{-}(\alpha\text{-}\beta)_q\text{-}\alpha_p$ in the polynucleotide represented by formula (I) has a nucleotide sequence identical to a target gene;
the nucleotide sequences of $X\text{-}(\alpha\text{-}\beta)_q$ in formula (I) and $(\beta\text{-}\alpha)_r\text{-}Y$ in formula (III) are complementary to each other.

6. The double-stranded polynucleotide or salt thereof of any one of claim 1, 2, or 5, wherein m is 0 and p is 0.

7. The double-stranded polynucleotide or salt thereof of any one of claim 1, 2, or 5, wherein α is a DNA, and β is a 2'-OMeRNA.

8. The double-stranded polynucleotide or salt thereof of any one of claim 1, 2, or 5, wherein m is 0, p is 0, s is 1, and n is 2.

9. The double-stranded polynucleotide or salt thereof of claim 7, wherein m is 0, p is 0, s is 1, and n is 2.

10. The double-stranded polynucleotide or salt thereof of any one of claim 1, 2, or 5, wherein λ and υ each independently comprise:
    a DNA selected from a thymine base, an adenine base, and a guanine base; or
    a 2'-OMeRNA selected from an uracil base, an adenine base, and a guanine base.

11. The double-stranded polynucleotide or salt thereof of claim 7, wherein λ and υ each independently comprise:
    a DNA selected from a thymine base, an adenine base, and a guanine base; or
    a 2'-OMeRNA selected from an uracil base, an adenine base, and a guanine base.

12. The double-stranded polynucleotide or salt thereof of claim 8, wherein λ and υ each independently comprise:
    a DNA selected from a thymine base, an adenine base, and a guanine base; or
    a 2'-OMeRNA selected from an uracil base, an adenine base, and a guanine base.

13. The double-stranded polynucleotide or salt thereof of claim 9, wherein λ and υ each independently comprise:
    a DNA selected from a thymine base, an adenine base, and a guanine base; or
    a 2'-OMeRNA selected from an uracil base, an adenine base, and a guanine base.

14. The double-stranded polynucleotide or salt thereof of any one of claim 1, 2, or 5, wherein m is 0, and n is 2.

15. The double-stranded polynucleotide or salt thereof of claim 7, wherein m is 0, and n is 2.

16. The double-stranded polynucleotide or salt thereof of any one of claim 1, 2, or 5, wherein one or more of the 1 to 4 2'-OMeRNA residues are substituted by an ENA or a 2',4'-BNA/LNA.

17. The double-stranded polynucleotide or salt thereof of claim 7, wherein one or more of the 1 to 4 2'-OMeRNA residues are substituted by an ENA or a 2',4'-BNA/LNA.

18. The double-stranded polynucleotide or salt thereof of claim 8, wherein one or more of the 1 to 4 2'-OMeRNA residues are substituted by an ENA or a 2',4'-BNA/LNA.

19. The double-stranded polynucleotide or salt thereof of claim 9, wherein one or more of the 1 to 4 2'-OMeRNA residues are substituted by an ENA or a 2',4'-BNA/LNA.

20. The double-stranded polynucleotide or salt thereof of any one of claim 1, 2, or 5, wherein one or more of the 1 to 4 DNA residues are substituted by an RNA, an ENA or a 2',4'-BNA/LNA.

21. The double-stranded polynucleotide or salt thereof of claim 7, wherein one or more of the 1 to 4 DNA residues are substituted by an RNA, an ENA or a 2',4'-BNA/LNA.

22. The double-stranded polynucleotide or salt thereof of claim 8, wherein one or more of the 1 to 4 DNA residues are substituted by an RNA, an ENA or a 2',4'-BNA/LNA.

23. The double-stranded polynucleotide or salt thereof of claim 9, wherein one or more of the 1 to 4 DNA residues are substituted by an RNA, an ENA or a 2',4'-BNA/LNA.

24. The double-stranded polynucleotide or salt thereof of any one of claim 1, 2, or 5, wherein the nucleotides are bonded to each other via a phosphodiester bond or a phosphorothioate bond.

25. The double-stranded polynucleotide or salt thereof of claim 7, wherein the nucleotides are bonded to each other via a phosphodiester bond or a phosphorothioate bond.

26. The double-stranded polynucleotide or salt thereof of claim 8, wherein the nucleotides are bonded to each other via a phosphodiester bond or a phosphorothioate bond.

27. The double-stranded polynucleotide or salt thereof of claim 9, wherein the nucleotides are bonded to each other via a phosphodiester bond or a phosphorothioate bond.

28. The double-stranded polynucleotide or salt thereof of any one of claim 1, 2, or 5, wherein the compound of formula (V), formula (VII) or formula (III) has a phosphorylated 5'-end.

29. The double-stranded polynucleotide or salt thereof of claim 7, wherein the compound of formula (V), formula (VII) or formula (III) has a phosphorylated 5'-end.

30. The double-stranded polynucleotide or salt thereof of claim 8, wherein the compound of formula (V), formula (VII) or formula (III) has a phosphorylated 5'-end.

31. The double-stranded polynucleotide or salt thereof of claim 9, wherein the compound of formula (V), formula (VII) or formula (III) has a phosphorylated 5'-end.

32. A pharmaceutical composition comprising the double-stranded polynucleotide or salt thereof of any one of claim 1, 2, or 5, and a pharmacologically acceptable additive.

33. A pharmaceutical composition comprising the double-stranded polynucleotide or salt thereof of claim 7, and a pharmacologically acceptable additive.

34. A pharmaceutical composition comprising the double-stranded polynucleotide or salt thereof of claim 8, and a pharmacologically acceptable additive.

35. A pharmaceutical composition comprising the double-stranded polynucleotide or salt thereof of claim 9, and a pharmacologically acceptable additive.

36. A pharmaceutical composition comprising the double-stranded polynucleotide or salt thereof of claim 13, and a pharmacologically acceptable additive.

37. A method for inhibiting the expression of a target gene, comprising administering the double-stranded polynucleotide or salt thereof of any one of claim 1, 2, or 5 to a mammal.

38. A method for inhibiting the expression of a target gene, comprising administering the double-stranded polynucleotide or salt thereof of claim 7 to a mammal.

39. A method for inhibiting the expression of a target gene, comprising administering the double-stranded polynucleotide or salt thereof of claim 8 to a mammal.

40. A method for inhibiting the expression of a target gene, comprising administering the double-stranded polynucleotide or salt thereof of claim 9 to a mammal.

* * * * *

UNITED STATES PATENT AND TRADEMARK OFFICE
CERTIFICATE OF CORRECTION

PATENT NO.       : 9,885,036 B2
APPLICATION NO.  : 13/001714
DATED            : February 6, 2018
INVENTOR(S)      : Koizumi et al.

Page 1 of 2

It is certified that error appears in the above-identified patent and that said Letters Patent is hereby corrected as shown below:

On the Title Page

In the "Inventors" section designated as Item (75), left column, Line 2, delete "Makoto Koizumi, Kanagawa (JP);" and insert therefor -- Makoto Koizumi, Tokyo (JP); --.

In the "Inventors" section designated as Item (75), left column, Line 3, delete "Yasuhide Hirota, Sakura (JP)" and insert therefor -- Yasuhide Hirota, Tokyo (JP) --.

In the "References Cited" section designated as Item (56), page 2, right column, Line 19, delete "siRNAs," RNA, 2004, vol. p. 766-771" and insert therefor -- siRNAs," RNA, 2004, vol. 10, p. 766-771 --.

In the "References Cited" section designated as Item (56), page 2, right column, Line 35, delete "Oligonucleotides fro Antisense Drug," Bioorganic & Medicinal" and insert therefor
-- Oligonucleotides for Antisense Drug," Bioorganic & Medicinal --.

In the "References Cited" section designated as Item (56), page 3, right column, Line 8, delete "Receptor Targetign and Avidin-Biotin Technology," Pharmaceutical" and insert therefor -- Receptor Targeting and Avidin-Biotin Technology," Pharmaceutical --.

In the Claims

In Claim 3, Column 239, Lines 64-65, delete "HO-$G^p$-$C^{m1p}$-$A^p$-$C^{m1p}$-$A^p$-$A^{m1p}$-$G^p$-$A^{m1p}$-$A^p$-$U^{m1p}$-$C^p$-$A^{m1p}$-$C^p$-$A^{m1t}$-H (SEQ ID NO: 60);" and insert therefor -- HO-$G^p$-$C^{m1p}$-$A^p$-$C^{m1p}$-$A^p$-$A^{m1p}$-$G^p$-$A^{m1p}$-$A^p$-$U^{m1p}$-$G^p$-$G^{m1p}$-$A^p$-$U^{m1p}$-$C^p$-$A^{m1p}$-$C^p$-$A^{m1t}$-H (SEQ ID NO: 60); --.

Signed and Sealed this
Twenty-second Day of May, 2018

Andrei Iancu
*Director of the United States Patent and Trademark Office*

CERTIFICATE OF CORRECTION (continued)
U.S. Pat. No. 9,885,036 B2

In Claim 3, Column 240, Lines 1-3, delete "HO-P(=O)(OH)-O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$T$^p$-U$^{m1t}$-H (SEQ ID NO: 54); and" and insert therefor -- HO-P(=O)(OH)-O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 54); and --.

In Claim 4, Column 240, Lines 23-25, delete "HO-P(=O)(OH)-O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-U$^{m1t}$-H (SEQ ID NO: 54); and" and insert therefor -- HO-P(=O)(OH)-O-U$^{m1p}$-T$^p$-G$^{m1p}$-T$^p$-G$^{m1p}$-A$^p$-U$^{m1p}$-C$^p$-C$^{m1p}$-A$^p$-U$^{m1p}$-T$^p$-C$^{m1p}$-T$^p$-U$^{m1p}$-G$^p$-U$^{m1p}$-G$^p$-C$^{m1p}$-T$^p$-U$^{m1t}$-H (SEQ ID NO: 54); and --.